(12) United States Patent
Kim et al.

(10) Patent No.: US 11,932,661 B2
(45) Date of Patent: Mar. 19, 2024

(54) COMPOSITION FOR ORGANIC OPTOELECTRONIC DEVICE, ORGANIC OPTOELECTRONIC DEVICE, AND DISPLAY DEVICE

(71) Applicant: SAMSUNG SDI CO., LTD., Yongin-si (KR)

(72) Inventors: Byungku Kim, Suwon-si (KR); Junmo Park, Suwon-si (KR); Min Seok Seo, Suwon-si (KR); Namheon Lee, Suwon-si (KR); Mijin Lee, Suwon-si (KR); Kipo Jang, Suwon-si (KR); Sung-Hyun Jung, Suwon-si (KR); Eunjeong Choi, Suwon-si (KR)

(73) Assignee: SAMSUNG SDI CO., LTD., Yongin-si (KR)

(*) Notice: Subject to any disclaimer, the term of this patent is extended or adjusted under 35 U.S.C. 154(b) by 547 days.

(21) Appl. No.: 17/204,094

(22) Filed: Mar. 17, 2021

(65) Prior Publication Data

US 2021/0300951 A1 Sep. 30, 2021

(30) Foreign Application Priority Data

Mar. 23, 2020 (KR) .......... 10-2020-0035035

(51) Int. Cl.
| | |
|---|---|
| *H01L 51/00* | (2006.01) |
| *C07F 7/08* | (2006.01) |
| *H10K 85/40* | (2023.01) |
| *H10K 85/60* | (2023.01) |
| *H10K 50/16* | (2023.01) |
| *H10K 50/17* | (2023.01) |

(52) U.S. Cl.
CPC .......... *C07F 7/0807* (2013.01); *C07F 7/0814* (2013.01); *H10K 85/40* (2023.02); *H10K 85/636* (2023.02); *H10K 85/654* (2023.02); *H10K 85/6572* (2023.02); *H10K 85/6574* (2023.02); *H10K 85/6576* (2023.02); *H10K 50/16* (2023.02); *H10K 50/171* (2023.02)

(58) Field of Classification Search
None
See application file for complete search history.

(56) References Cited

U.S. PATENT DOCUMENTS

| | | |
|---|---|---|
| 5,061,569 A | 10/1991 | Vanslyke et al. |
| 6,229,012 B1 | 5/2001 | Hu et al. |
| 8,951,647 B2 | 2/2015 | Parham et al. |
| 2022/0407010 A1* | 12/2022 | Park ............ C07D 209/80 |
| 2023/0167137 A1* | 6/2023 | Kim ............ H10K 85/6576 |
| | | 257/40 |

FOREIGN PATENT DOCUMENTS

| | | | |
|---|---|---|---|
| CN | 108409773 A | | 8/2018 |
| CN | 110872313 A | * | 3/2020 ............ C07F 7/0816 |
| EP | 3174123 A1 | | 5/2017 |
| JP | 1993-009471 A | | 1/1993 |
| JP | 1995-126615 A | | 5/1995 |
| JP | 1998-095973 A | | 4/1998 |
| JP | 3817632 B2 | | 9/2006 |
| JP | 4978003 B2 | | 7/2012 |
| KR | 10-2013-0025190 A | | 3/2013 |
| KR | 10-1399636 B1 | | 5/2014 |
| KR | 10-2015-0030511 A | | 3/2015 |
| KR | 10-2015-0130651 A | | 11/2015 |
| KR | 10-2017-0061238 A | | 6/2017 |
| KR | 10-2018-0027468 A | | 3/2018 |
| KR | 10-2018-0031874 A | | 3/2018 |
| KR | 10-2018-0040080 A | | 4/2018 |
| WO | WO 1995/009147 A1 | | 4/1995 |
| WO | WO 2010/126270 A1 | | 11/2010 |
| WO | WO 2011/055912 A1 | | 5/2011 |
| WO | WO 2018/087020 A1 | | 5/2018 |
| WO | WO 2019/027212 A1 | | 2/2019 |
| WO | WO 2019/121483 A1 | | 6/2019 |

* cited by examiner

Primary Examiner — Robert S Loewe
(74) Attorney, Agent, or Firm — Lee IP Law, P.C.

(57) ABSTRACT

A composition for an organic photoelectronic device, an organic photoelectronic device, and a display device, the composition comprising a first compound represented by Chemical Formula 1, and a second compound represented by Chemical Formula 2:

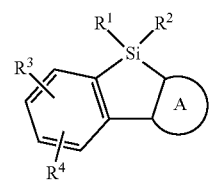

[Chemical Formula 1]

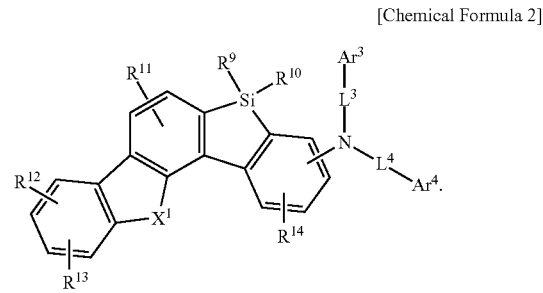

[Chemical Formula 2]

14 Claims, 1 Drawing Sheet

COMPOSITION FOR ORGANIC OPTOELECTRONIC DEVICE, ORGANIC OPTOELECTRONIC DEVICE, AND DISPLAY DEVICE

CROSS-REFERENCE TO RELATED APPLICATION

Korean Patent Application No. 10-2020-0035035, filed on Mar. 23, 2020, in the Korean Intellectual Property Office, and entitled: "Composition for Organic Optoelectronic Device, Organic Optoelectronic Device, and Display Device," is incorporated by reference herein in its entirety.

BACKGROUND

1. Field

Embodiments relate to a composition for an organic photoelectronic device, an organic photoelectronic device, and a display device.

2. Description of the Related Art

An organic optoelectronic device (e.g., organic optoelectronic diode) is a device capable of converting electrical energy and optical energy to each other.

Organic optoelectronic devices may be largely divided into two types according to a principle of operation. One is a photoelectric device that generates electrical energy by separating excitons formed by light energy into electrons and holes, and transferring the electrons and holes to different electrodes, respectively and the other is light emitting device that generates light energy from electrical energy by supplying voltage or current to the electrodes.

Examples of the organic optoelectronic device may include an organic photoelectric element, an organic light emitting diode, an organic solar cell, and an organic photo conductor drum.

Among them, organic light emitting diodes (OLEDs) are attracting much attention in recent years due to increasing demands for flat panel display devices. The organic light emitting diode is a device that converts electrical energy into light, and the performance of the organic light emitting diode is greatly influenced by an organic material between electrodes.

SUMMARY

The embodiments may be realized by providing a composition for an organic photoelectronic device, the composition including a first compound represented by Chemical Formula 1, and a second compound represented by Chemical Formula 2:

[Chemical Formula 1]

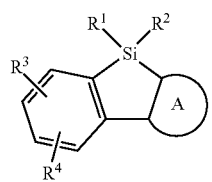

wherein $R^1$ and $R^2$ are each independently a substituted or unsubstituted C1 to C10 alkyl group, a substituted or unsubstituted C3 to C10 cycloalkyl group, a substituted or unsubstituted C6 to C20 aryl group, or a combination thereof, $R^3$ and $R^4$ are each independently hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof, and ring A is a moiety of the following Group A, Group A

[A-1]

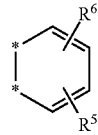

[A-2]

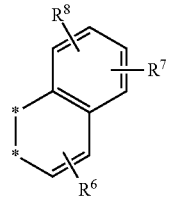

[A-3]

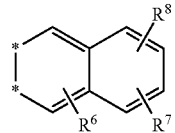

[A-4]

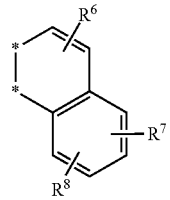

wherein $R^5$ to $R^8$ are each independently hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof, * is a linking point, and at least one of $R^3$ to $R^8$ is a substituent represented by Chemical Formula B,

[Chemical Formula B]

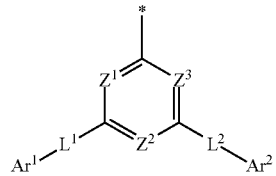

wherein $Z^1$ to $Z^3$ are each independently N or $CR^a$, at least two of $Z^1$ to $Z^3$ being N, each $R^a$ is independently hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof, $L^1$ and $L^2$ are each independently a single bond or a substituted or unsubstituted C6 to C30 arylene group, $Ar^1$ and $Ar^2$ are each independently a substituted or unsubstituted C6 to C30 aryl group, a substituted or unsubstituted C2 to C30 heterocyclic group, or a combination thereof;

[Chemical Formula 2]

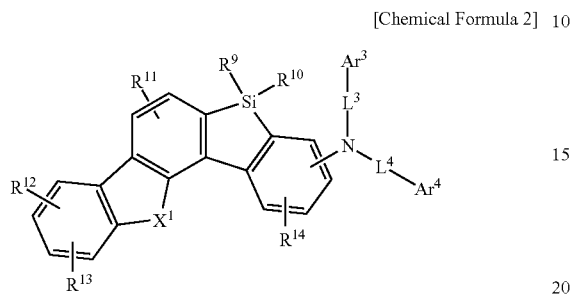

$X^1$ is O or S, $R^9$ and $R^{10}$ are each independently a substituted or unsubstituted C1 to C10 alkyl group, a substituted or unsubstituted C3 to C10 cycloalkyl group, a substituted or unsubstituted C6 to C20 aryl group, or a combination thereof, $R^{11}$ to $R^{14}$ are each independently hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof, $L^3$ and $L^4$ are each independently a single bond or a substituted or unsubstituted C6 to C30 arylene group, and $Ar^3$ and $Ar^4$ are each independently a substituted or unsubstituted C6 to C30 aryl group, a substituted or unsubstituted C2 to C30 heterocyclic group, or a combination thereof.

The first compound may be represented by Chemical Formula 1A, Chemical Formula 1E, Chemical Formula 1F, or Chemical Formula 1G,

[Chemical Formula 1A]

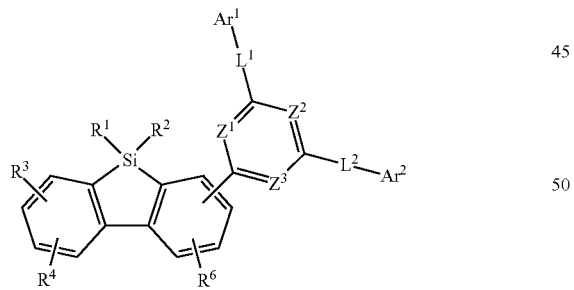

[Chemical Formula 1E]

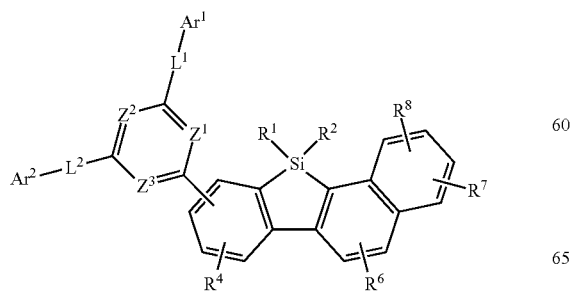

[Chemical Formula 1F]

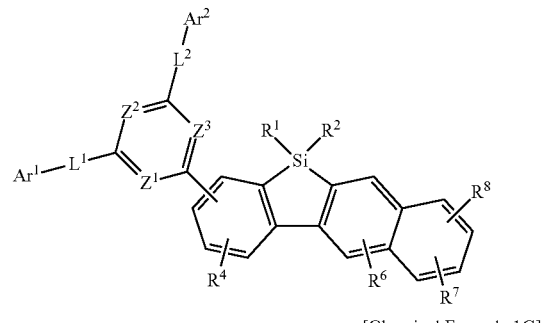

[Chemical Formula 1G]

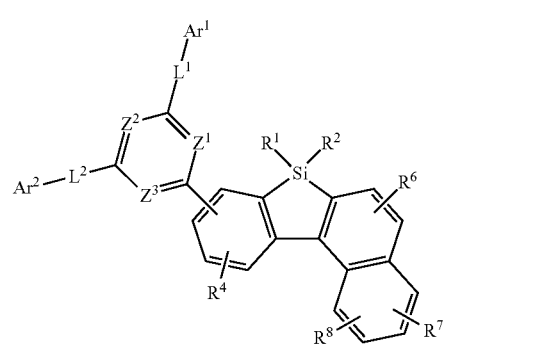

in Chemical Formula 1A and Chemical Formula 1E to Chemical Formula 1G, $R^1$ to $R^4$, $R^6$ to $R^8$, $Z^1$ to $Z^3$, $L^1$, $L^2$, $Ar^1$, and $Ar^2$ may be defined the same as those of Chemical Formula 1.

The first compound may be represented by Chemical Formula 1A-2, Chemical Formula 1A-4, Chemical Formula 1E-2, Chemical Formula 1E-4, Chemical Formula 1F-2, Chemical Formula 1F-4, Chemical Formula 1G-2, or Chemical Formula 1G-4:

[Chemical Formula 1A-2]

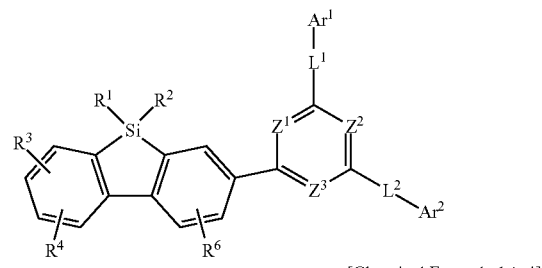

[Chemical Formula 1A-4]

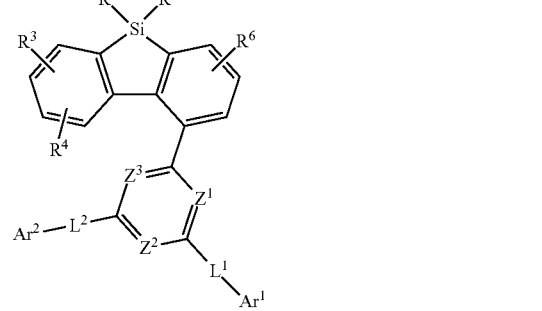

[Chemical Formula 1E-2]

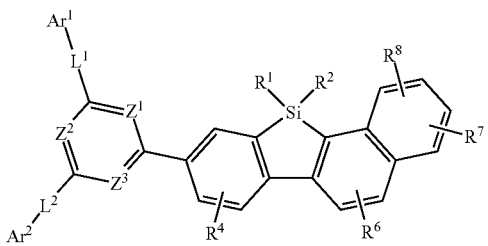

[Chemical Formula 1E-4]

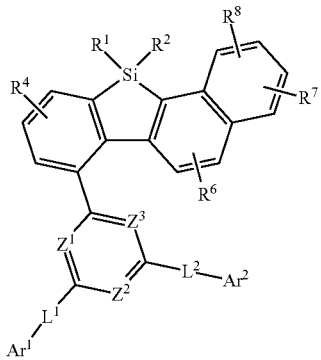

[Chemical Formula 1F-2]

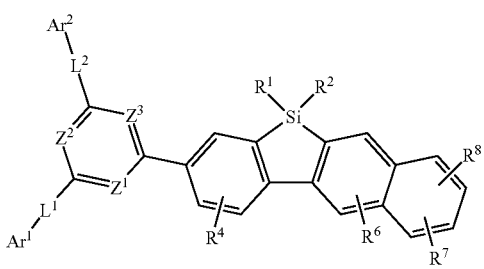

[Chemical Formula 1F-4]

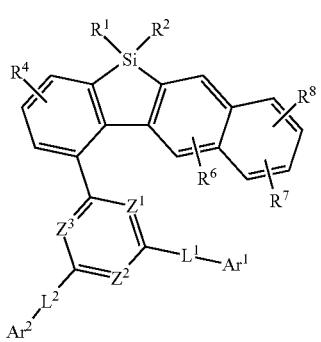

[Chemical Formula 1G-2]

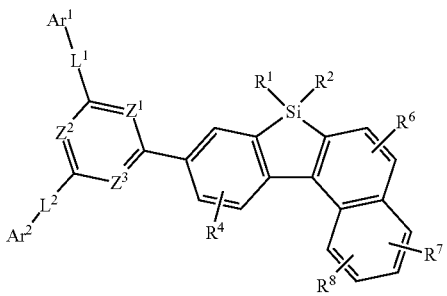

[Chemical Formula 1G-4]

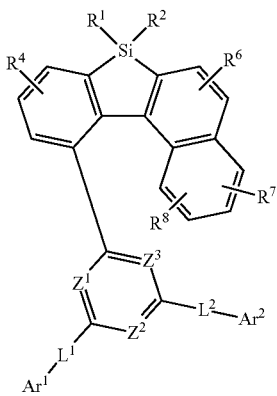

in Chemical Formula 1A-2, Chemical Formula 1A-4, Chemical Formula 1E-2, Chemical Formula 1E-4, Chemical Formula 1F-2, Chemical Formula 1F-4, Chemical Formula 1G-2, and Chemical Formula 1G-4, $R^1$ to $R^4$, $R^6$ to $R^8$, $Z^1$ to $Z^3$, $L^1$, $L^2$, $Ar^1$, and $Ar^2$ may be defined the same as those of Chemical Formula 1.

The first compound may be represented by Chemical Formula 1A-2 or Chemical Formula 1A-4, $Ar^1$ and $Ar^2$ may be each independently a substituted or unsubstituted phenyl group, a substituted or unsubstituted biphenyl group, or a substituted or unsubstituted naphthyl group, $R^1$ and $R^2$ may be each independently a substituted or unsubstituted C1 to C5 alkyl group or a substituted or unsubstituted phenyl group, $R^3$, $R^4$, and $R^6$ may be each independently hydrogen or a substituted or unsubstituted phenyl group, and $L^1$ and $L^2$ may be each independently a single bond or a substituted or unsubstituted phenylene group.

The first compound may be represented by Chemical Formula 1E-2, Chemical Formula 1E-4, Chemical Formula 1F-2, Chemical Formula 1F-4, Chemical Formula 1G-2, or Chemical Formula 1G-4, $Ar^1$ and $Ar^2$ may be each independently a substituted or unsubstituted phenyl group, a substituted or unsubstituted biphenyl group, or a substituted or unsubstituted naphthyl group, $R^1$ and $R^2$ may be each independently a substituted or unsubstituted C1 to C5 alkyl group or a substituted or unsubstituted phenyl group, $R^4$ and $R^6$ to $R^8$ may be each independently hydrogen or a substituted or unsubstituted phenyl group, and $L^1$ and $L^2$ may be each independently a single bond or a substituted or unsubstituted phenylene group.

The second compound may be represented by Chemical Formula 2-2:

[Chemical Formula 2-2]

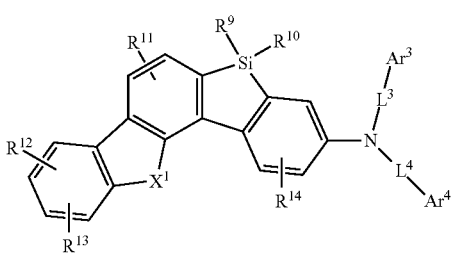

in Chemical Formula 2-2, $X^1$, $R^9$ to $R^{14}$, $L^3$, $L^4$, $Ar^3$, and $Ar^4$ may be defined the same as those of Chemical Formula 2.

Ar³ and Ar⁴ may be each independently a substituted or unsubstituted phenyl group, a substituted or unsubstituted biphenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted dibenzofuranyl group, a substituted or unsubstituted dibenzothiophenyl group, a substituted or unsubstituted carbazolyl group, or a substituted or unsubstituted dibenzosilole group, L³ and L⁴ may be each independently a single bond, a substituted or unsubstituted phenylene group, or a substituted or unsubstituted naphthylene group, R⁹ and R¹⁰ may be each independently a substituted or unsubstituted C1 to C5 alkyl group or a substituted or unsubstituted phenyl group, and R¹¹ to R¹⁴ may be each independently hydrogen or a substituted or unsubstituted phenyl group.

Ar³ and Ar⁴ may be each independently a substituted or unsubstituted phenyl group, a substituted or unsubstituted biphenyl group, a substituted or unsubstituted naphthyl group, a substituted or unsubstituted fluorenyl group, a substituted or unsubstituted dibenzofuranyl group, a substituted or unsubstituted dibenzothiophenyl group, a substituted or unsubstituted carbazolyl group, or a substituted or unsubstituted dibenzosilole group, L³ and L⁴ may be each independently a single bond or a substituted or unsubstituted phenylene group, R⁹ and R¹⁰ may be each independently a substituted or unsubstituted methyl group or a substituted or unsubstituted phenyl group, and R¹¹ to R¹⁴ may be each hydrogen.

The first compound may be represented by Chemical Formula 1A-2, Chemical Formula 1A-4, Chemical Formula 1E-2, Chemical Formula 1E-4, Chemical Formula 1F-2, Chemical Formula 1F-4, Chemical Formula 1G-2, or Chemical Formula 1G-4, the second compound may be represented by Chemical Formula 2-2:

[Chemical Formula 1A-2]

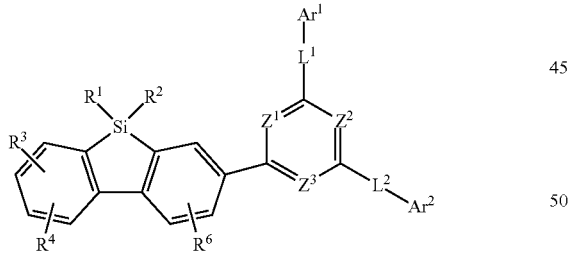

[Chemical Formula 1A-4]

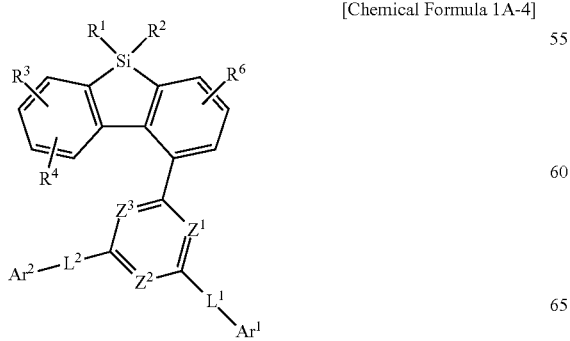

[Chemical Formula 1E-2]

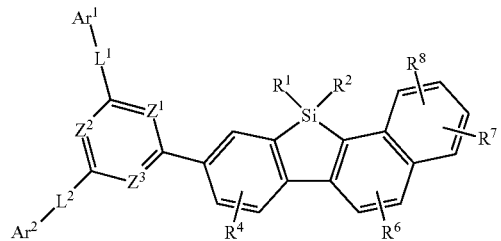

[Chemical Formula 1E-4]

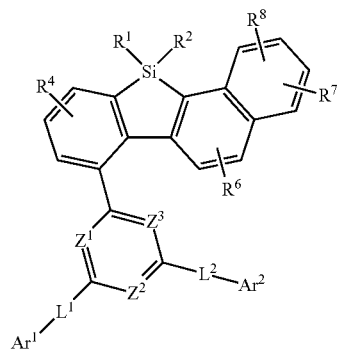

[Chemical Formula 1F-2]

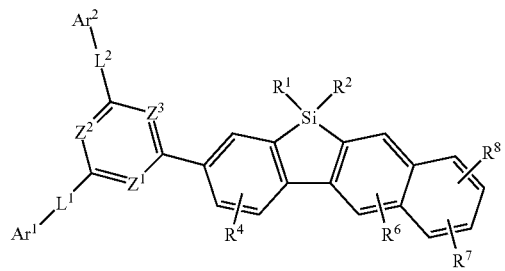

[Chemical Formula 1F-4]

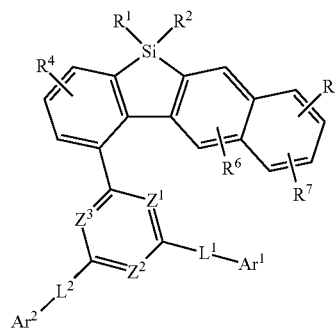

[Chemical Formula 1G-2]

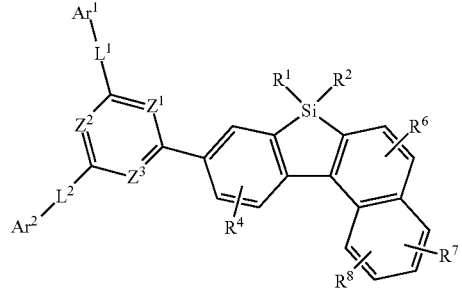

-continued

[Chemical Formula 1G-4]

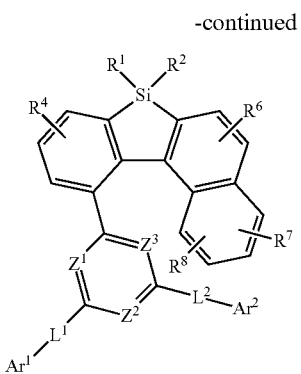

[Chemical Formula 2-2]

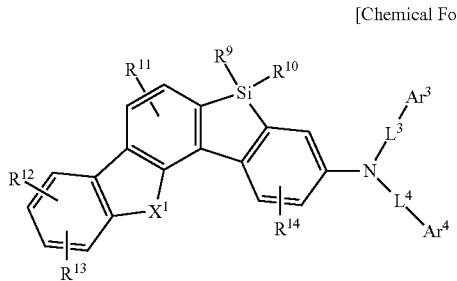

in Chemical Formula 1A-2, Chemical Formula 1A-4, Chemical Formula 1E-2, Chemical Formula 1E-4, Chemical Formula 1F-2, Chemical Formula 1F-4, Chemical Formula 1G-2, and Chemical Formula 1G-4, $R^1$ to $R^4$, $R^6$ to $R^8$, $Z^1$ to $Z^3$, $L^1$, $L^2$, $Ar^1$, and $Ar^2$ may be defined the same as those of Chemical Formula 1, and in Chemical Formula 2-2, $X^1$, $R^9$ to $R^{14}$, $L^3$, $L^4$, $Ar^3$, and $Ar^4$ may be defined the same as those of Chemical Formula 2.

In Chemical Formula 1A-2 and Chemical Formula 1A-4, $Ar^1$ and $Ar^2$ may be each independently a substituted or unsubstituted phenyl group, a substituted or unsubstituted biphenyl group, or a substituted or unsubstituted naphthyl group, $R^1$ and $R^2$ may be each independently a substituted or unsubstituted C1 to C5 alkyl group or a substituted or unsubstituted phenyl group, $R^3$, $R^4$, and $R^6$ may be each independently hydrogen or a substituted or unsubstituted phenyl group, and $L^1$ and $L^2$ may be each independently a single bond or a substituted or unsubstituted phenylene group, in Chemical Formula 1E-2, Chemical Formula 1E-4, Chemical Formula 1F-2, Chemical Formula 1F-4, Chemical Formula 1G-2, and Chemical Formula 1G-4, $Ar^1$ and $Ar^2$ may be each independently a substituted or unsubstituted phenyl group, a substituted or unsubstituted biphenyl group, or a substituted or unsubstituted naphthyl group, $R^1$ and $R^2$ may be each independently a substituted or unsubstituted C1 to C5 alkyl group or a substituted or unsubstituted phenyl group, $R^4$ and $R^6$ to $R^1$ may be each independently hydrogen or a substituted or unsubstituted phenyl group, and $L^1$ and $L^2$ may be each independently a single bond or a substituted or unsubstituted phenylene group, and in Chemical Formula 2-2, $Ar^3$ may be $Ar^4$ are each independently a substituted or unsubstituted phenyl group, a substituted or unsubstituted biphenyl group, a substituted or unsubstituted naphthyl group, a substituted or unsubstituted fluorenyl group, a substituted or unsubstituted dibenzofuranyl group, a substituted or unsubstituted dibenzothiophenyl group, a substituted or unsubstituted carbazolyl group, or a substituted or unsubstituted dibenzosilole group, $L^3$ and $L^4$ may be each independently a single bond or a substituted or unsubstituted phenylene group, and $R^9$ and $R^{10}$ may be each independently a substituted or unsubstituted methyl group or a substituted or unsubstituted phenyl group, and $R^{11}$ to $R^{14}$ may be each hydrogen.

The embodiments may be realized by providing an organic photoelectronic device including an anode and a cathode facing each other; and at least one organic layer between the anode and the cathode, wherein the at least one organic layer includes a light emitting layer, and the light emitting layer includes the composition for an organic photoelectronic device according to an embodiment.

The composition for an organic photoelectronic device may be a host of the light emitting layer.

The composition may include the first compound and the second compound in a weight ratio of about 70:30 to about 40:60.

The embodiments may be realized by providing a display device including the organic photoelectronic device according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
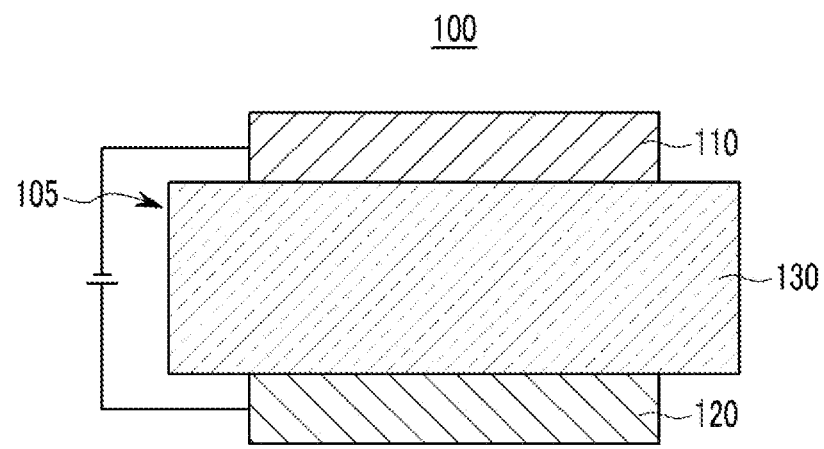
FIGS. 1 and 2 are cross-sectional views of an organic light emitting diode according to embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout. As used herein, the term "or" is not an exclusive term, e.g., "A or B" would include A, B, or A and B.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In addition, in specific examples, "substituted" refers to replacement of at least one hydrogen of a substituent or a compound by deuterium, a C1 to C20 alkyl group, a C6 to C30 aryl group, or a cyano group. In addition, in specific examples, "substituted" refers to replacement of at least one hydrogen of a substituent or a compound by deuterium, a C1 to C5 alkyl group, a C6 to C18 aryl group, or a cyano group. In addition, in specific examples, "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

As used herein, when a definition is not otherwise provided, "hetero" refers to one including one to three heteroatoms selected from N, O, S, P, and Si, and remaining carbons in one functional group.

As used herein, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like, a group in which two or more hydrocarbon aromatic moieties may be linked by a sigma bond, for example a biphenyl group, a terphenyl group, a quarterphenyl group, and the like, and a group in which two or more hydrocarbon aromatic moieties are fused directly or indirectly to provide a non-aromatic fused ring, for example, a fluorenyl group, and the like.

The aryl group may include a monocyclic, polycyclic, or fused ring polycyclic (i.e., rings sharing adjacent pairs of carbon atoms) functional group.

As used herein, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" refers to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, or a combination thereof.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, a substituted or unsubstituted dibenzothiophenyl group, a substituted or unsubstituted dibenzosilole group, or a combination thereof.

In the present specification, hole characteristics refer to an ability to donate an electron to form a hole when an electric field is applied and that a hole formed in the anode may be easily injected into the light emitting layer and transported in the light emitting layer due to conductive characteristics according to the highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to the lowest unoccupied molecular orbital (LUMO) level.

Hereinafter, a composition for an organic optoelectronic device according to an embodiment is described.

The composition for an organic optoelectronic device according to an embodiment may include a first compound represented by Chemical Formula 1 and a second compound represented by Chemical Formula 2.

[Chemical Formula 1]

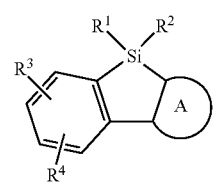

In Chemical Formula 1,
$R^1$ and $R^2$ may each independently be or include, e.g., a substituted or unsubstituted C1 to C10 alkyl group, a substituted or unsubstituted C3 to C10 cycloalkyl group, a substituted or unsubstituted C6 to C20 aryl group, or a combination thereof.
$R^3$ and $R^4$ may each independently be or include, e.g., hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof.

ring A may be, e.g., a moiety of the following Group A.

Group A

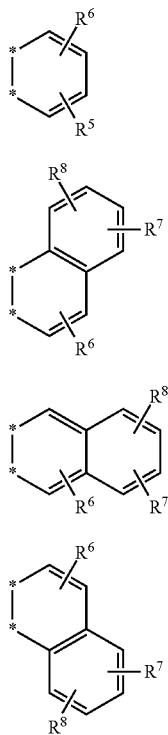

[A-1]

[A-2]

[A-3]

[A-4]

In A-1 to A-4 of Group A, $R^5$ to $R^8$ may each independently be or include, e.g., hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof.

Each * is a linking point (e.g., to the 5-membered, silicon containing ring of Chemical Formula 1). For example, each * may be a carbon shared between the 5-membered, silicon containing ring of Chemical Formula 1 and the moiety of Group A.

In an implementation, in Chemical Formula 1 and Group A, at least one of $R^3$ to $R^8$ may be, e.g., a substituent represented by Chemical Formula B.

[Chemical Formula B]

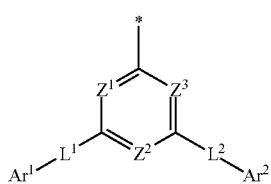

In Chemical Formula B, $Z^1$ to $Z^3$ may each independently be, e.g., N or $CR^a$. In an implementation, at least two of $Z^1$ to $Z^3$ may be N.

Each $R^a$ may independently be or include, e.g., hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof.

$L^1$ and $L^2$ may each independently be or include, e.g., a single bond or a substituted or unsubstituted C6 to C30 arylene group.

$Ar^1$ and $Ar^2$ may each independently be or include, e.g., a substituted or unsubstituted C6 to C30 aryl group, a substituted or unsubstituted C2 to C30 heterocyclic group, or a combination thereof.

[Chemical Formula 2]

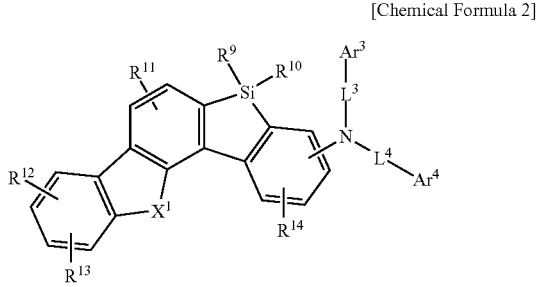

In Chemical Formula 2, $X^1$ may be, e.g., O or S.

$R^9$ and $R^{10}$ may each independently be or include, e.g., a substituted or unsubstituted C1 to C10 alkyl group, a substituted or unsubstituted C3 to C10 cycloalkyl group, a substituted or unsubstituted C6 to C20 aryl group, or a combination thereof.

$R^{11}$ to $R^{14}$ may each independently be or include, e.g., hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof.

$L^3$ and $L^4$ may each independently be or include, e.g., a single bond or a substituted or unsubstituted C6 to C30 arylene group.

$Ar^3$ and $Ar^4$ may each independently be or include, e.g., a substituted or unsubstituted C6 to C30 aryl group, a substituted or unsubstituted C2 to C30 heterocyclic group or a combination thereof.

The first compound represented by Chemical Formula 1 may secure a high molecular weight by including a dibenzosilole moiety, thereby increasing a glass transition temperature.

In an implementation, the dibenzosilole moiety may be substituted with the nitrogen-containing six-membered (e.g., hexagonal) ring (e.g., the substituent represented by Chemical Formula B) to help increase the planarity of the molecule, thereby increasing the dipole moment to help improve lattice accumulation, resulting in a high glass transition temperature as well as a low deposition process temperature relative to the molecular weight.

As a result, stability of the device in the device manufacturing process and stability against Joule heat generated when the device is driven may be increased, so that improved life-span characteristics in a low driving may be realized.

The first compound (having enhanced electron characteristics) and the second compound in which a dibenzosilole moiety is fused with benzofuran (or a dibenzosilole moiety is fused with benzothiophene) is substituted with an amine derivative to enhance hole characteristics are introduced together, and thus an appropriate balance of charges between holes and electrons may be achieved, thereby exhibiting high efficiency/long life-span/low voltage driving characteristics.

In an implementation, the first compound may be represented by one of Chemical Formula 1A to Chemical Formula 1G, e.g., depending on the substitution position and direction of the nitrogen-containing six-membered ring.

[Chemical Formula 1A]

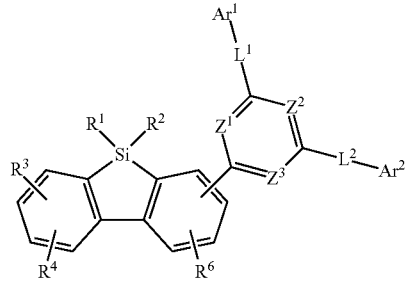

[Chemical Formula 1B]

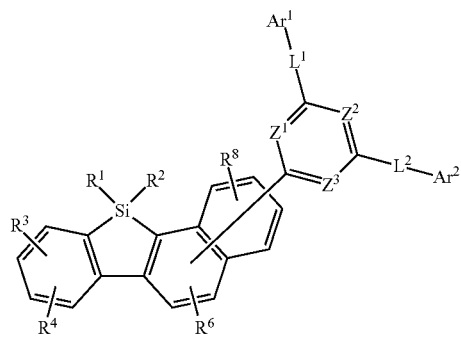

[Chemical Formula 1C]

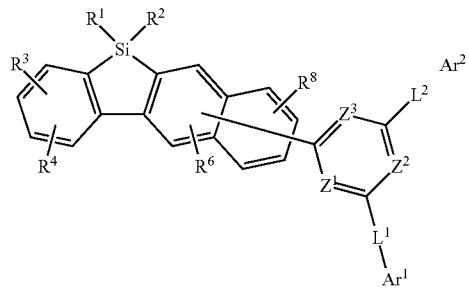

[Chemical Formula 1D]

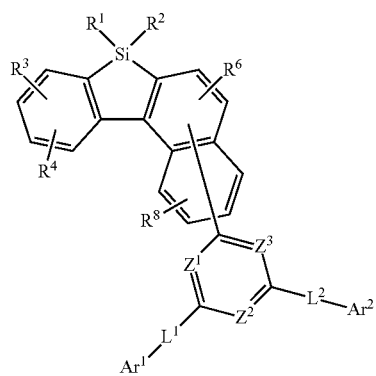

[Chemical Formula 1E]

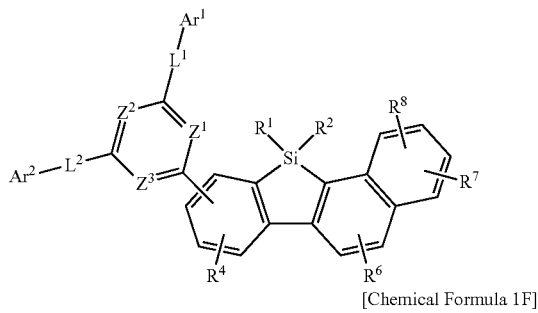

[Chemical Formula 1F]

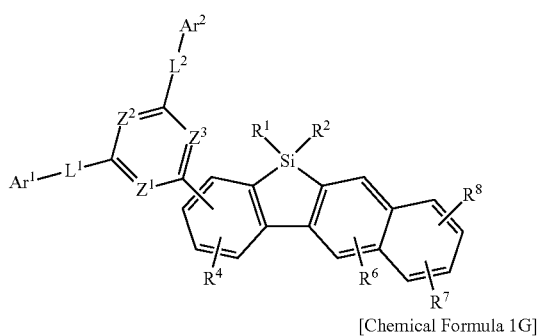

[Chemical Formula 1G]

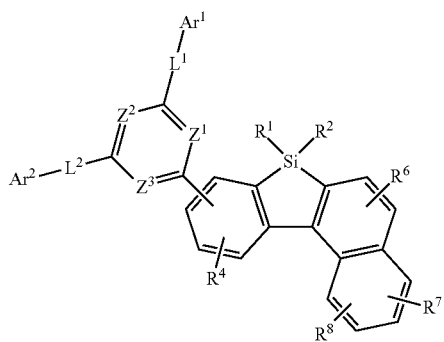

In Chemical Formula 1A to Chemical Formula 1G, $R^1$ to $R^4$, $R^6$ to $R^8$, $Z^1$ to $Z^3$, $L^1$, $L^2$, $Ar^1$, and $Ar^2$ may be defined the same as those of Chemical Formula 1.

In an implementation, $Ar^1$ and $Ar^2$ may each independently be or include, e.g., a substituted or unsubstituted C6 to C30 aryl group. In an implementation, $Ar^1$ and $Ar^2$ may each independently be or include, e.g., a substituted or unsubstituted C6 to C12 aryl group. In an implementation, $Ar^1$ and $Ar^2$ may each independently be or include, e.g., a substituted or unsubstituted phenyl group, a substituted or unsubstituted biphenyl group, or a substituted or unsubstituted naphthyl group.

In an implementation, $L^1$ and $L^2$ may each independently be or include, e.g., a single bond or a substituted or unsubstituted C6 to C12 arylene group. In an implementation, $L^1$ and $L^2$ may each independently be or include, e.g., a single bond, a substituted or unsubstituted phenylene group, or a substituted or unsubstituted naphthylene group.

In an implementation, the first compound may be represented by Chemical Formula 1A, Chemical Formula 1E, Chemical Formula 1F, or Chemical Formula 1G.

In an implementation, Chemical Formula 1A may be represented by any one of Chemical Formula 1A-1 to Chemical Formula 1A-4, depending on the specific substitution position of the nitrogen-containing six-membered ring.

[Chemical Formula 1A-1]

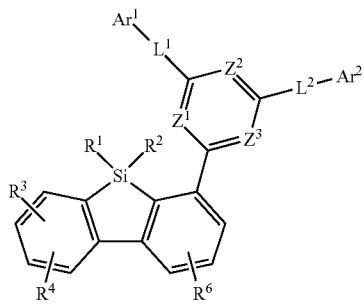

[Chemical Formula 1A-2]

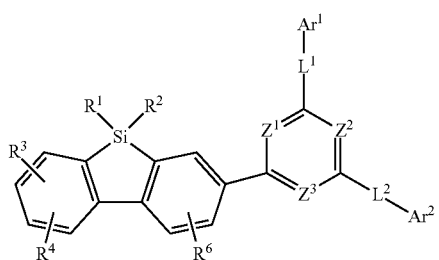

[Chemical Formula 1A-3]

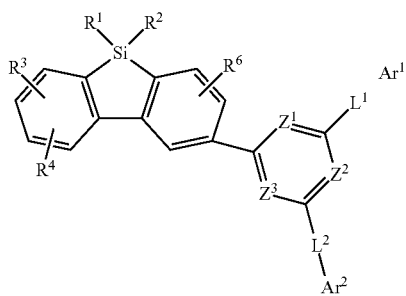

[Chemical Formula 1A-4]

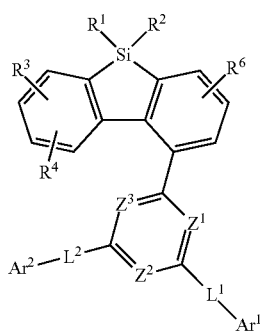

In Chemical Formula 1A-1 to Chemical Formula 1A-4, $Z^1$ to $Z^3$, $L^1$, $L^2$, $Ar^1$, $Ar^2$, $R^1$ to $R^4$, and $R^6$ may be defined the same as those of Chemical Formula 1.

Chemical Formula 1E may be represented by any one of Chemical Formula 1E-1 to Chemical Formula 1E-4, depending on the specific substitution position of the nitrogen-containing six-membered ring.

[Chemical Formula 1E-1]

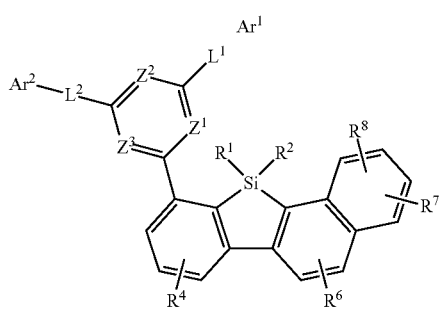

[Chemical Formula 1E-2]

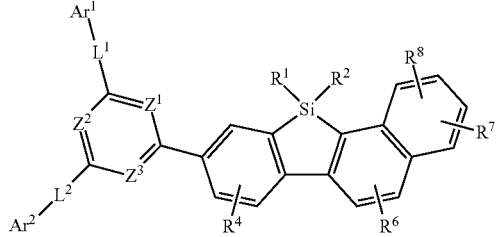

[Chemical Formula 1E-3]

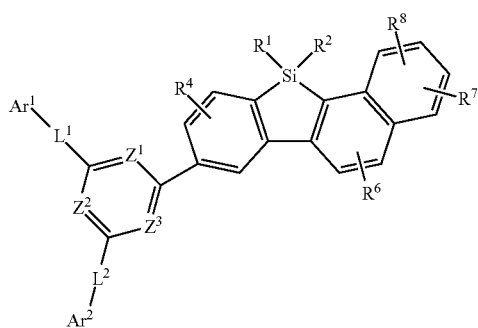

[Chemical Formula 1E-4]

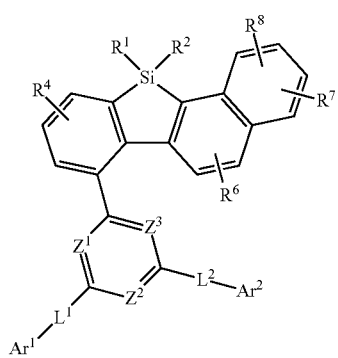

In Chemical Formula 1E-1 to Chemical Formula 1E-4, $Z^1$ to $Z^3$, $L^1$, $L^2$, $Ar^1$, $Ar^2$, $R^4$, and $R^6$ to $R^8$ may be defined the same as those of Chemical Formula 1.

Chemical Formula 1F may be represented by any one of Chemical Formula 1F-1 to Chemical Formula 1F-4, depending on the specific substitution position of the nitrogen-containing six-membered ring.

[Chemical Formula 1F-1]

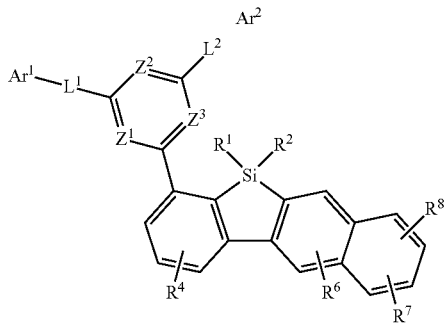

[Chemical Formula 1F-2]

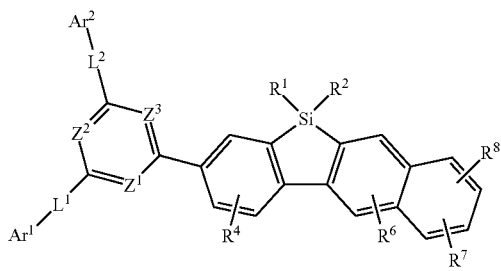

[Chemical Formula 1F-3]

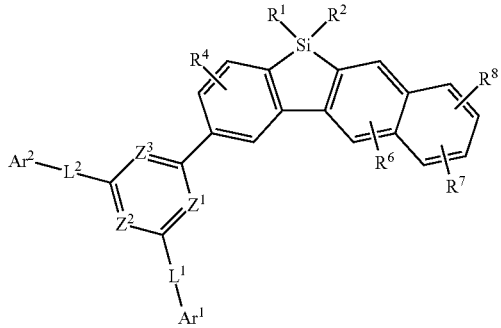

[Chemical Formula 1F-4]

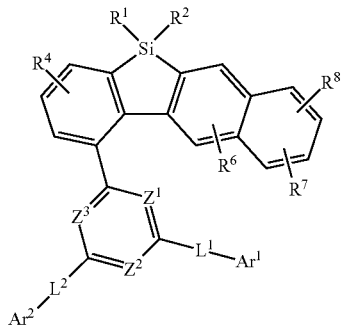

In Chemical Formula 1F-1 to Chemical Formula 1F-4, the definitions of $Z^1$ to $Z^3$, $L^1$, $L^2$, $Ar^1$, $Ar^2$, $R^4$, and $R^6$ to $R^1$ may be defined the same as those of Chemical Formula 1.

Chemical Formula 1G may be represented by any one of Chemical Formula 1G-1 to Chemical Formula 1G-4, depending on the specific substitution position of the nitrogen-containing six-membered ring.

[Chemical Formula 1G-1]

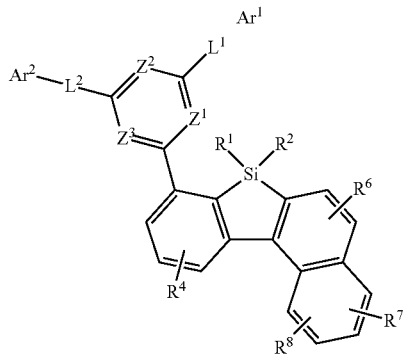

[Chemical Formula 1G-2]

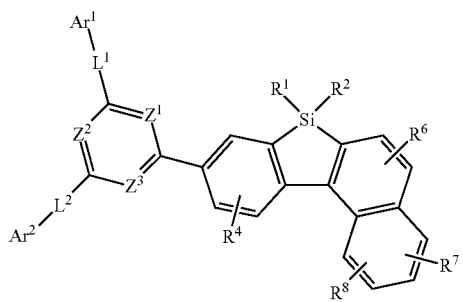

[Chemical Formula 1G-3]

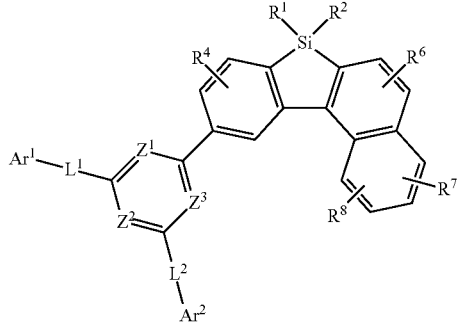

[Chemical Formula 1G-4]

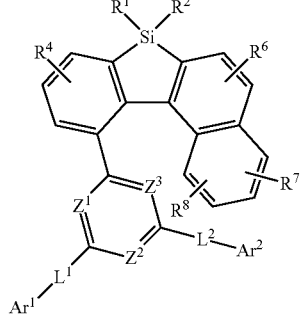

In Chemical Formula 1G-1 to Chemical Formula 1G-4, the definitions of $Z^1$ to $Z^3$, $L^1$, $L^2$, $Ar^1$, $Ar^2$, $R^4$, and $R^6$ to $R^1$ may be defined the same as those of Chemical Formula 1.

In an implementation, the first compound may be represented by Chemical Formula 1A-2, Chemical Formula 1A-4, Chemical Formula 1E-2, Chemical Formula 1E-4, Chemical Formula 1F-2, Chemical Formula 1F-4, Chemical Formula 1G-2, or Chemical Formula 1G-4.

In an implementation, $Ar^1$ and $Ar^2$ of Chemical Formula 1A-2 and Chemical Formula 1A-4 may each independently be or include, e.g., a substituted or unsubstituted phenyl group, a substituted or unsubstituted biphenyl group, or a substituted or unsubstituted naphthyl group.

$R^1$ and $R^2$ of Chemical Formula 1A-2 and Chemical Formula 1A-4 may each independently be or include, e.g., a substituted or unsubstituted C1 to C5 alkyl group or a substituted or unsubstituted phenyl group.

$R^3$, $R^4$, and $R^6$ of Chemical Formula 1A-2 may each independently be or include, e.g., hydrogen or a substituted or unsubstituted phenyl group.

$L^1$ and $L^2$ of Chemical Formula 1A-2 may each independently be or include, e.g., a single bond or a substituted or unsubstituted phenylene group.

In an implementation, $Ar^1$ and $Ar^2$ of Chemical Formula 1E-2 and Chemical Formula 1E-4 may each independently be or include, e.g., a substituted or unsubstituted phenyl group, a substituted or unsubstituted biphenyl group, or a substituted or unsubstituted naphthyl group.

$R^1$ and $R^2$ of Chemical Formula 1E-2 and Chemical Formula 1E-4 may each independently be or include, e.g., a substituted or unsubstituted C1 to C5 alkyl group or a substituted or unsubstituted phenyl group.

$R^4$ and $R^6$ to $R^8$ of Chemical Formula 1E-2 and Chemical Formula 1E-4 may each independently be or include, e.g., hydrogen or a substituted or unsubstituted phenyl group.

$L^1$ and $L^2$ of above Chemical Formula 1E-2 and Chemical Formula 1E-4 may each independently be or include, e.g., a single bond, or a substituted or unsubstituted phenylene group.

In an implementation, $Ar^1$ and $Ar^2$ of Chemical Formula 1F-2 and Chemical Formula 1F-4 may each independently be or include, e.g., a substituted or unsubstituted phenyl group, a substituted or unsubstituted biphenyl group, or a substituted or unsubstituted naphthyl group.

$R^1$ and $R^2$ of Chemical Formula 1F-2 and Chemical Formula 1F-4 may each independently be or include, e.g., a substituted or unsubstituted C1 to C5 alkyl group or a substituted or unsubstituted phenyl group.

$R^4$ and $R^6$ to $R^8$ of Chemical Formula 1F-2 and Chemical Formula 1F-4 may each independently be or include, e.g., hydrogen or a substituted or unsubstituted phenyl group.

$L^1$ and $L^2$ of Chemical Formula 1F-2 and Chemical Formula 1F-4 may each independently be or include, e.g., a single bond or a substituted or unsubstituted phenylene group.

In an implementation, $Ar^1$ and $Ar^2$ of Chemical Formula 1G-2 and Chemical Formula 1G-4 may each independently be or include, e.g., a substituted or unsubstituted phenyl group, a substituted or unsubstituted biphenyl group, or a substituted or unsubstituted naphthyl group.

$R^1$ and $R^2$ of Chemical Formula 1G-2 and Chemical Formula 1G-4 may each independently be or include, e.g., a substituted or unsubstituted C1 to C5 alkyl group or a substituted or unsubstituted phenyl group.

$R^4$ and $R^6$ to $R^8$ of Chemical Formula 1G-2 and Chemical Formula 1G-4 may each independently be or include, e.g., hydrogen or a substituted or unsubstituted phenyl group.

$L^1$ and $L^2$ of Chemical Formula 1G-2 and Chemical Formula 1G-4 may each independently be or include, e.g., a single bond or a substituted or unsubstituted phenylene group.

In an implementation, the first compound may be a compound of the following Group 1.

[Group 1]

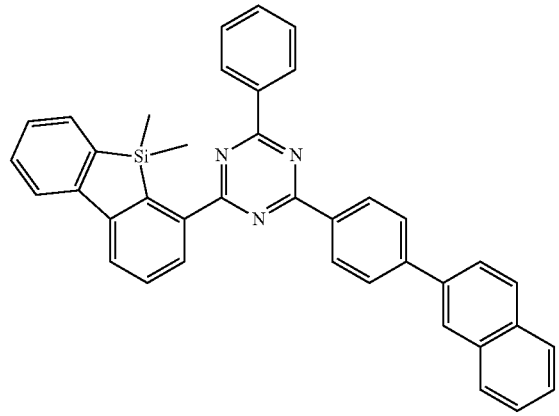

A-1

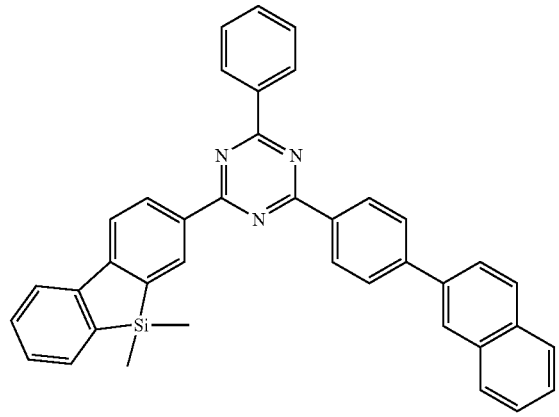

A-2

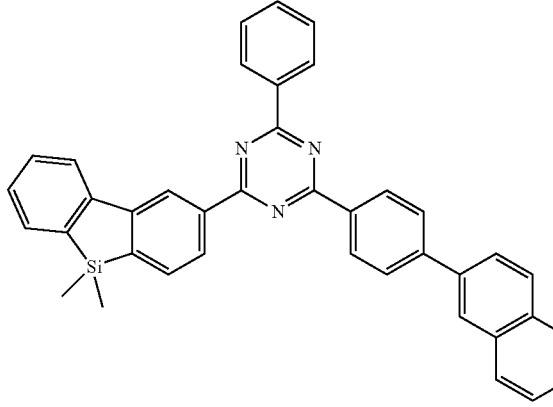

A-3

A-4
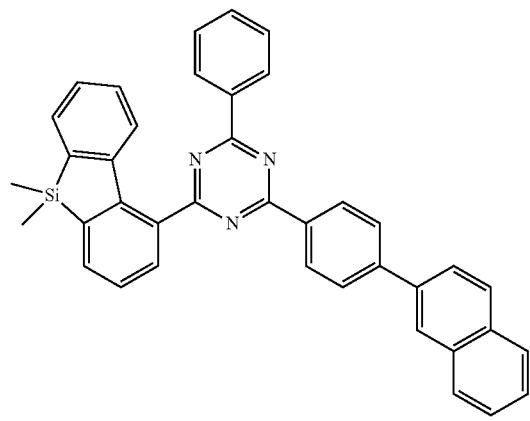
A-5
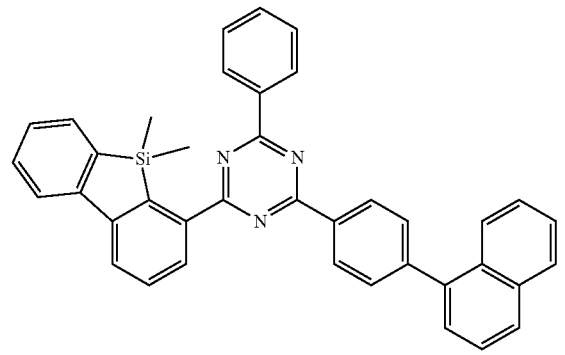
A-6
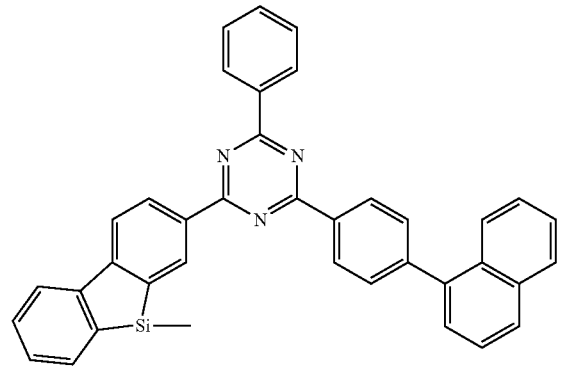
A-7
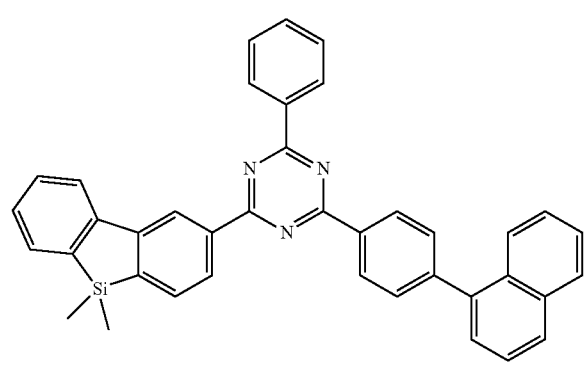
A-8
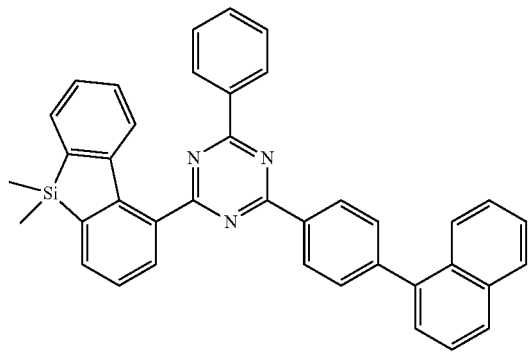
A-9
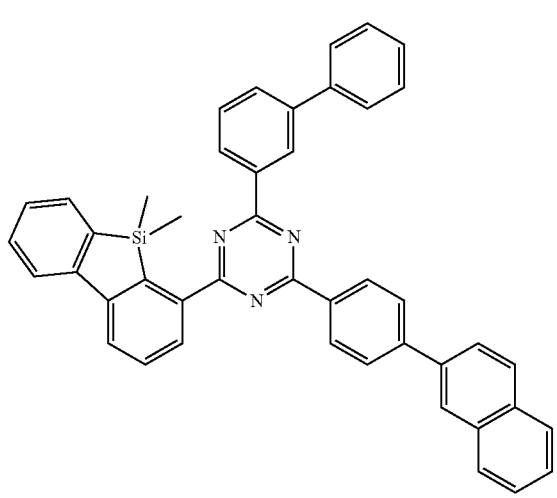
A-10
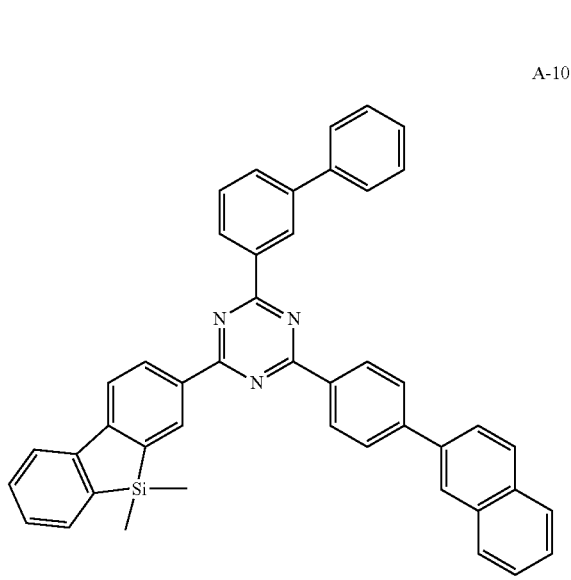

-continued
A-11
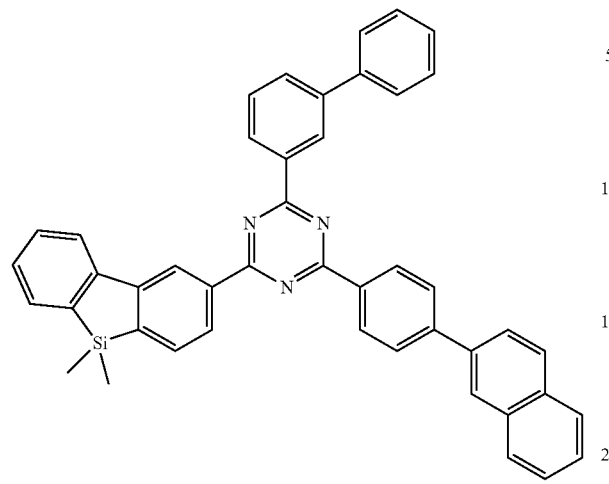
A-14
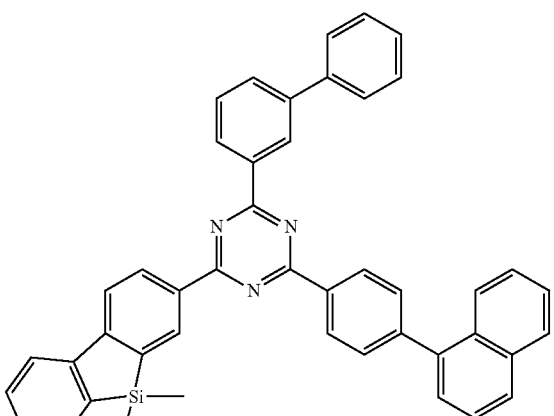
A-12
A-15
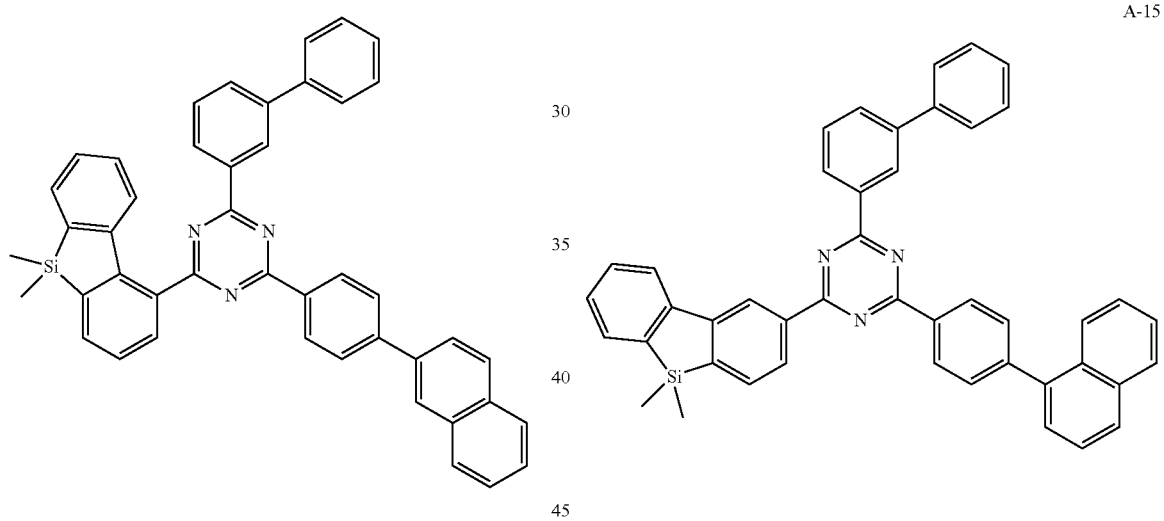
A-13
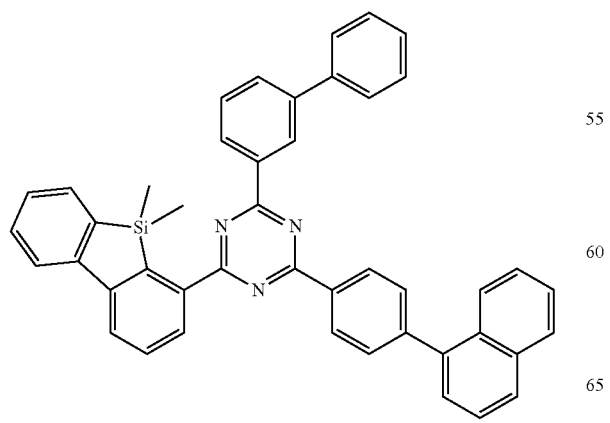
A-16
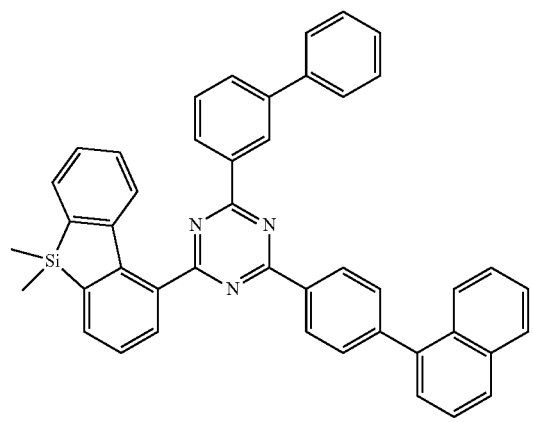

-continued
A-17
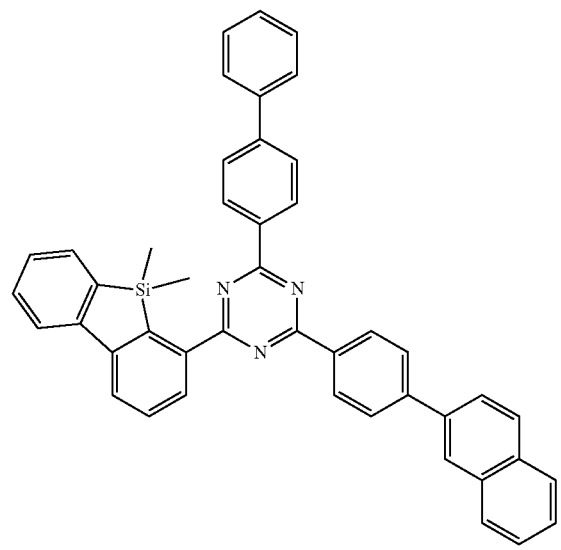
A-18
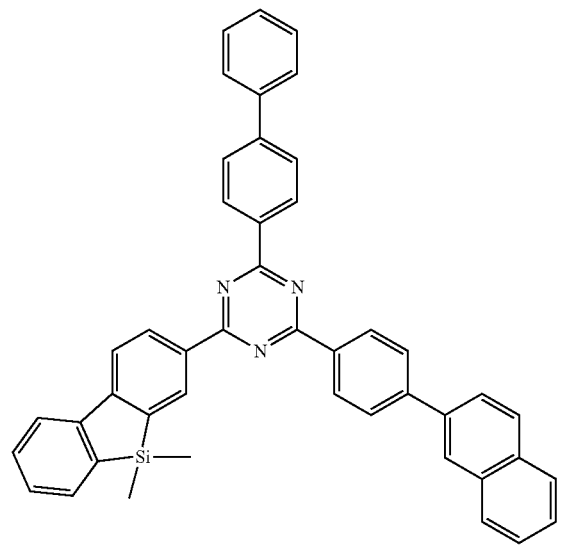
A-19
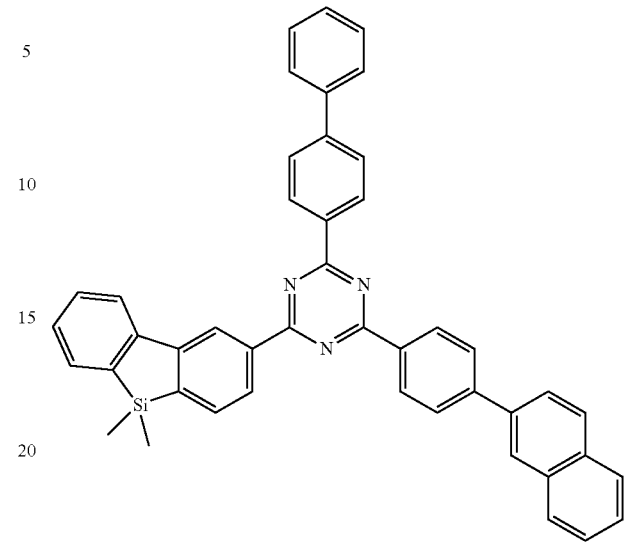
A-20
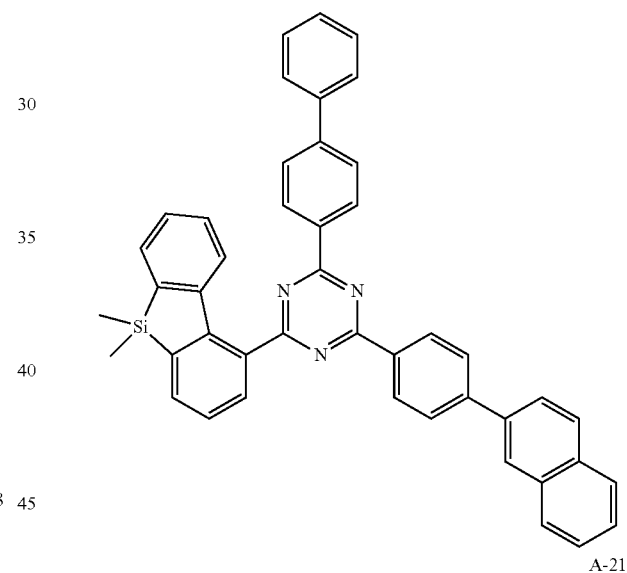
A-21
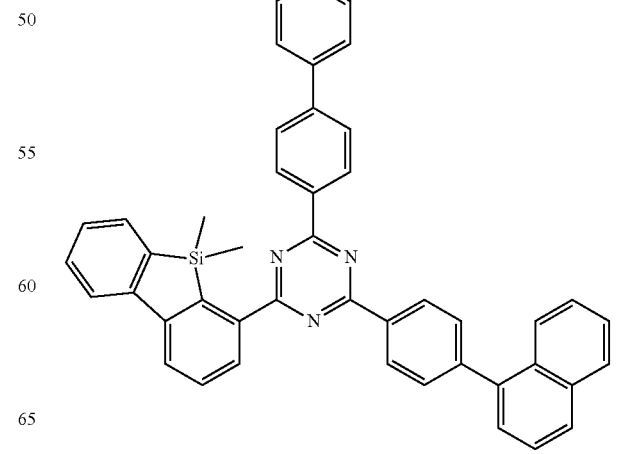

A-22
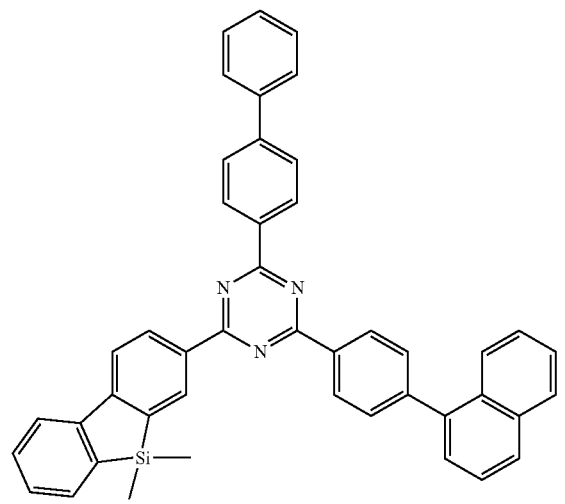
A-25
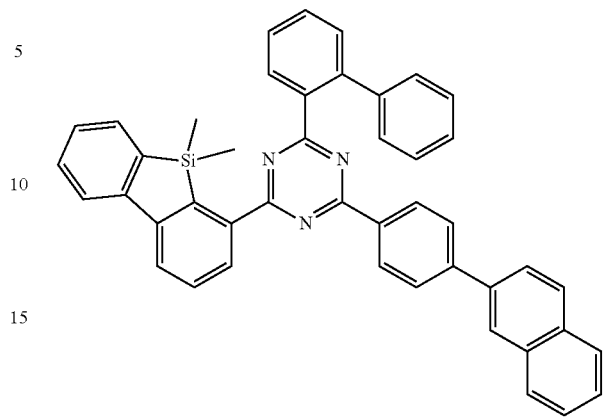
A-23
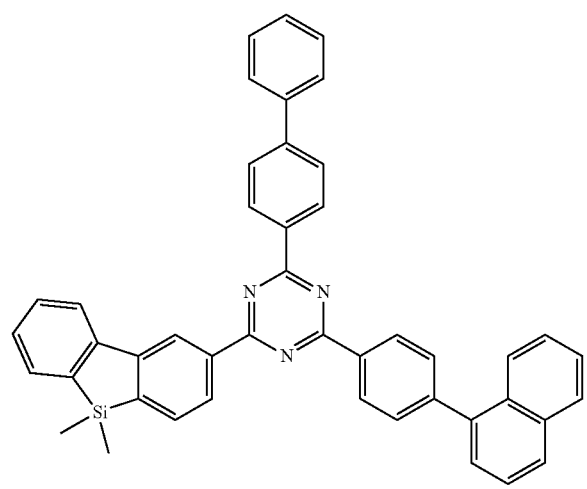
A-26
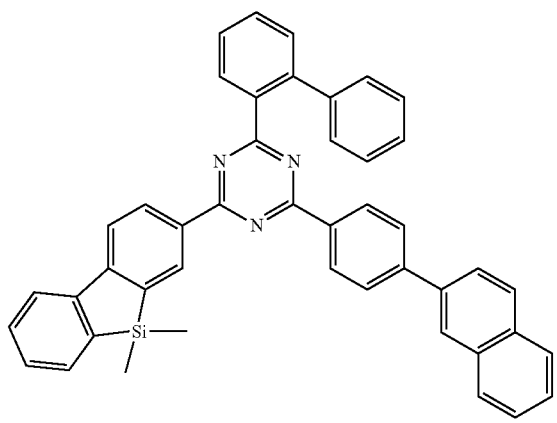
A-24
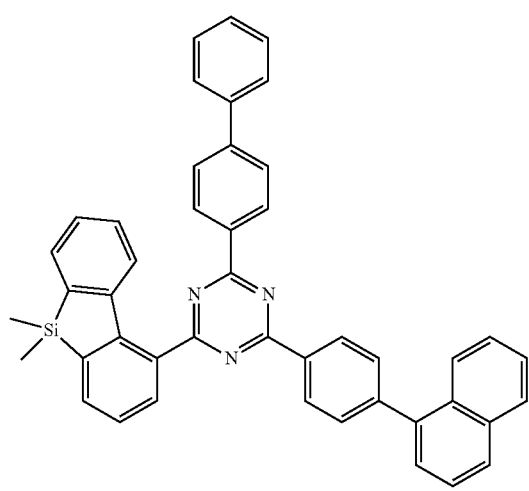
A-27
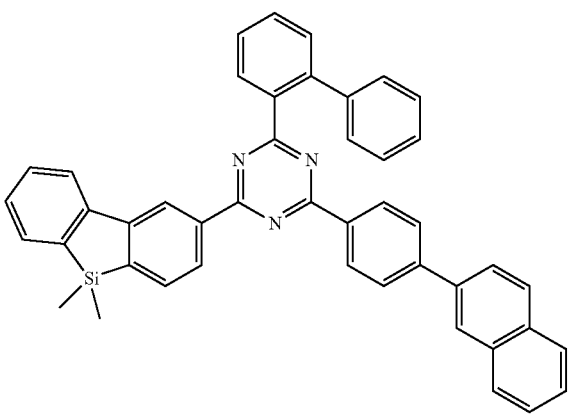

A-28
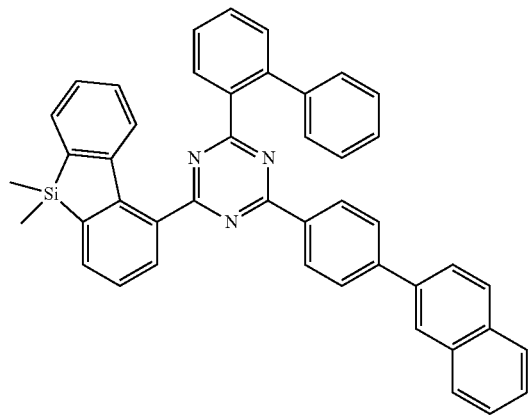
A-29
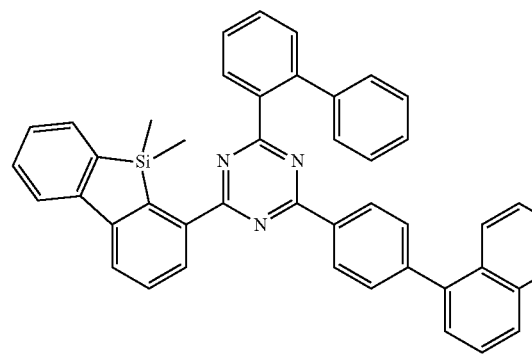
A-30
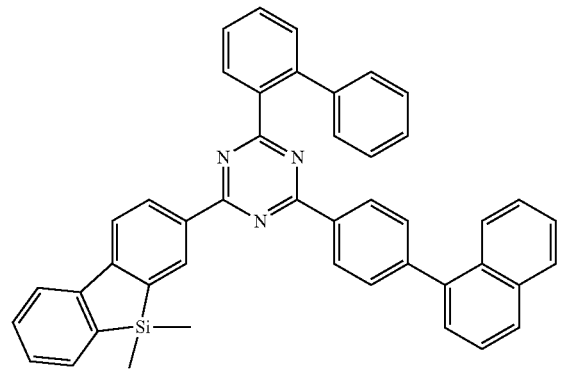
A-31
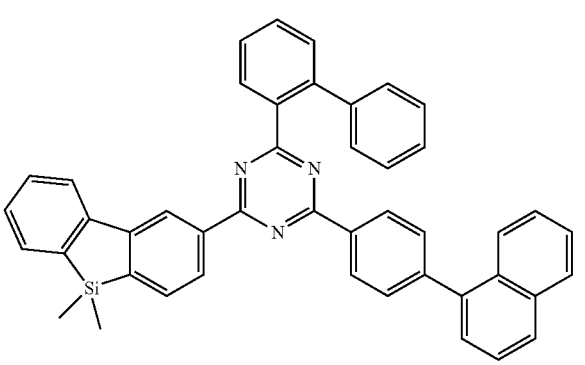
A-32
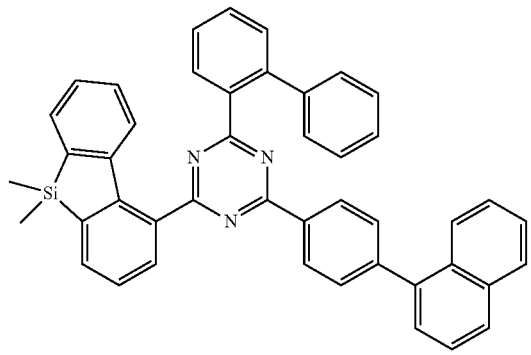
A-33
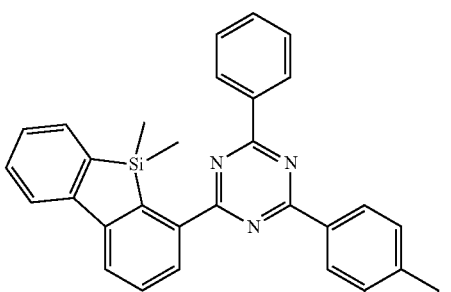
A-34
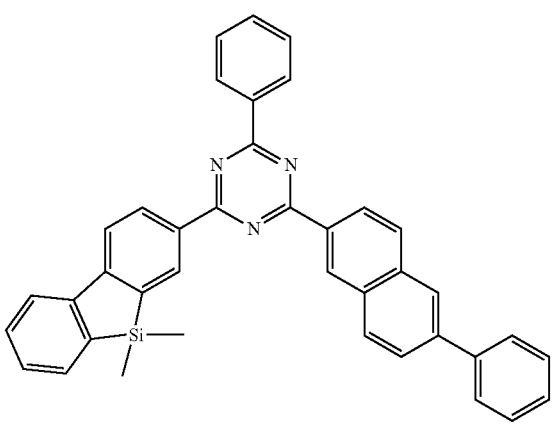

A-35
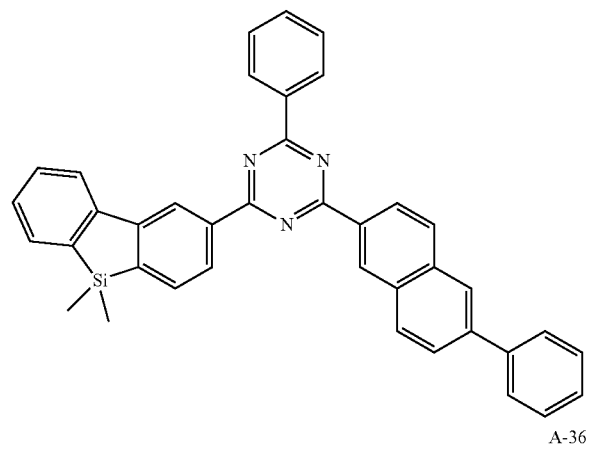
A-39
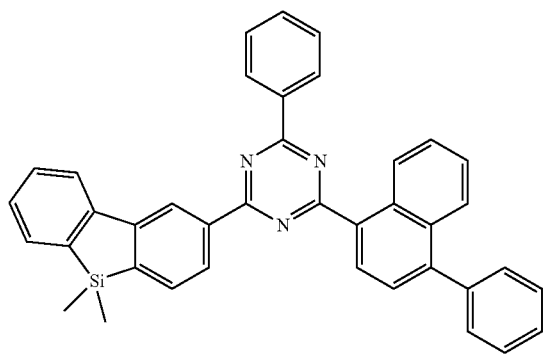
A-36
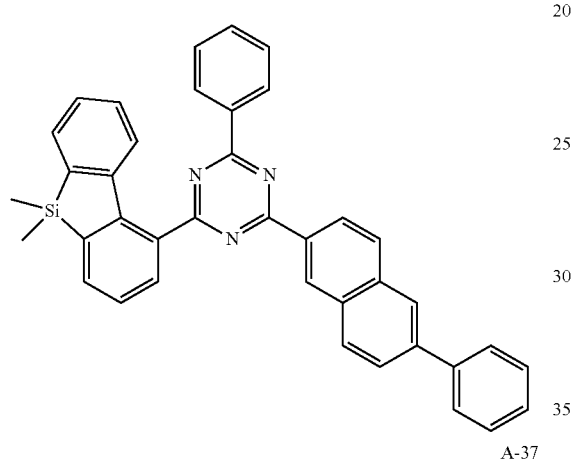
A-40
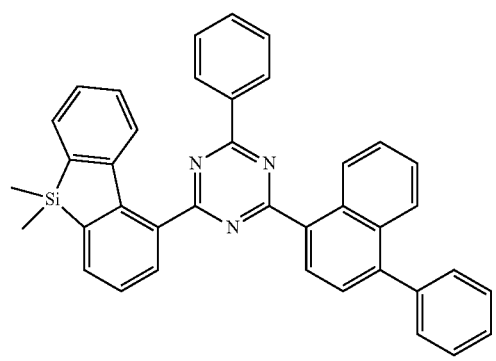
A-37
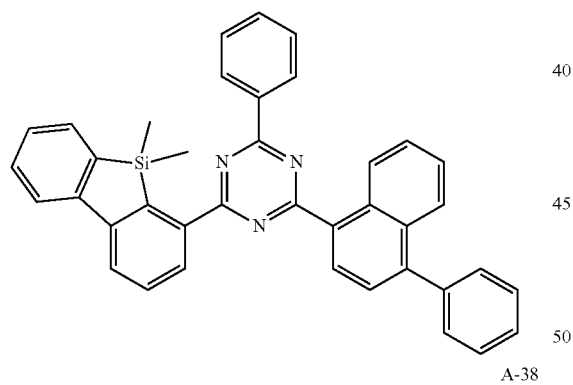
A-41
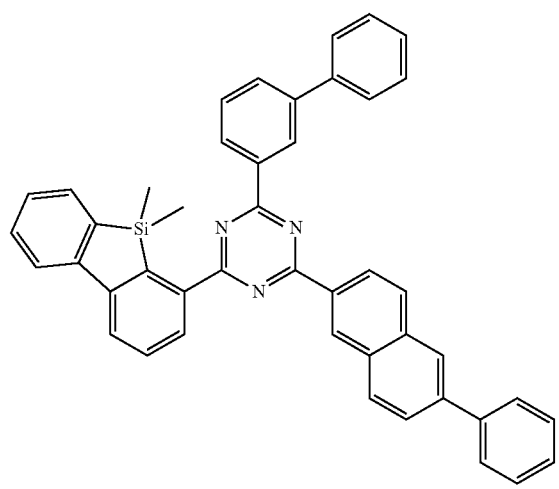
A-38
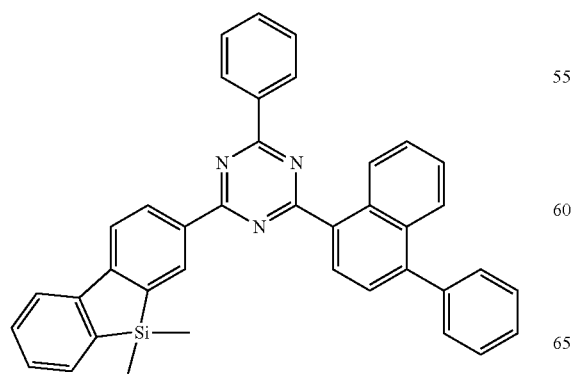

A-42
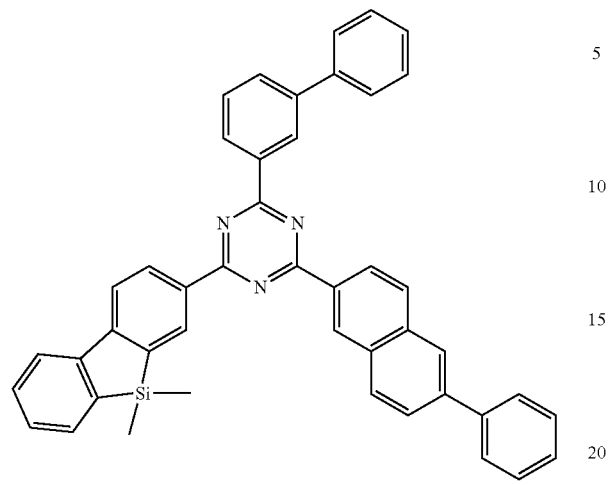
A-43
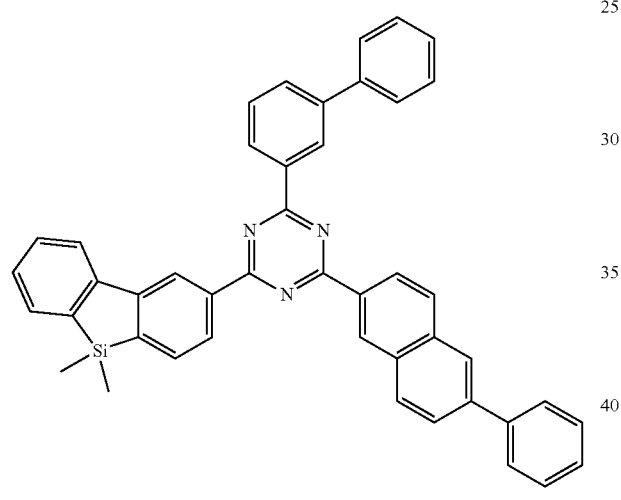
A-44
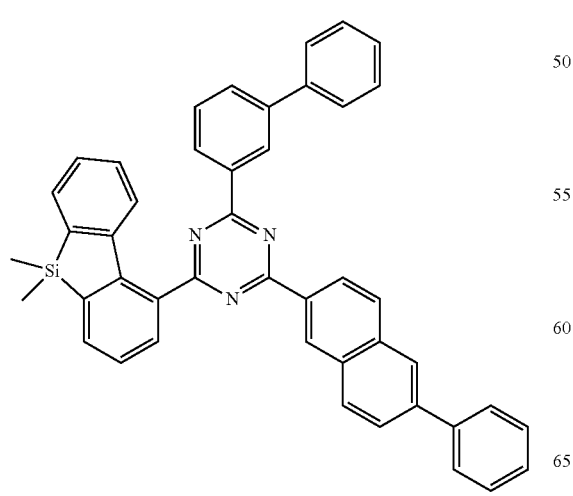
A-45
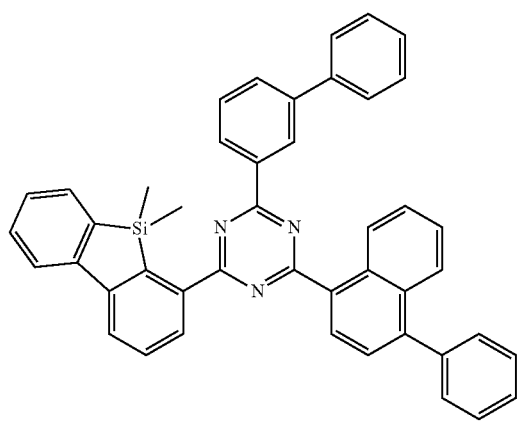
A-46
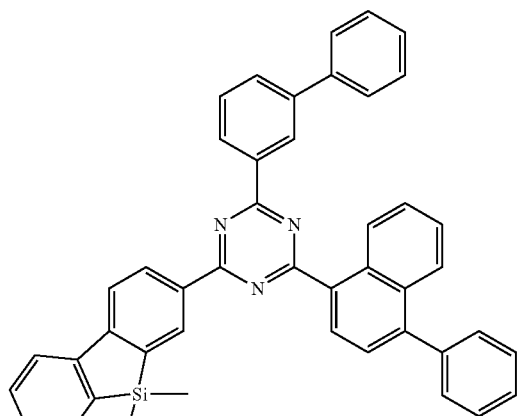
A-47
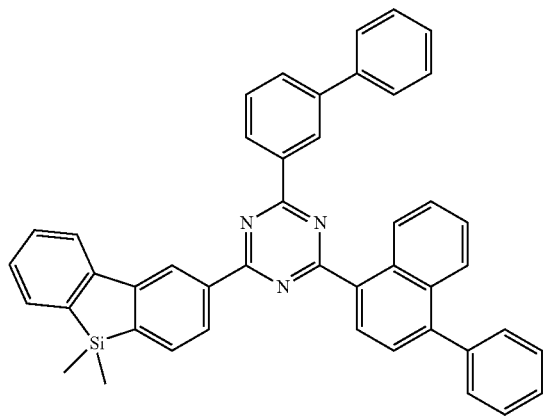

A-48
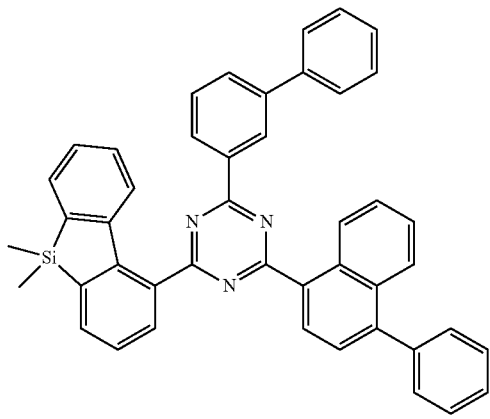
A-49
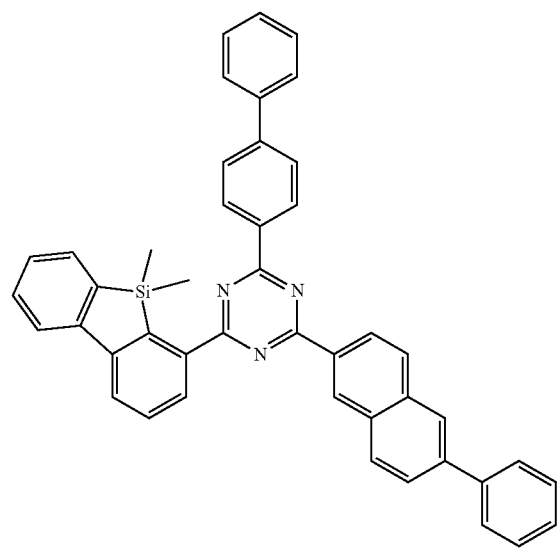
A-50
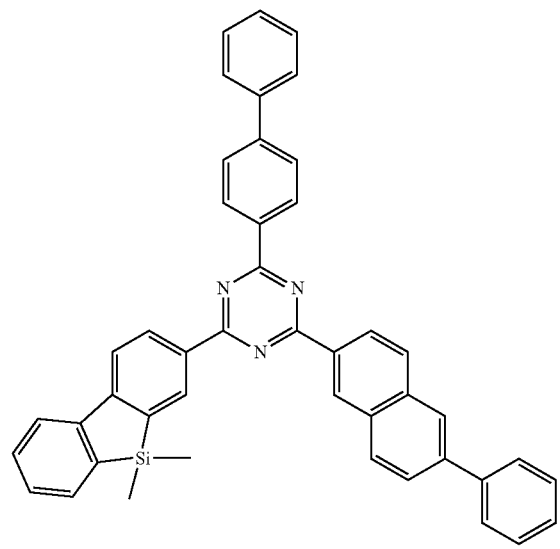
A-51
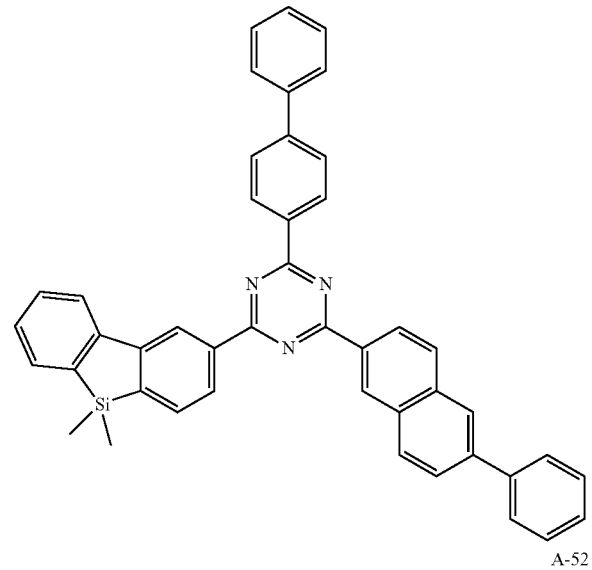
A-52
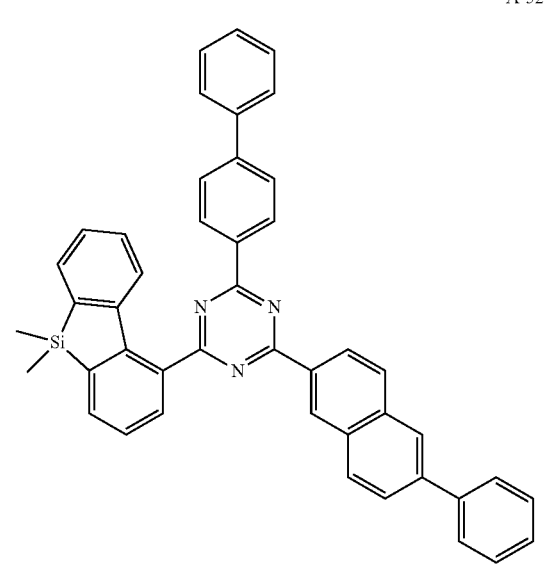
A-53
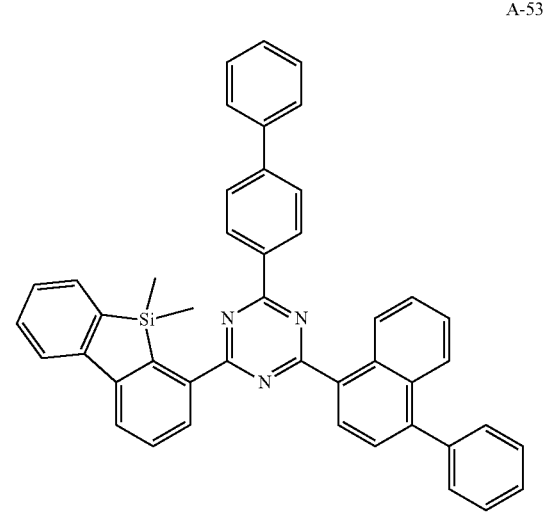

A-54
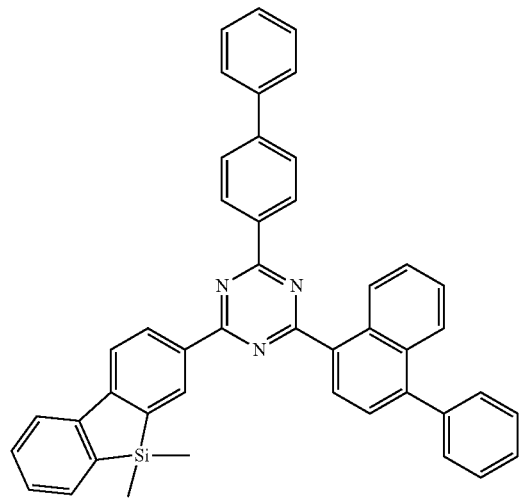
A-55
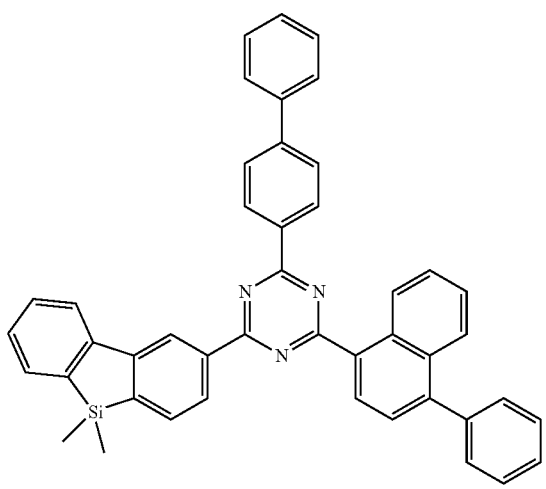
A-56
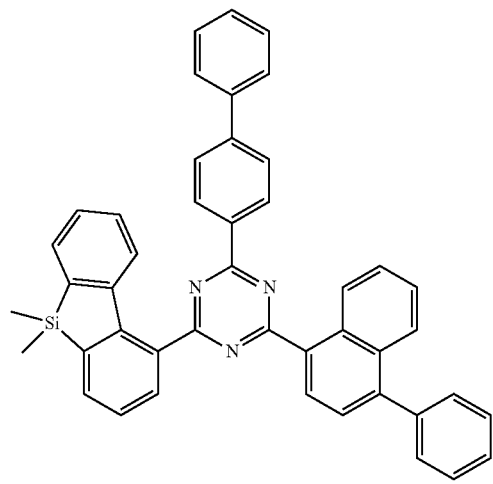
A-57
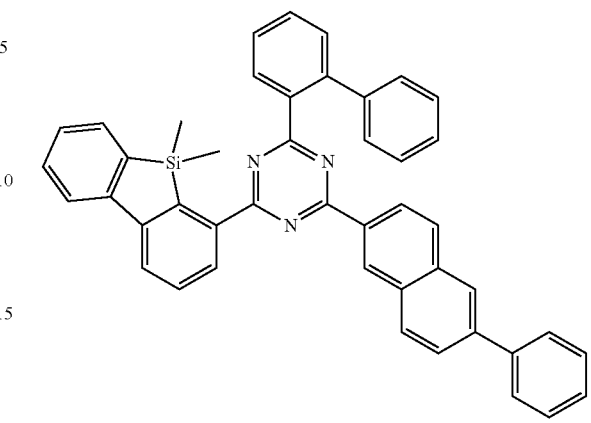
A-58
A-59

A-60
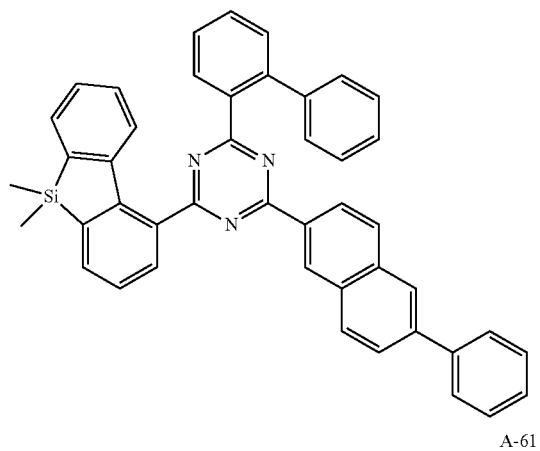
A-61
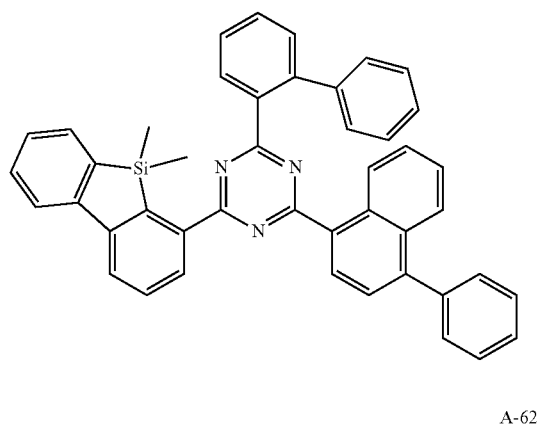
A-62
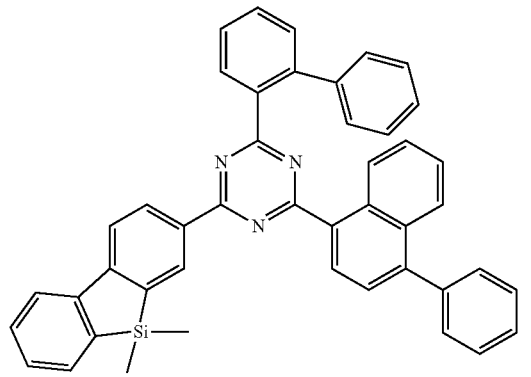
A-63
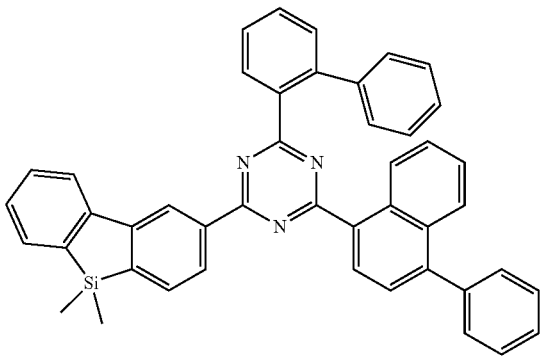
A-64
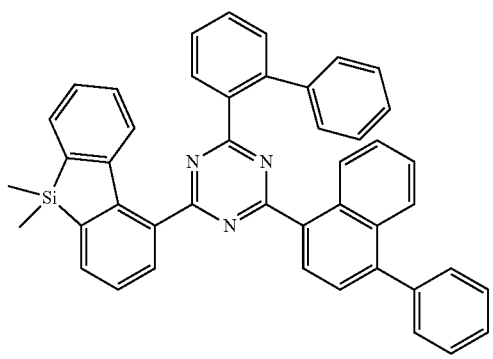
A-65
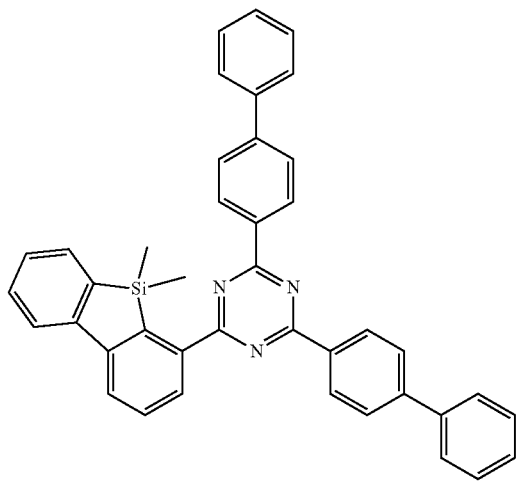
A-66
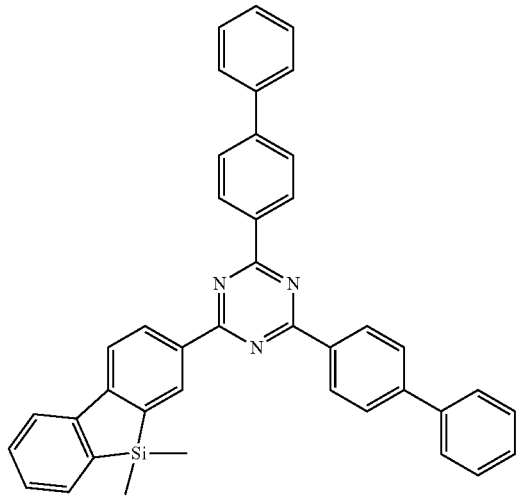

A-67
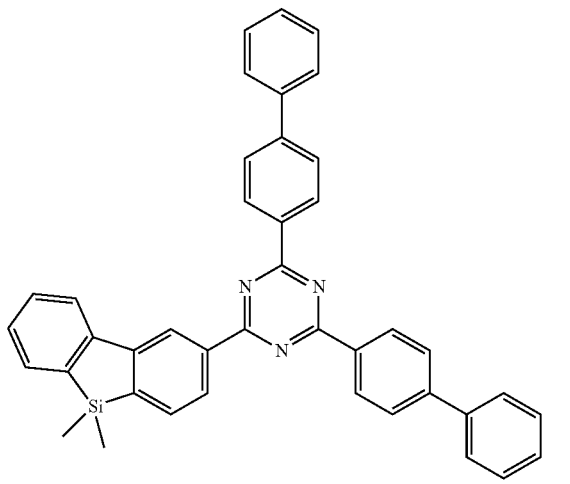
A-70
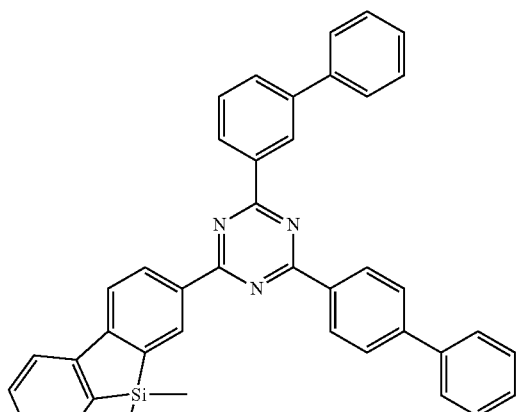
A-68
A-71
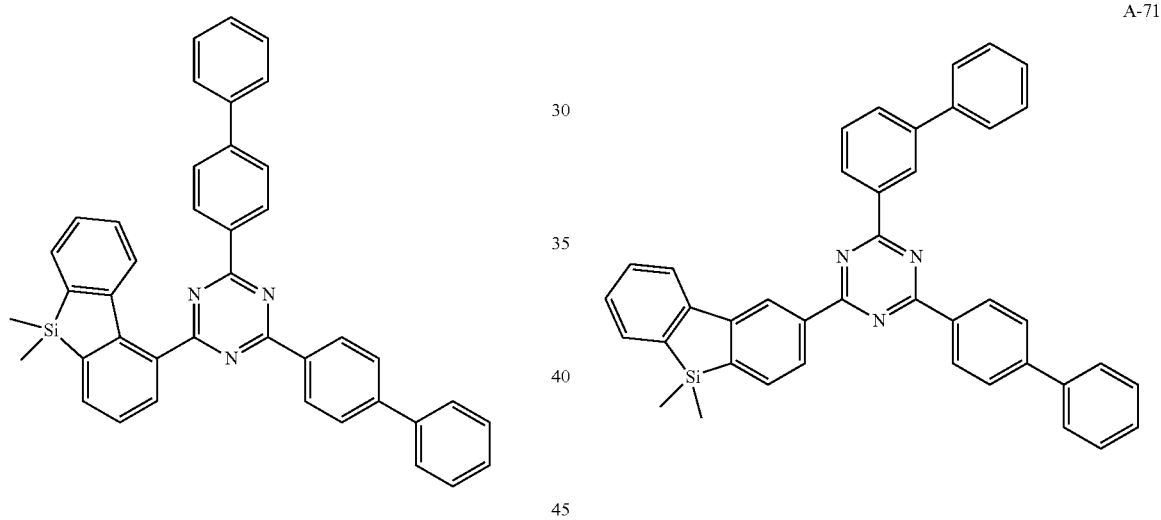
A-69
A-72
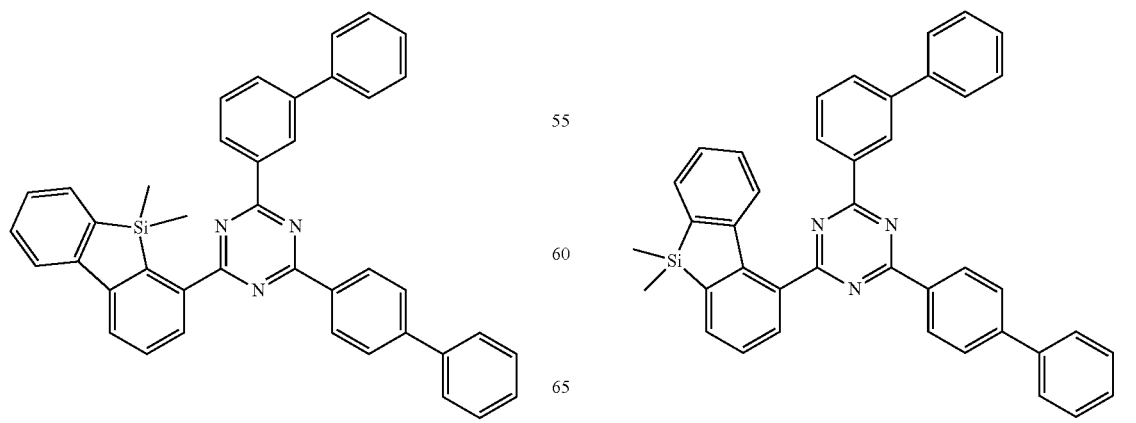

B-1
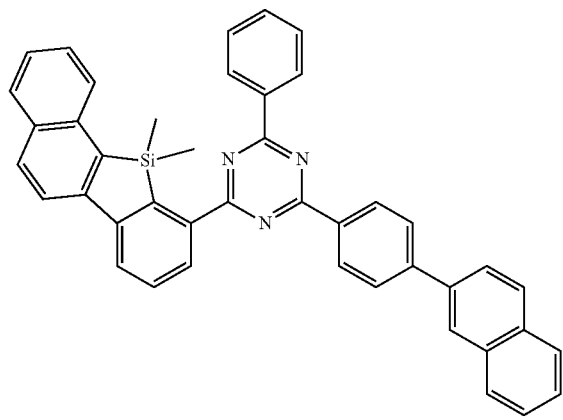
B-2
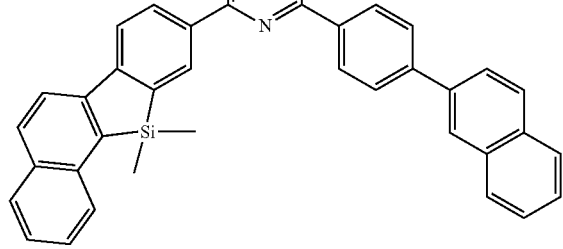
B-3
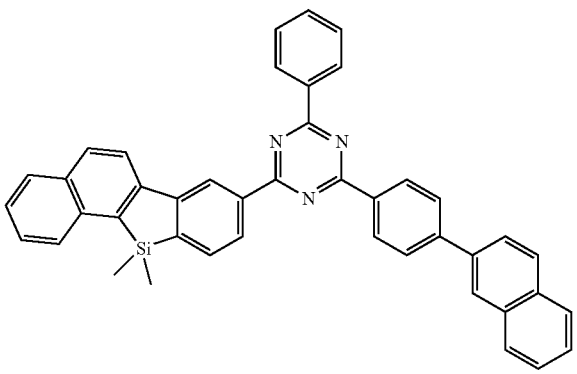
B-4
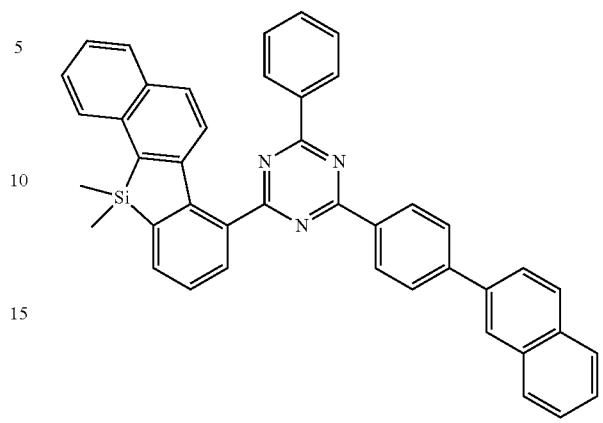
B-5
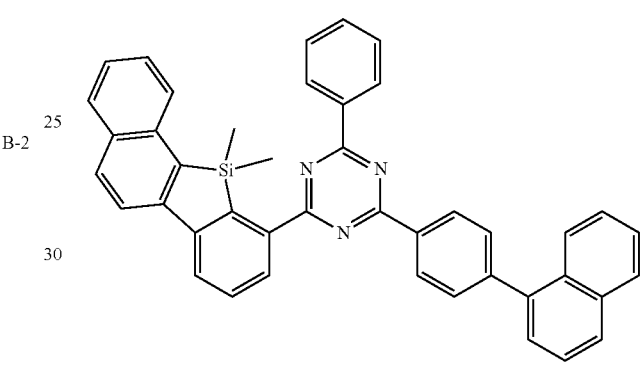
B-6
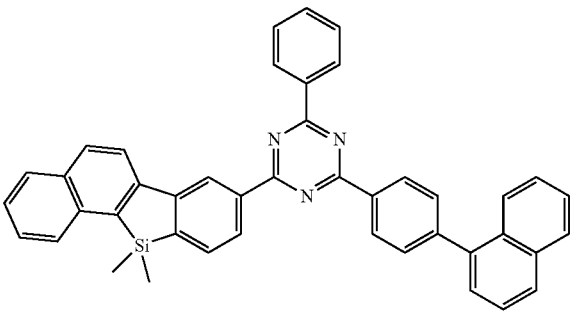
B-7

B-8
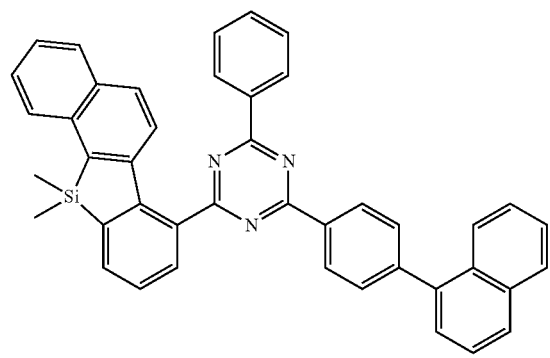
B-9
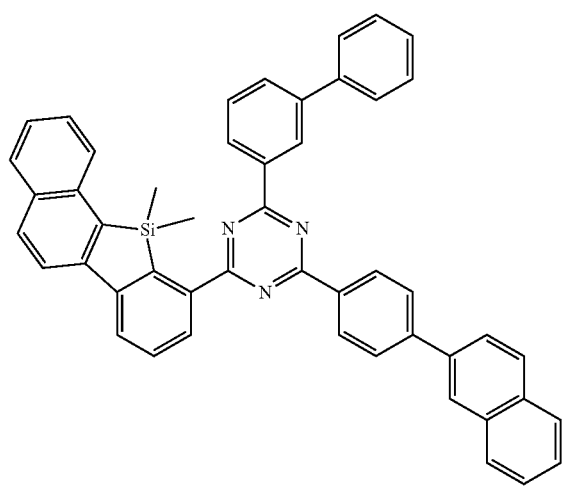
B-10
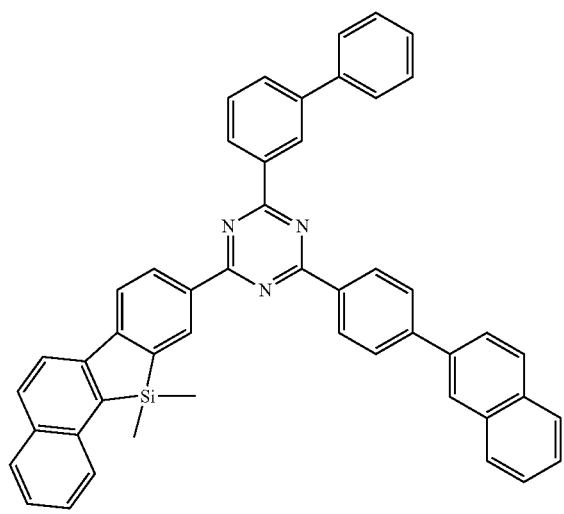
B-11
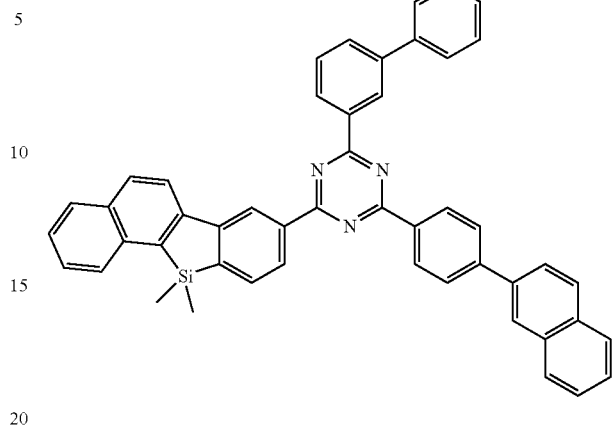
B-12
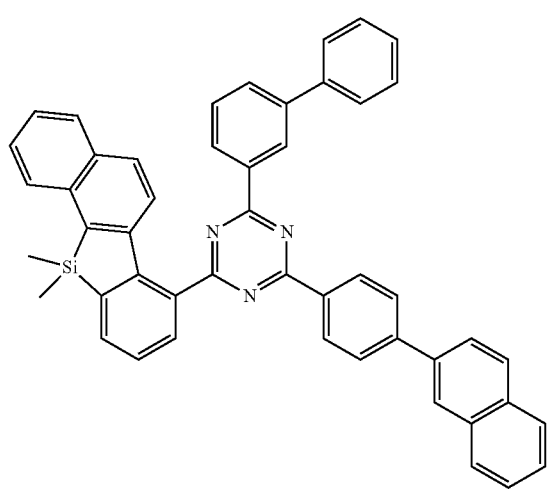
B-13
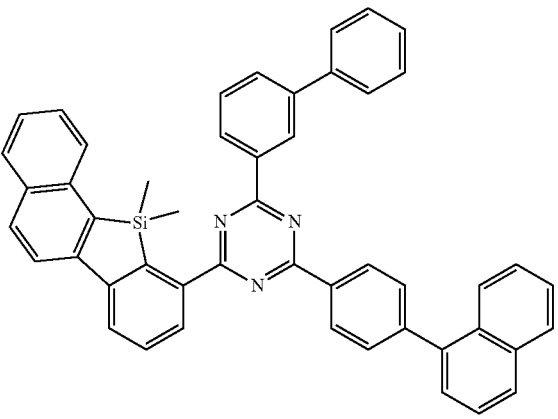

B-14
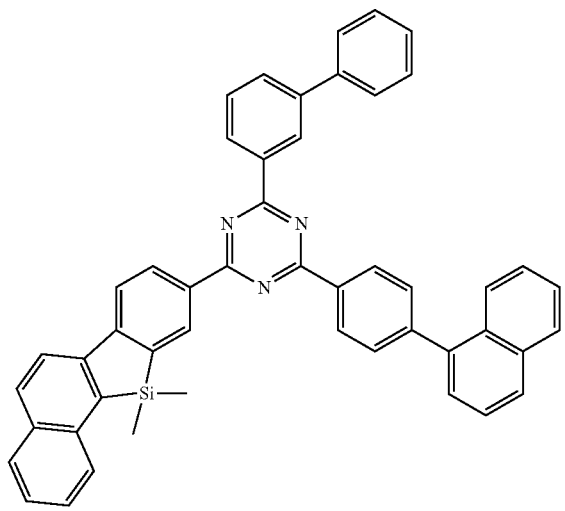
B-17
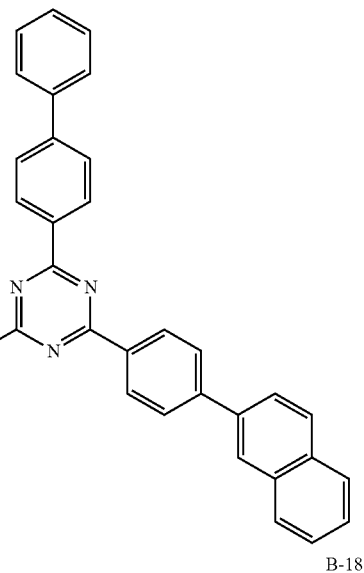
B-15
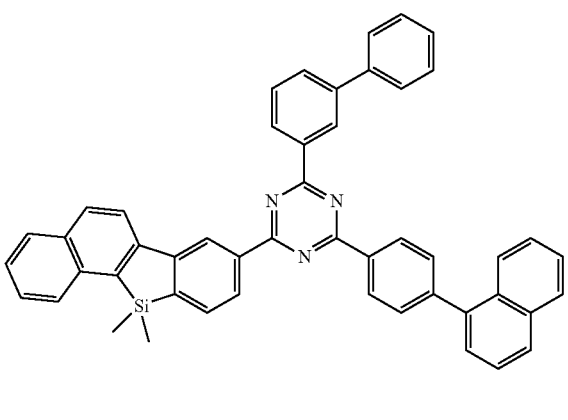
B-18
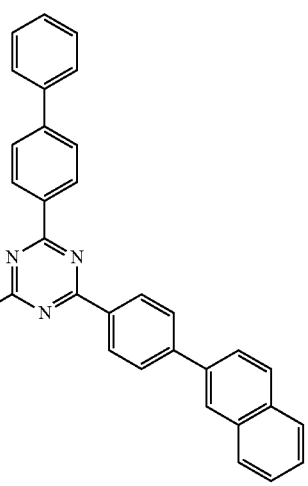
B-16
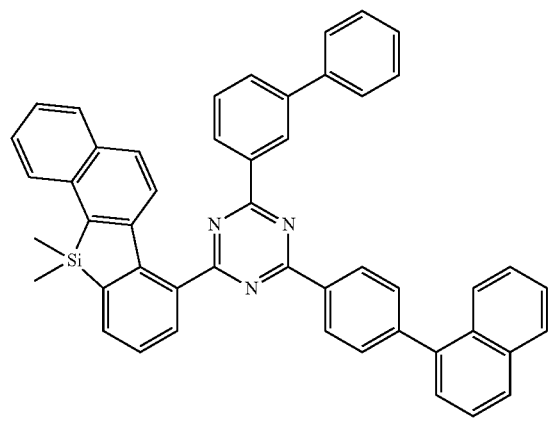
B-19

-continued
B-20
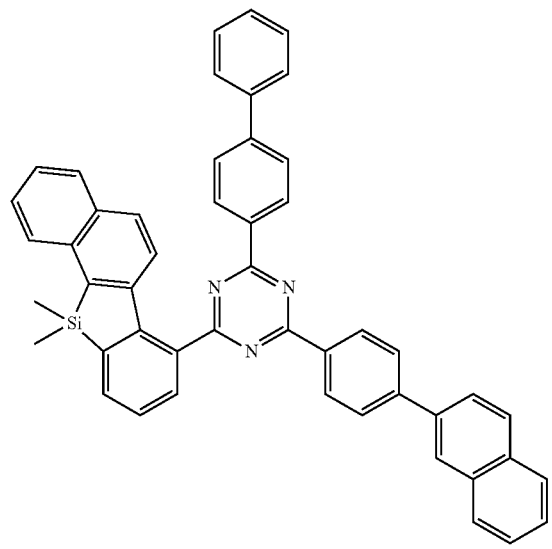
B-21
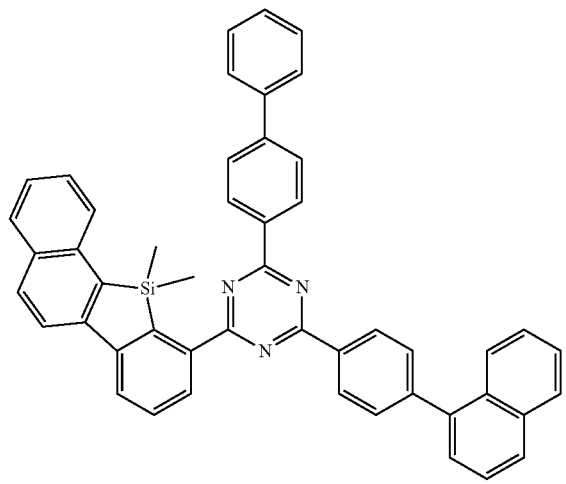
B-22
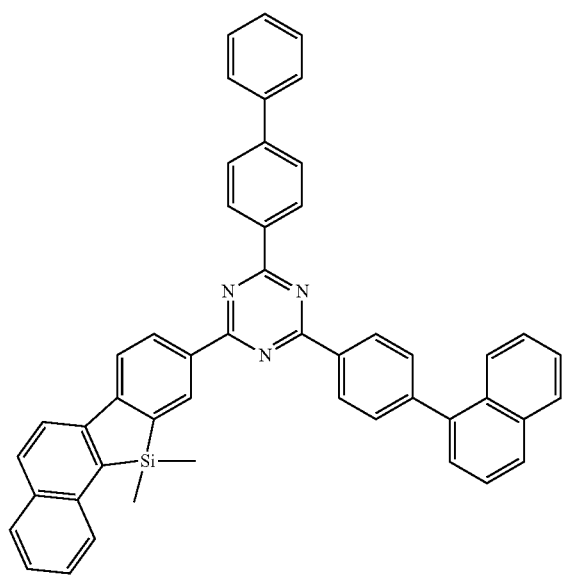
B-23
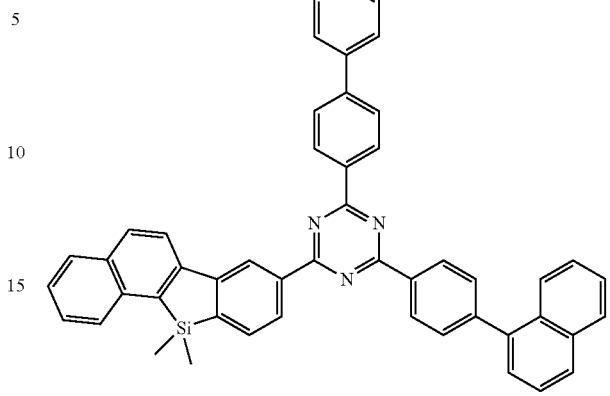
B-24
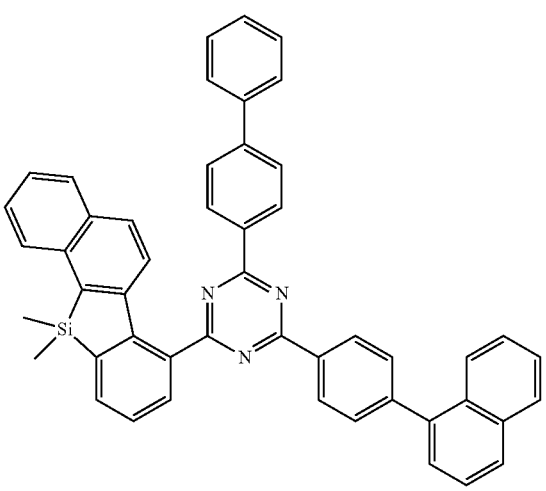
B-25
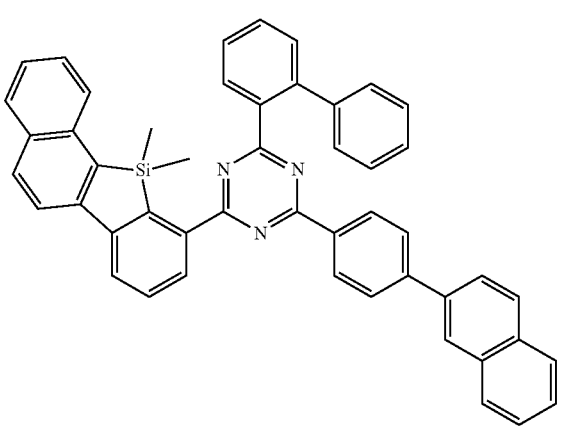

B-26
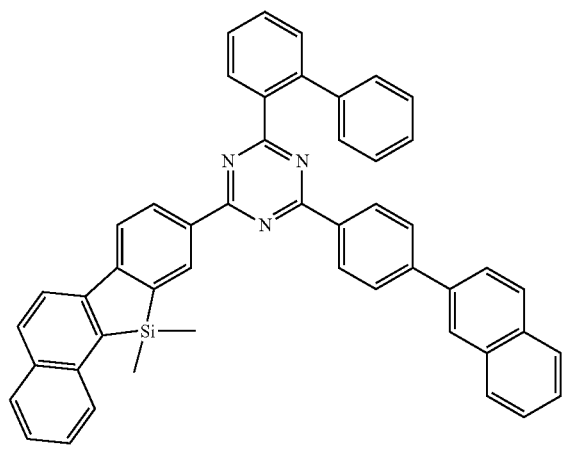
B-29
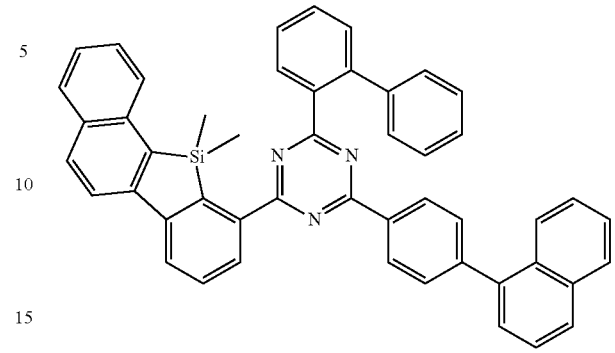
B-27
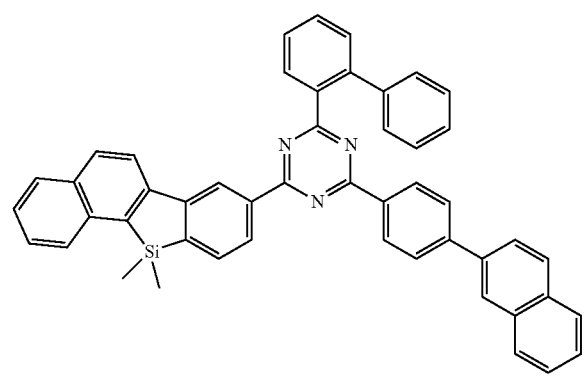
B-30
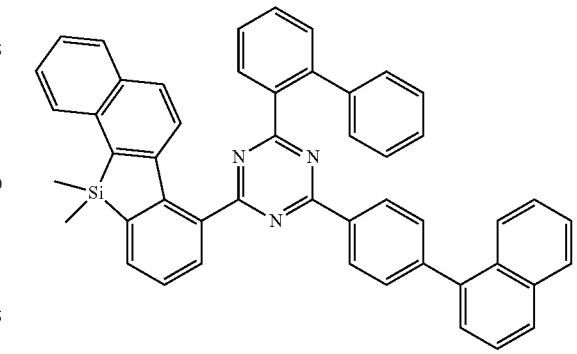
B-31
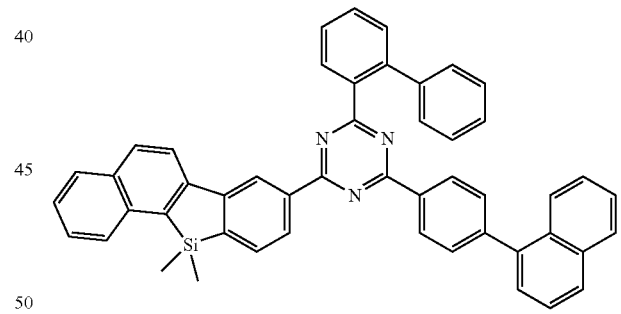
B-28
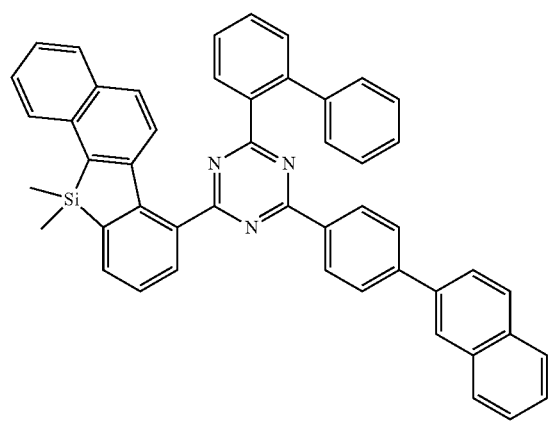
B-32

B-33
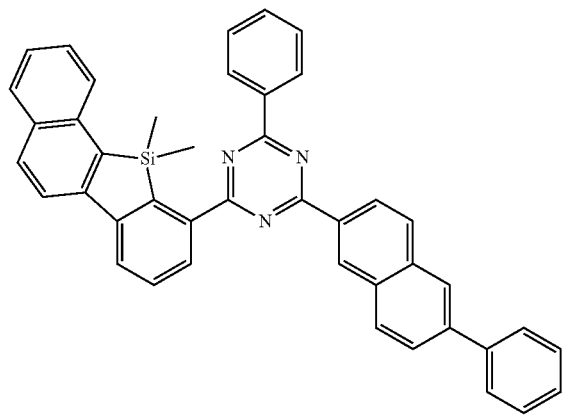
B-34
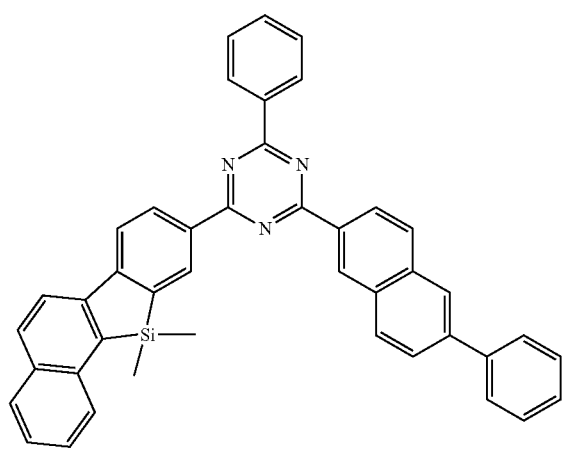
B-35
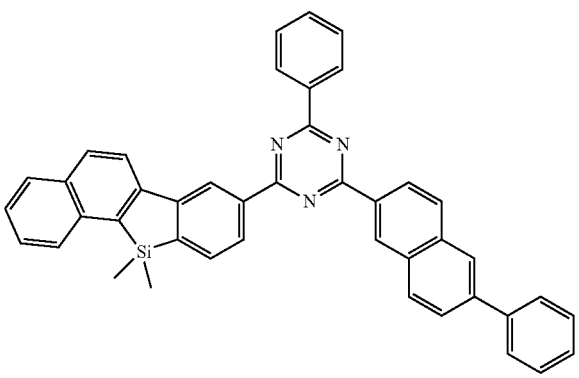
B-36
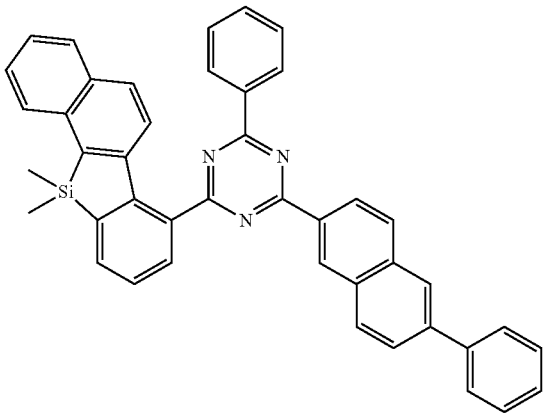
B-37
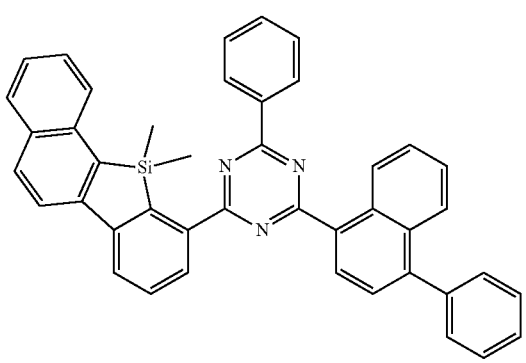
B-38
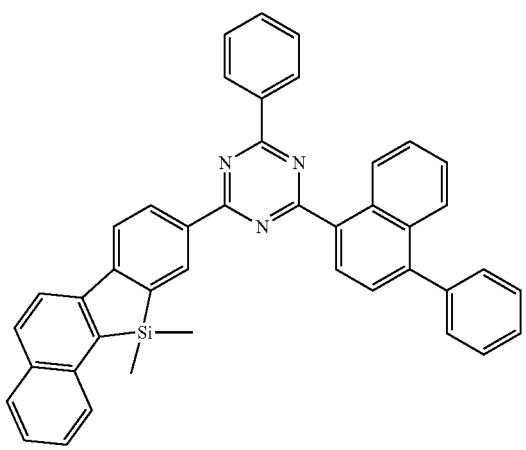
B-39
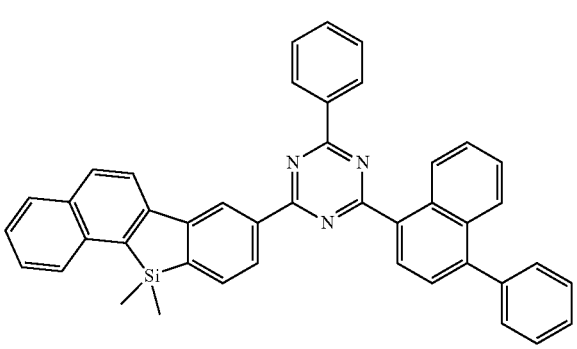

B-40
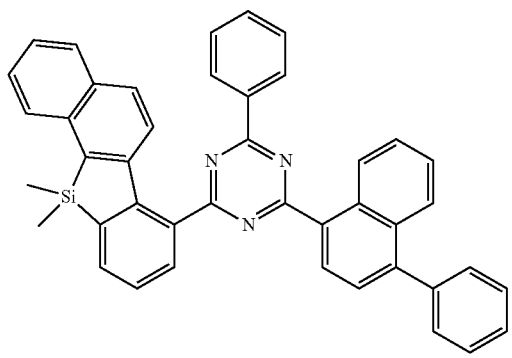
B-41
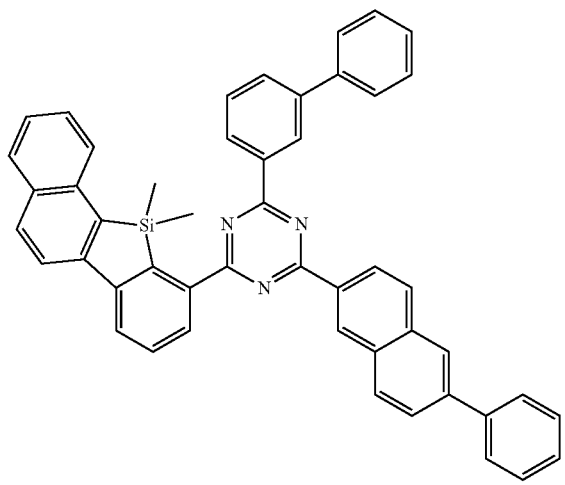
B-42
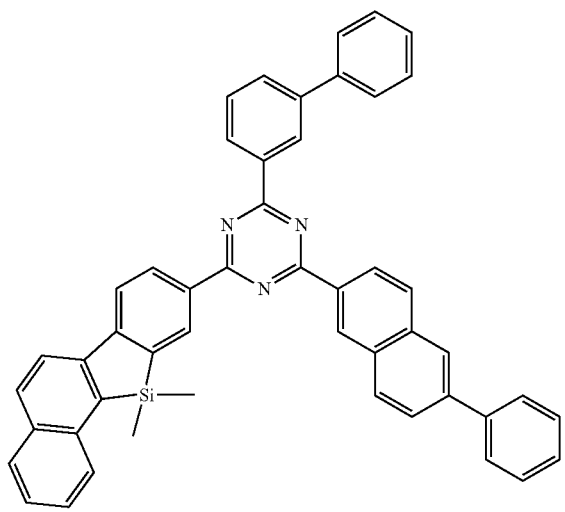
B-43
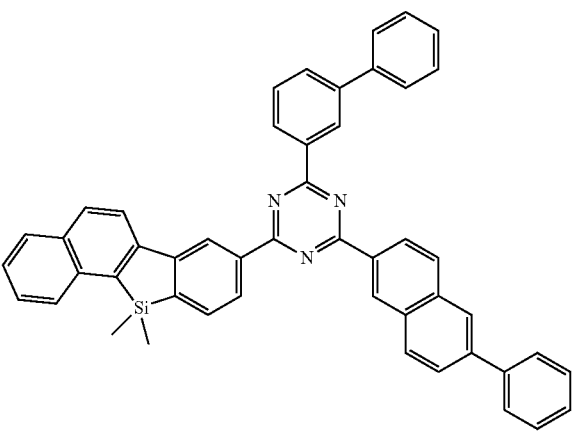
B-44
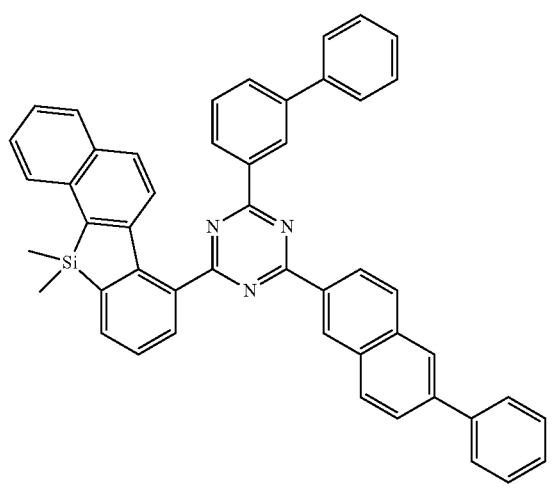
B-45
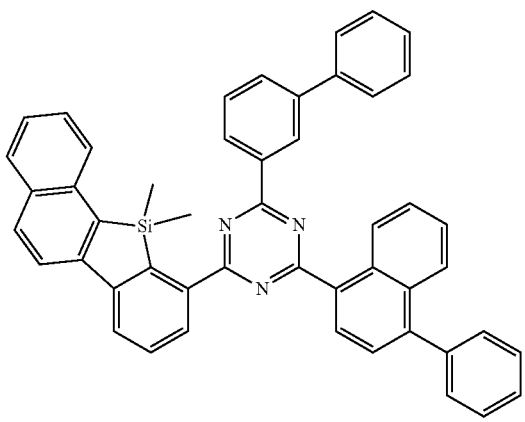

B-46
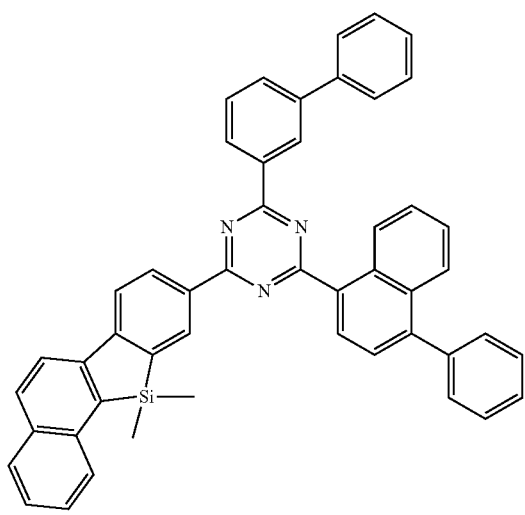
B-47
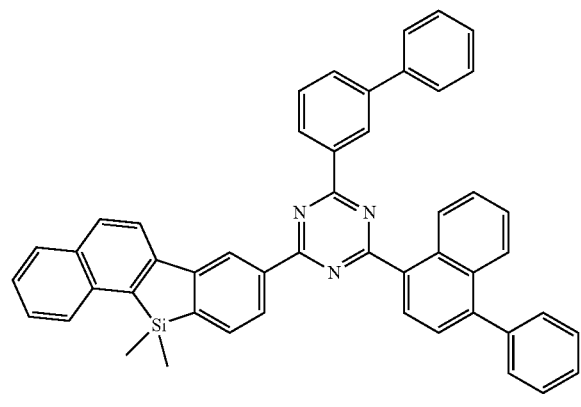
B-48
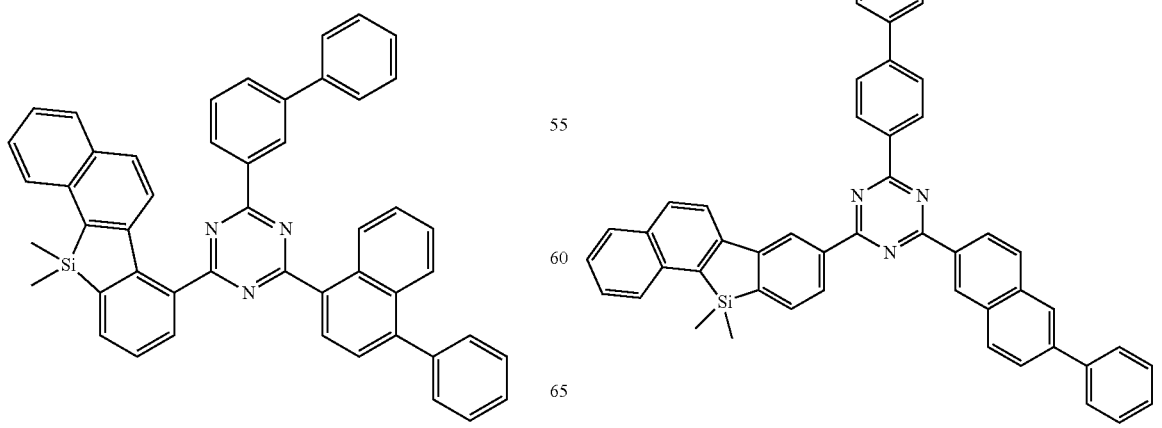
B-49
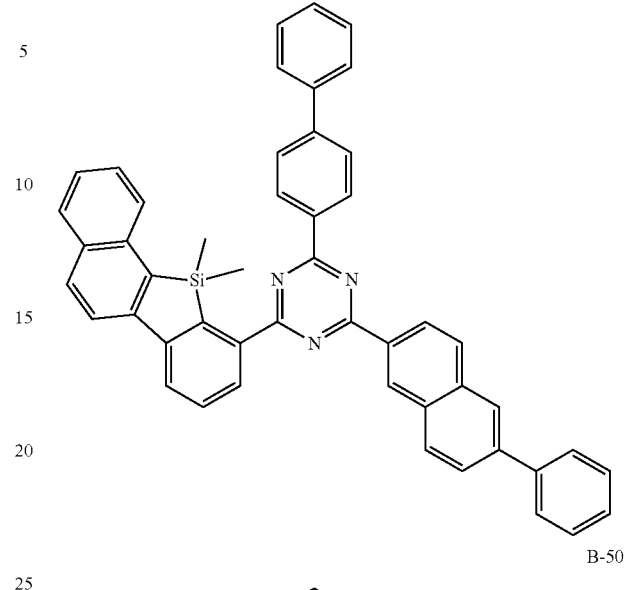
B-50
B-51

-continued
B-52
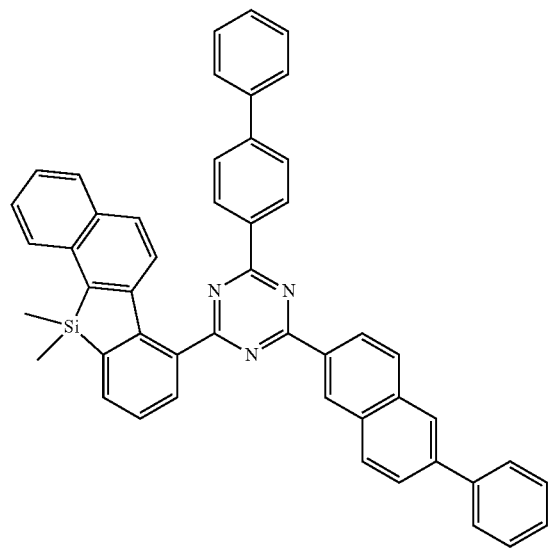
B-53
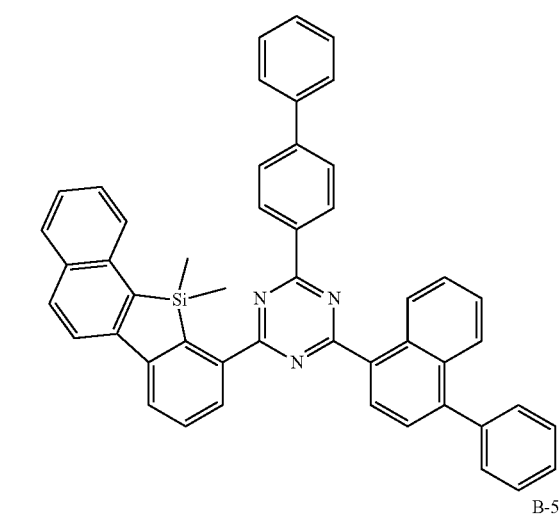
B-54
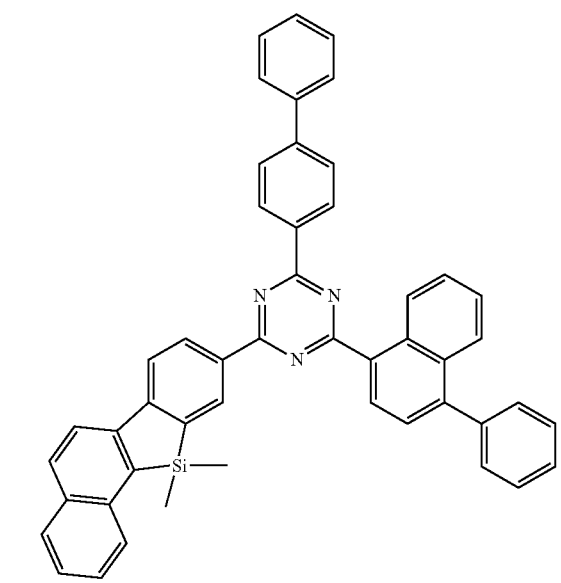
-continued
B-55
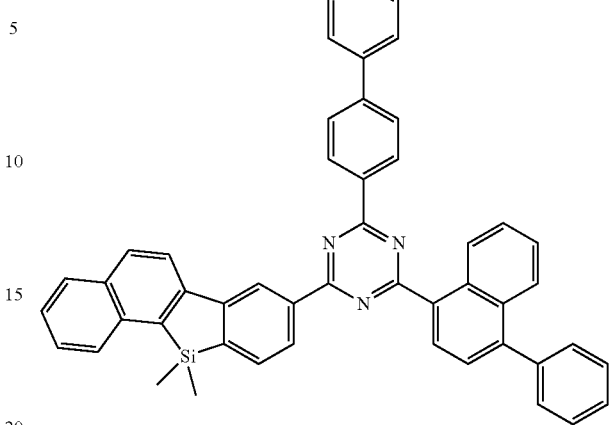
B-56
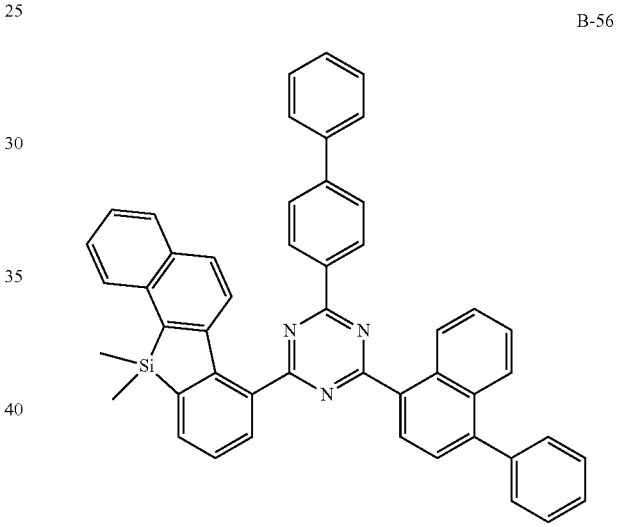
B-57
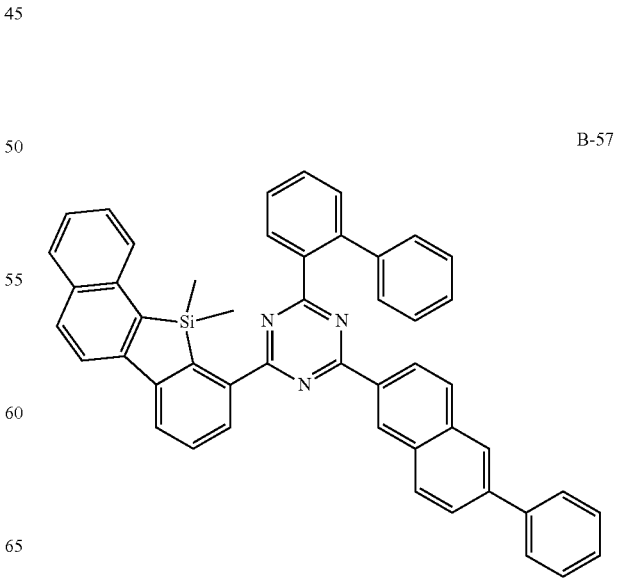

B-58
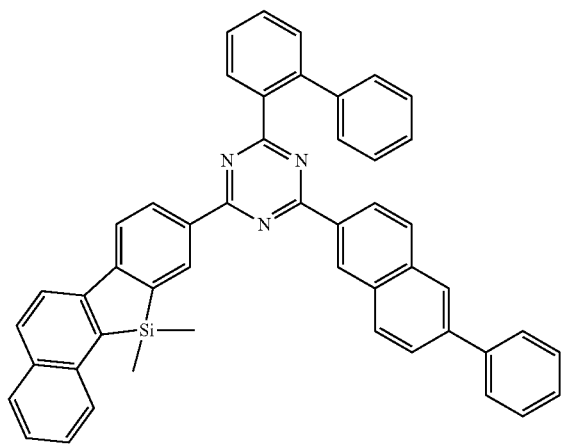
B-59
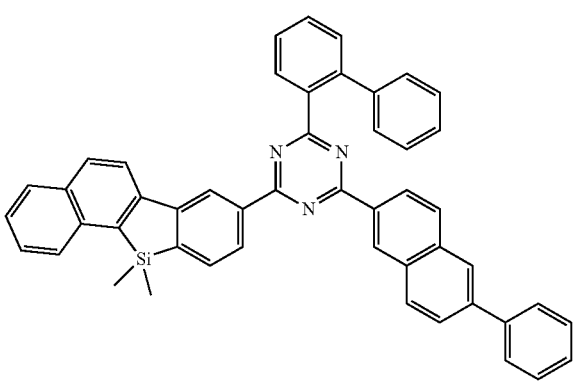
B-60
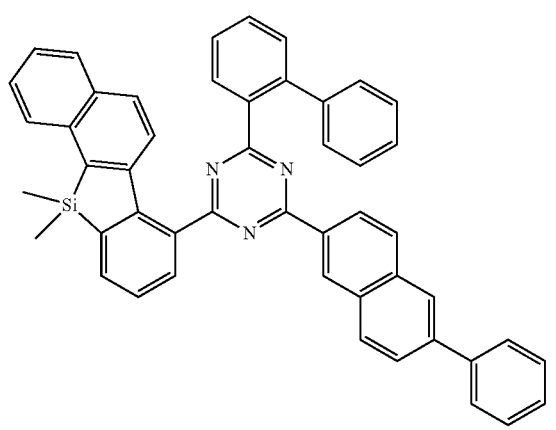
B-61
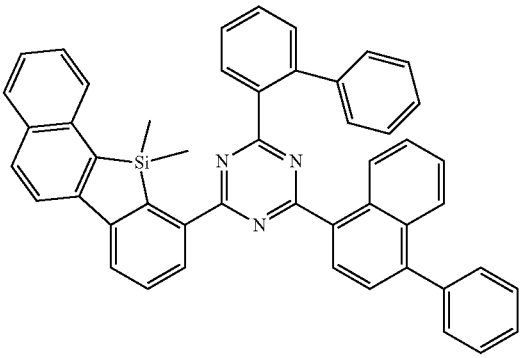
B-62
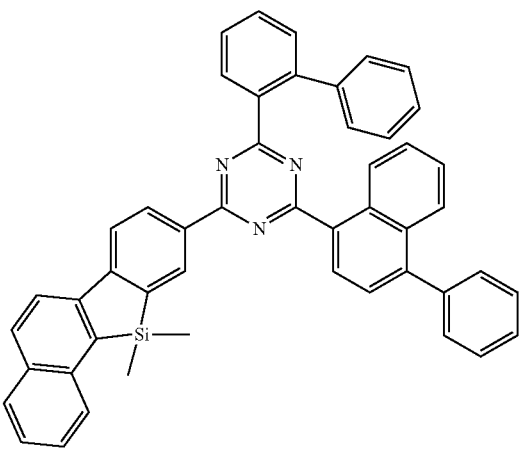
B-63
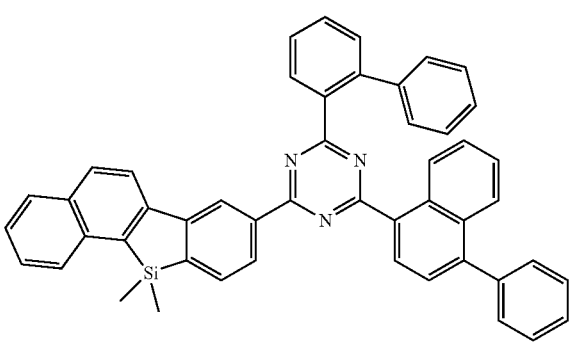
B-64
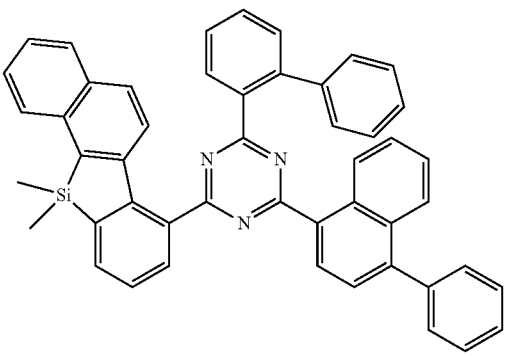

B-65
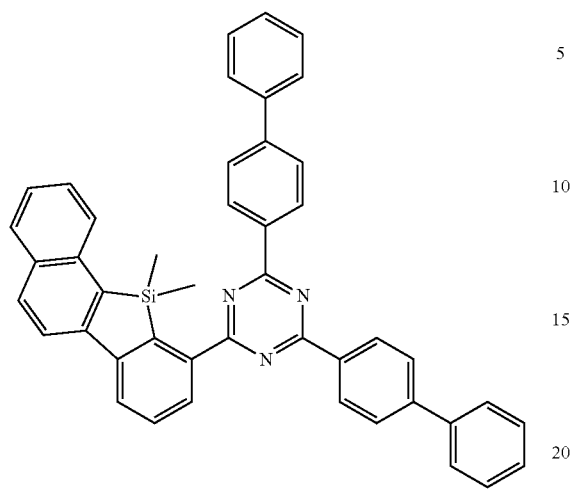
B-66
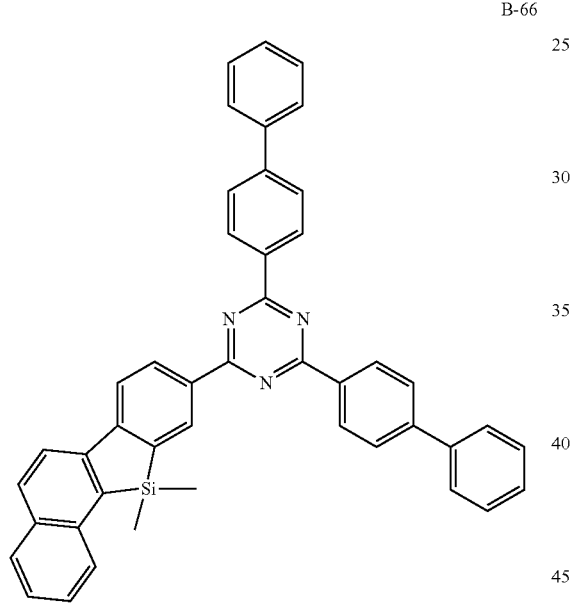
B-67
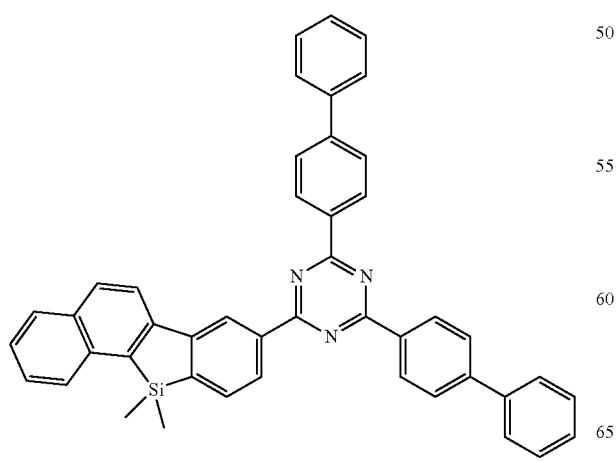
B-68
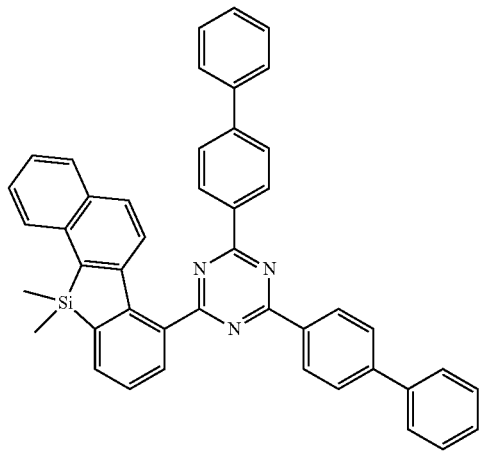
B-69
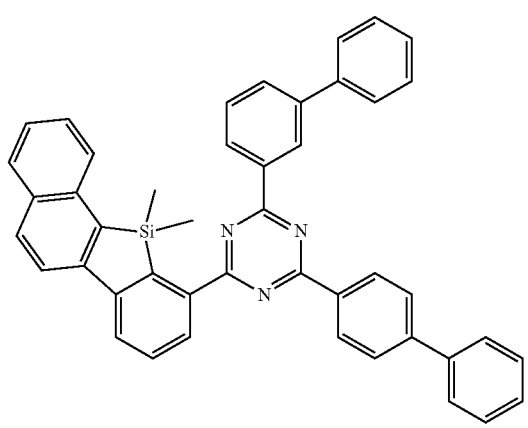
B-70
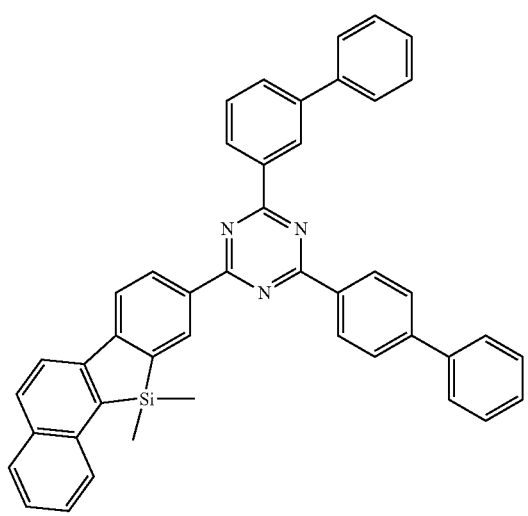

B-71
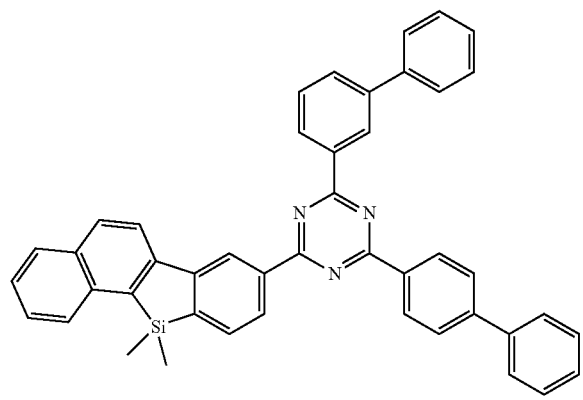
B-72
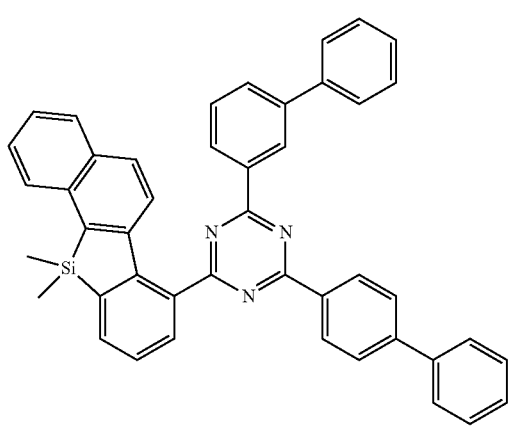
C-1
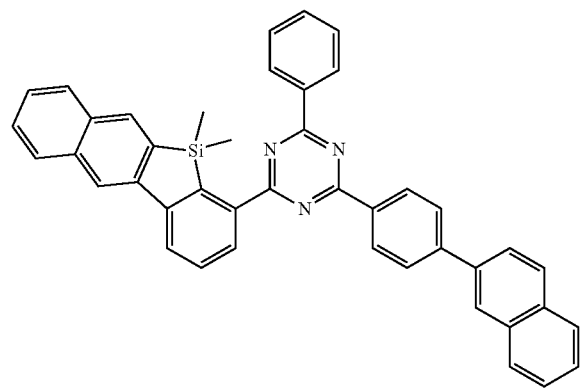
C-2
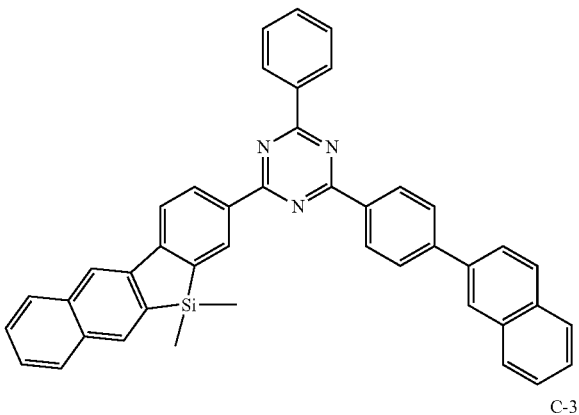
C-3
C-4
C-5
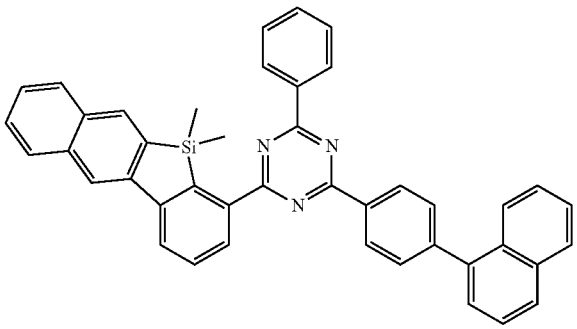

C-6
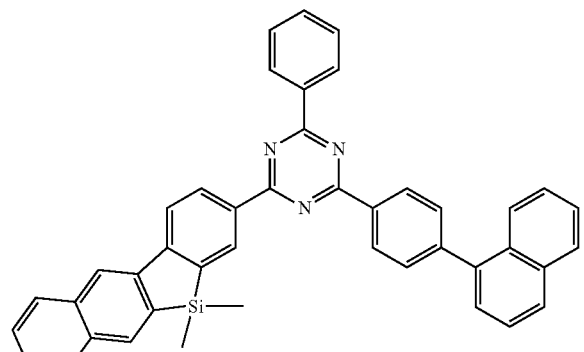
C-7
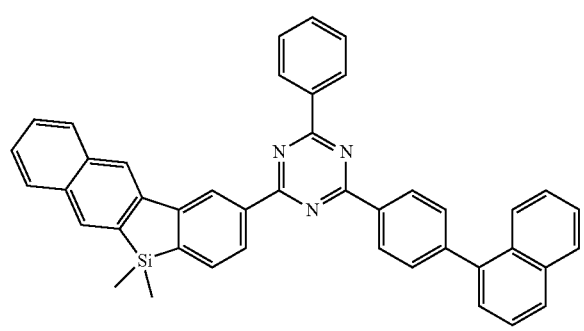
C-8
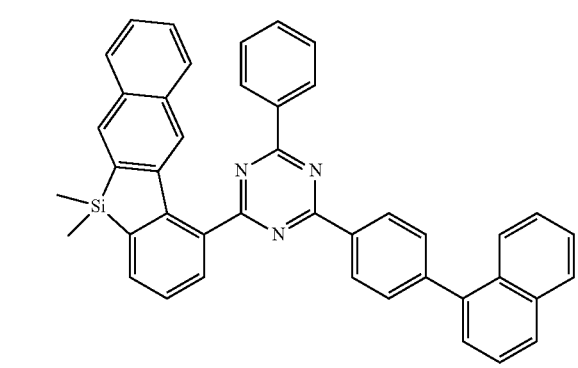
C-9
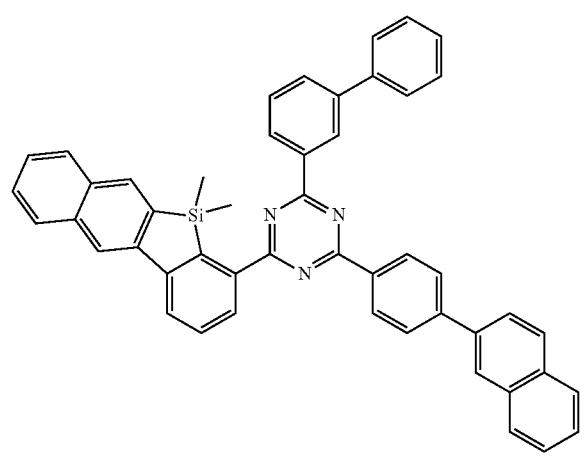
C-10
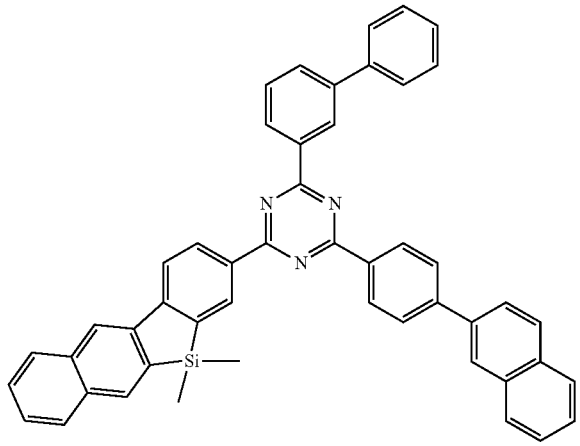
C-11
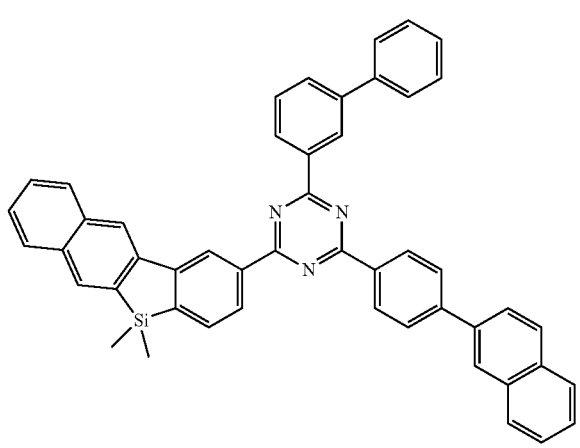
C-12
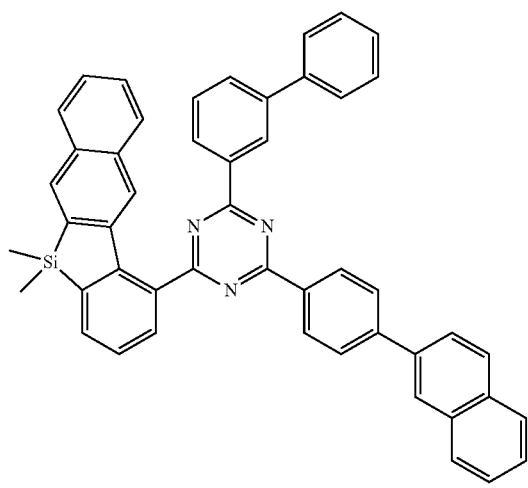

C-13
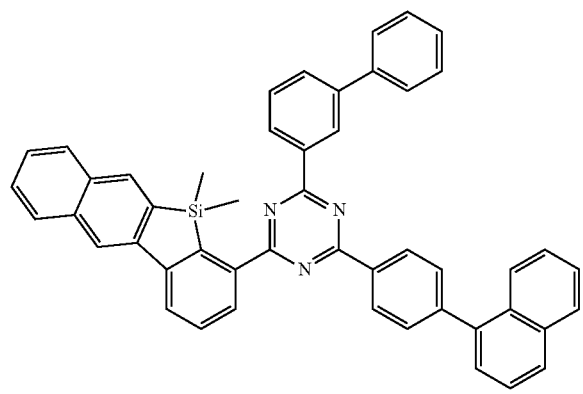
C-14
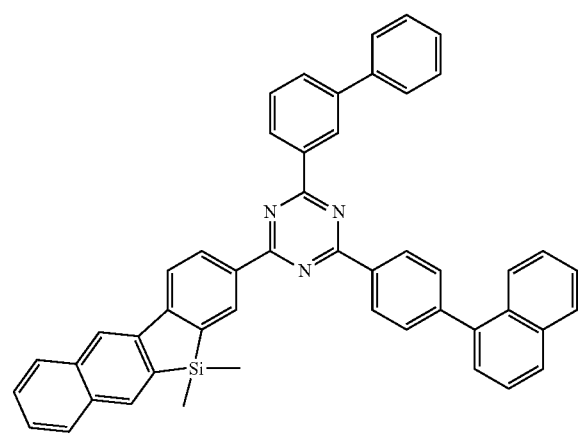
C-15
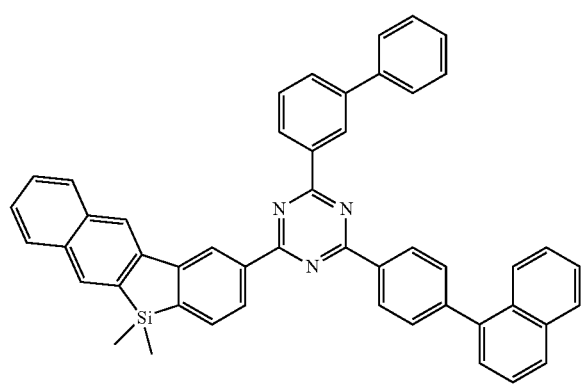
C-16
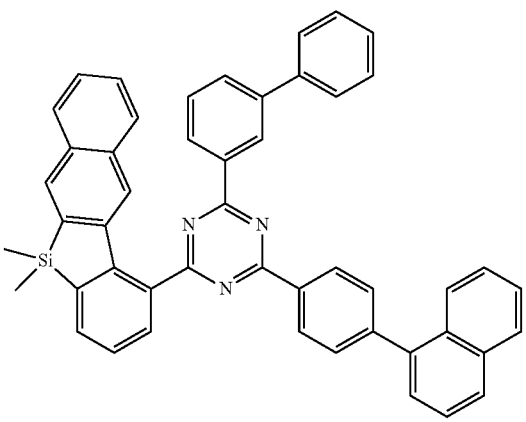
C-17
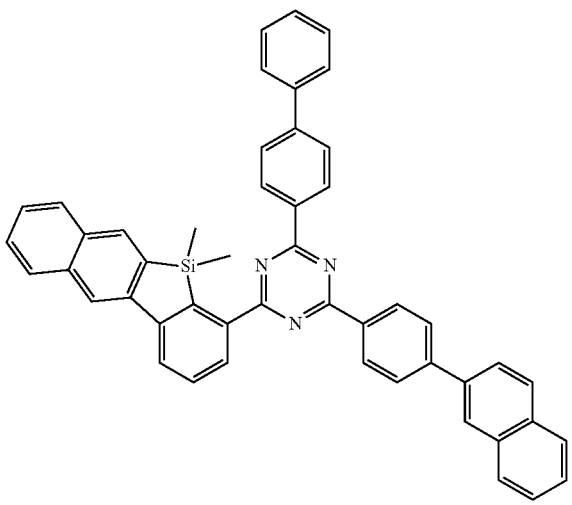
C-18
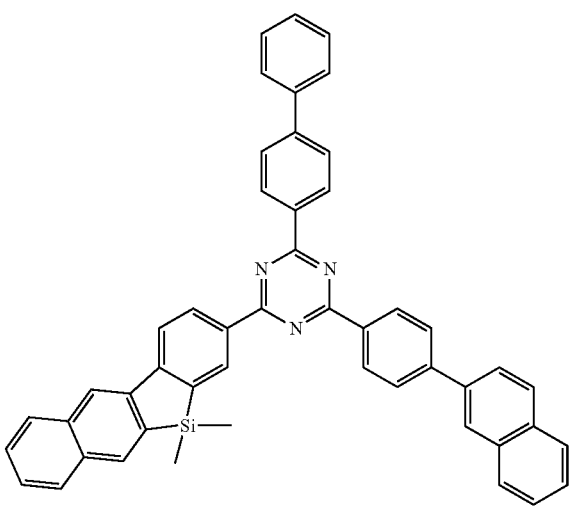

-continued
C-19
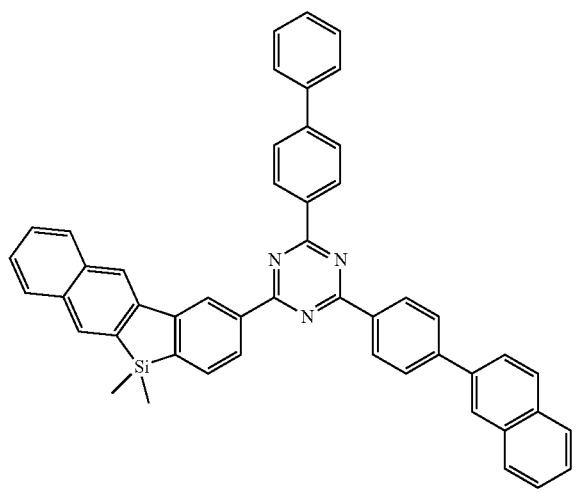
C-20
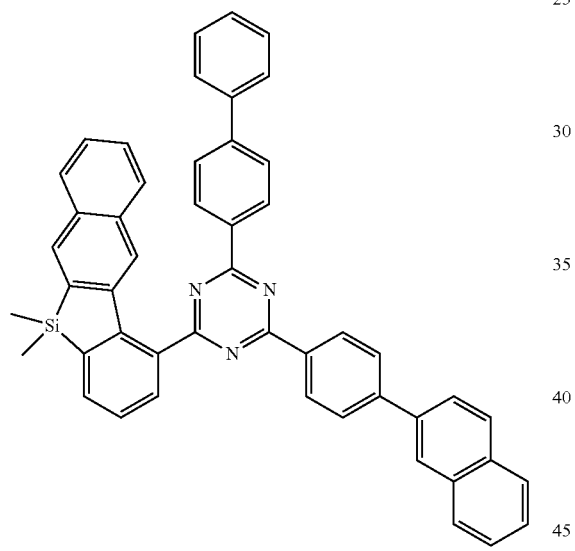
C-21
C-22
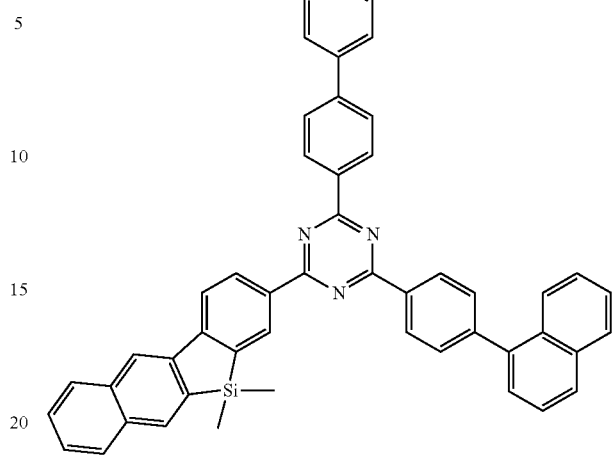
C-23
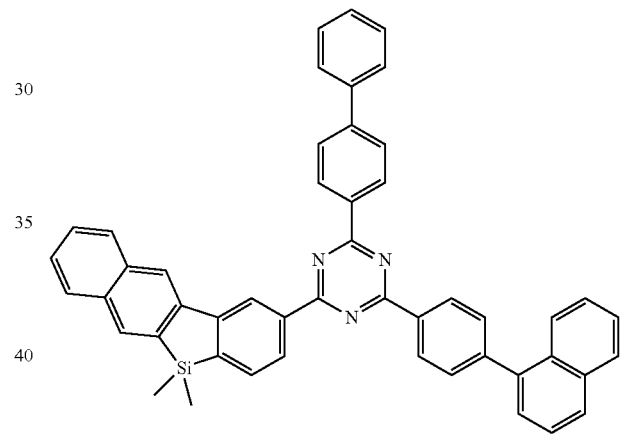
C-24
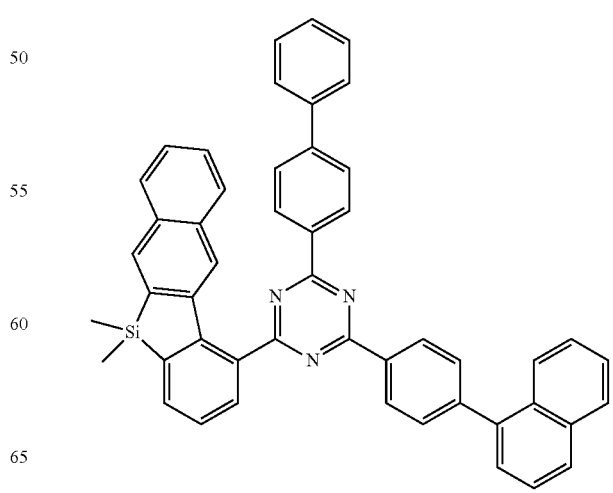

-continued
C-25
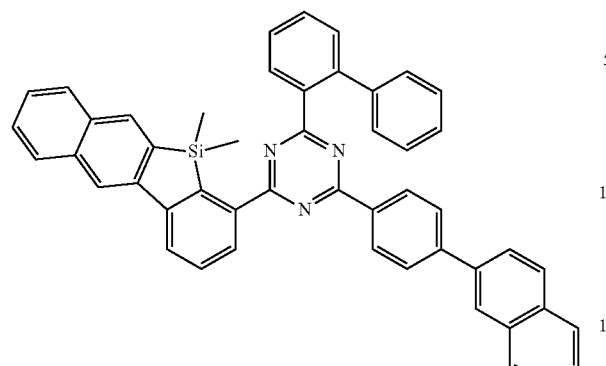
C-26
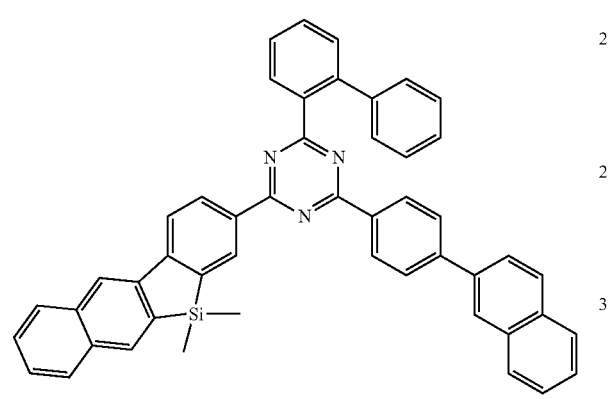
C-27
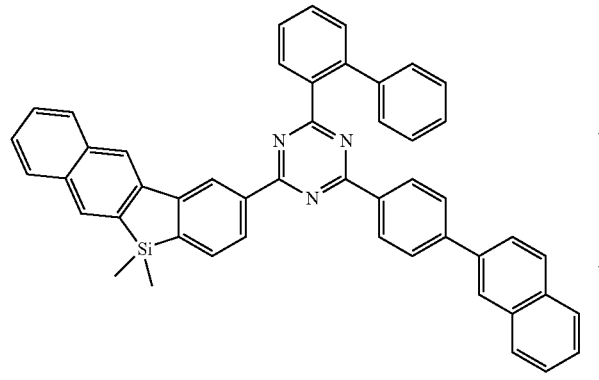
C-28
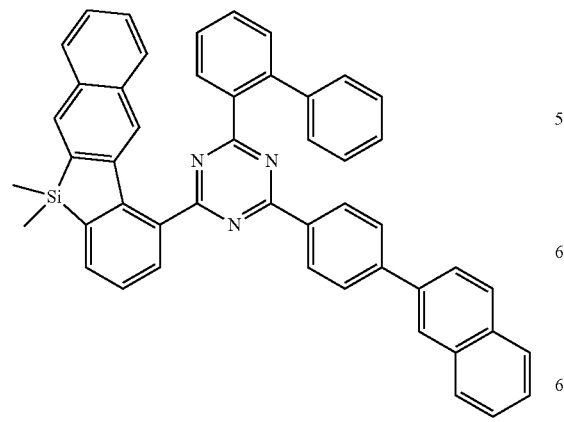
-continued
C-29
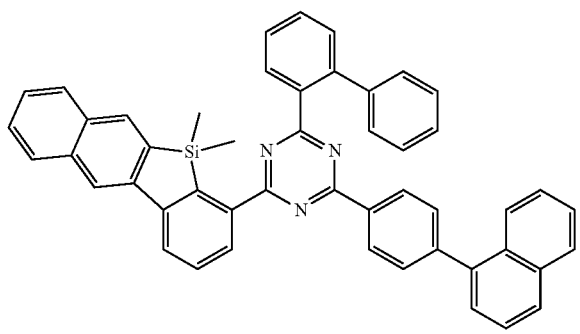
C-30
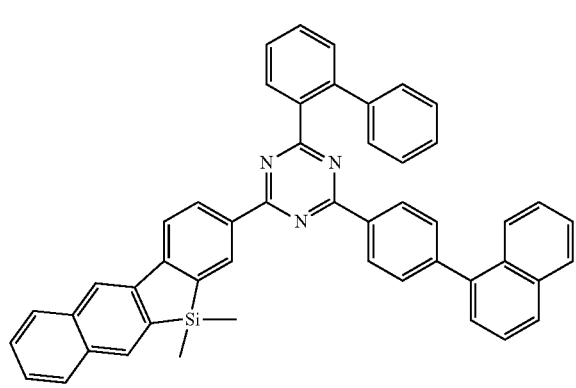
C-31
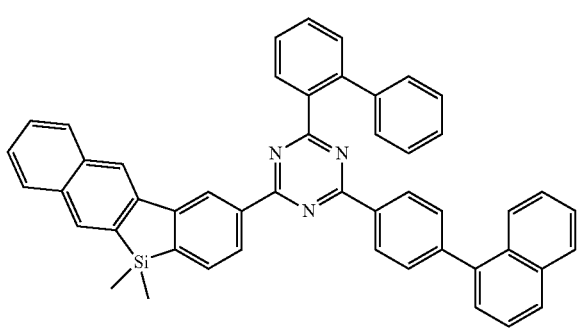
C-32
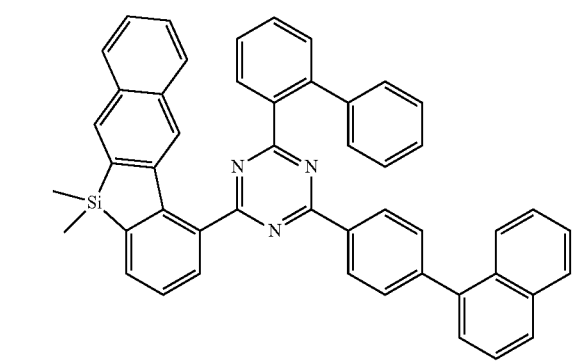

C-33
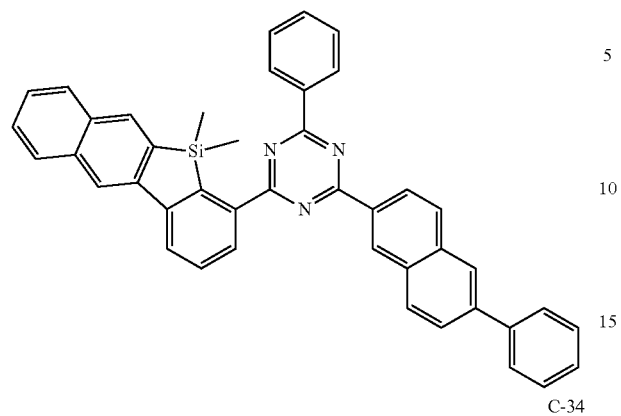
C-34
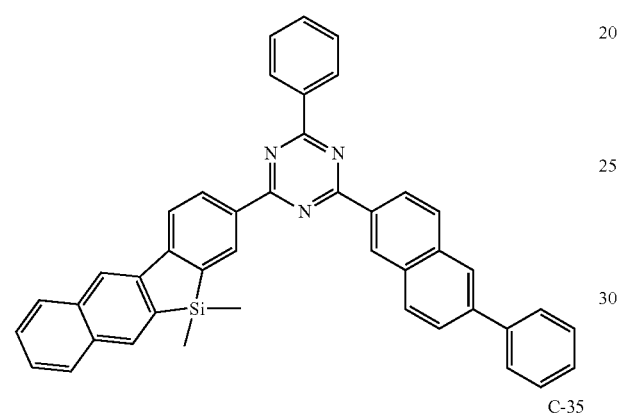
C-35
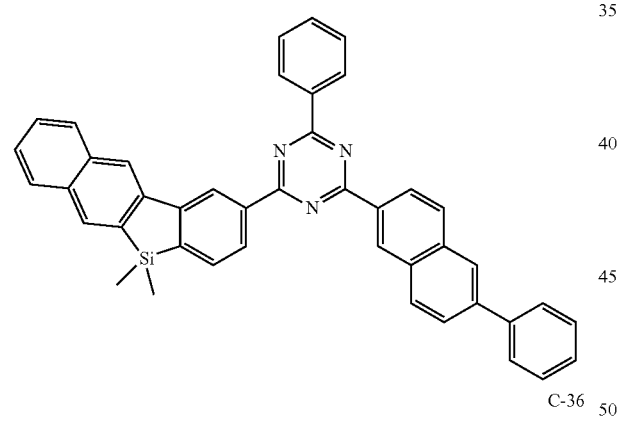
C-36
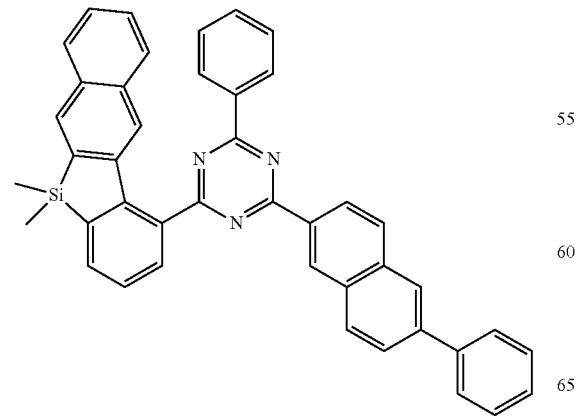
C-37
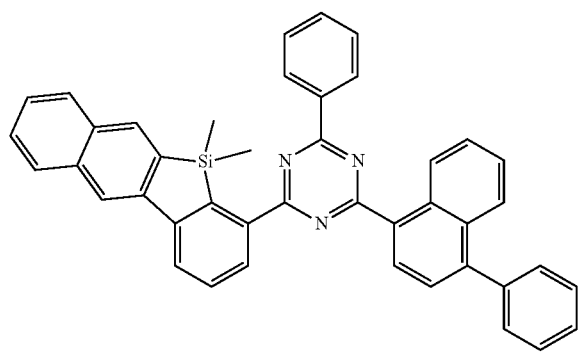
C-38
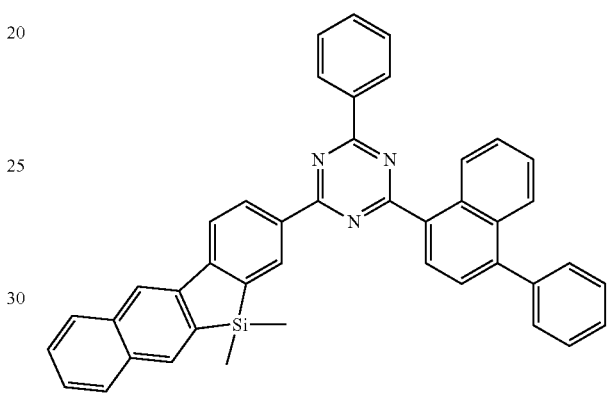
C-39
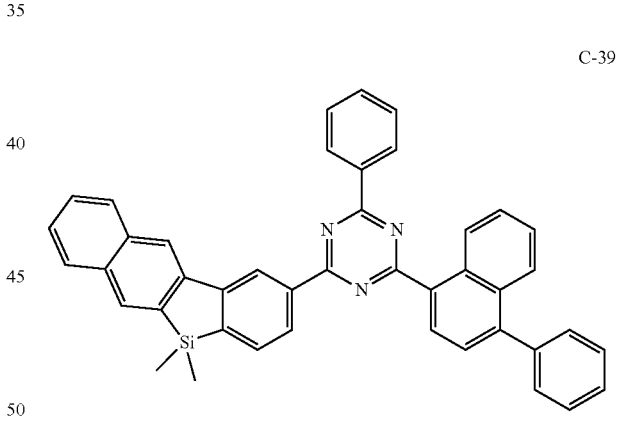
C-40
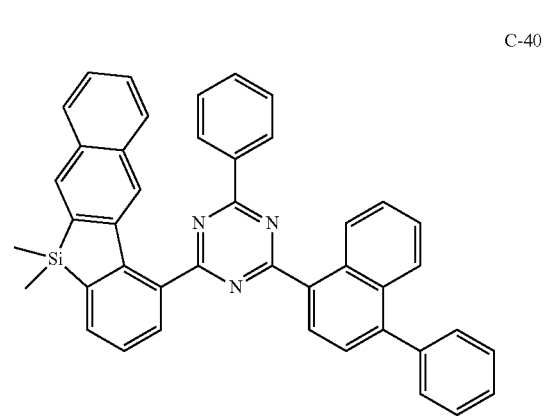

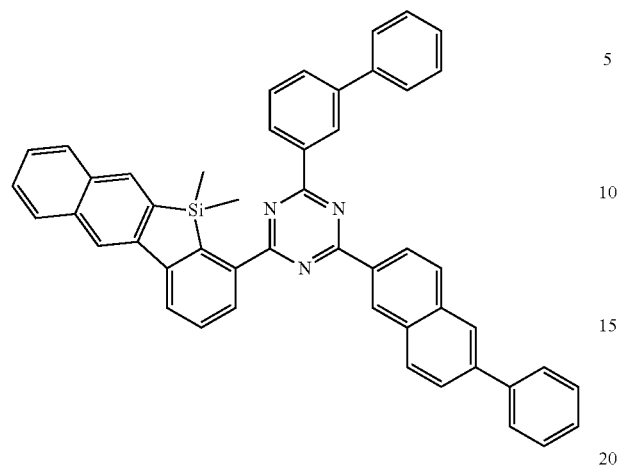
C-41
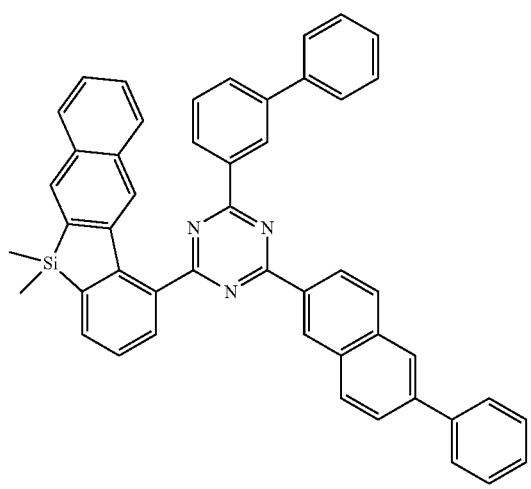
C-44
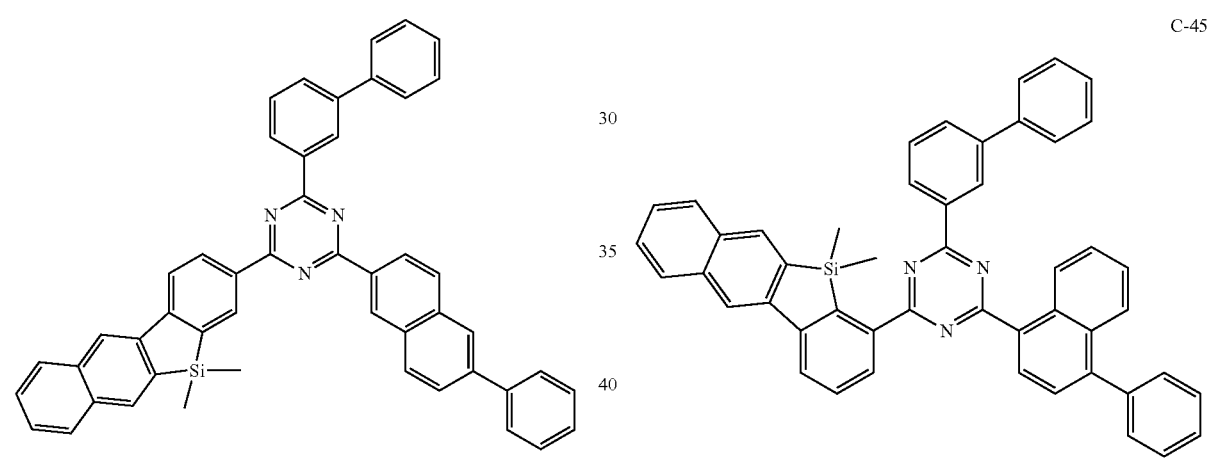
C-42
C-45
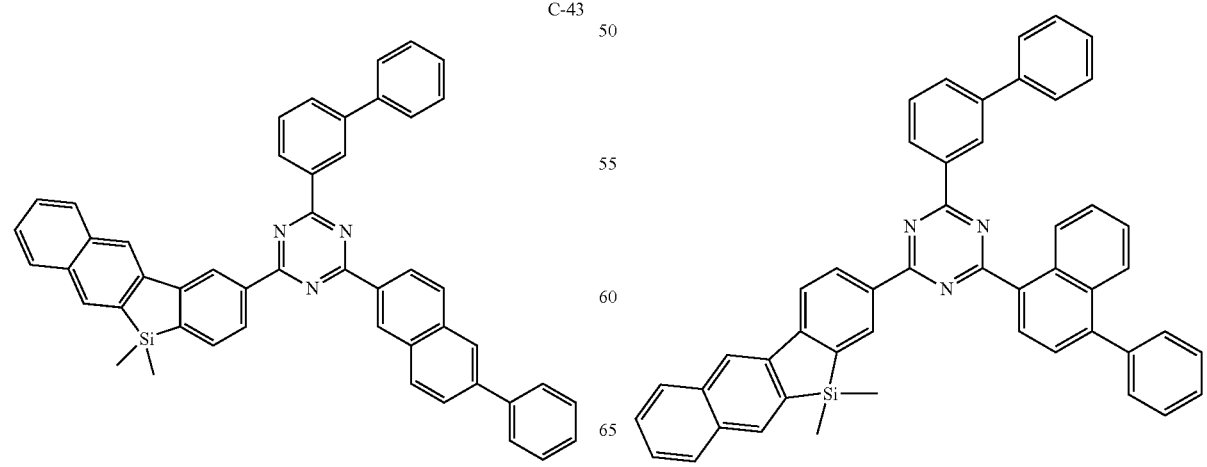
C-43
C-46

C-47
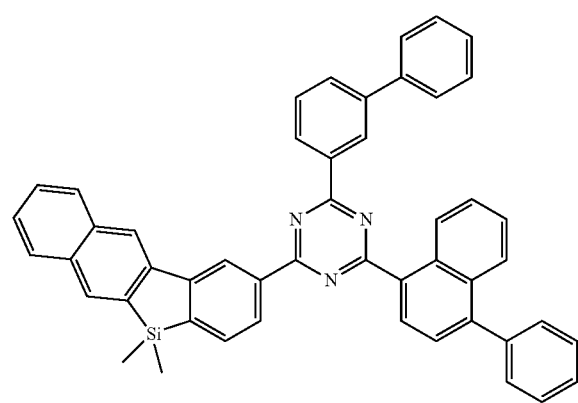
C-50
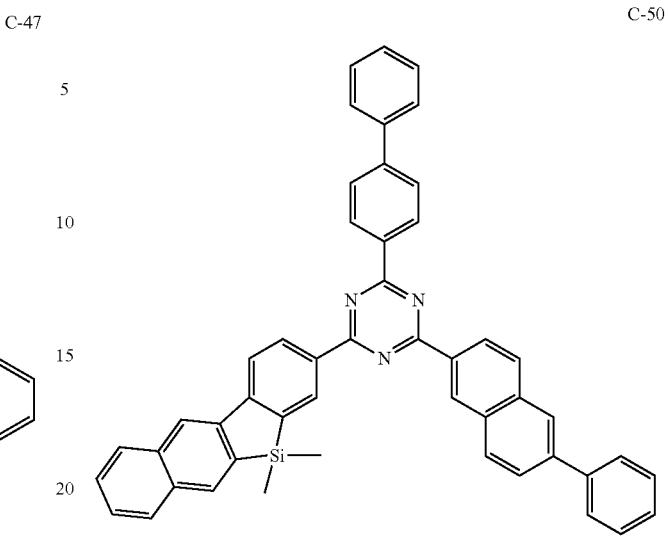
C-48
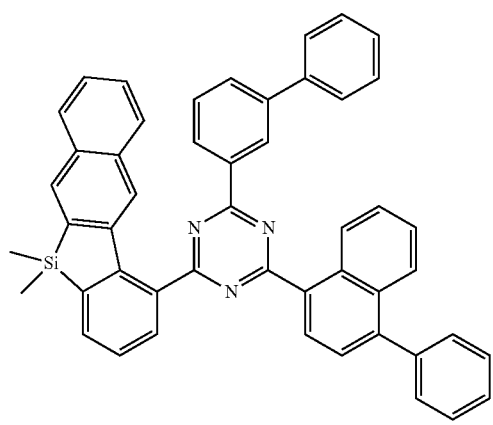
C-51
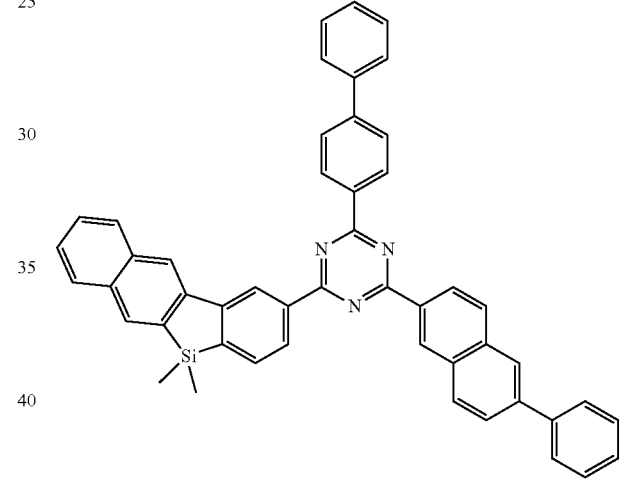
C-49
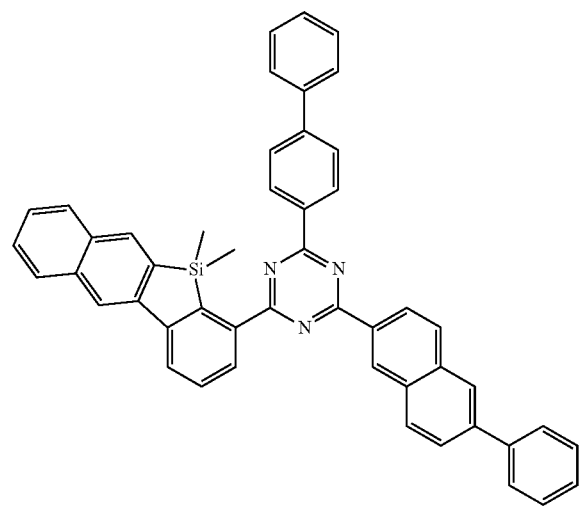
C-52
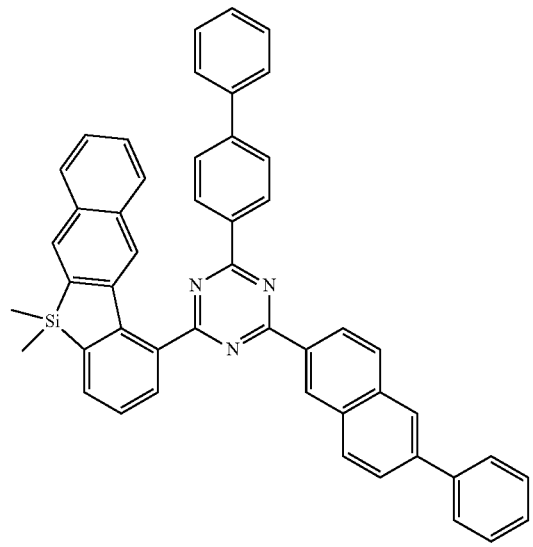

C-53
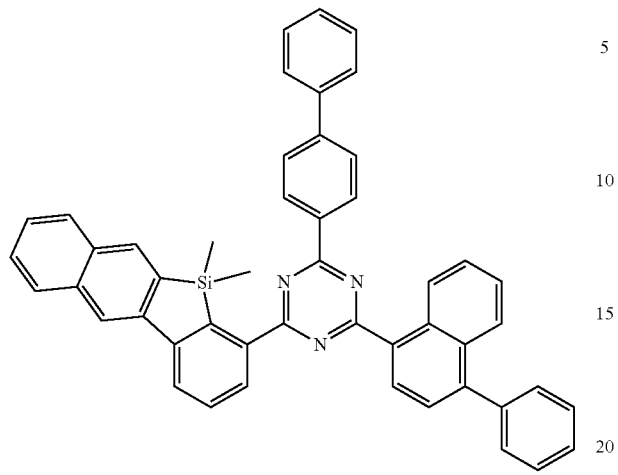
C-54
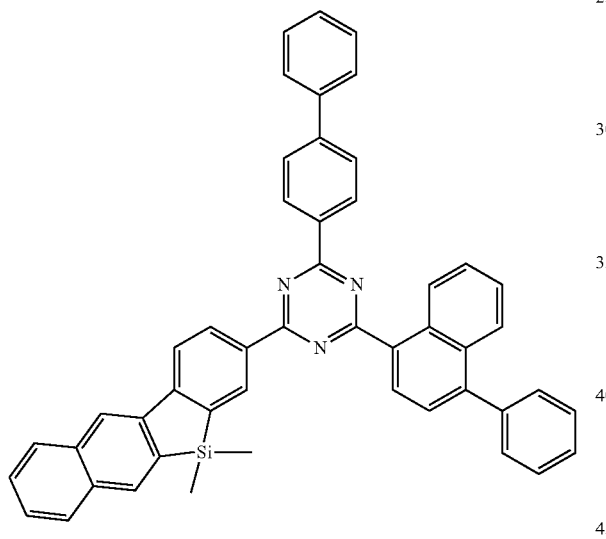
C-55
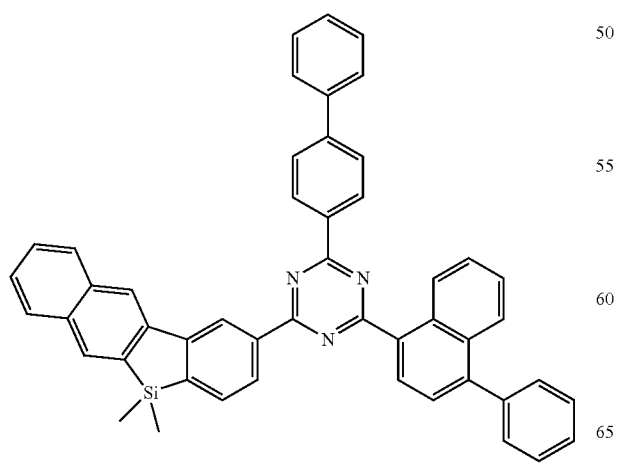
C-56
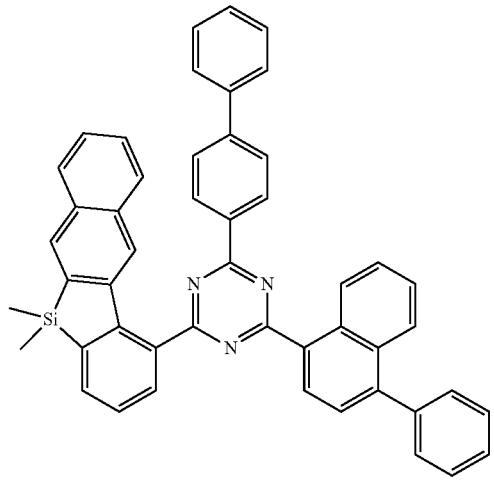
C-57
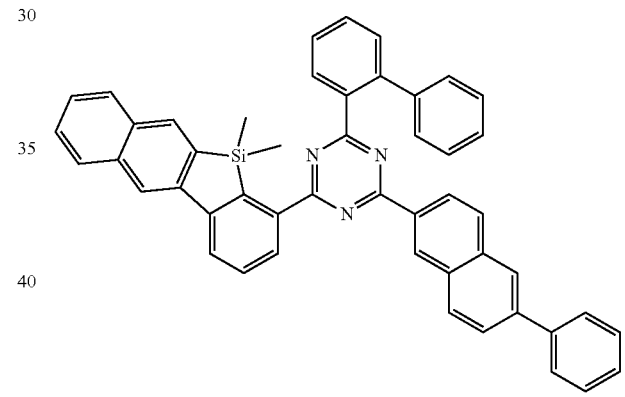
C-58
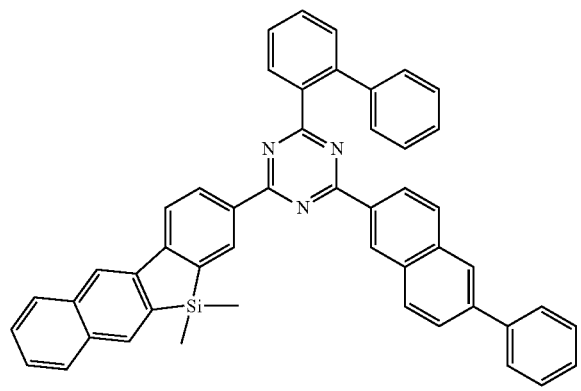

C-59
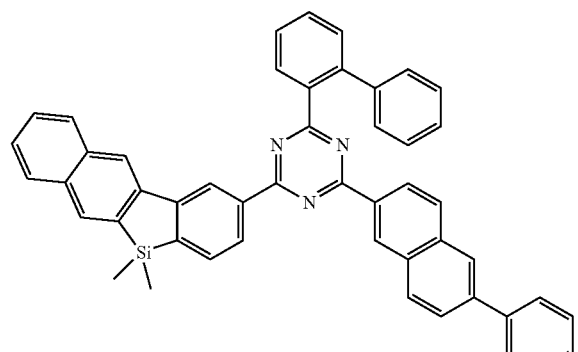
C-60
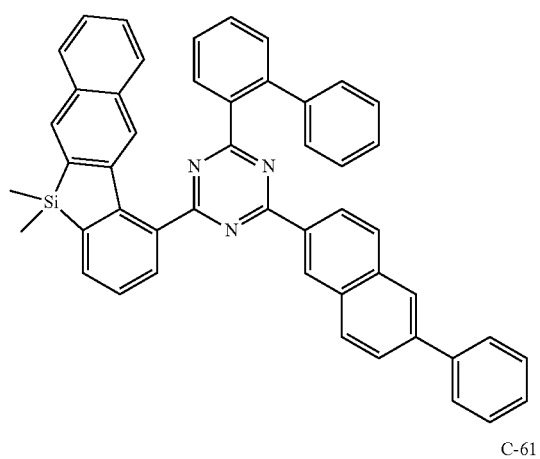
C-61
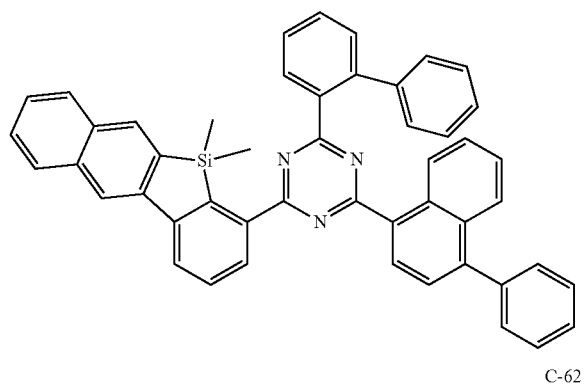
C-62
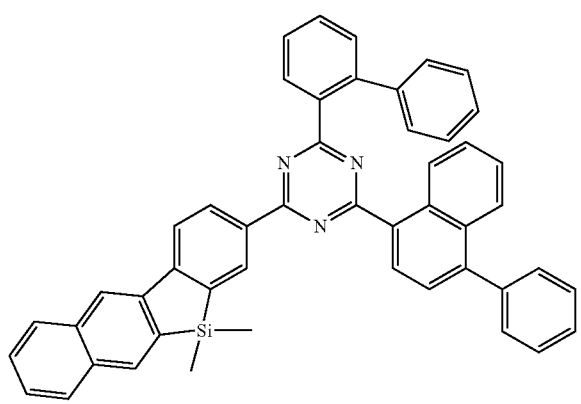
C-63
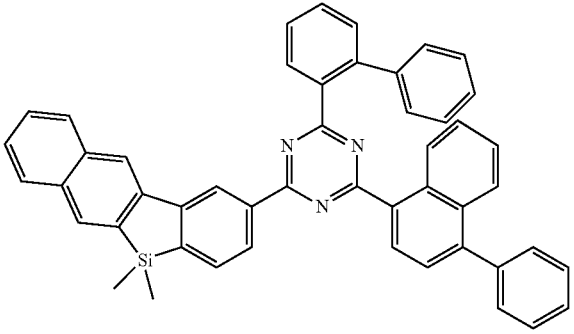
C-64
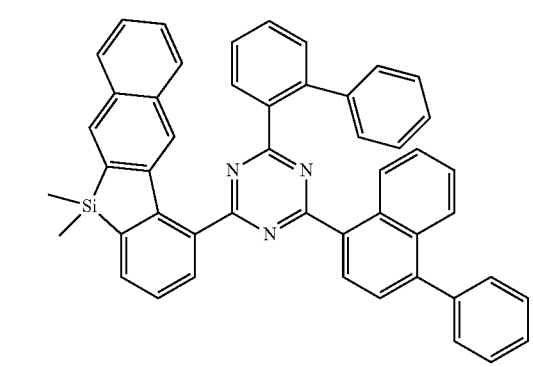
C-65

C-66
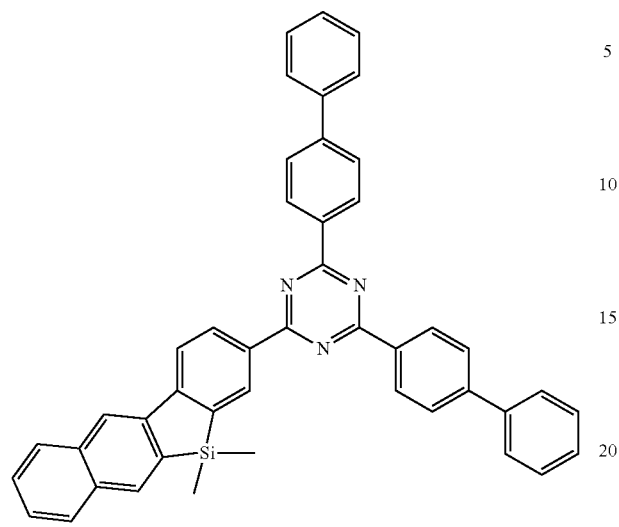
C-69
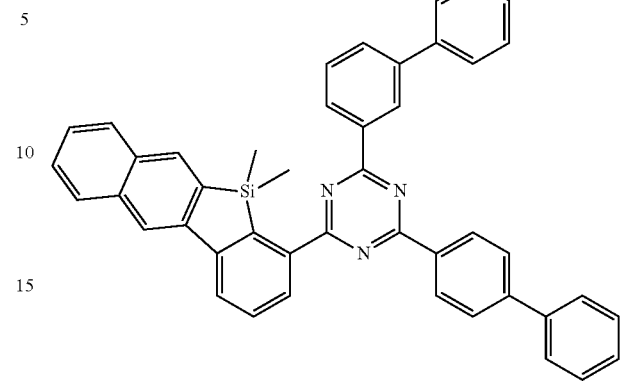
C-67
C-70
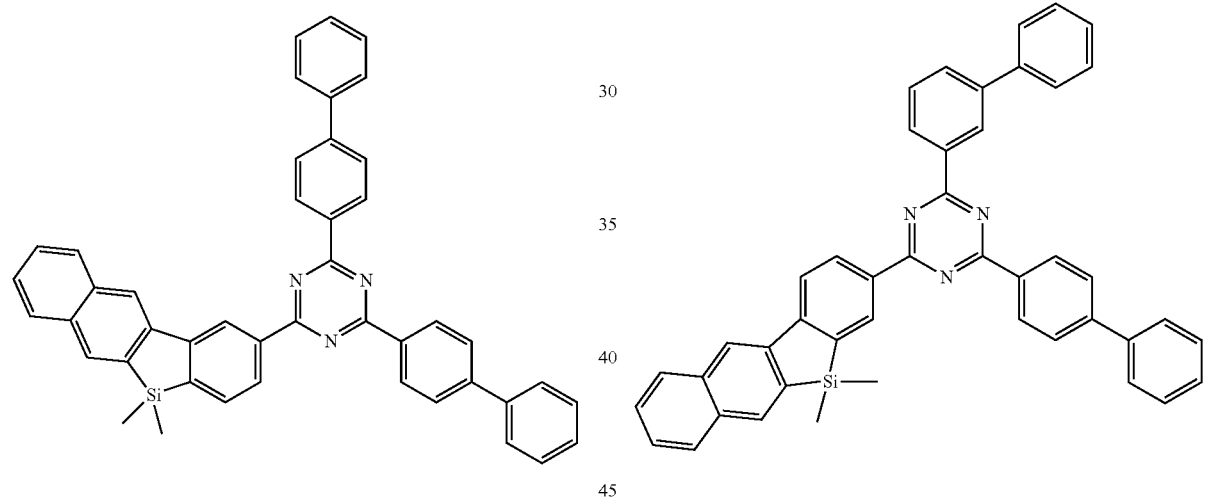
C-68
C-71
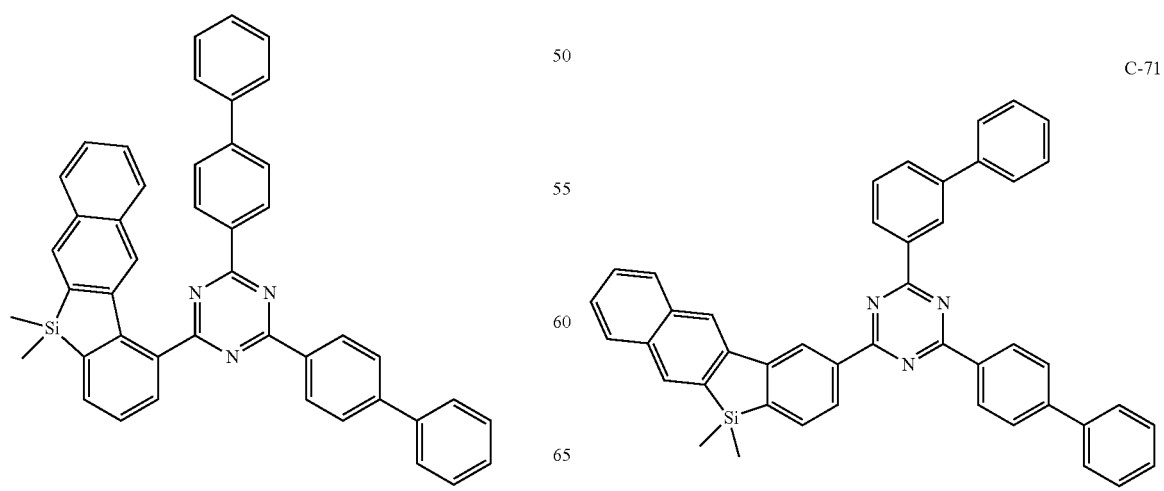

C-72
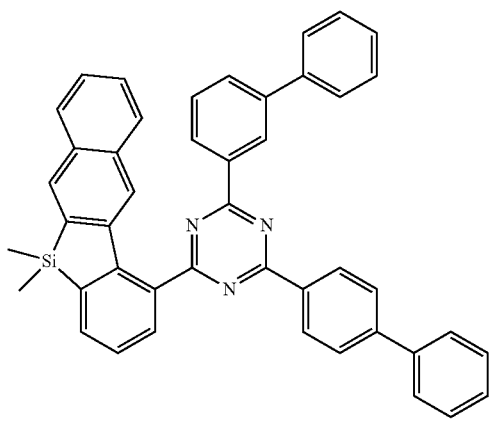
D-3
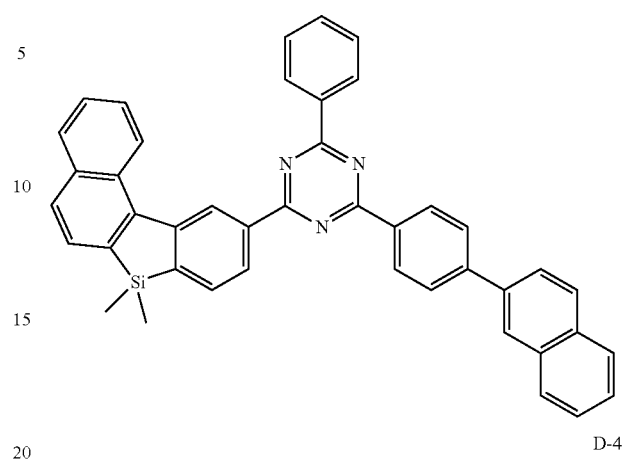
D-1
D-4
D-5
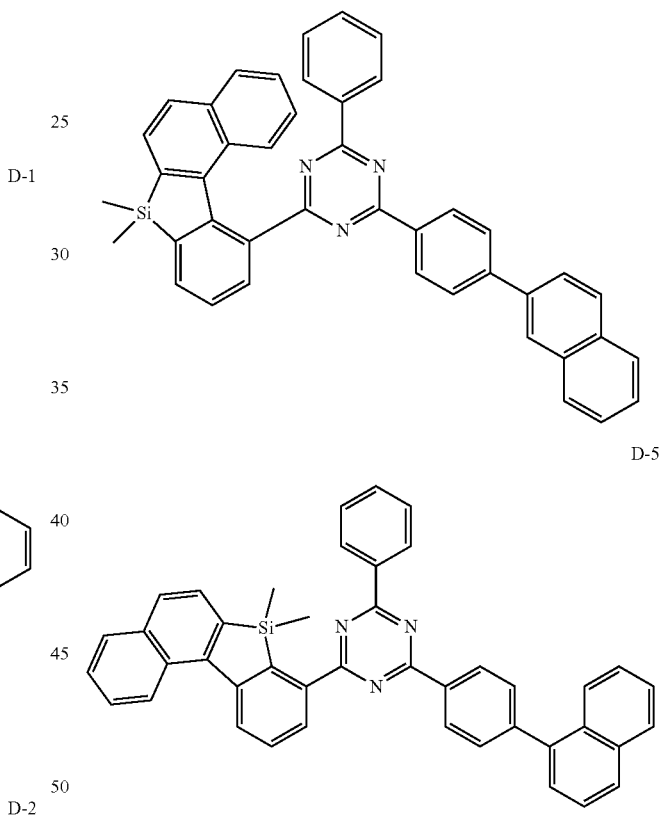
D-2
D-6
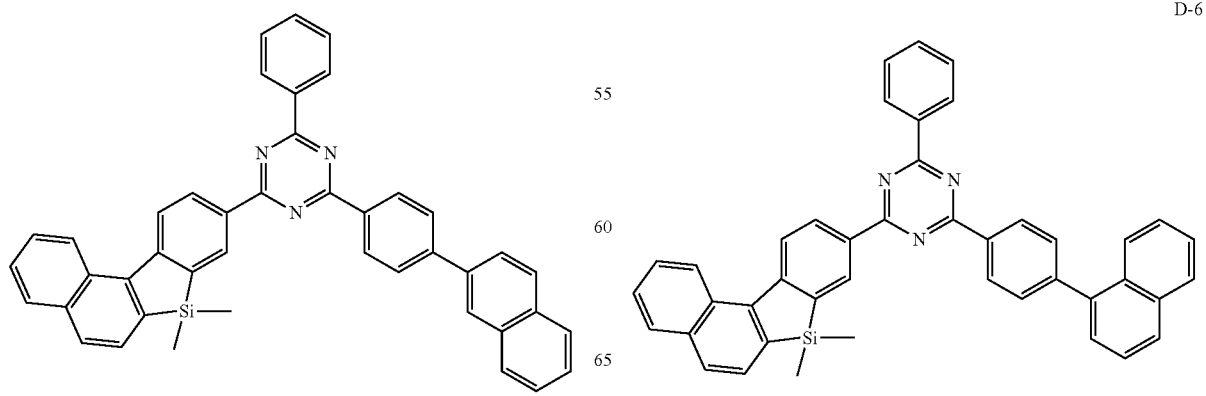

-continued
D-7
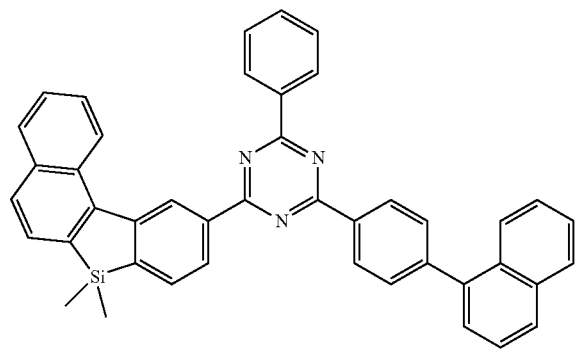
D-8
D-9
-continued
D-10
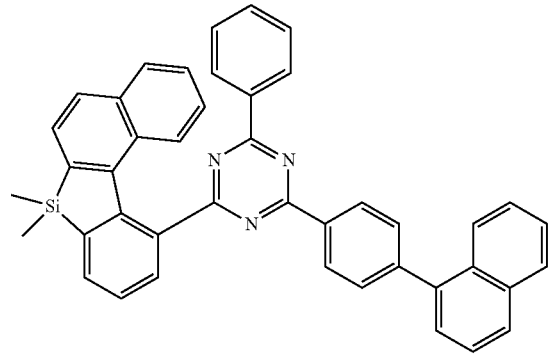
D-11
D-12
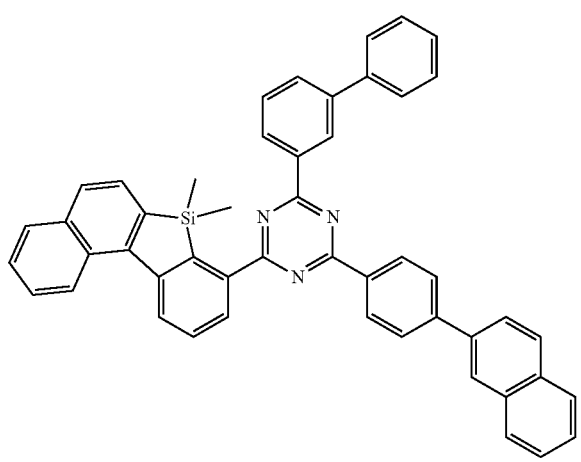

D-13
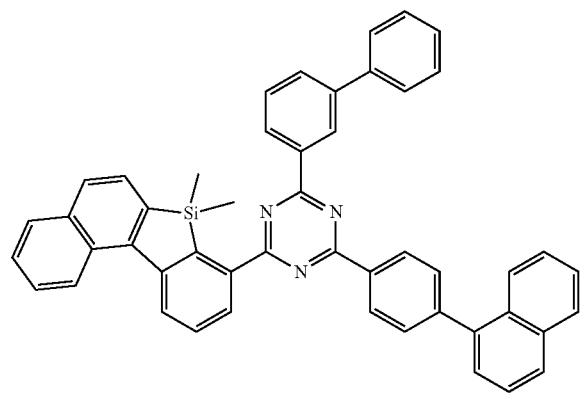
D-14
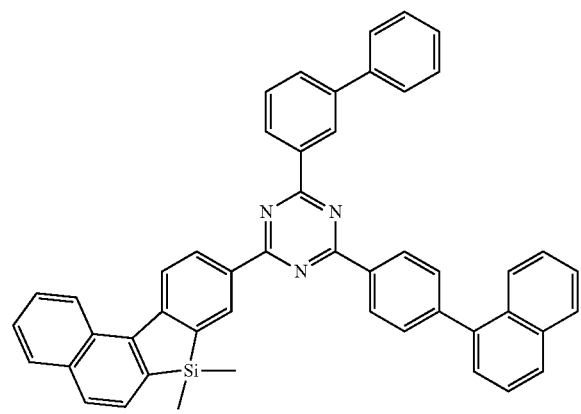
D-15
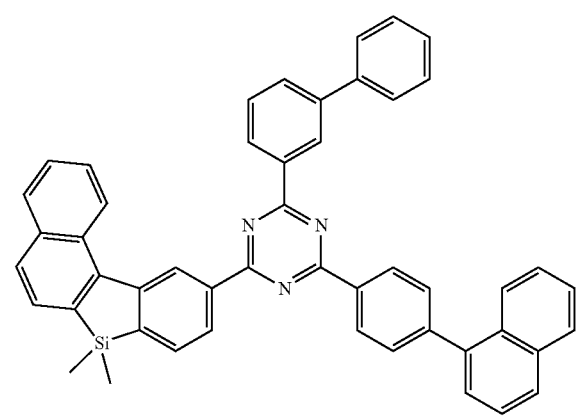
D-16
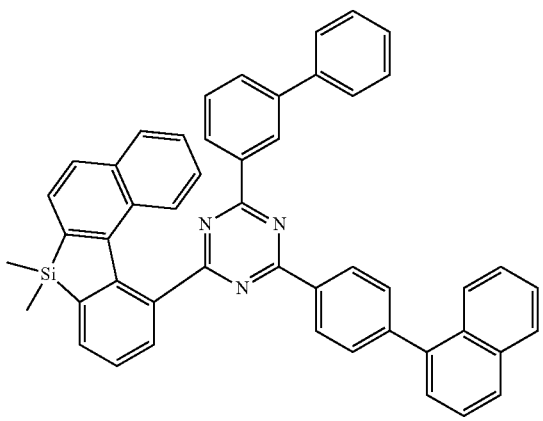
D-17
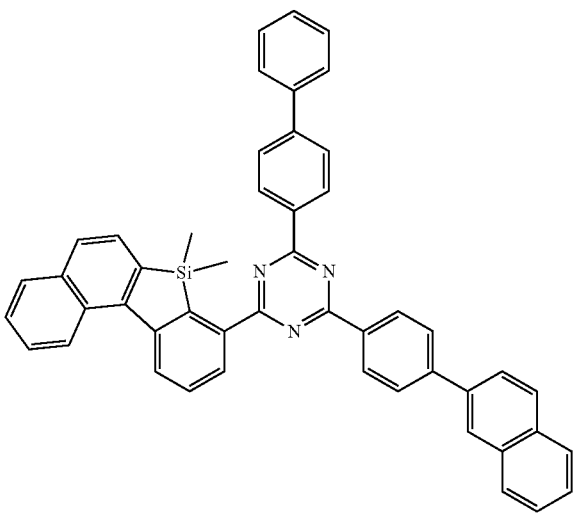
D-18
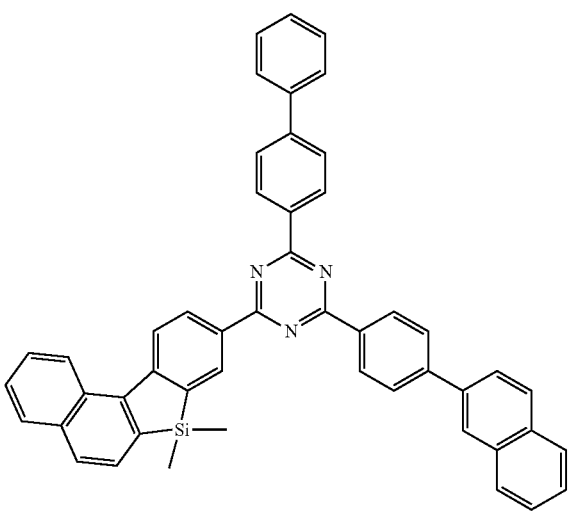

D-19
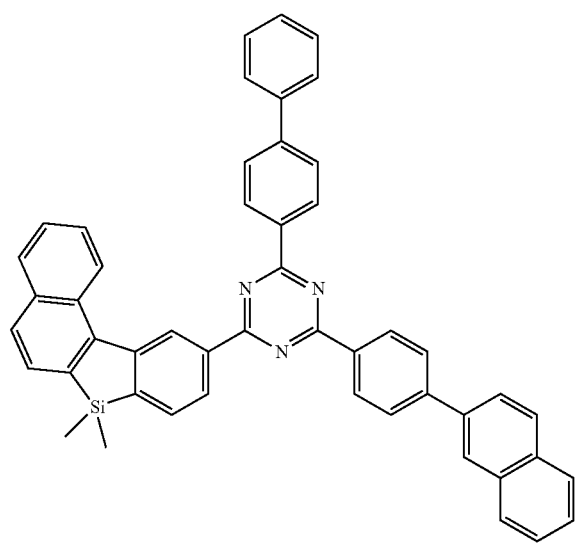
D-20
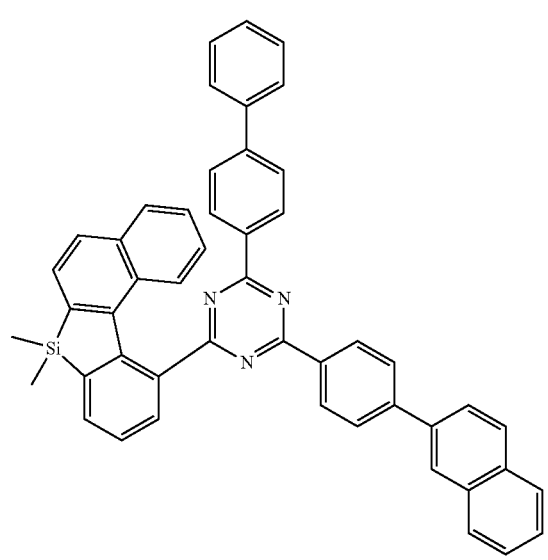
D-21
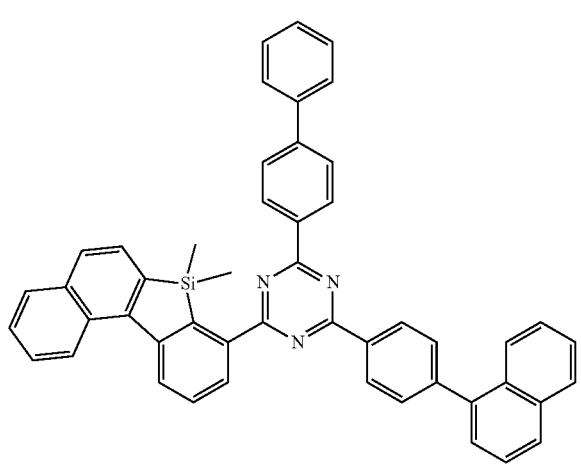
D-22
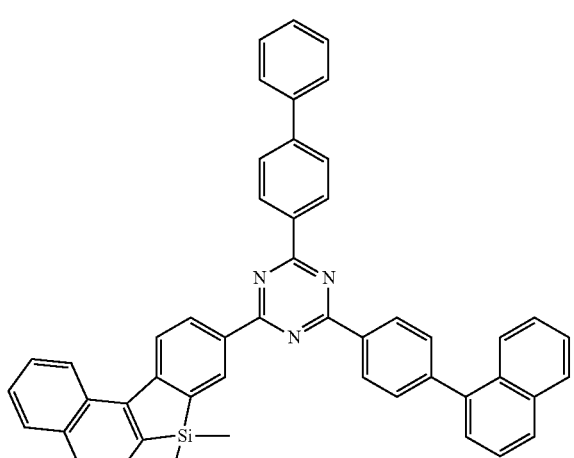
D-23
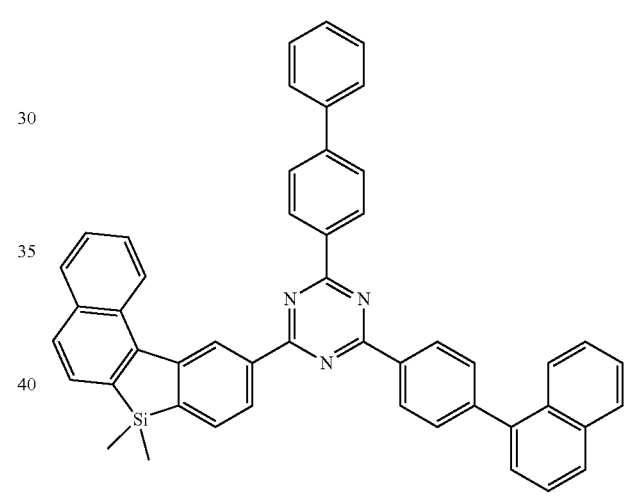
D-24
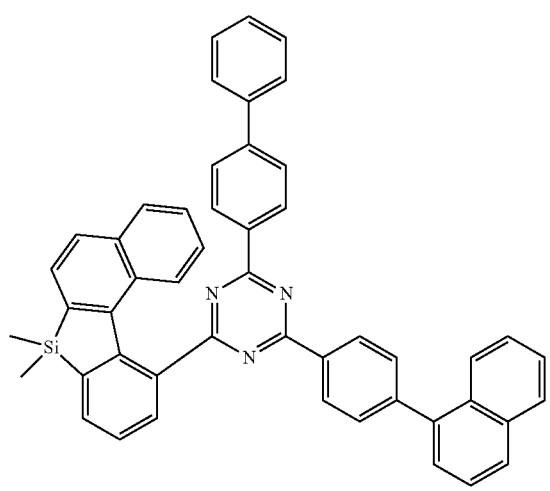

D-25
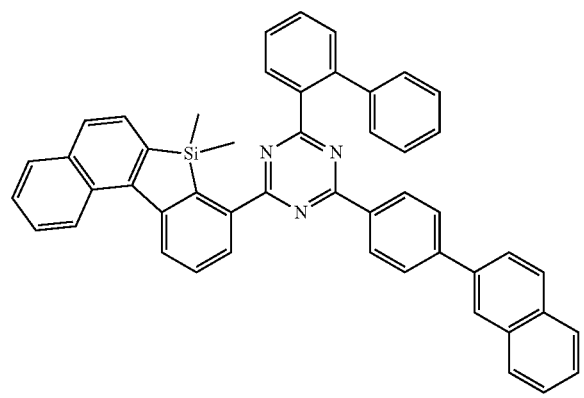
D-26
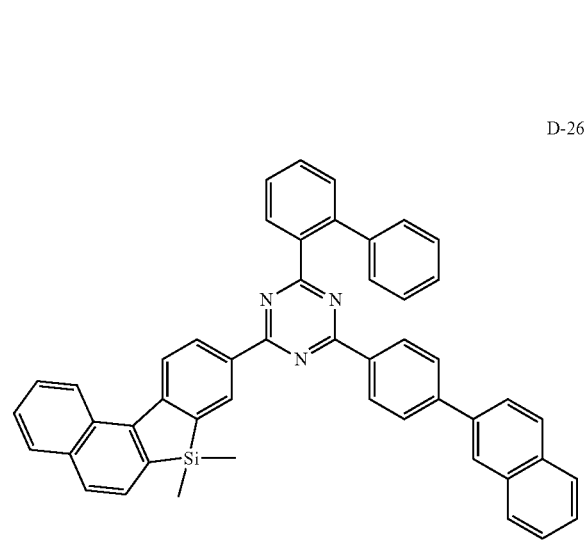
D-27
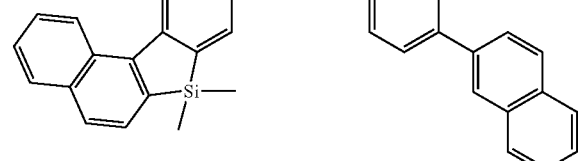
D-28
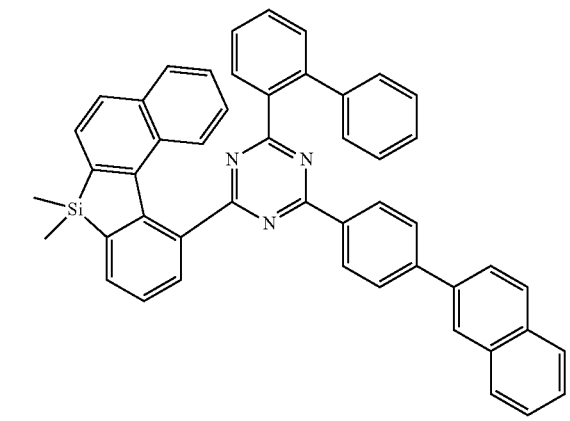
D-29
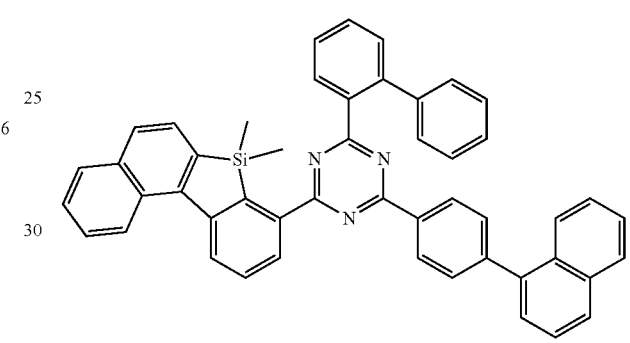
D-30
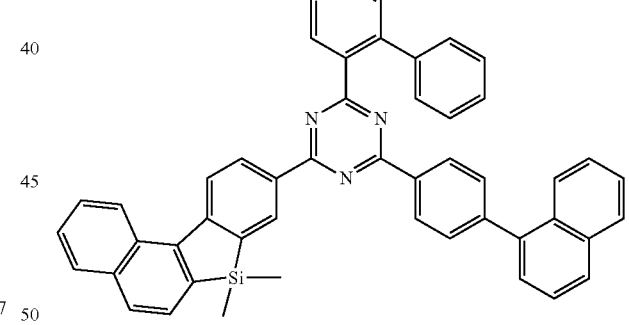
C-31
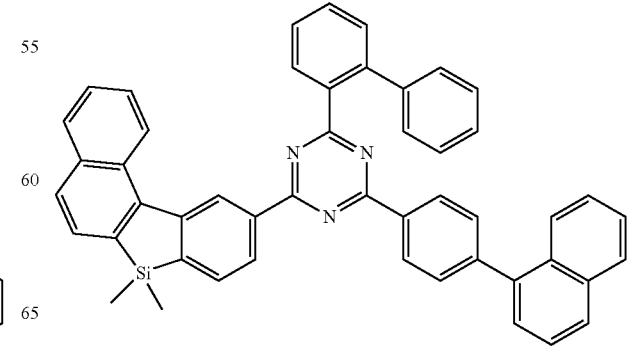

D-32
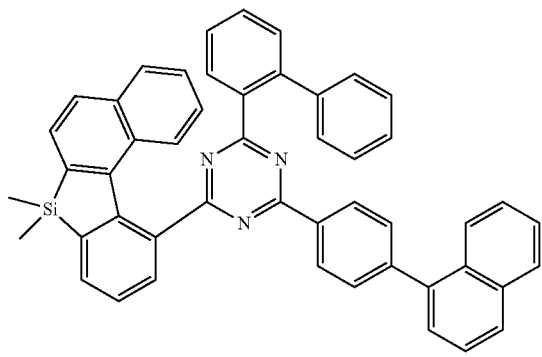
D-33
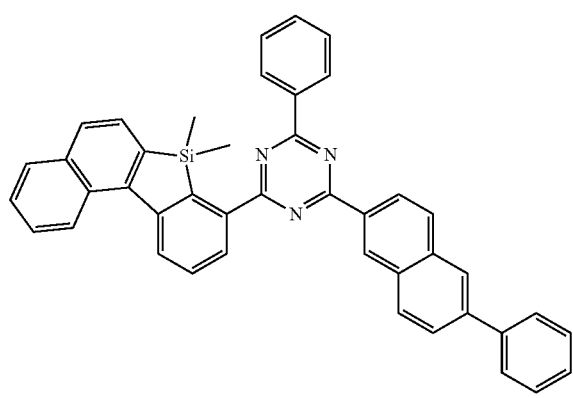
D-34
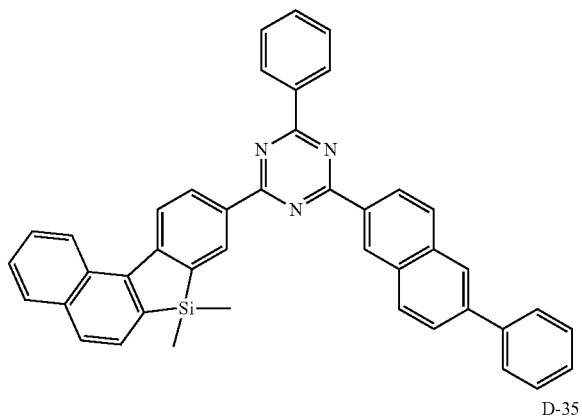
D-35
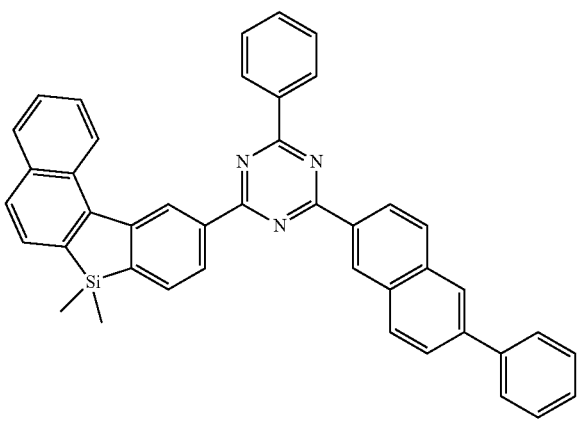
D-36
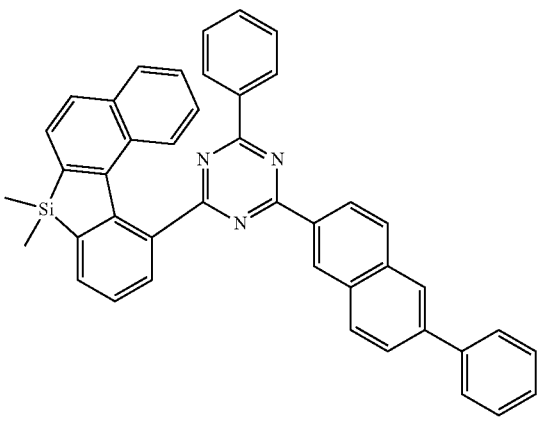
D-37
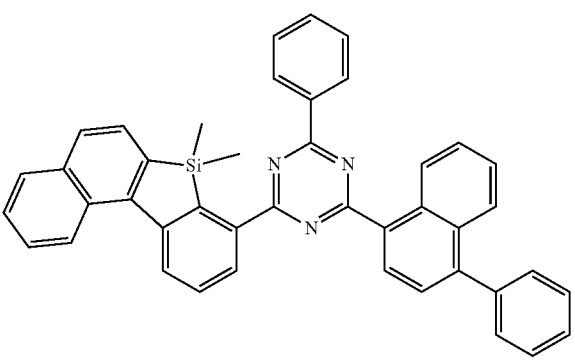
D-38
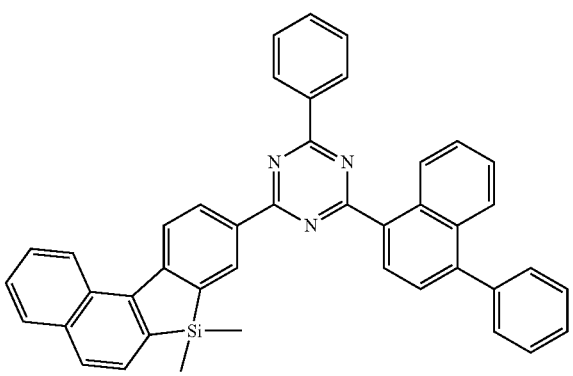
D-39
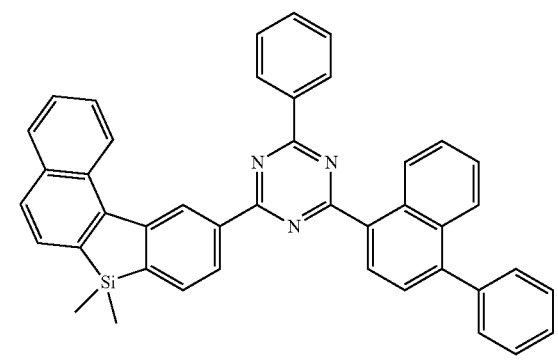

D-40
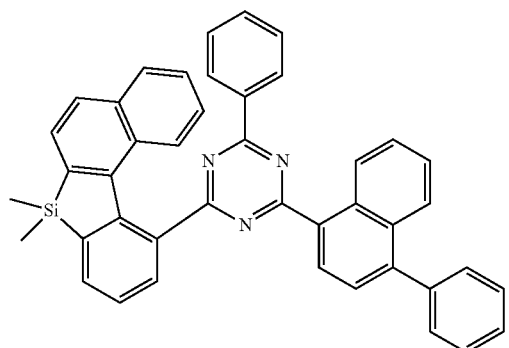
D-41
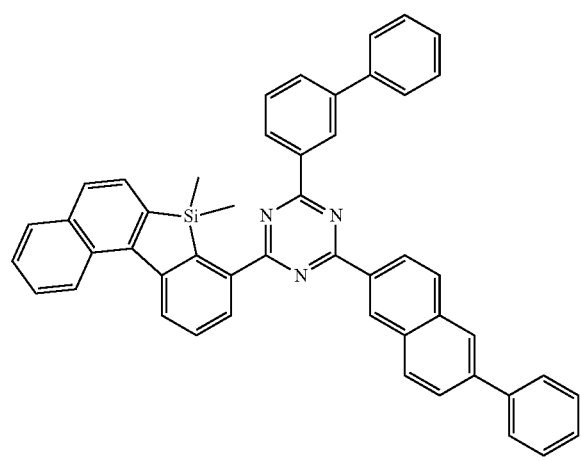
D-42
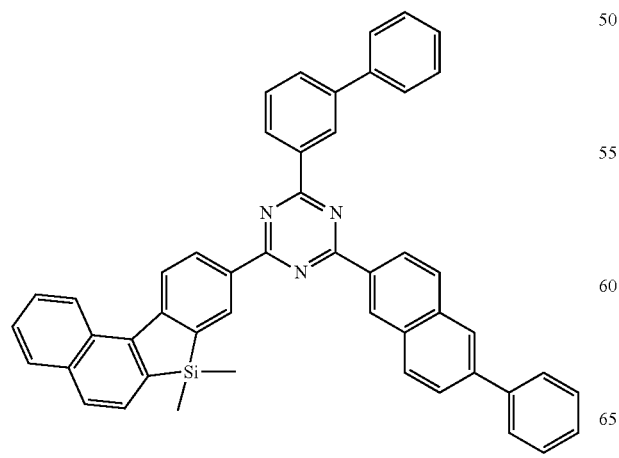
D-43
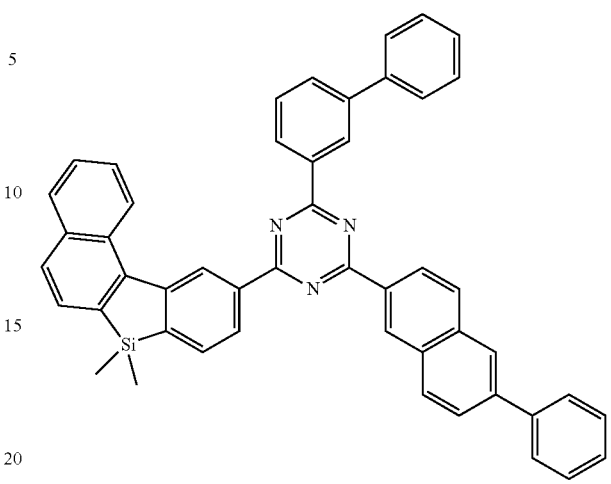
D-44
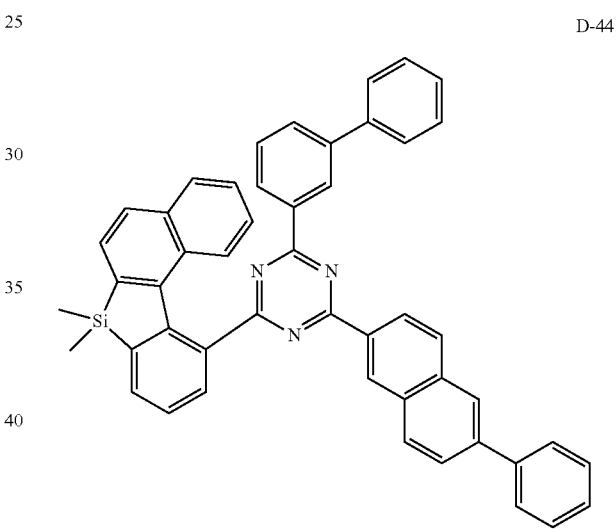
D-45

-continued
D-46
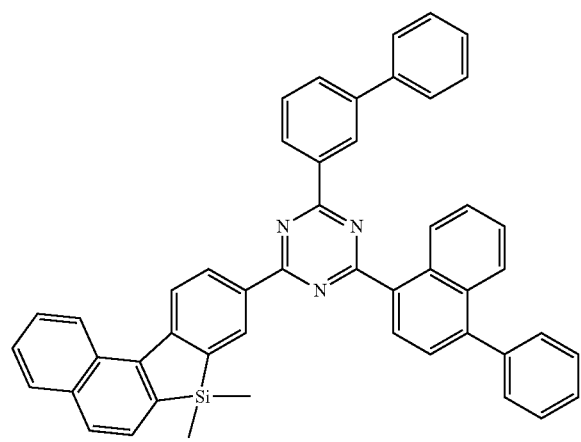
D-47
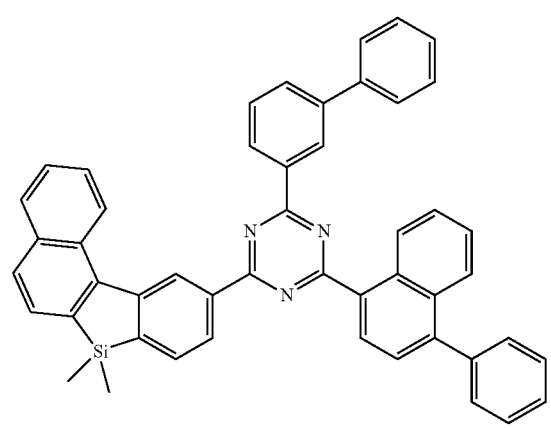
D-48
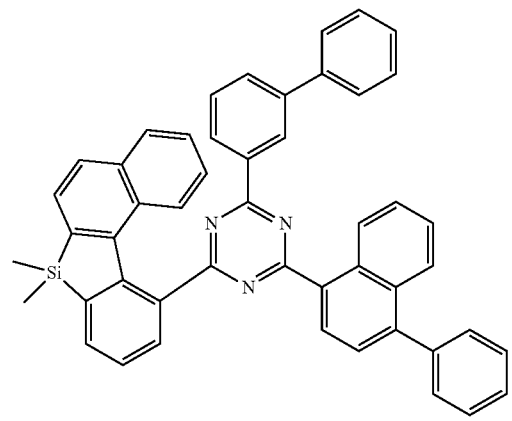
-continued
D-49
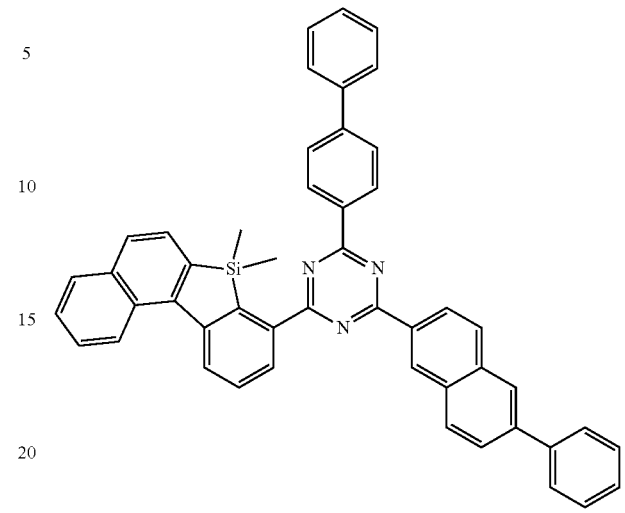
D-50
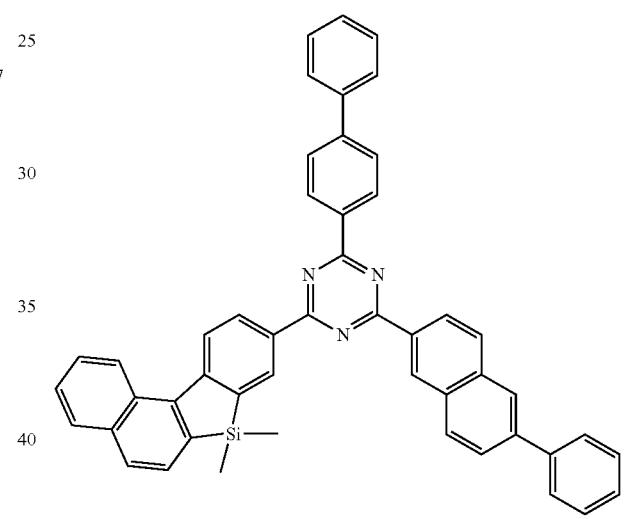
D-51
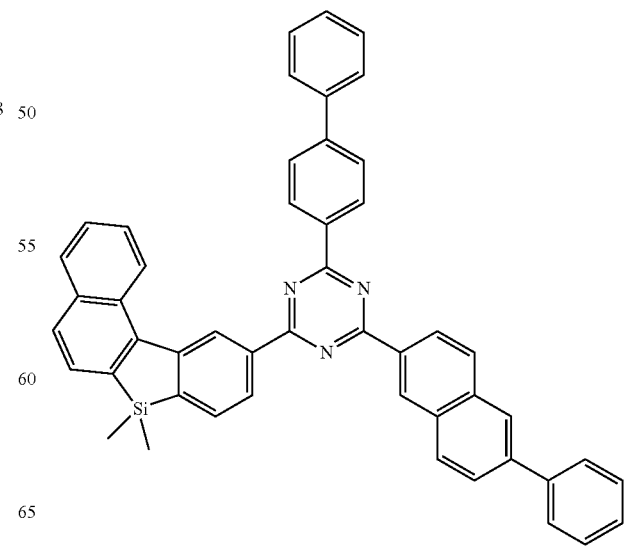

D-52
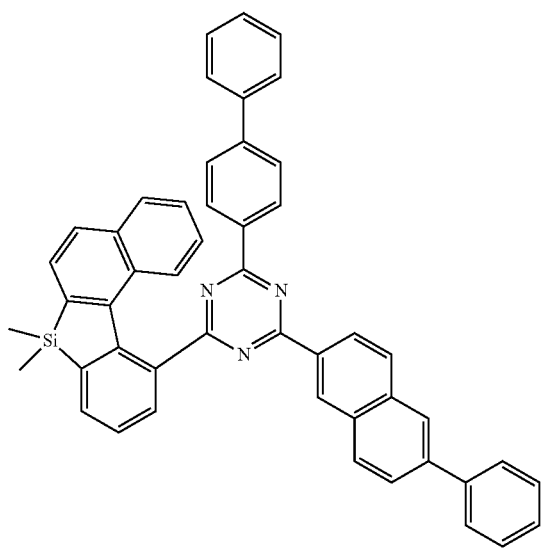
D-55
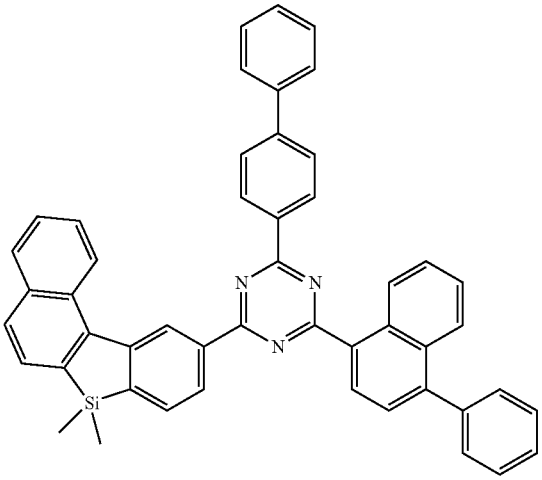
D-53
D-56
D-54
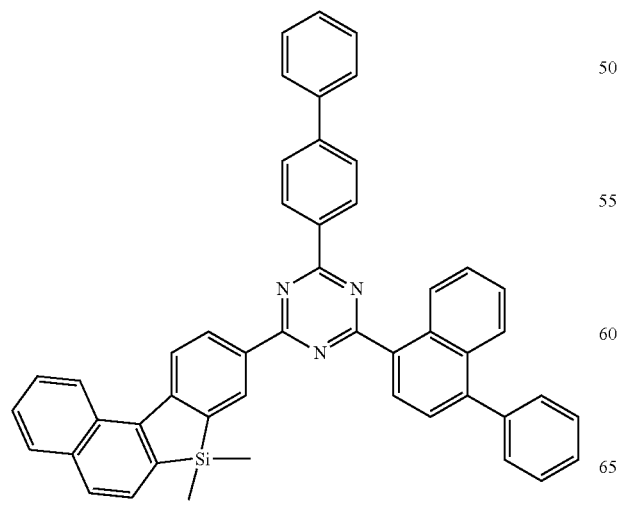
D-57

D-58
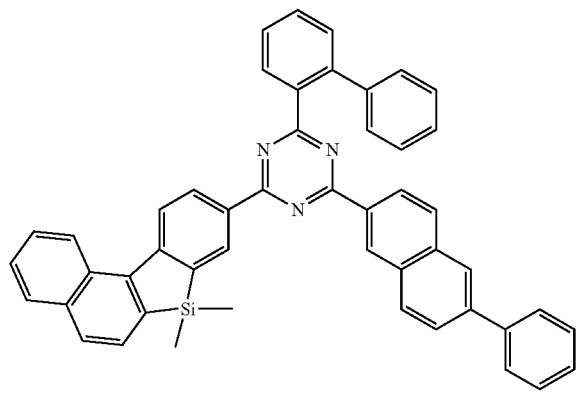
D-59
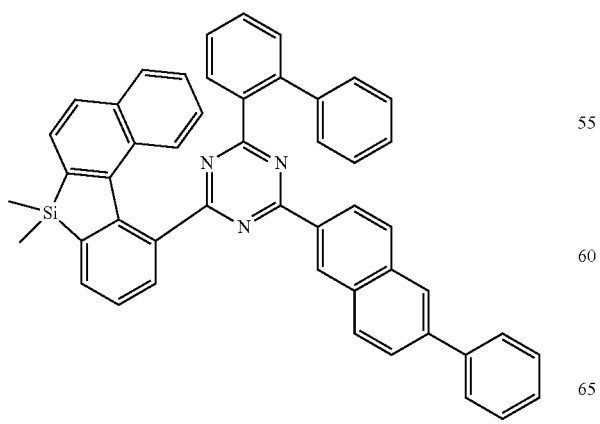
D-60
D-61
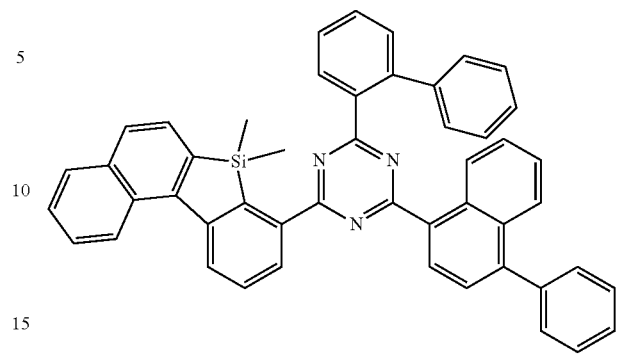
D-62
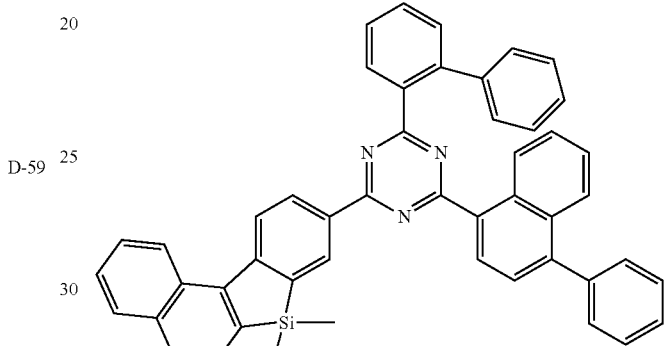
D-63
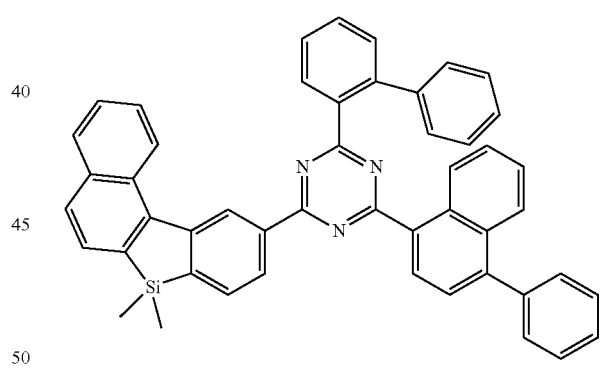
D-64
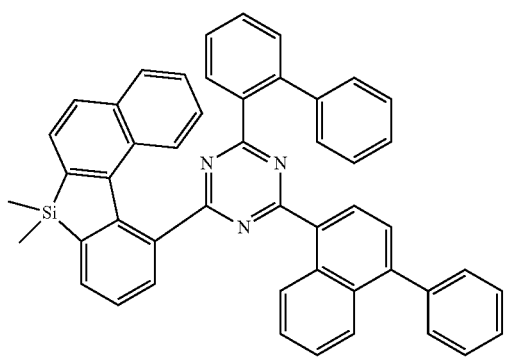

D-65
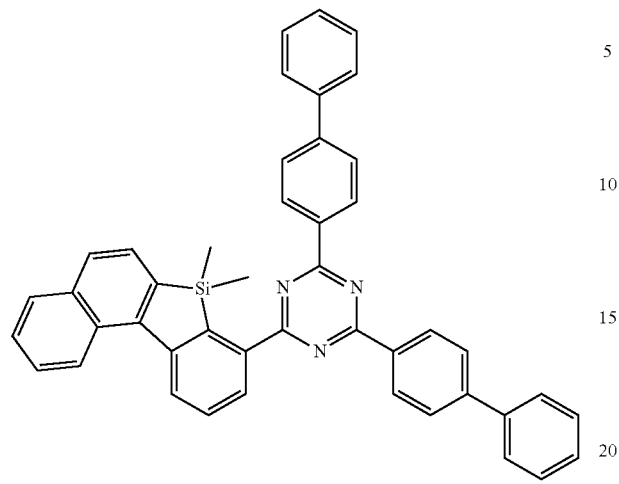
D-68
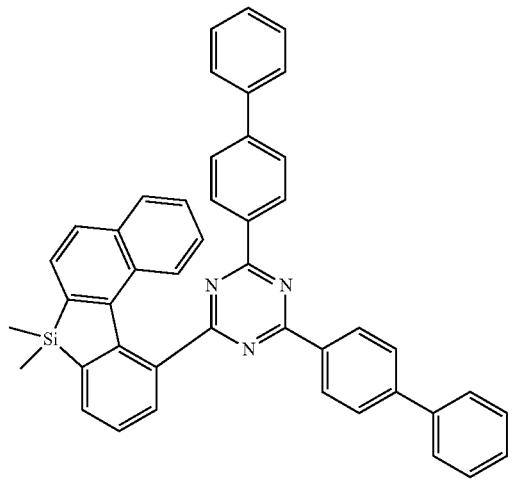
D-66
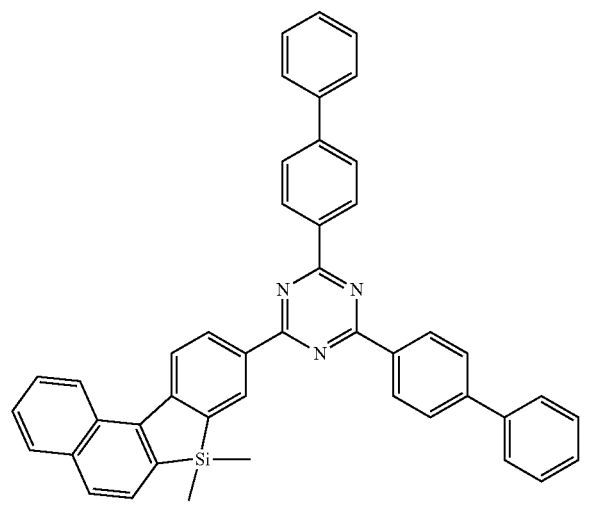
D-69
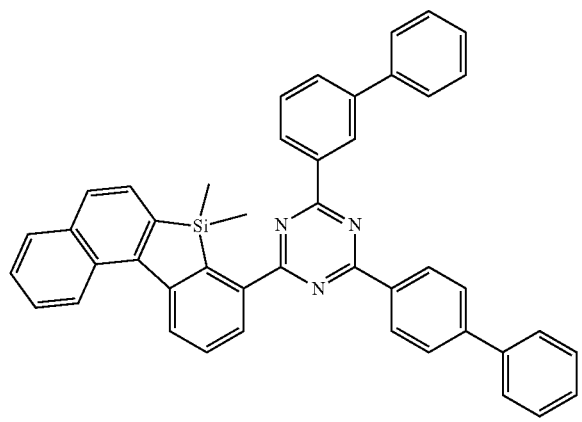
D-67
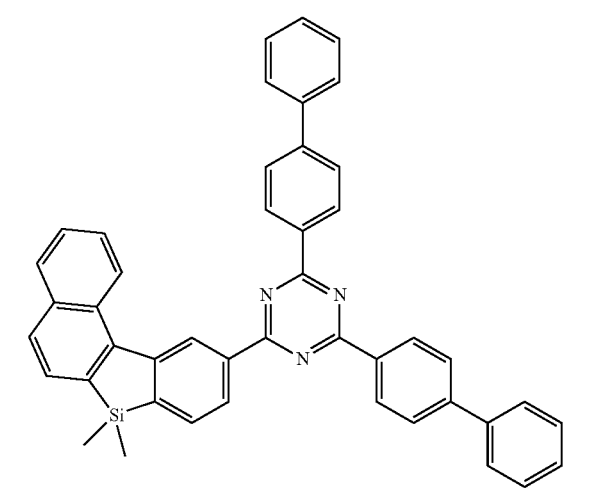
D-70
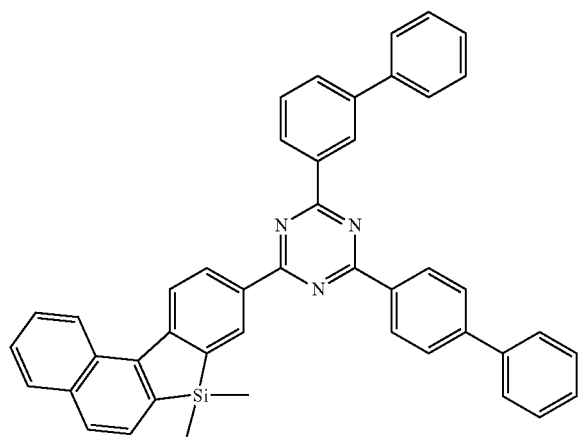

D-71
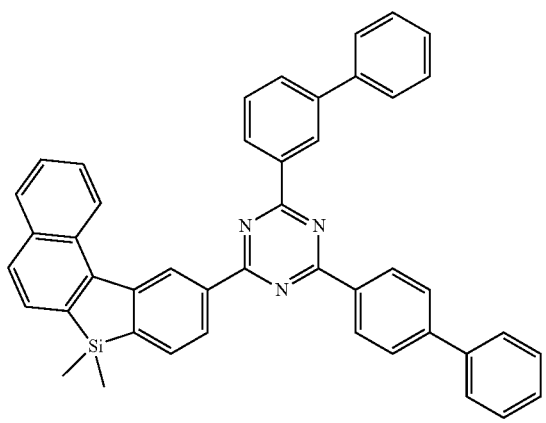
D-72
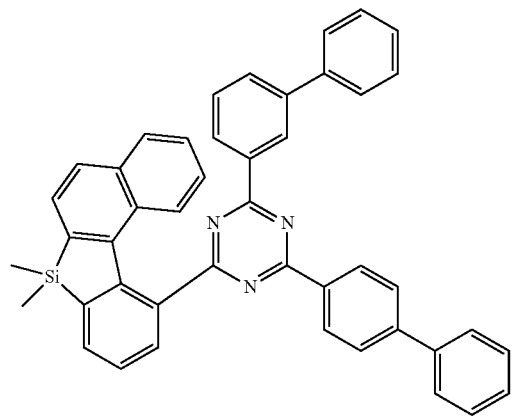
E-1
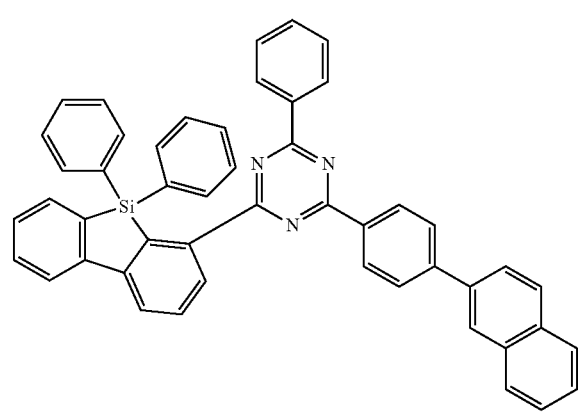
E-2
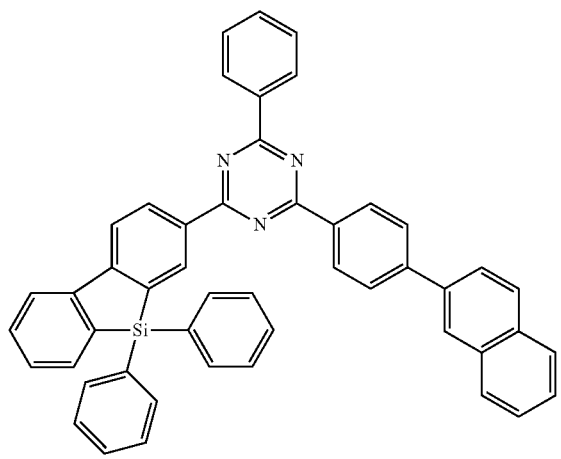
E-3
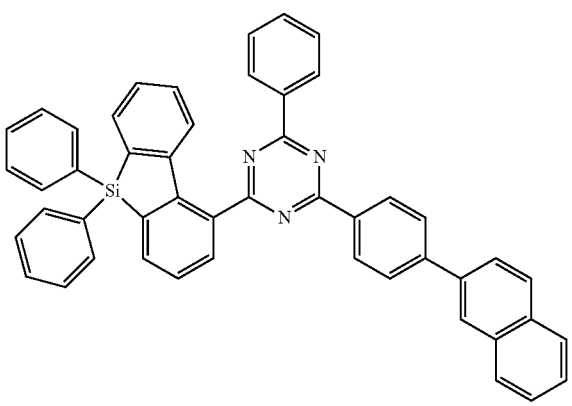
E-4
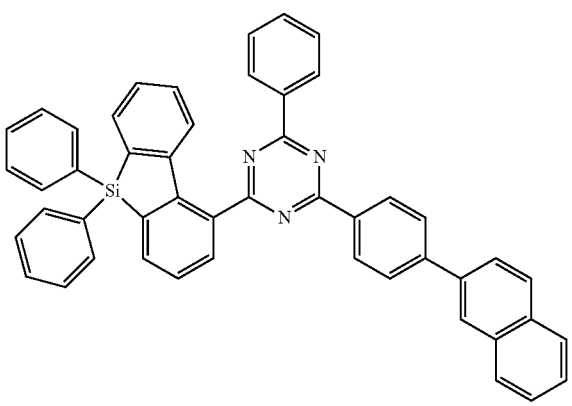

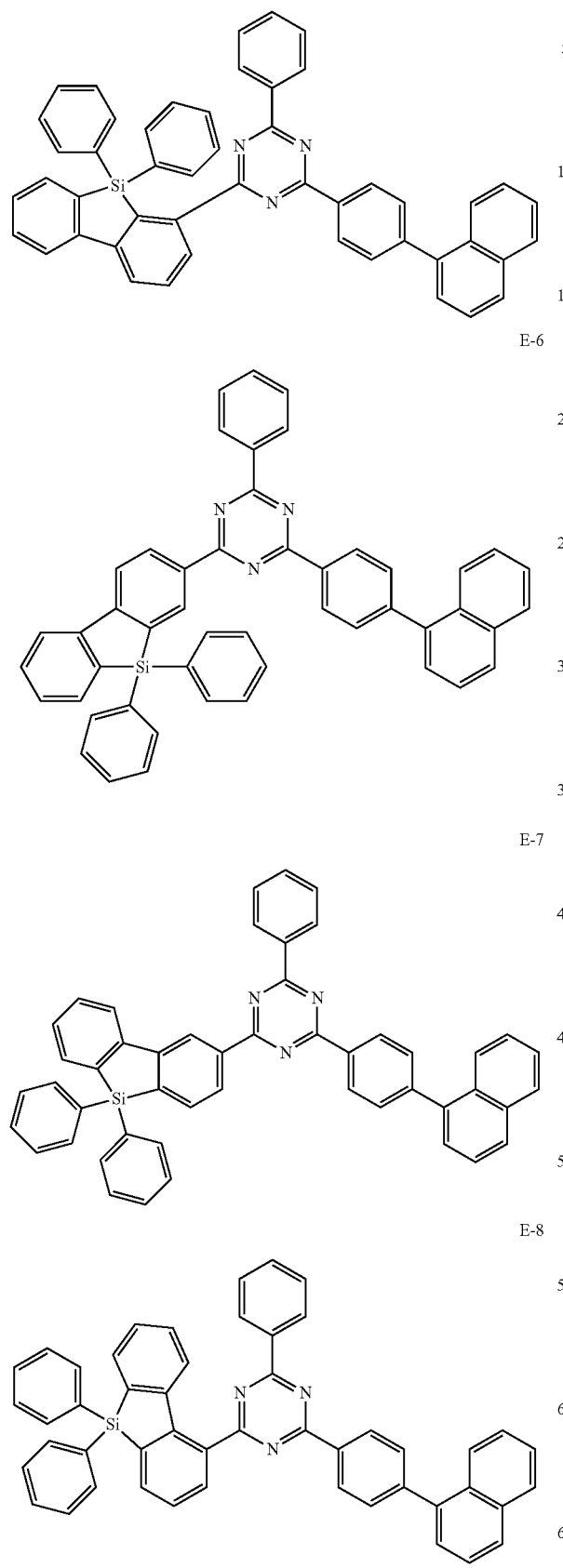
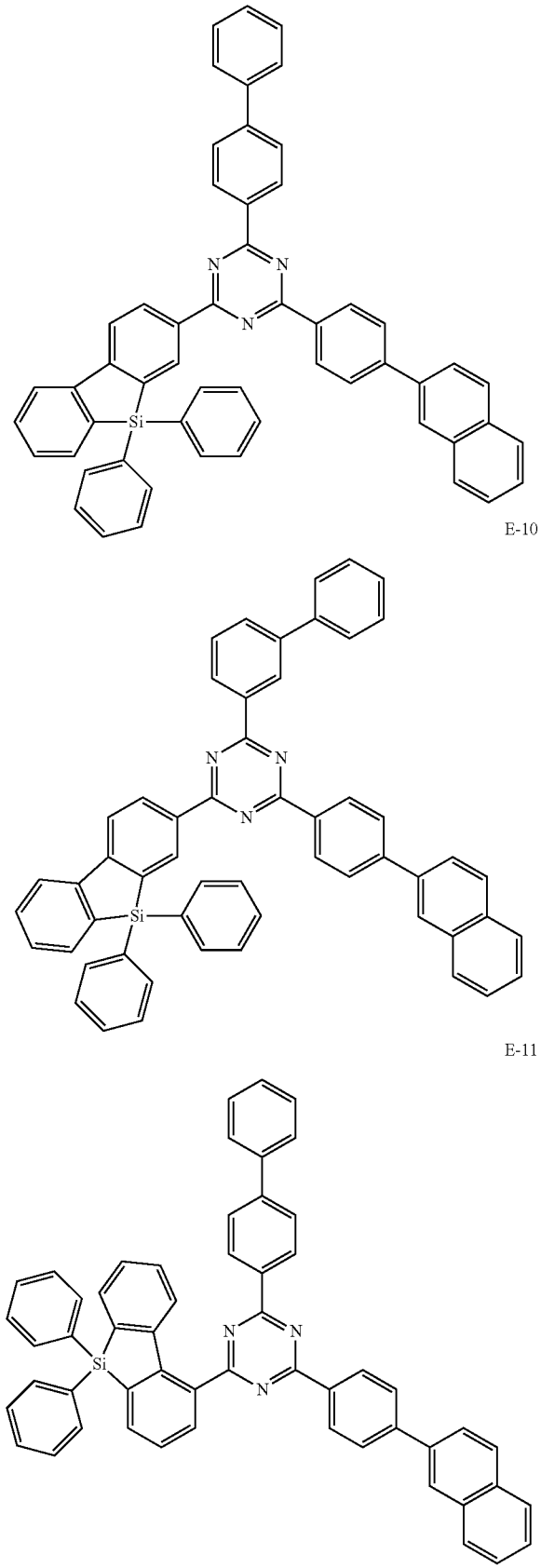

-continued
E-12
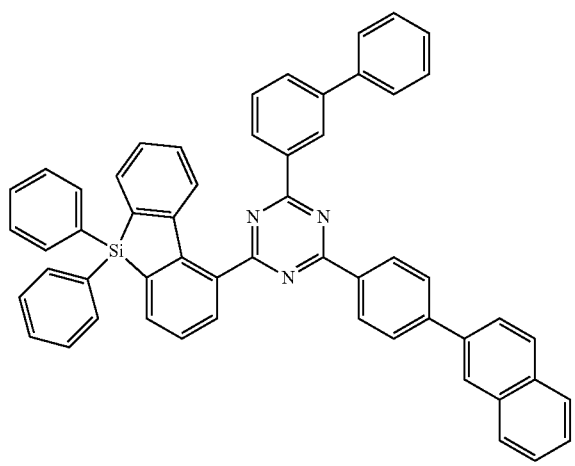
E-13
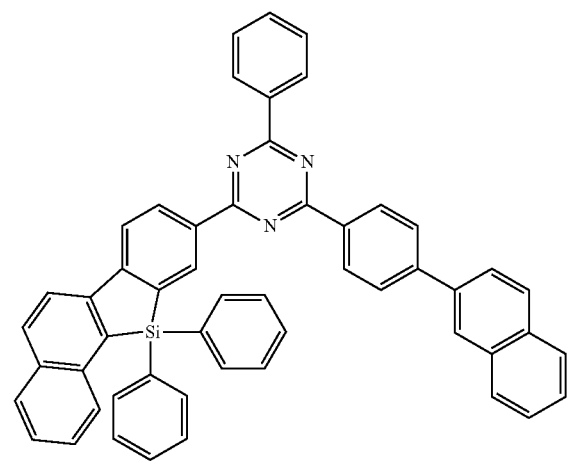
E-14
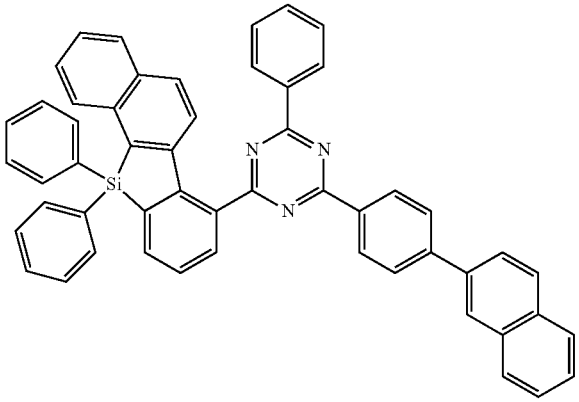
E-15
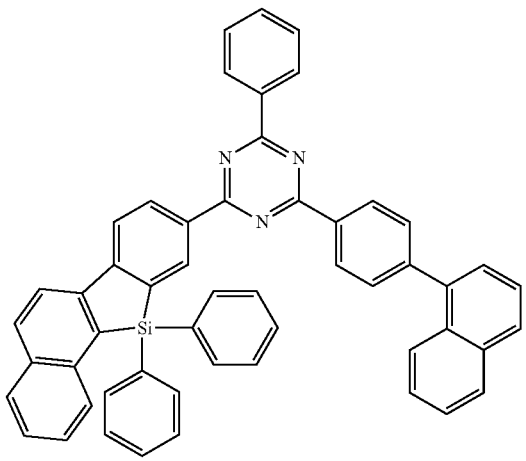
E-16
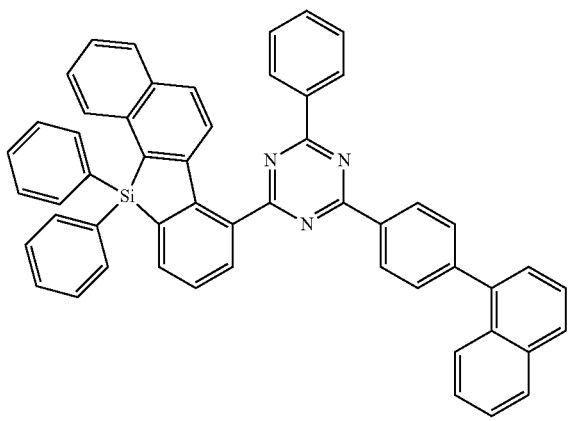
E-17
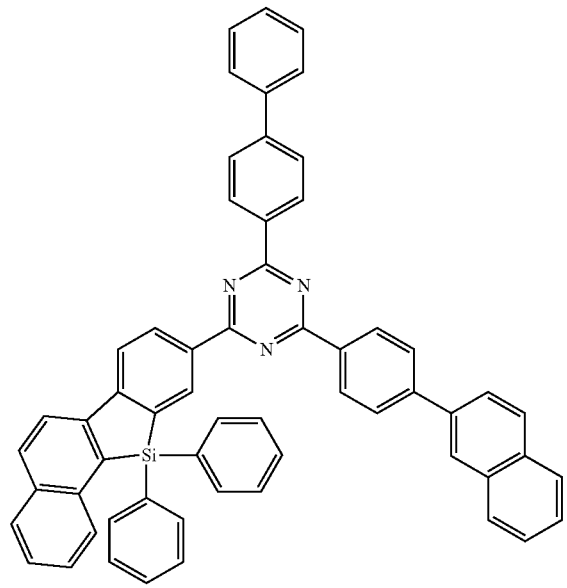

E-18
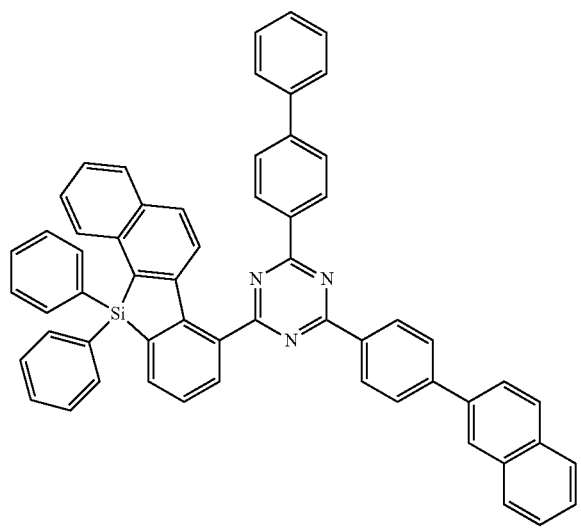
E-21
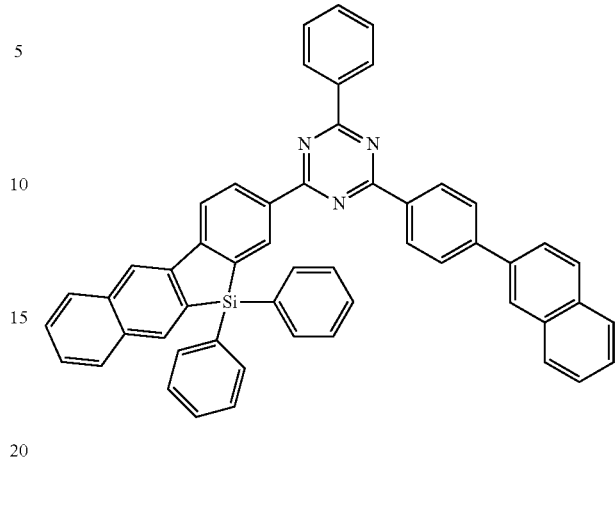
E-19
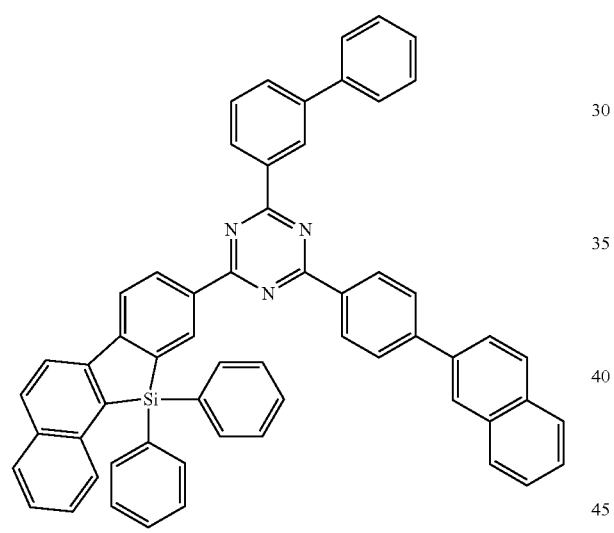
E-22
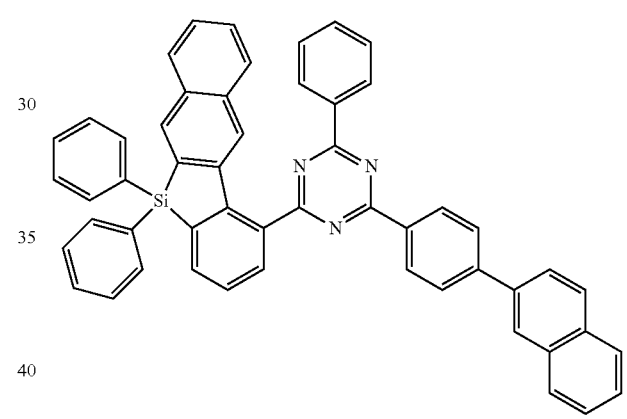
E-20
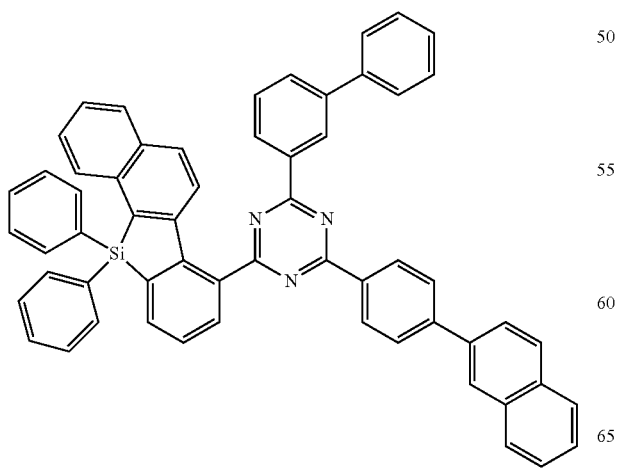
E-23
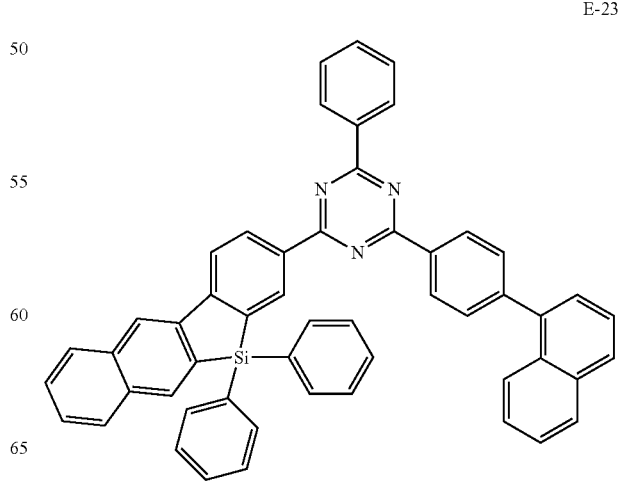

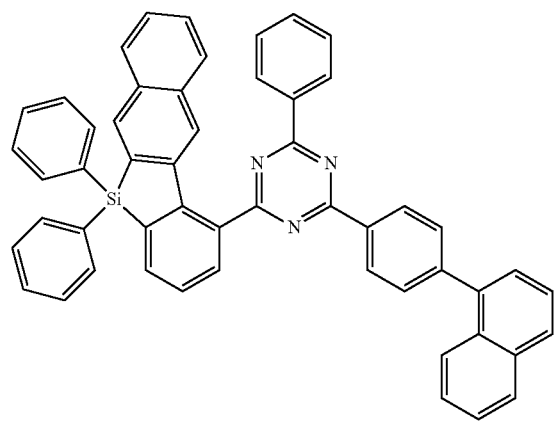
E-24
E-25
E-26
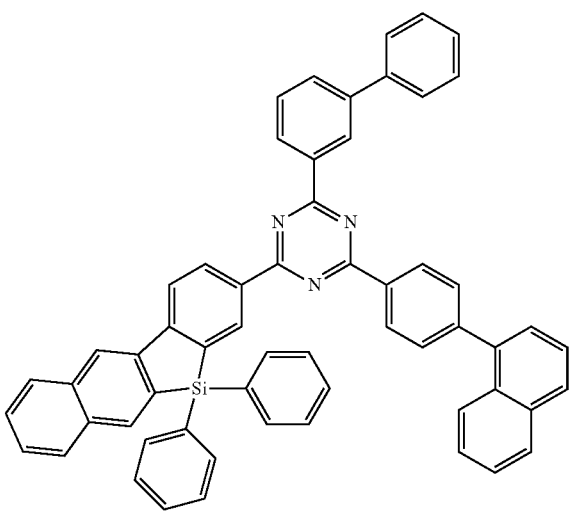
E-27
E-28
E-29
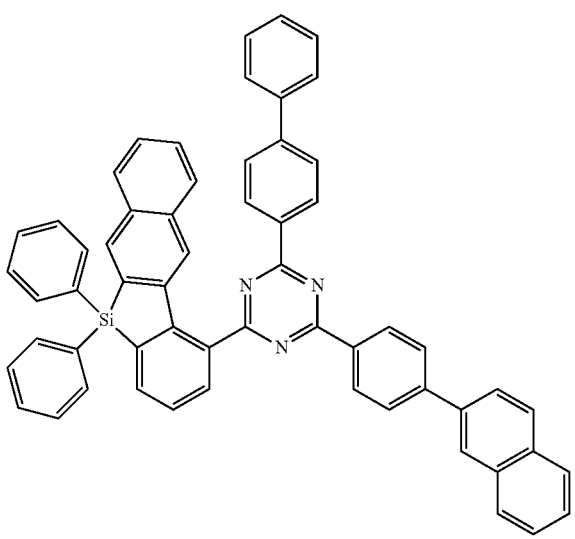

-continued
E-30
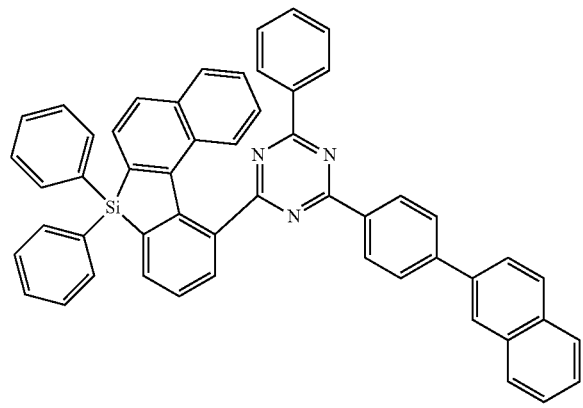
E-31
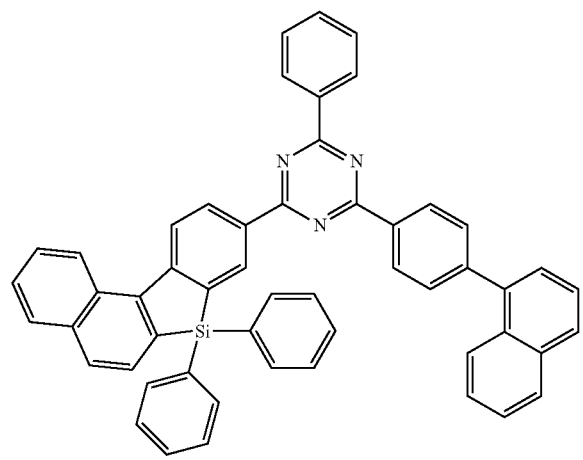
E-32
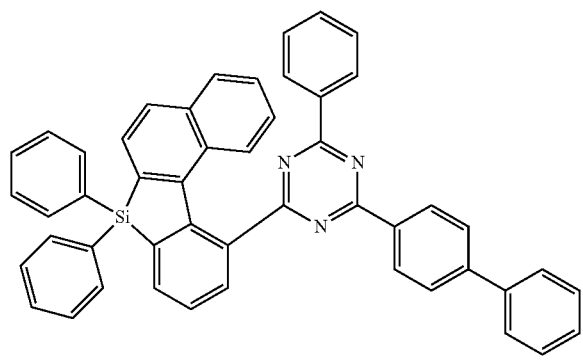
-continued
E-33
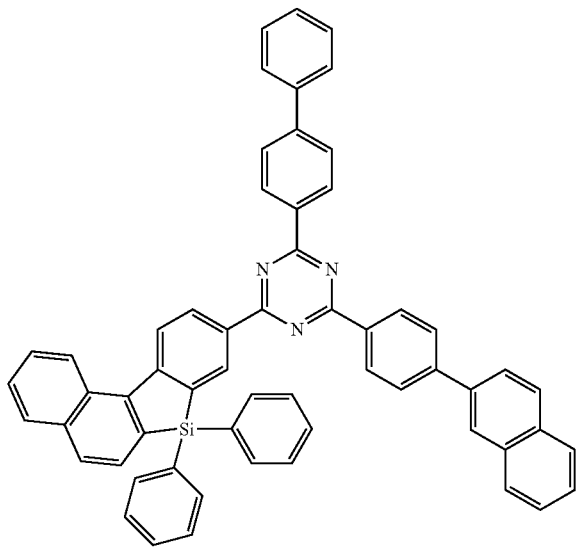
E-34
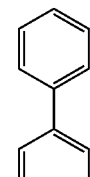
E-35
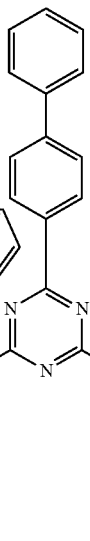

E-36

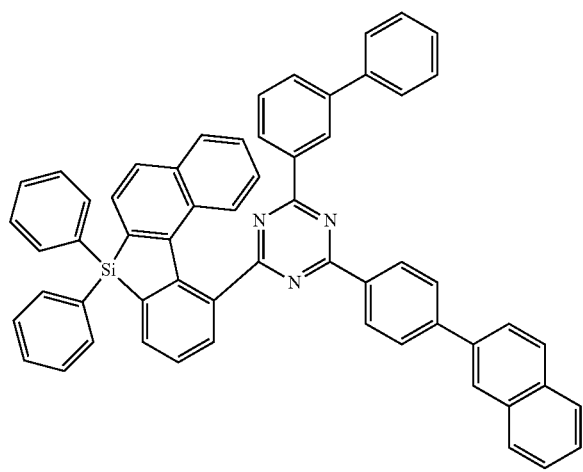

In an implementation, the second compound represented by Chemical Formula 2 may be, e.g., represented by one of Chemical Formula 2-1 to Chemical Formula 2-4, depending on the substitution position of the amine group.

[Chemical Formula 2-1]

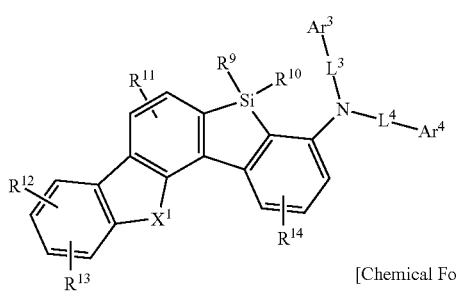

[Chemical Formula 2-2]

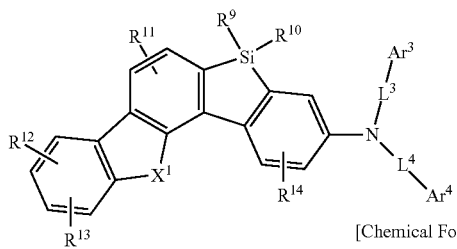

[Chemical Formula 2-3]

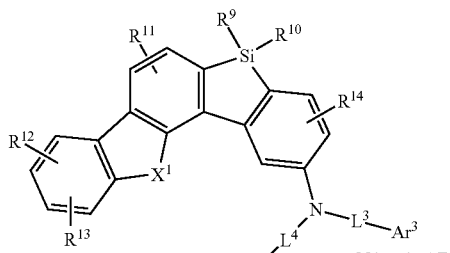

[Chemical Formula 2-4]

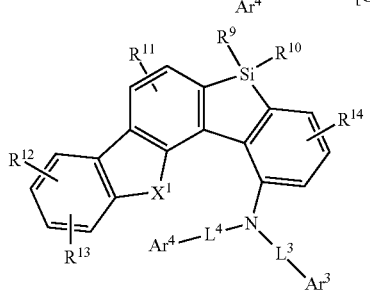

In Chemical Formula 2-1 to Chemical Formula 2-4, $X^1$, $R^9$ to $R^{14}$, $L^3$, $L^4$, $Ar^3$, and $Ar^4$ may be defined the same as those of Chemical Formula 2.

In an implementation, the second compound may be represented by Chemical Formula 2-2.

In an implementation, $Ar^3$ and $Ar^4$ of Chemical Formula 2-2 may each independently be or include, e.g., a substituted or unsubstituted phenyl group, a substituted or unsubstituted biphenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted dibenzofuranyl group, a substituted or unsubstituted dibenzothiophenyl group, a substituted or unsubstituted carbazolyl group, or a substituted or unsubstituted dibenzosilole group.

In an implementation, $Ar^3$ and $Ar^4$ in Chemical Formula 2-2 may each independently be or include, e.g., a substituted or unsubstituted phenyl group, a substituted or unsubstituted biphenyl group, a substituted or unsubstituted naphthyl group, a substituted or unsubstituted fluorenyl group, a substituted or unsubstituted dibenzofuranyl group, a substituted or unsubstituted dibenzothiophenyl group, a substituted or unsubstituted carbazolyl group, or a substituted or unsubstituted dibenzosilole group.

In an implementation, $L^3$ and $L^4$ of Chemical Formula 2-2 may each independently be or include, e.g., a single bond, a substituted or unsubstituted phenylene group, or a substituted or unsubstituted naphthylene group.

In an implementation, $L^3$ and $L^4$ of Chemical Formula 2-2 may each independently be or include, e.g., a single bond or a substituted or unsubstituted phenylene group.

In an implementation, $R^9$ and $R^{10}$ of Chemical Formula 2-2 may each independently be or include, e.g., a substituted or unsubstituted C1 to C5 alkyl group or a substituted or unsubstituted phenyl group.

In an implementation, $R^9$ and $R^{10}$ of Chemical Formula 2-2 may each independently be or include, e.g., a substituted or unsubstituted methyl group or a substituted or unsubstituted phenyl group.

In an implementation, $R^{11}$ to $R^{14}$ of Chemical Formula 2-2 may each independently be or include, e.g., hydrogen or a phenyl group.

In an implementation, $R^{11}$ to $R^{14}$ of Chemical Formula 2-2 may each be hydrogen.

In an implementation, the second compound may be, e.g., a compound of the following Group 2.

[Group 2]

F-1

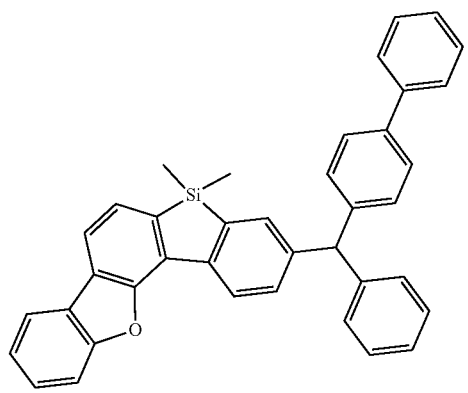

F-2
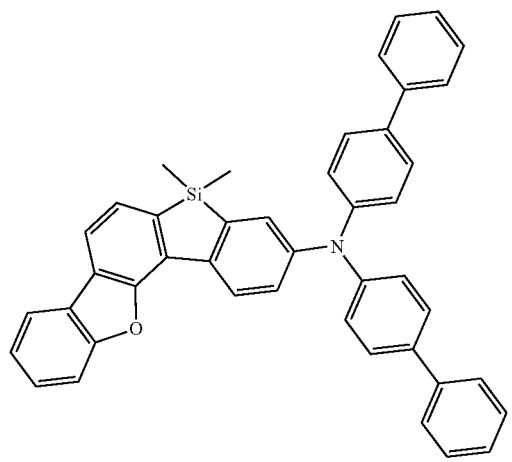
F-3
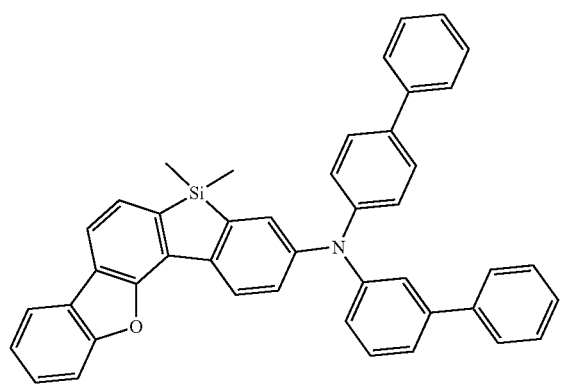
F-4
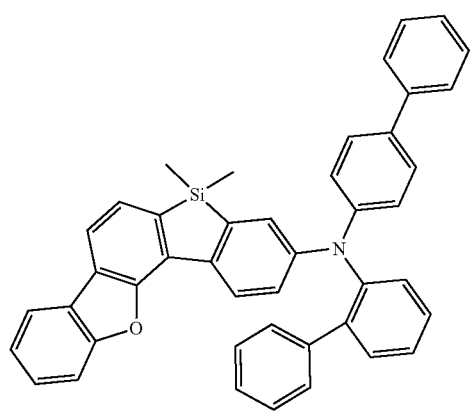
F-5
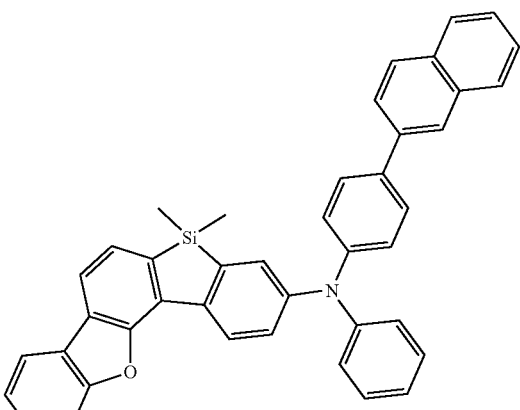
F-6
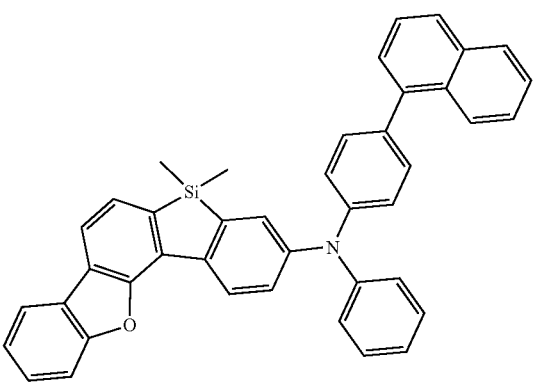
F-7
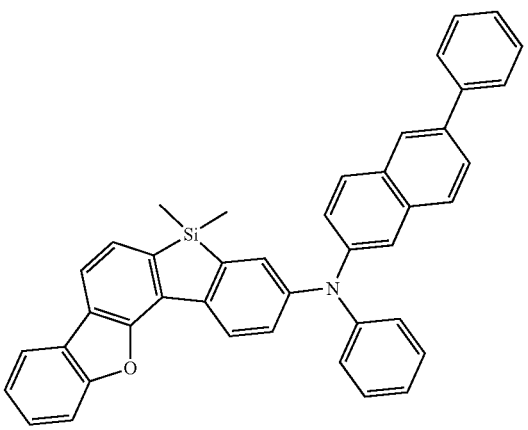

127
-continued
F-8
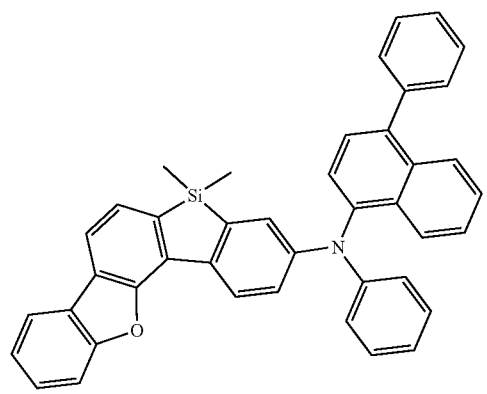
F-9
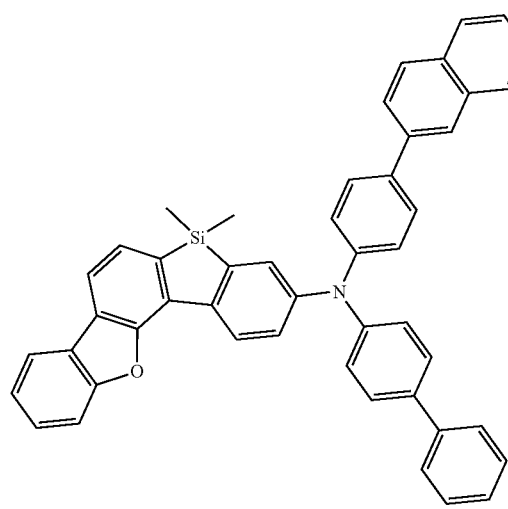
F-10
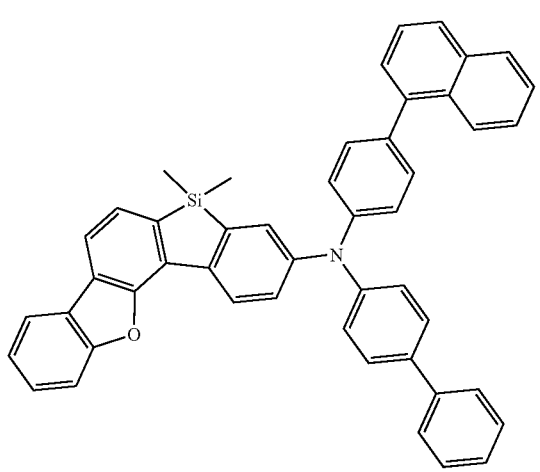
128
-continued
F-11
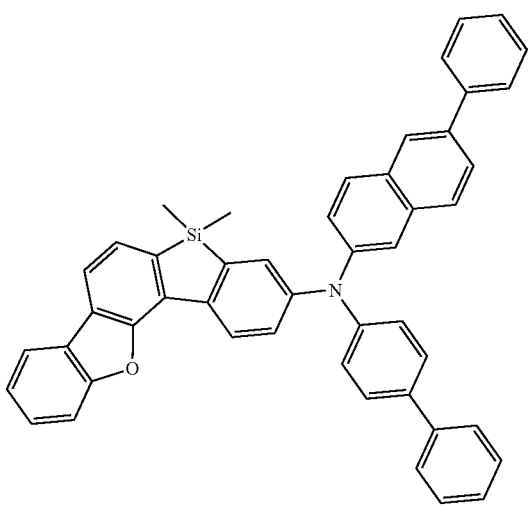
F-12
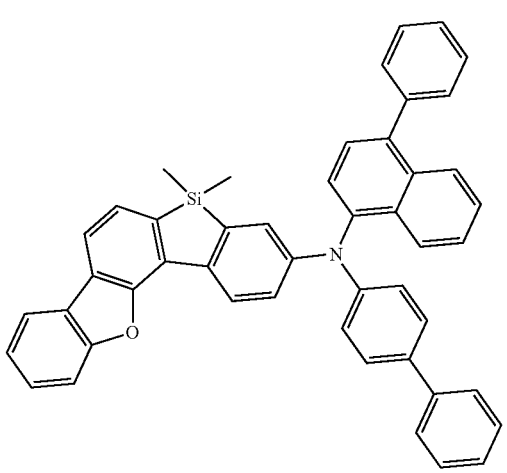
F-13
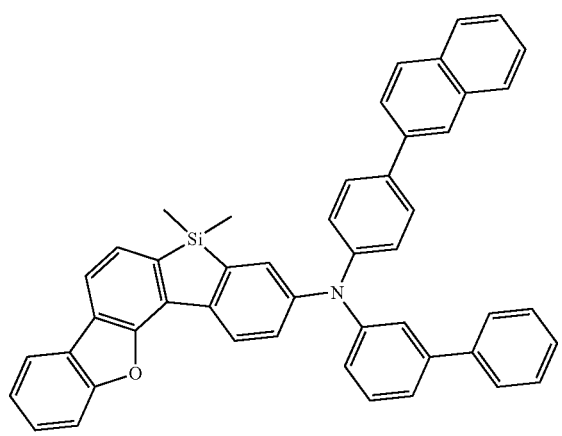

F-14
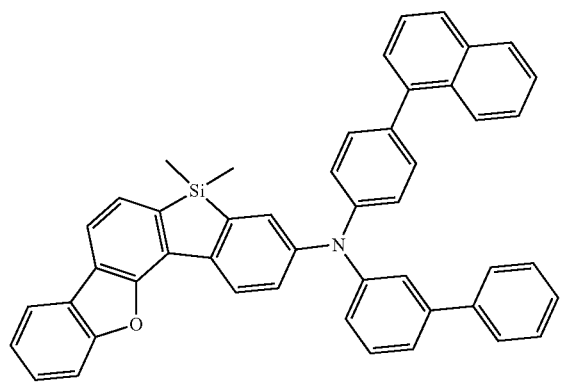
F-17
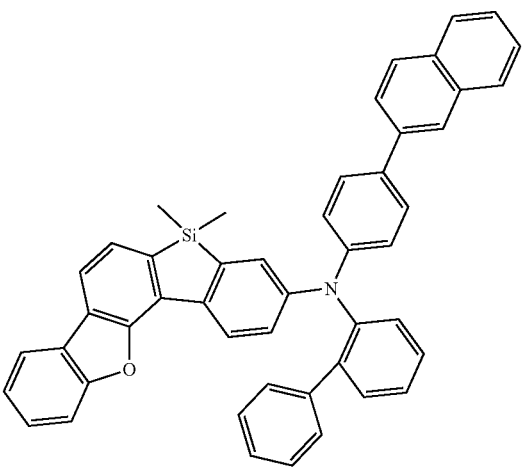
F-15
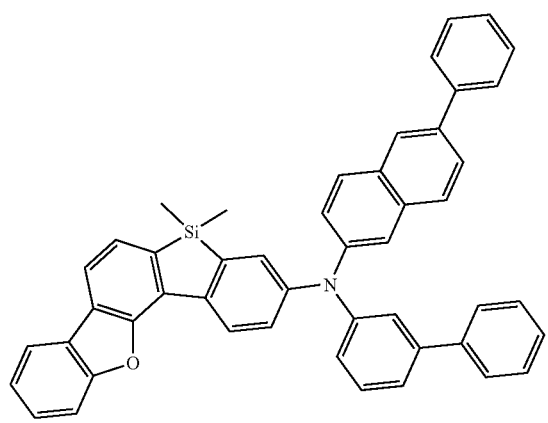
F-18
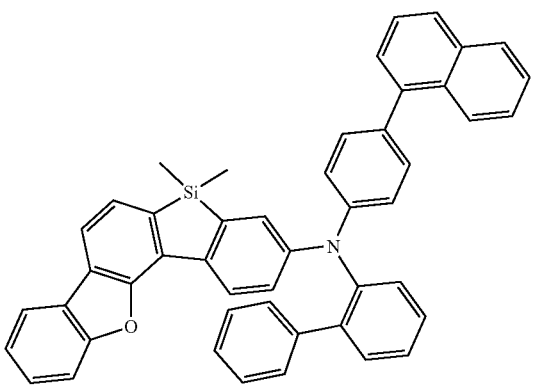
F-16
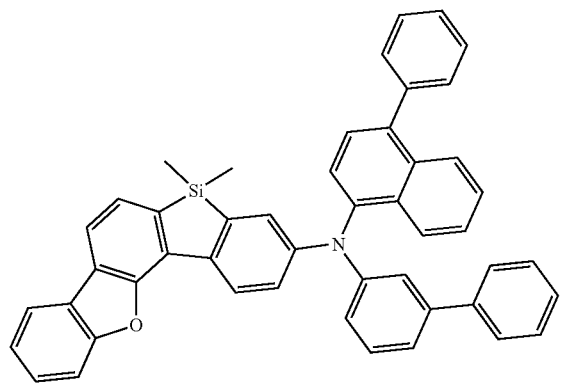
F-19
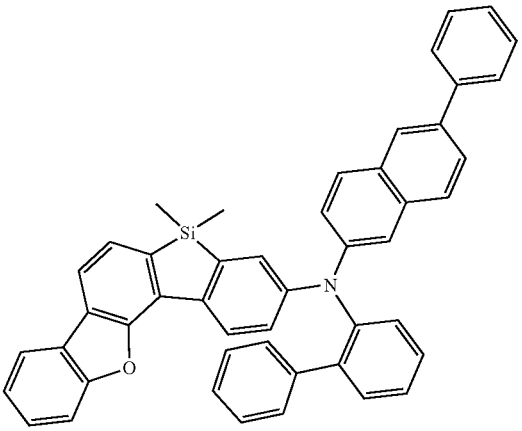

F-20
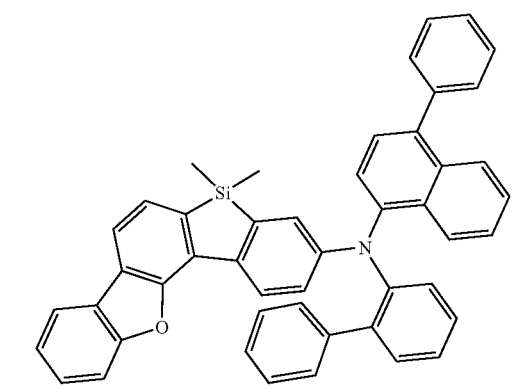
F-21
F-22
F-23
F-24
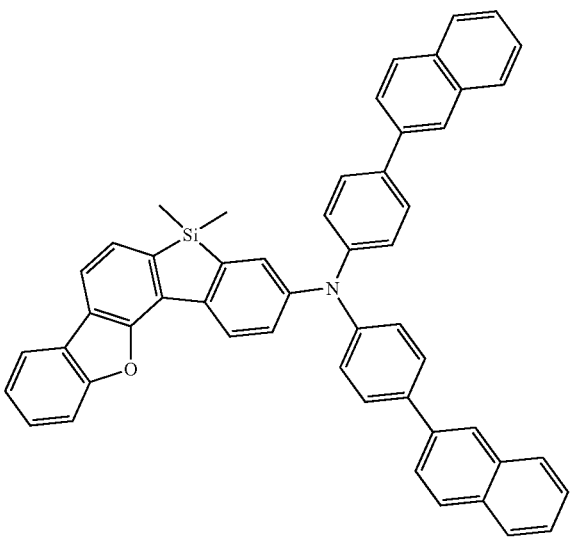
F-25
F-26
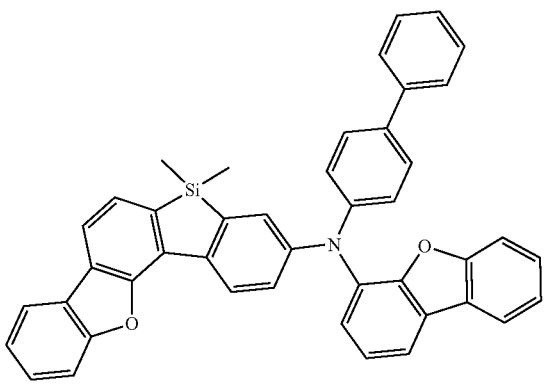
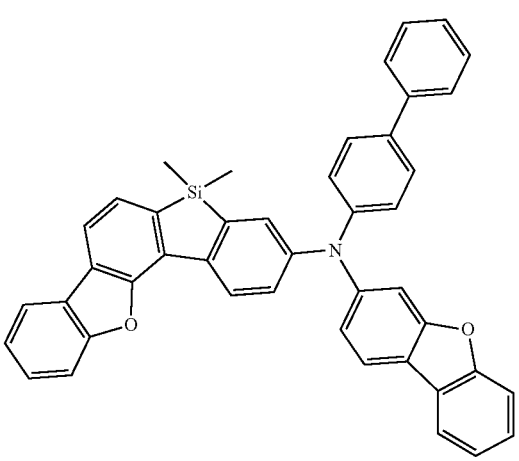

F-27
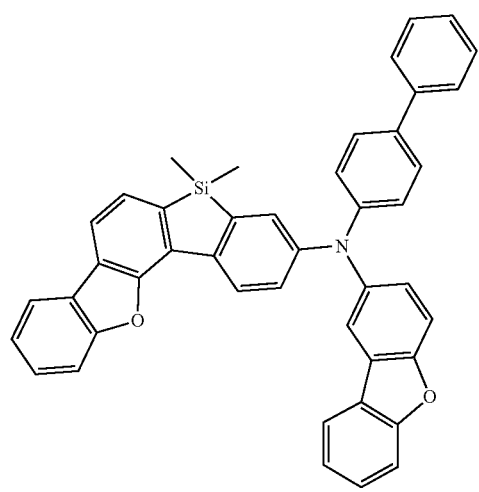
F-28
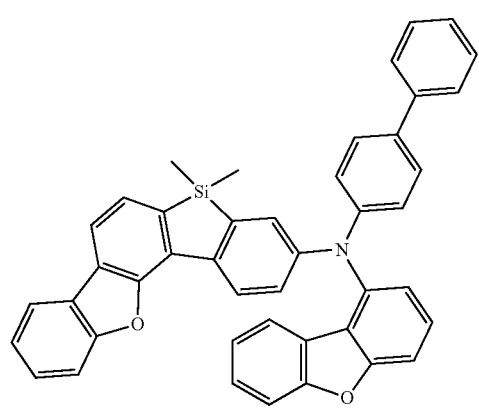
F-29
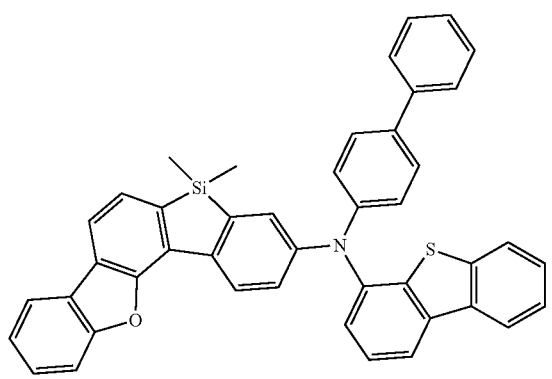
F-30
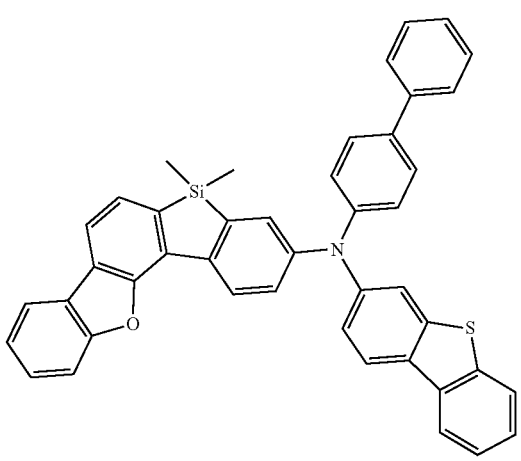
F-31
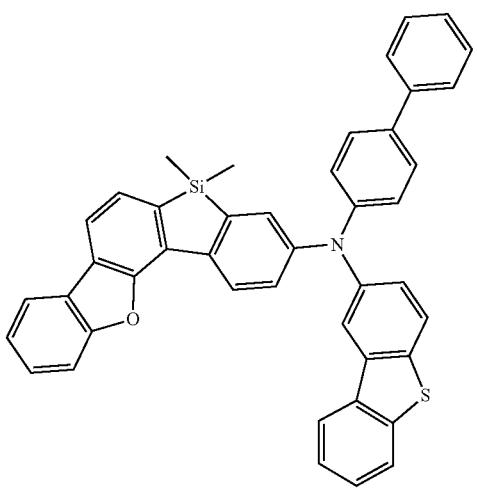
F-32
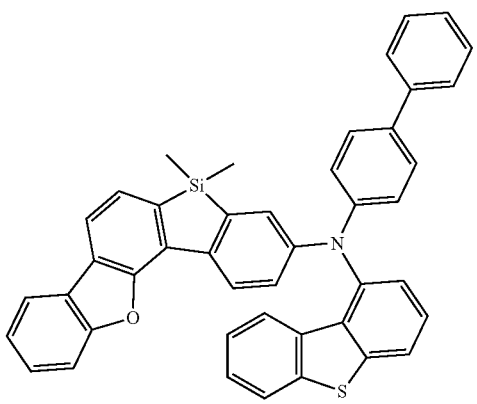

F-33
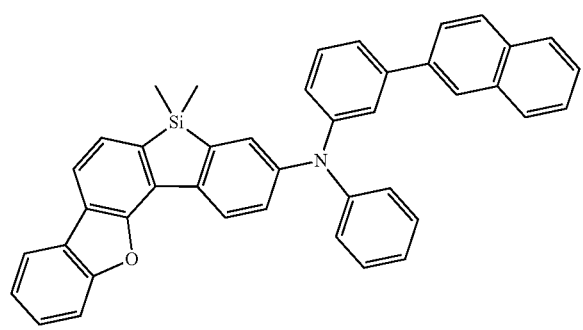
F-34
F-37
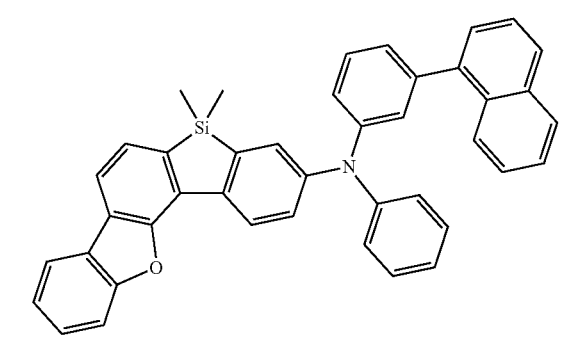
F-38
F-35
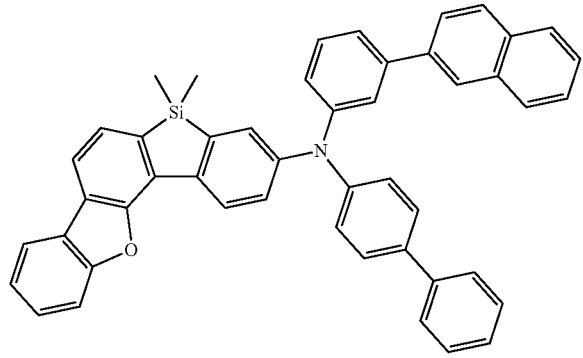
F-39
F-36
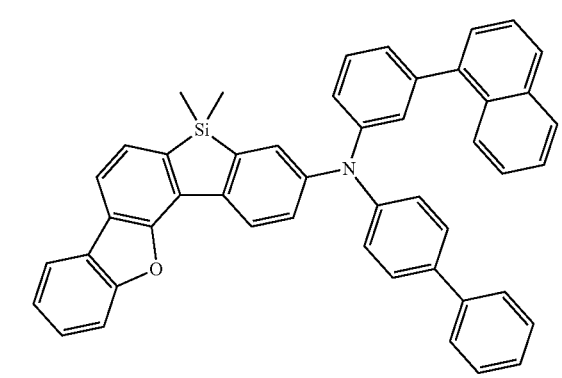
F-40

-continued
F-41
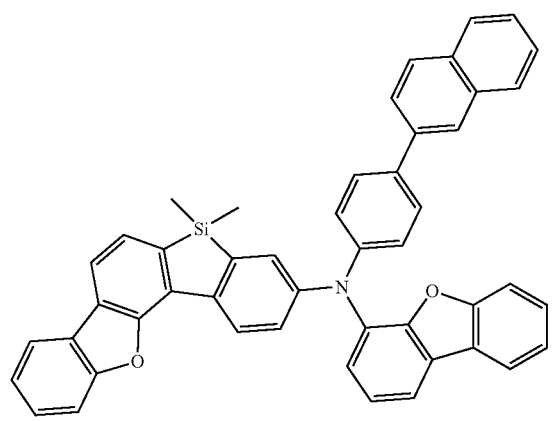
F-42
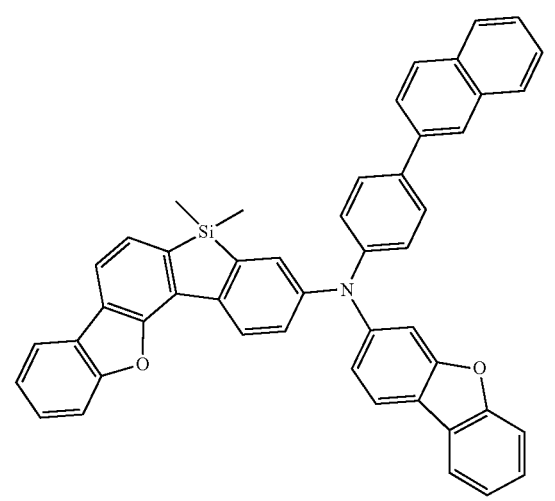
F-43
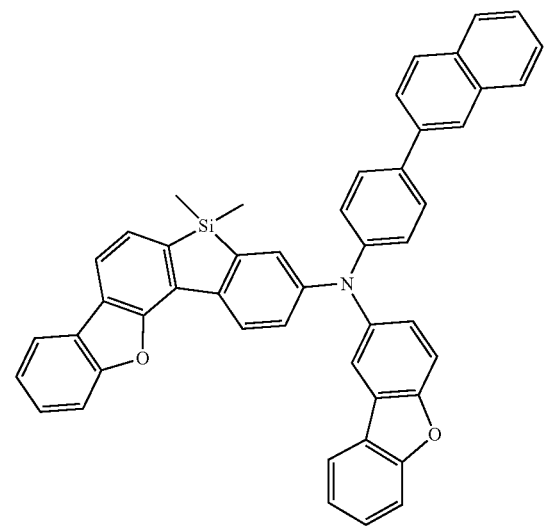
-continued
F-44
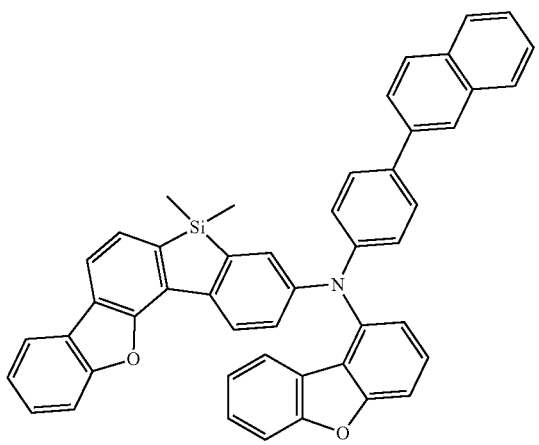
F-45
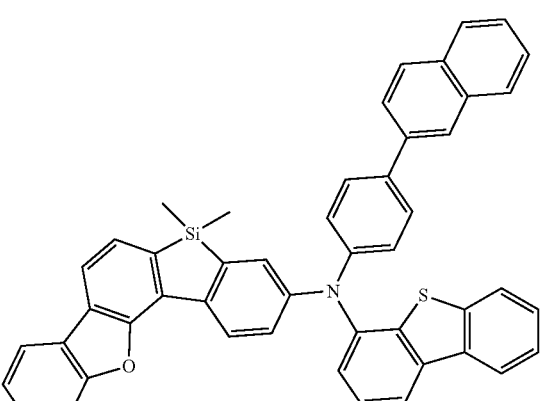
F-46
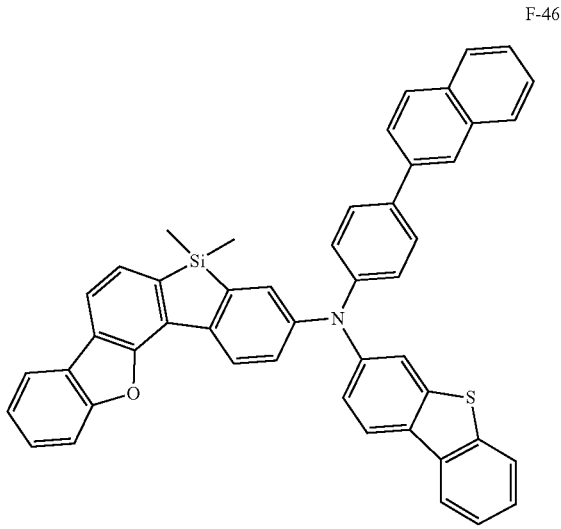

F-47
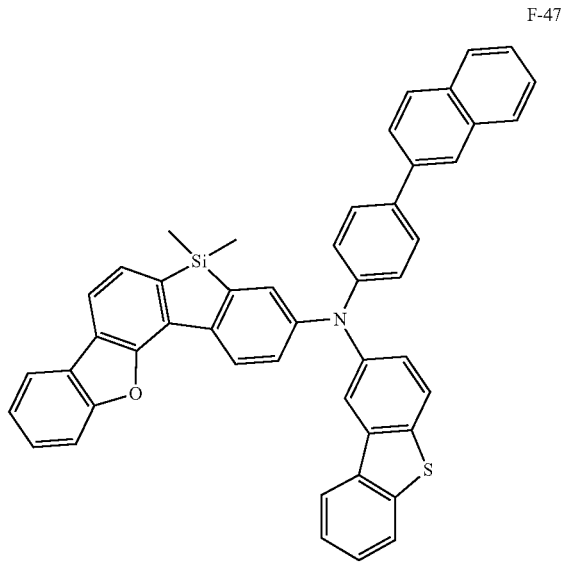
F-48
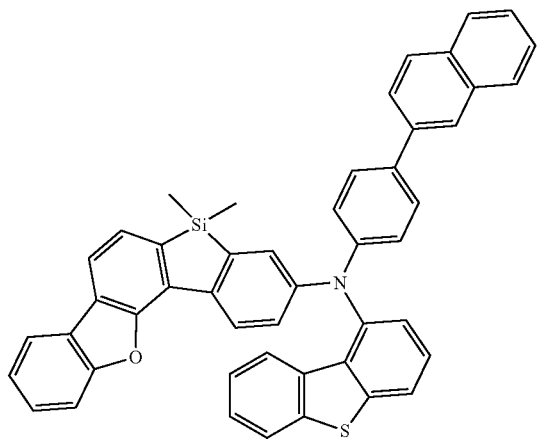
F-49
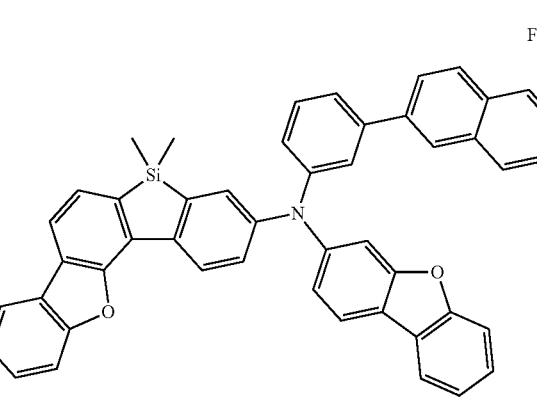
F-50
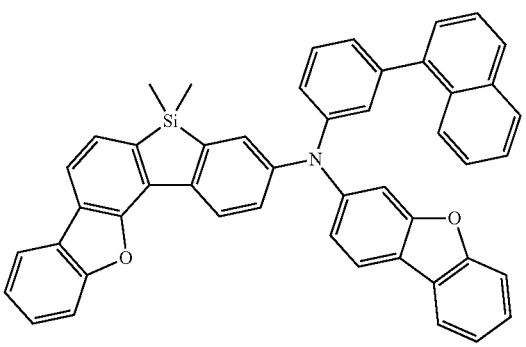
F-51
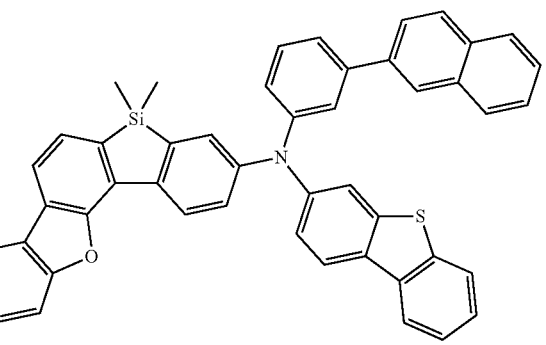
F-52
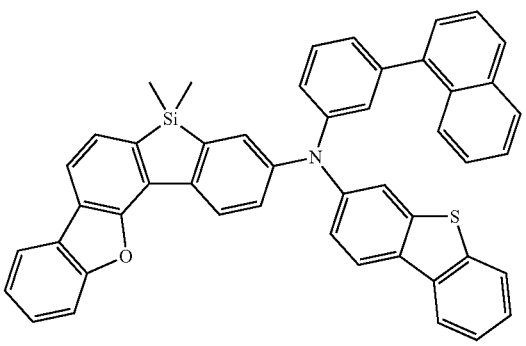
F-53
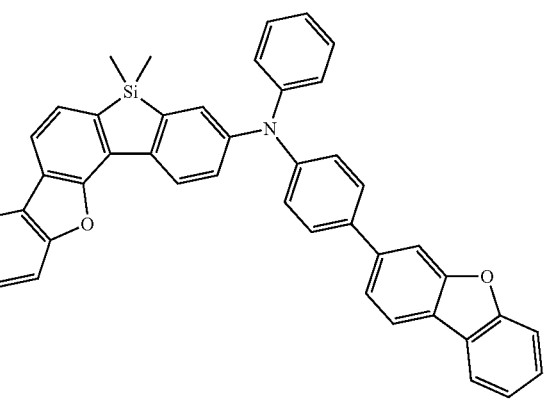

F-54
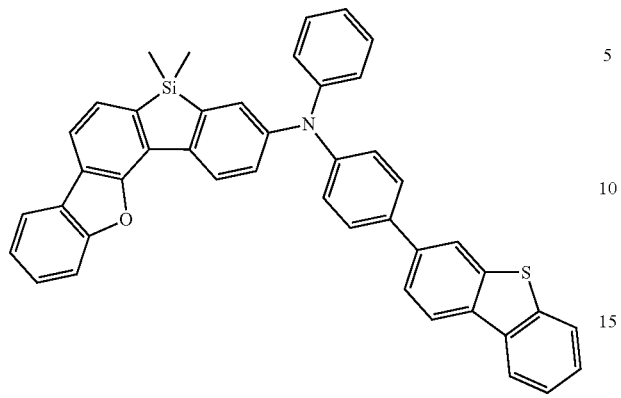
F-55
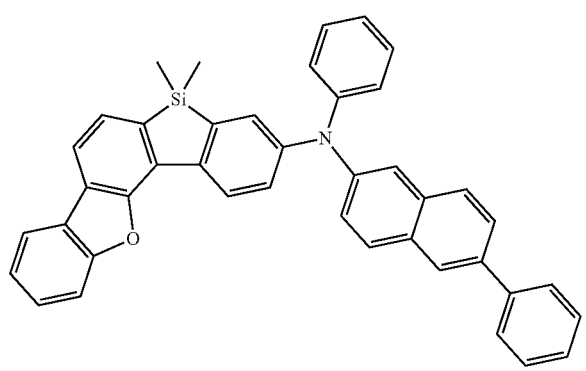
F-56
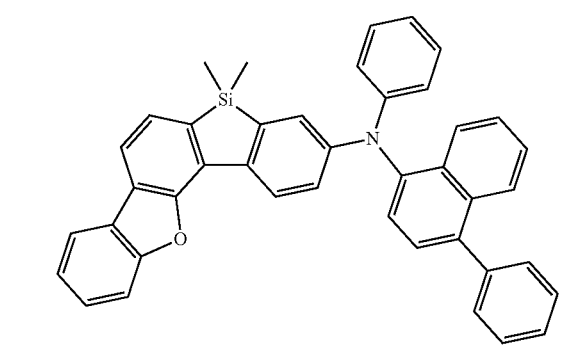
F-57
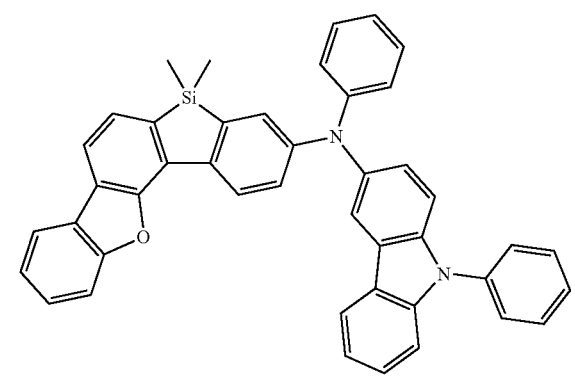
F-58
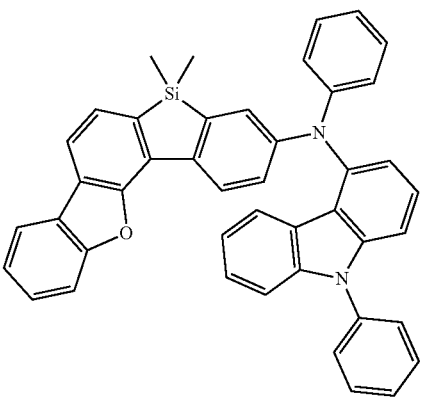
F-59
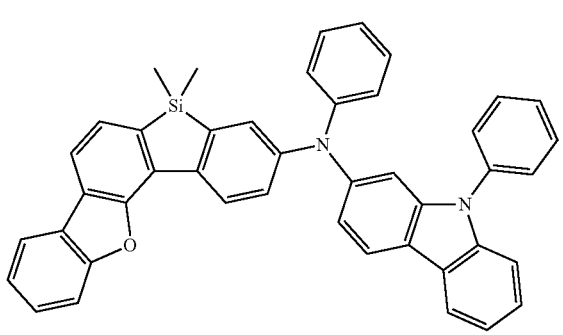
F-60
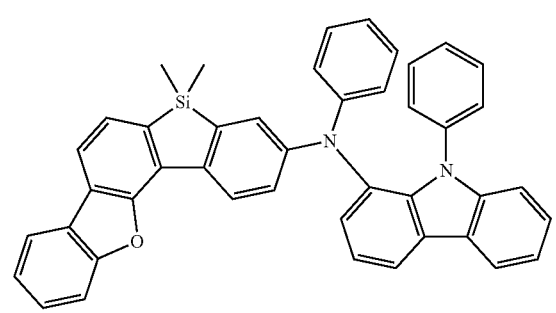
F-61
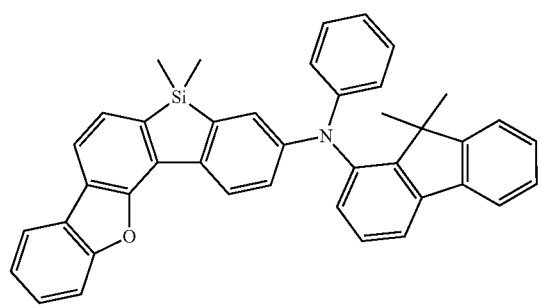

F-62
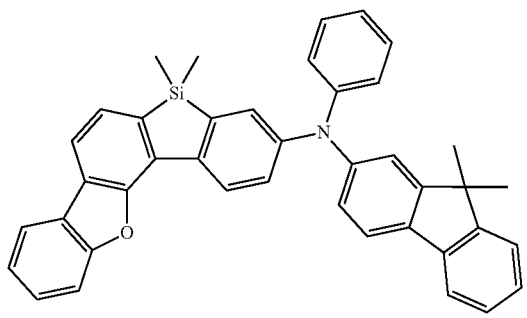
F-63
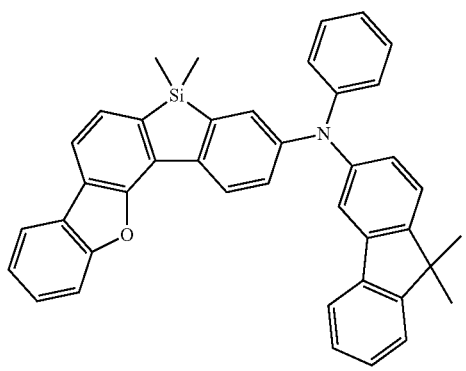
F-64
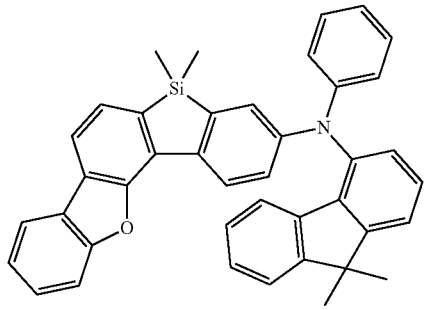
F-65
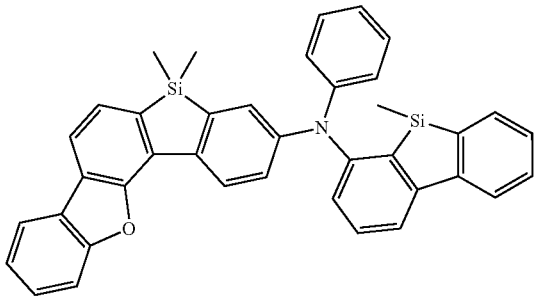
F-66
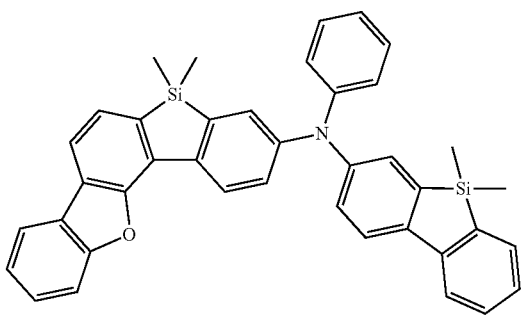
F-67
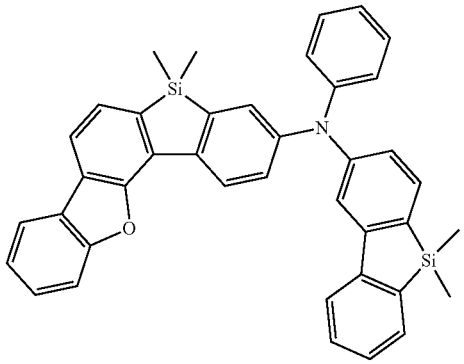
F-68
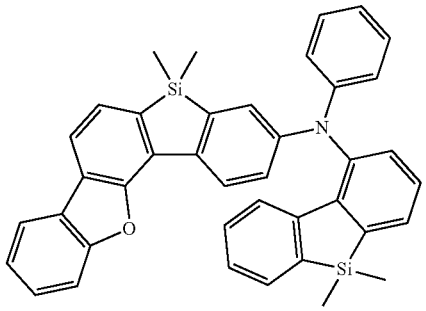
F-69
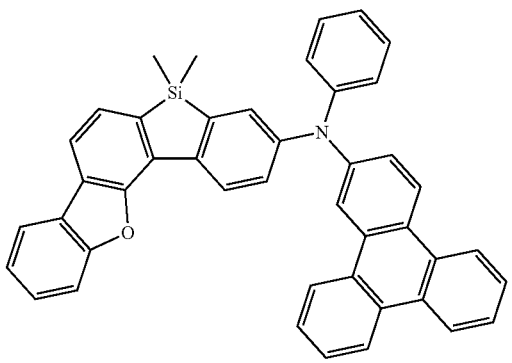

F-70
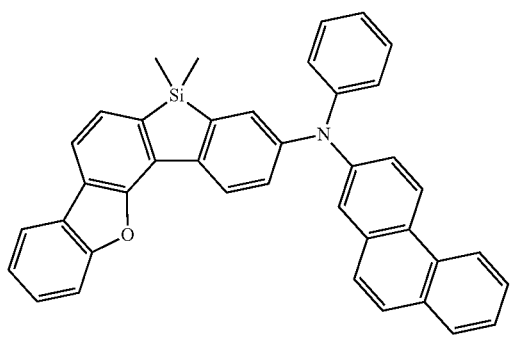
F-71
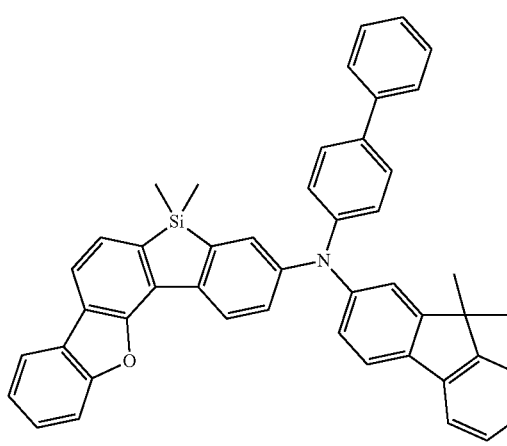
F-72
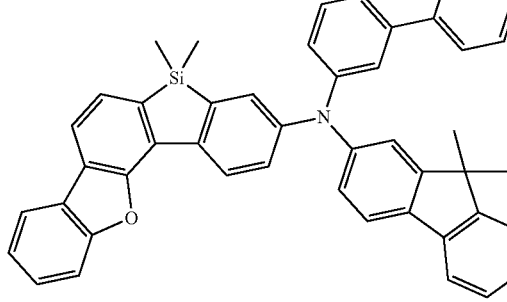
G-1
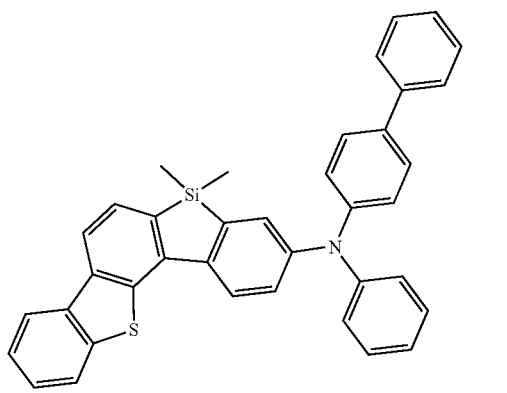
G-2
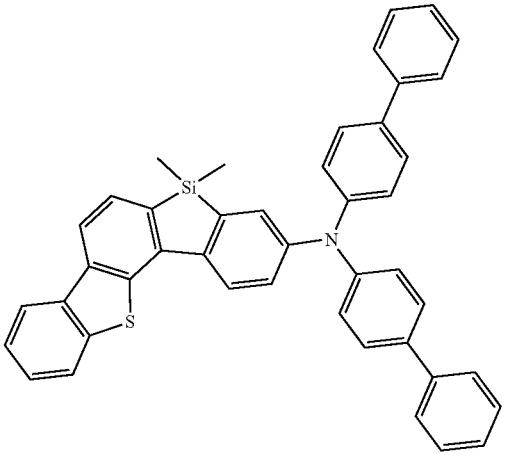
G-3
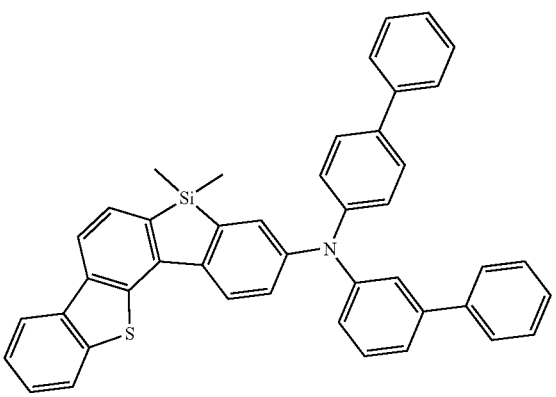
G-4
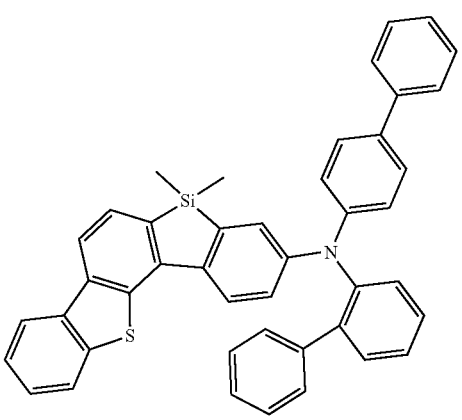

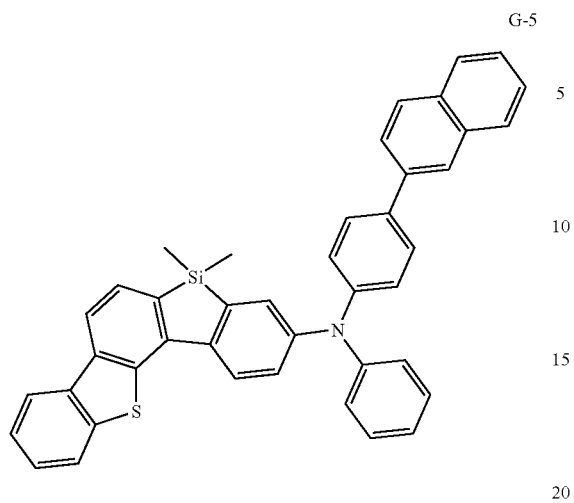
G-5
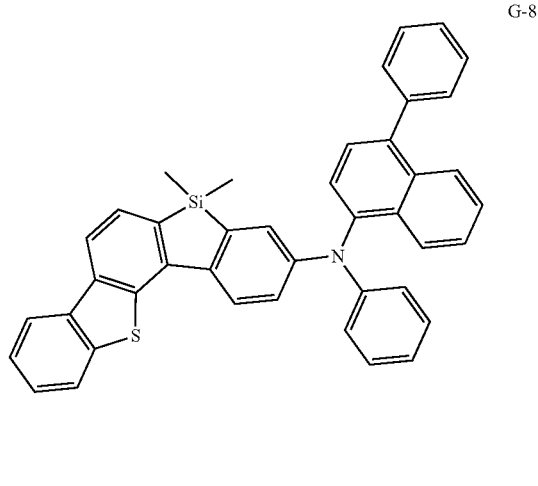
G-8
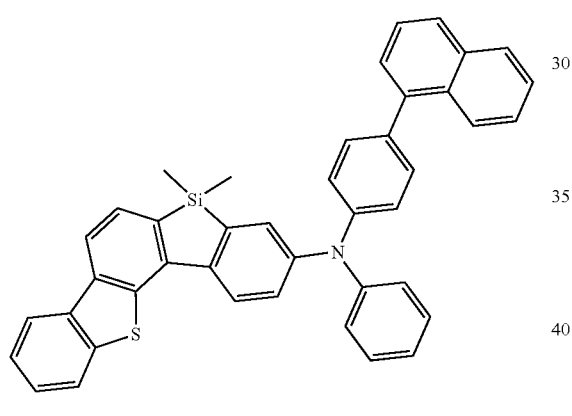
G-6
G-9
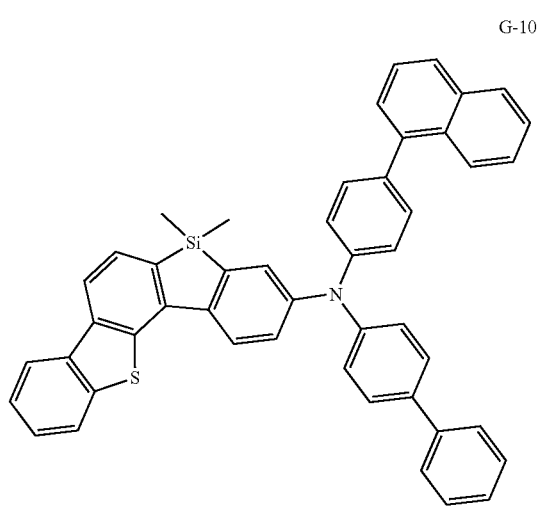
G-10
G-7

G-11
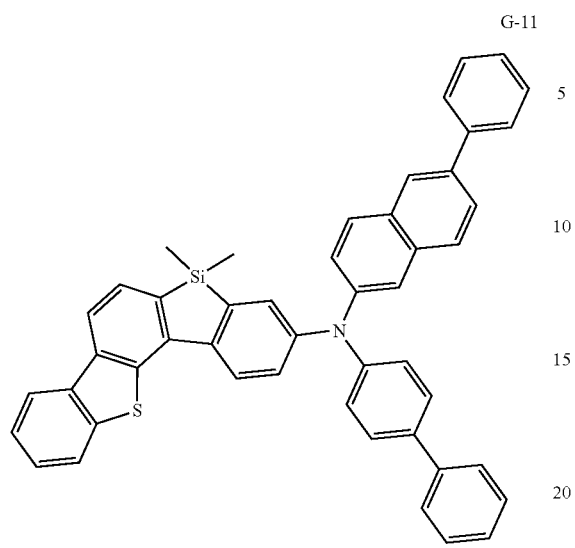
G-12
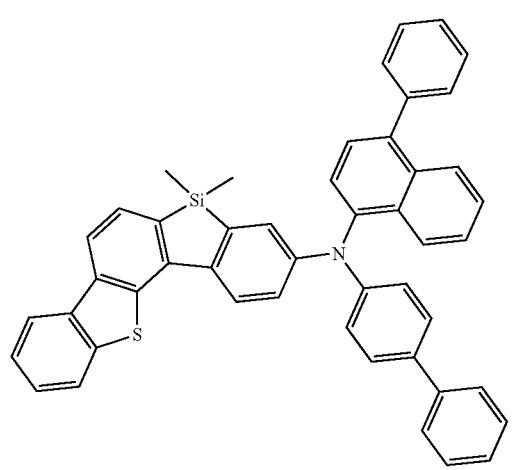
G-13
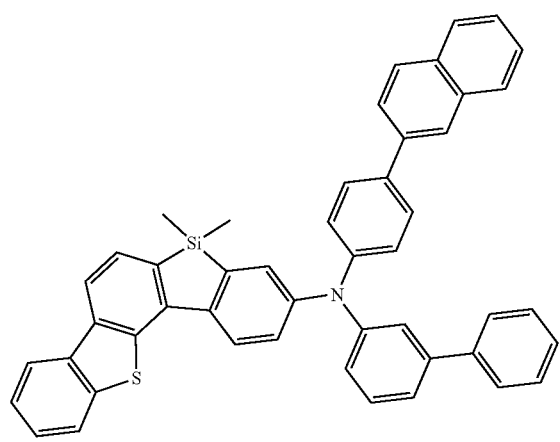
G-14
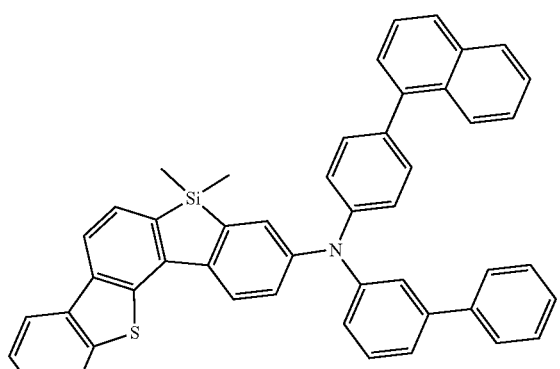
G-15
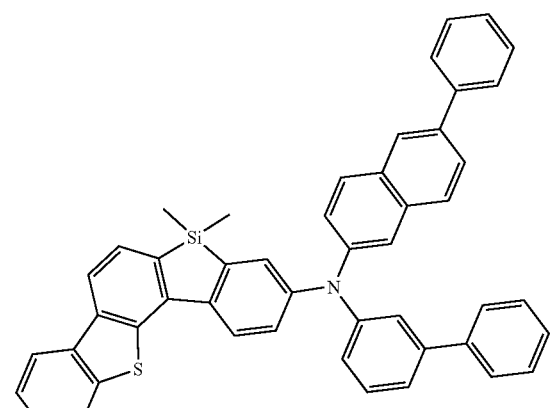
G-16
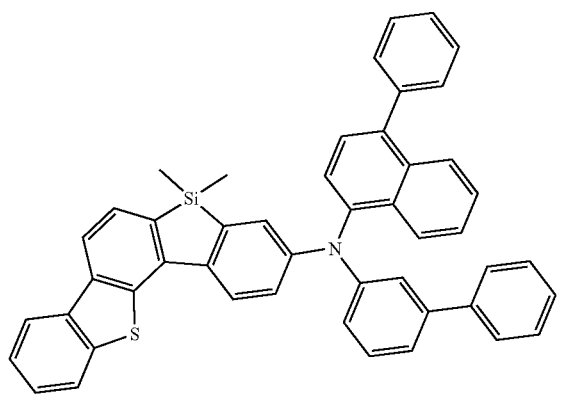

G-17
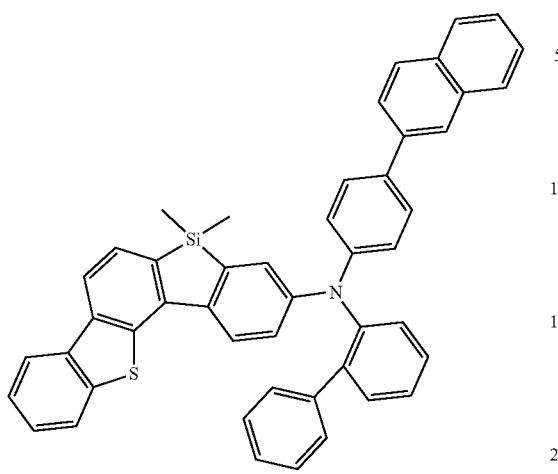
G-18
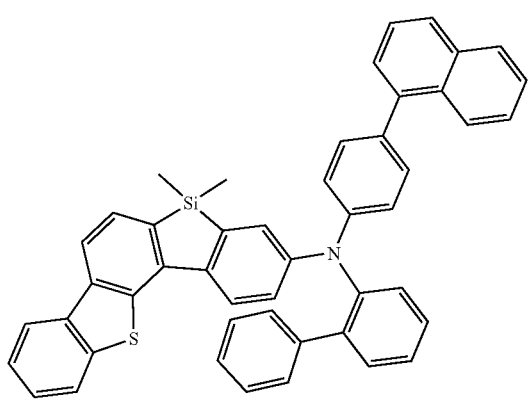
G-19
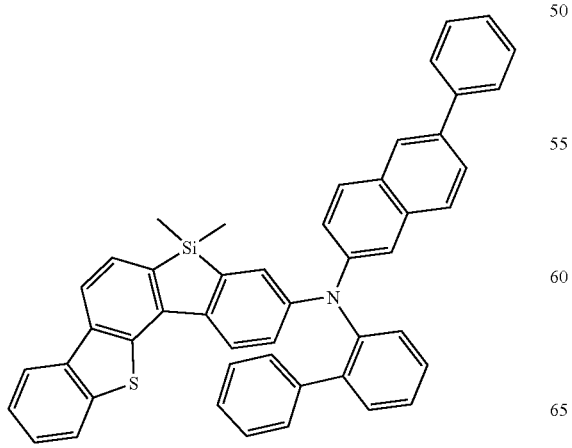
G-20
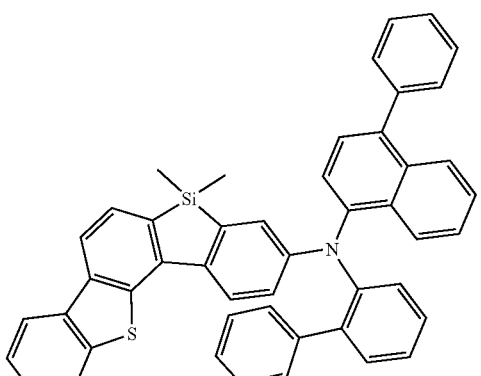
G-21
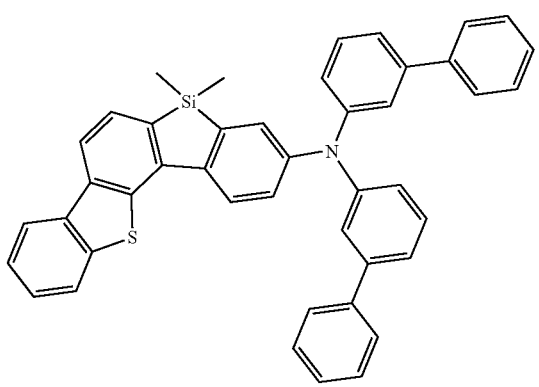
G-22
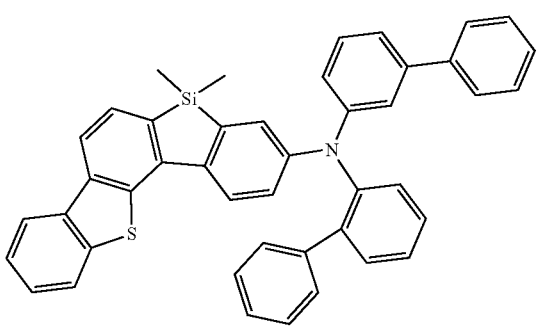
G-23
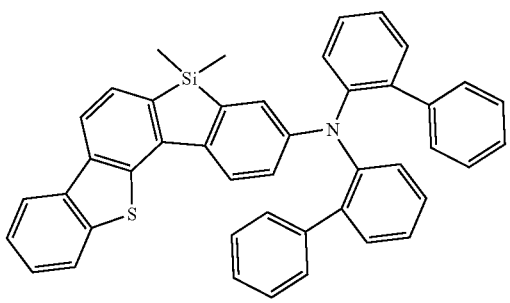

G-24
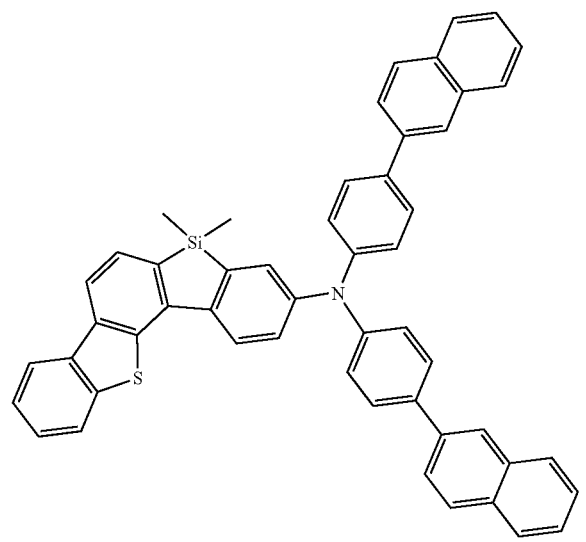
G-25
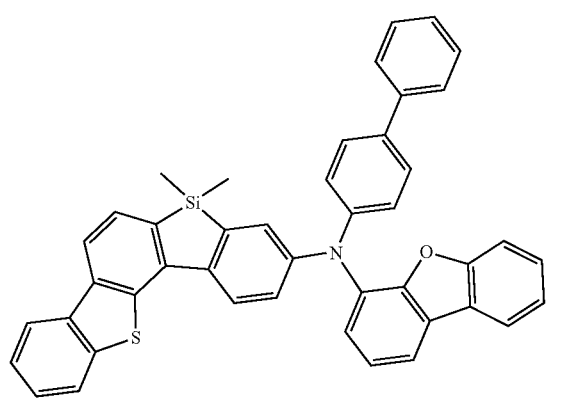
G-26
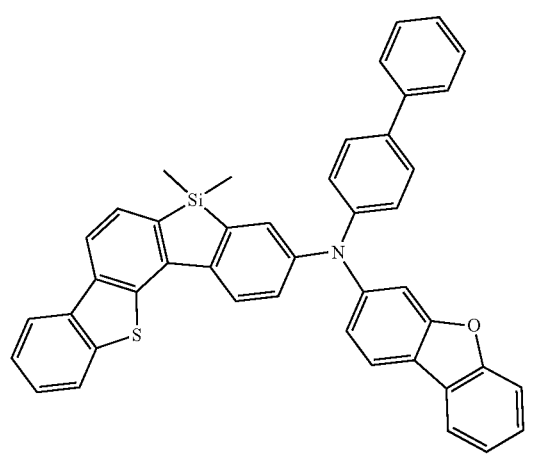
G-27
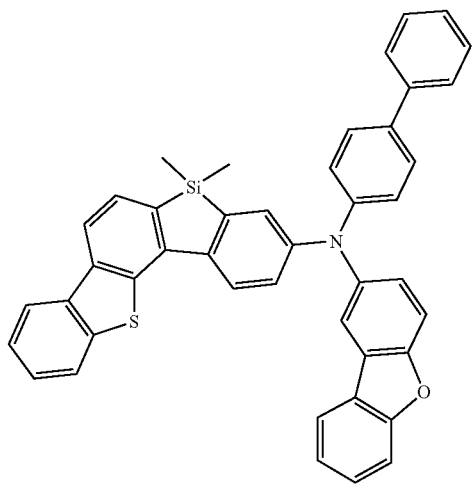
G-28
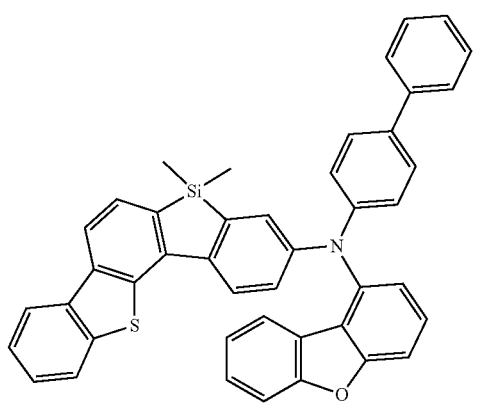
G-29
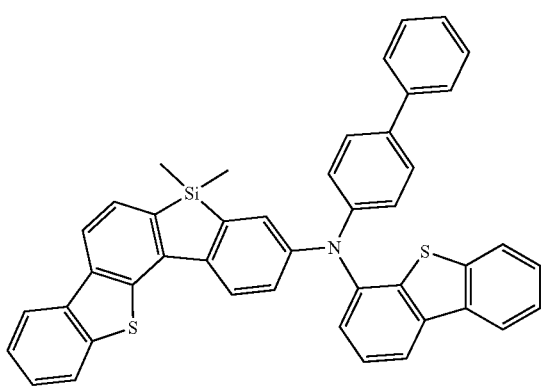

G-30
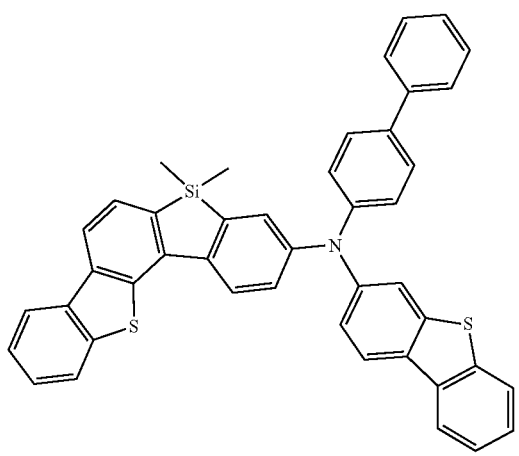
G-31
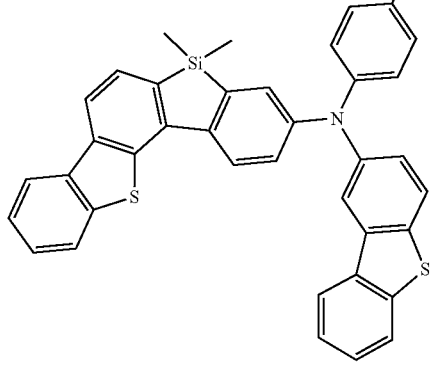
G-32
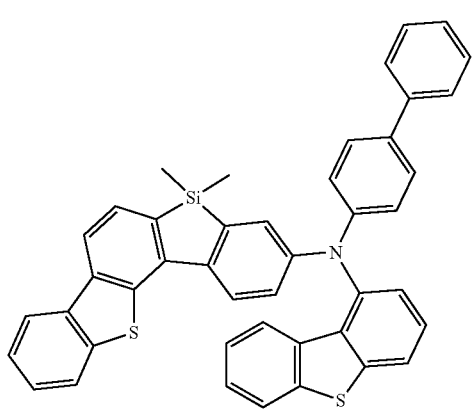
G-33
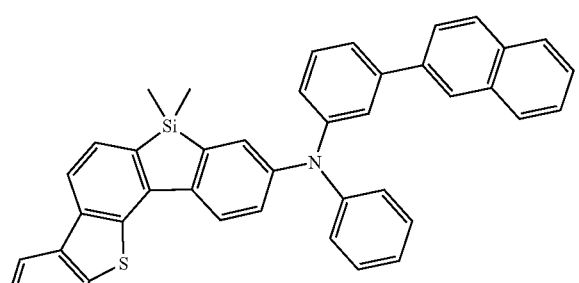
G-34
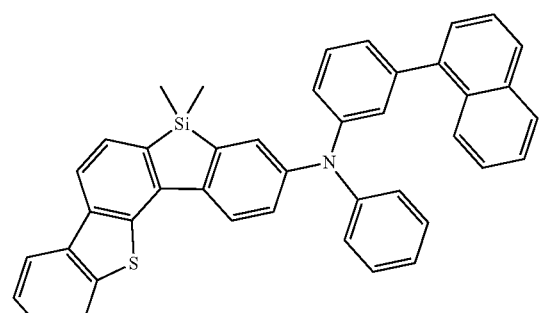
G-35
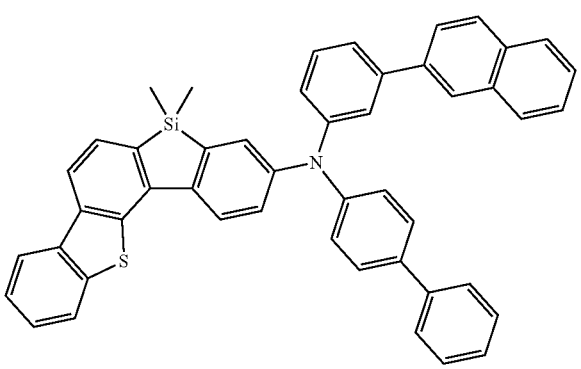
G-36
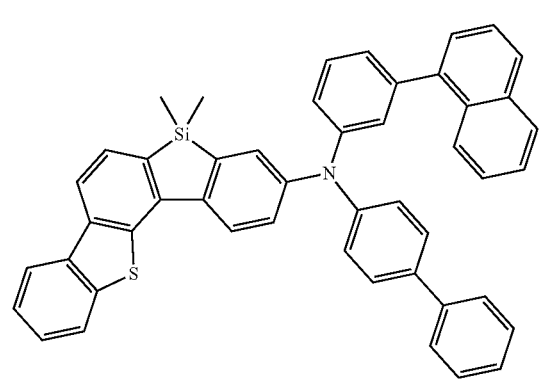

-continued
G-37
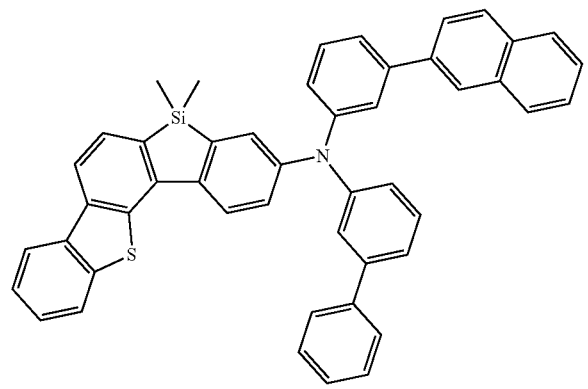
G-38
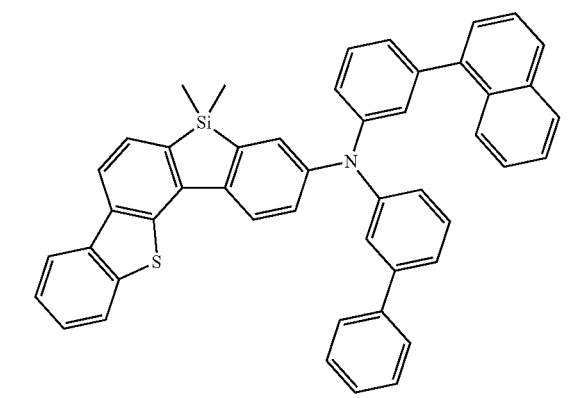
G-39
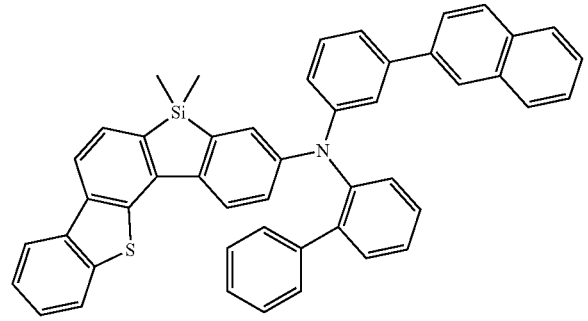
G-40
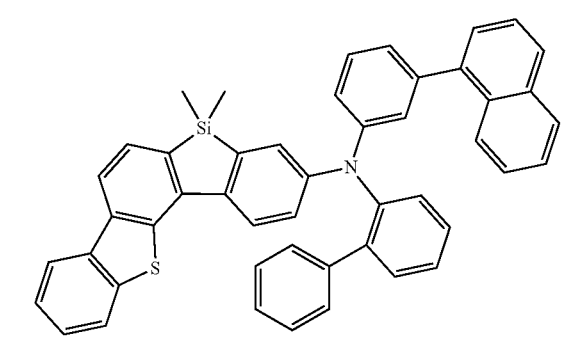
-continued
G-41
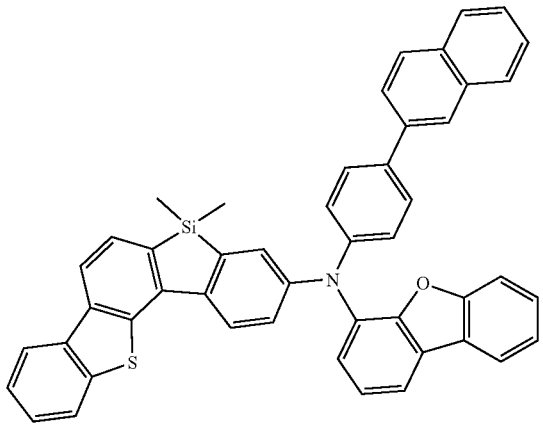
G-42
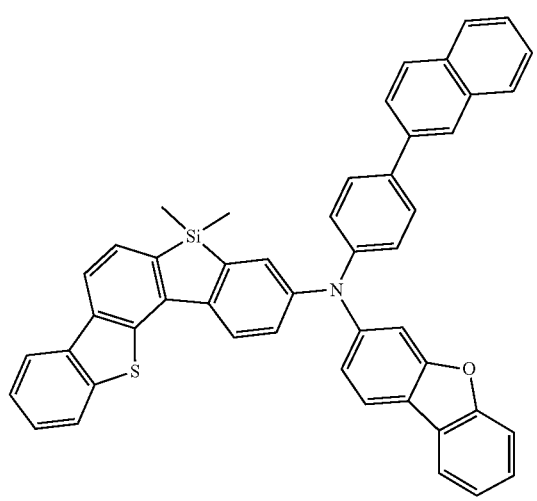
G-43
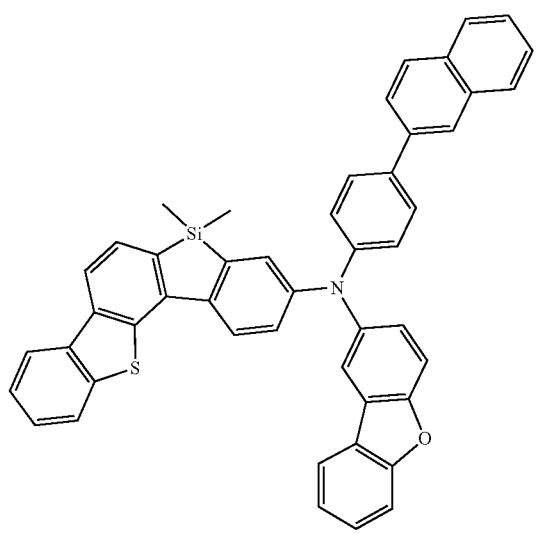

G-44
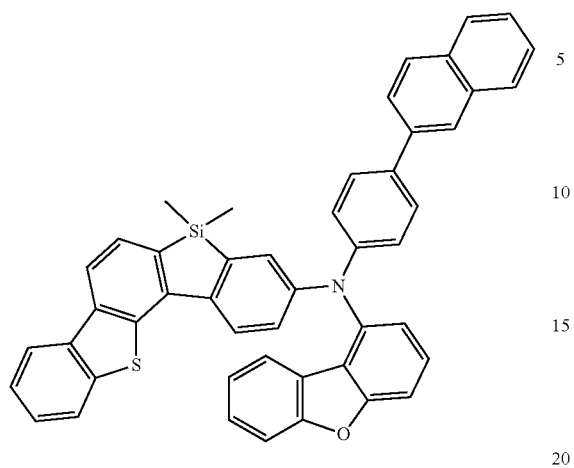
G-45
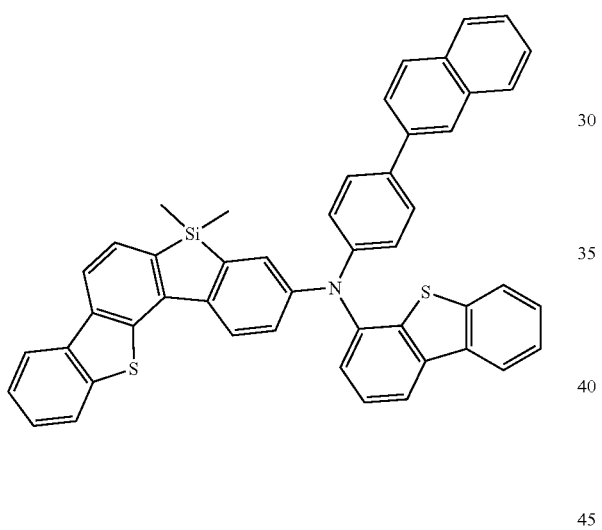
G-46
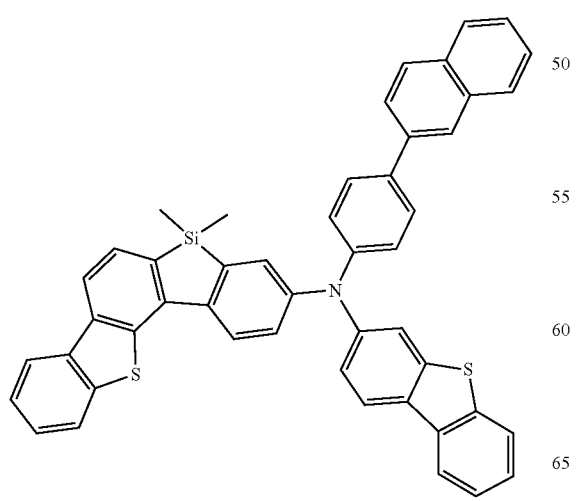
G-47
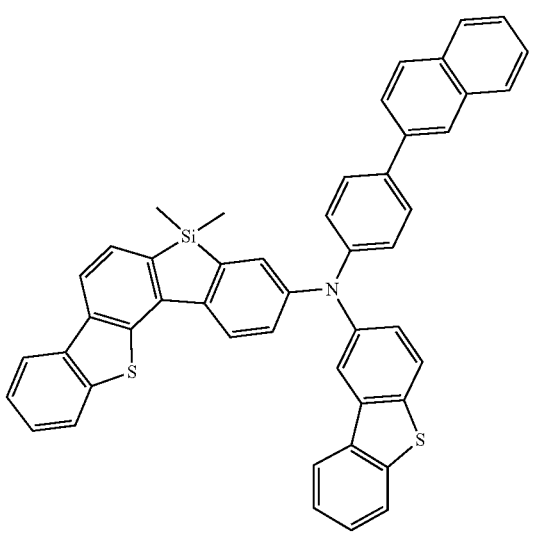
G-48
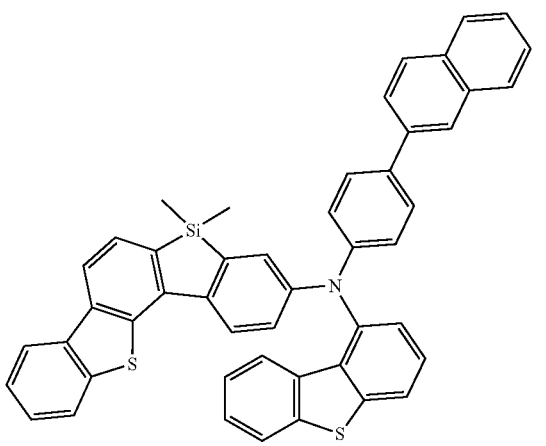
G-49
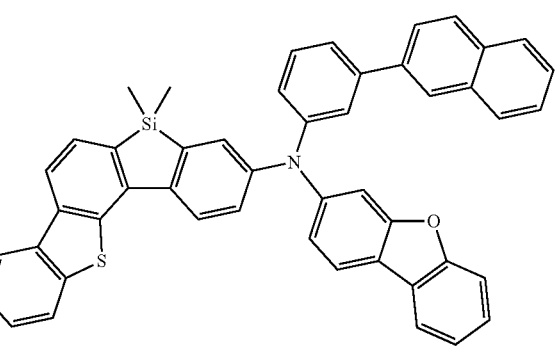

G-50
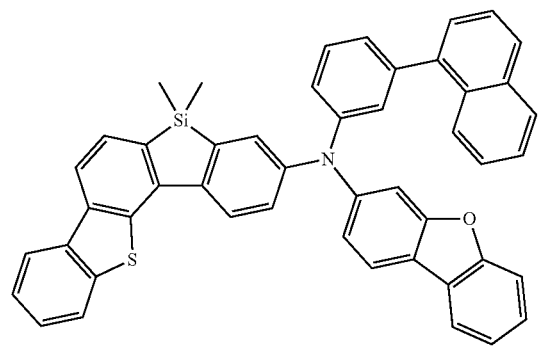
G-54
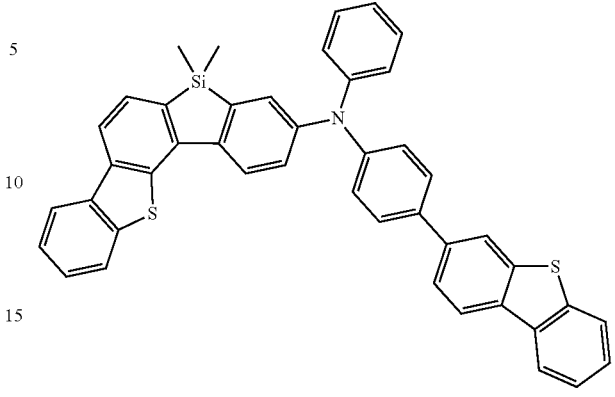
G-51
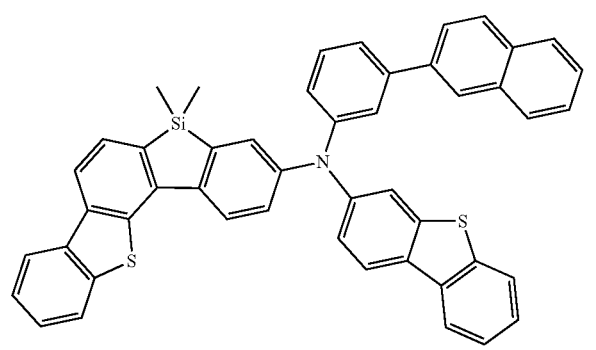
G-55
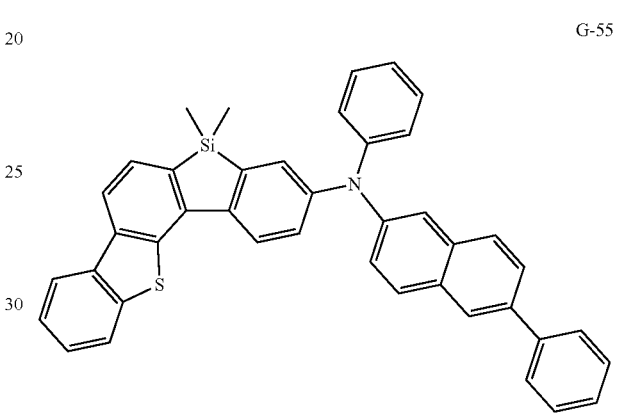
G-52
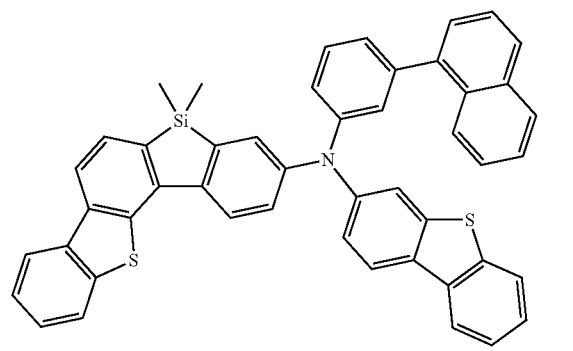
G-56
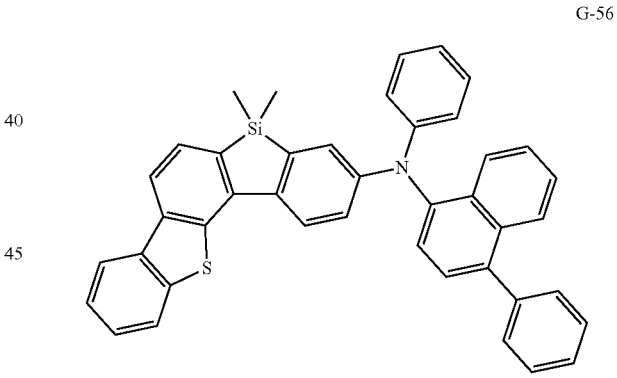
G-53
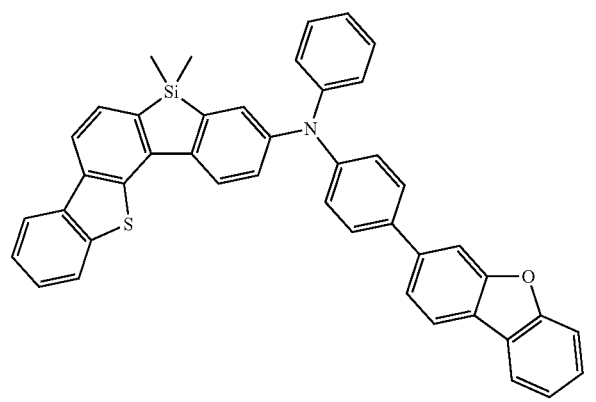
G-57
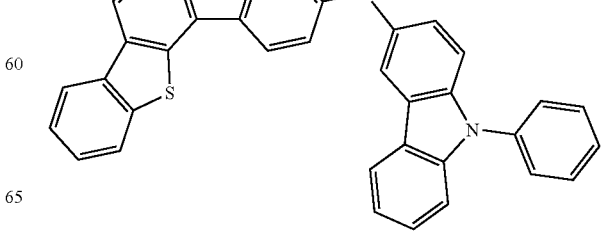

G-58
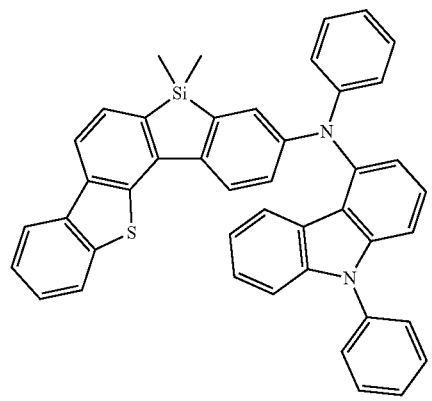
G-59
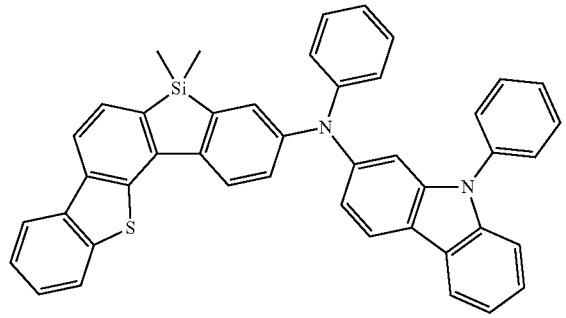
G-60
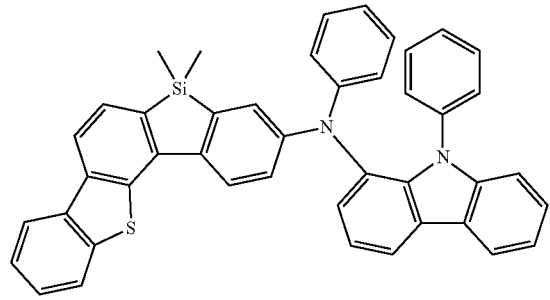
G-61
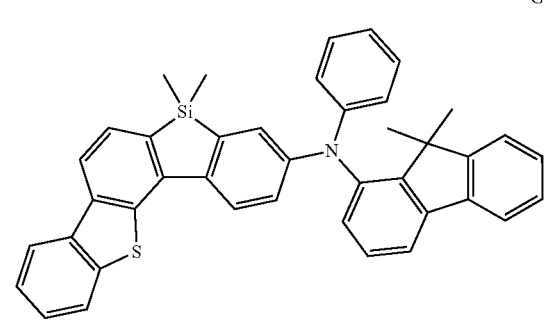
G-62
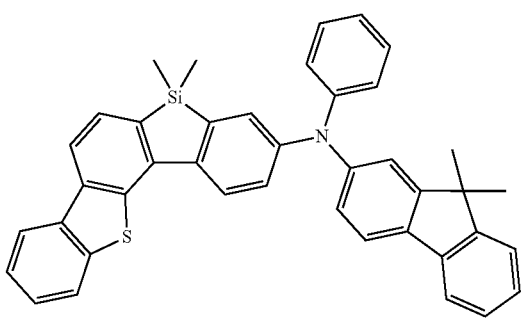
G-63
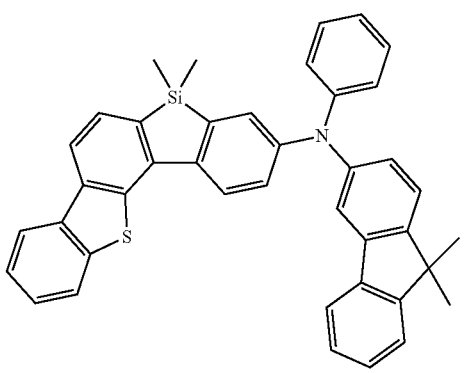
G-64
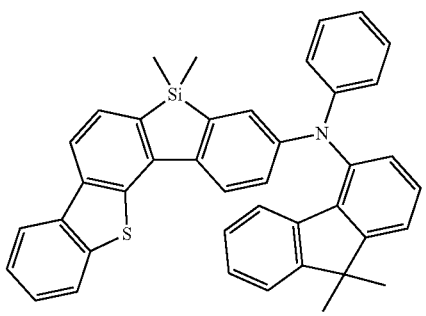
G-65
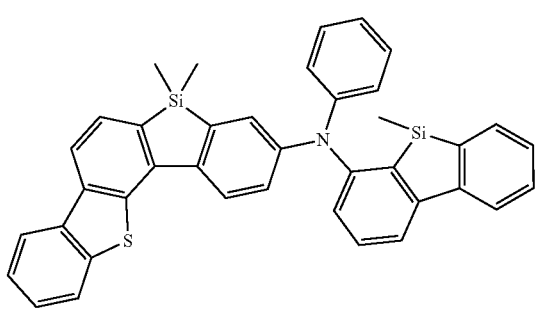

G-66
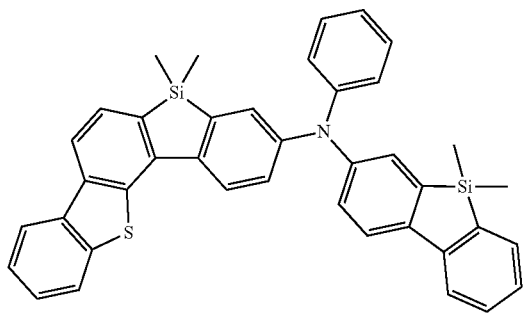
G-67
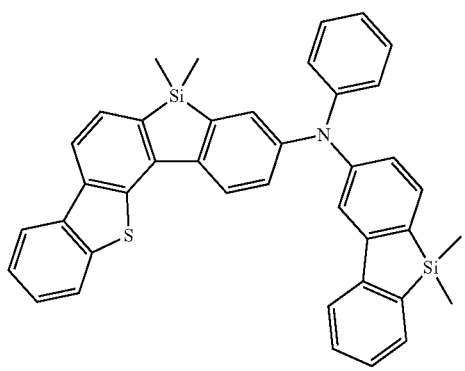
G-68
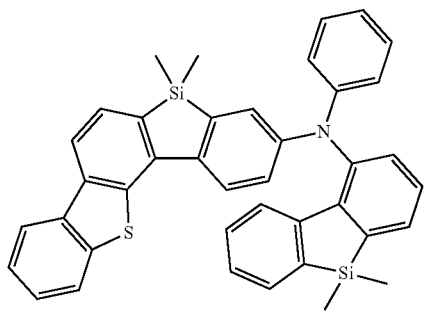
G-69
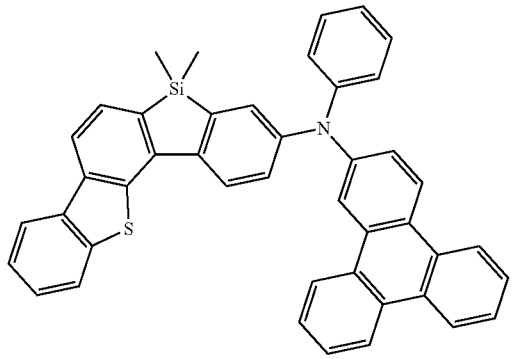
G-70
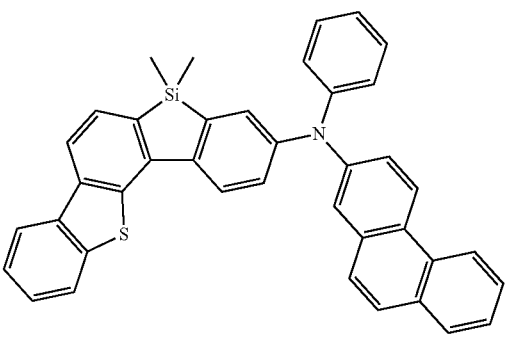
G-71
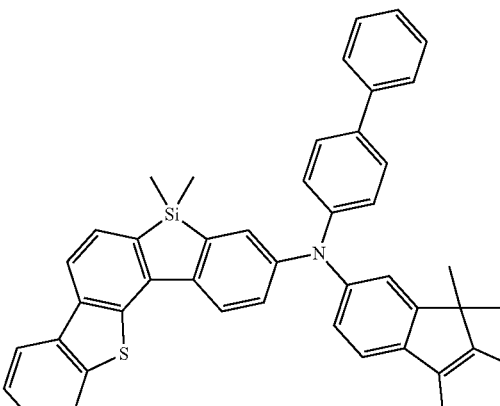
G-72
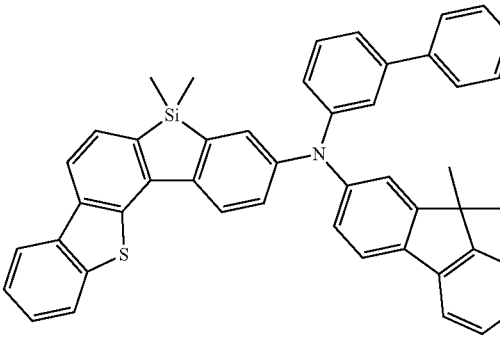
H-1
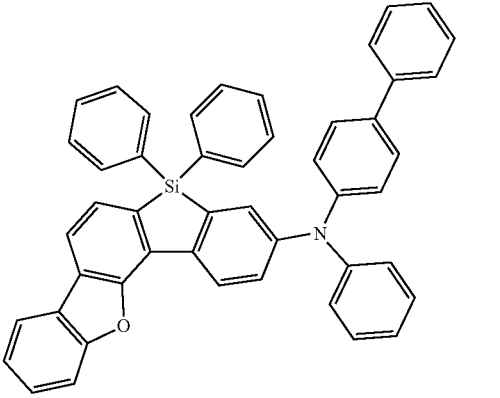

H-2
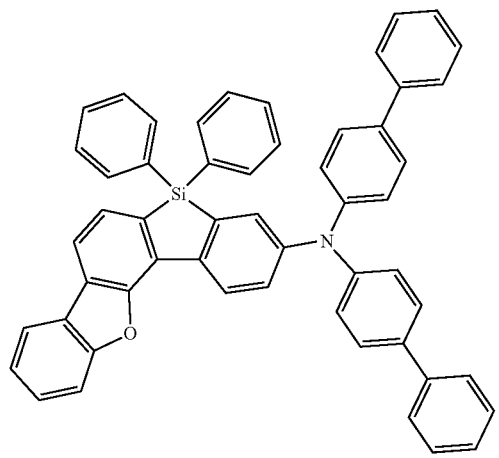
H-3
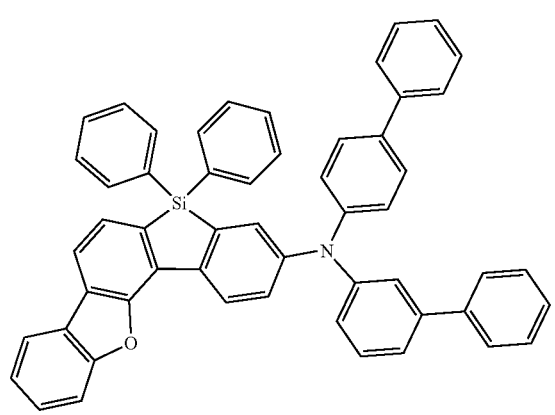
H-4
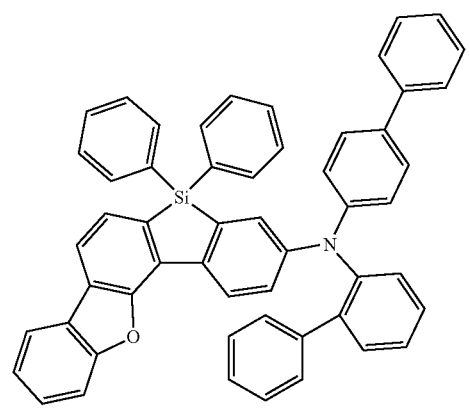
H-5
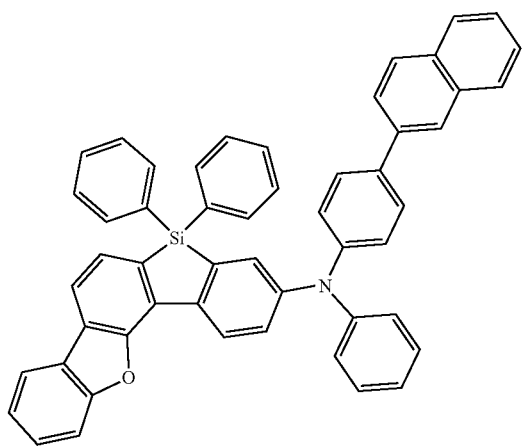
H-6
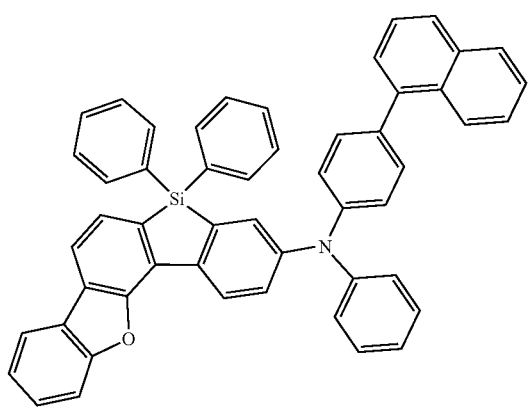
H-7
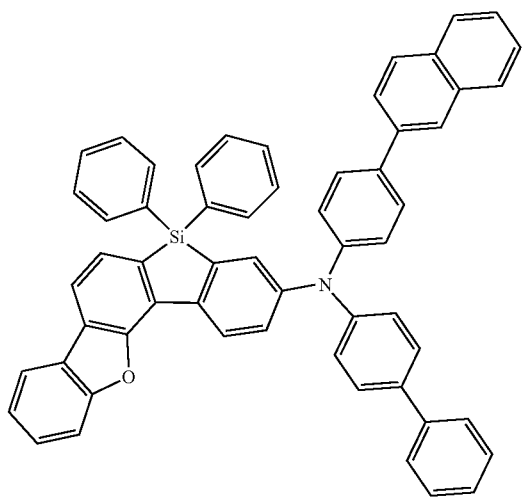

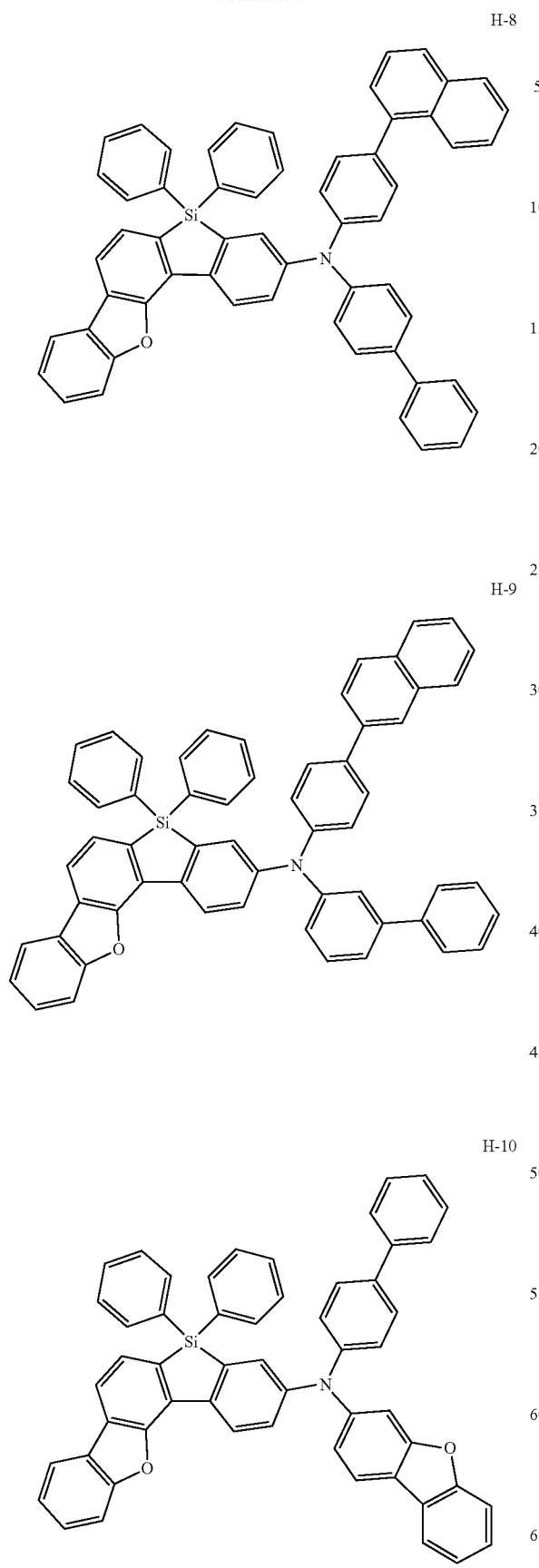
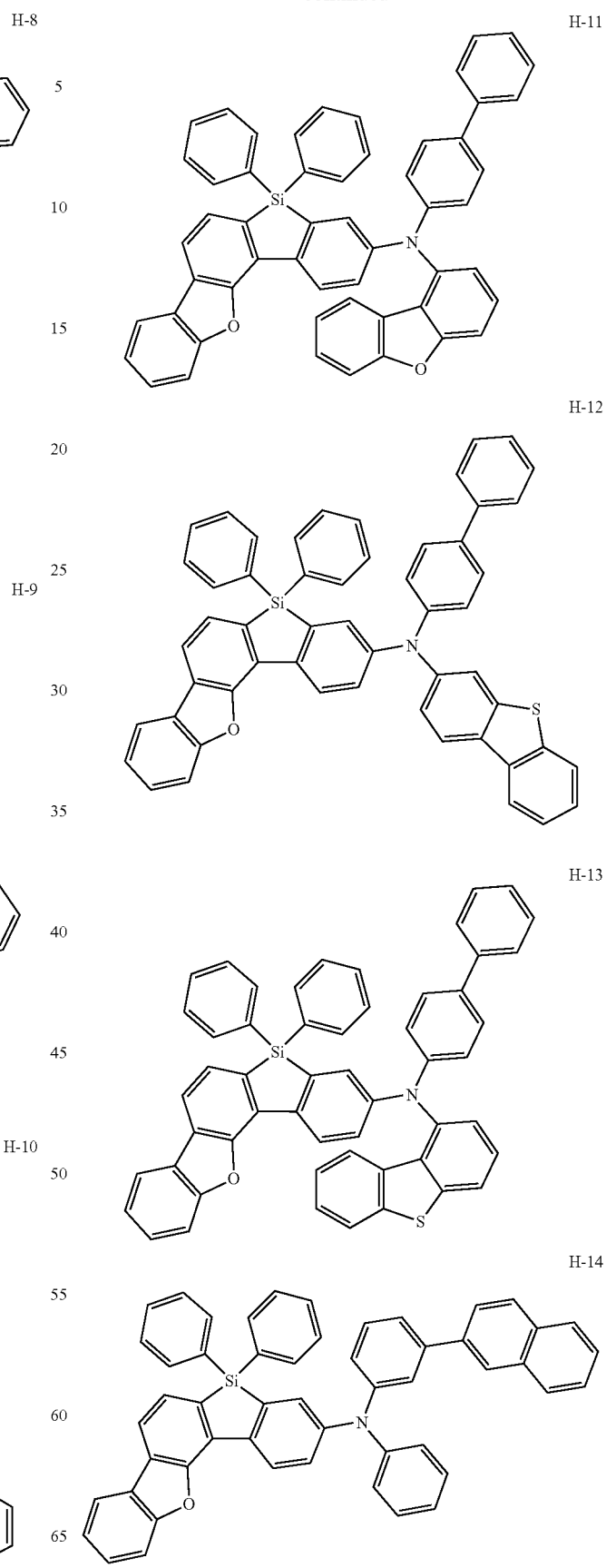

H-15
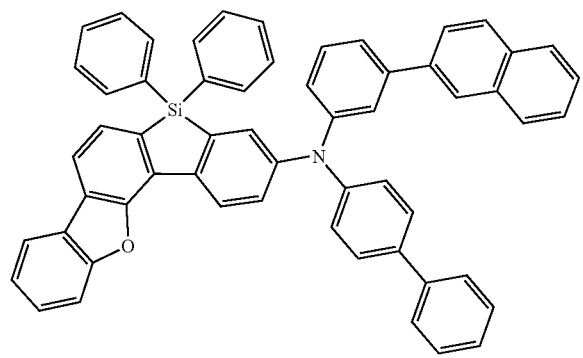
H-16
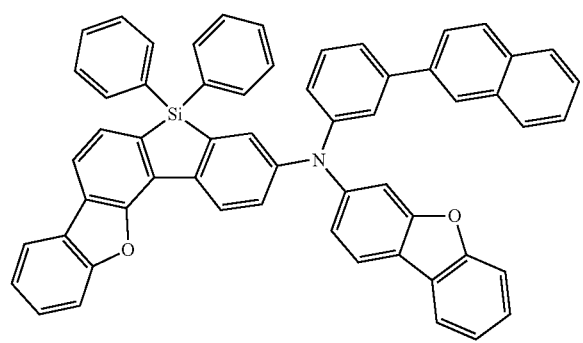
H-17
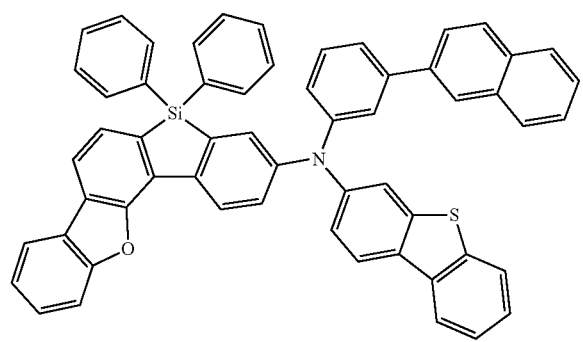
H-18
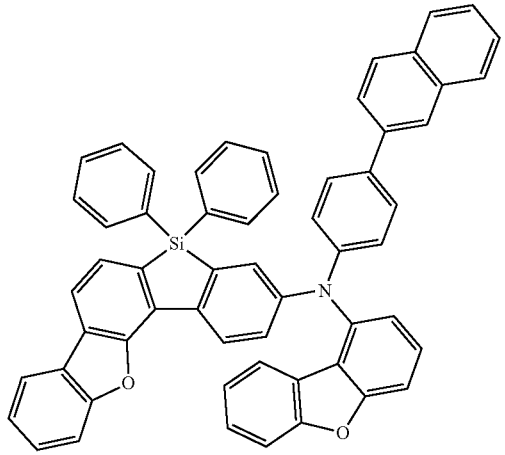
H-19
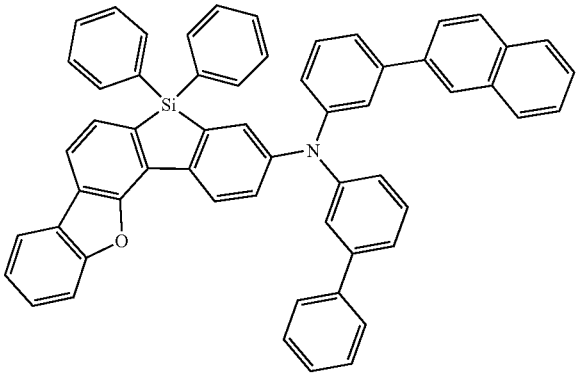
H-20
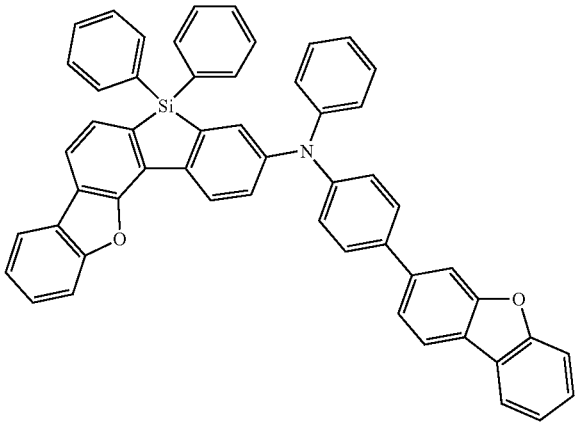
H-21
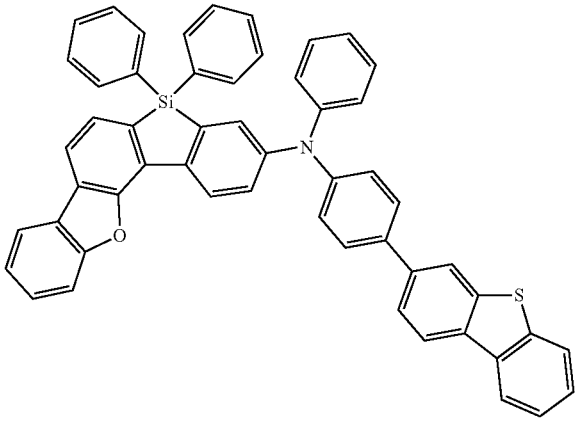

H-22
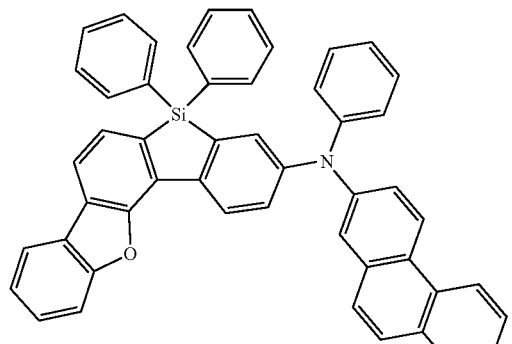
H-23
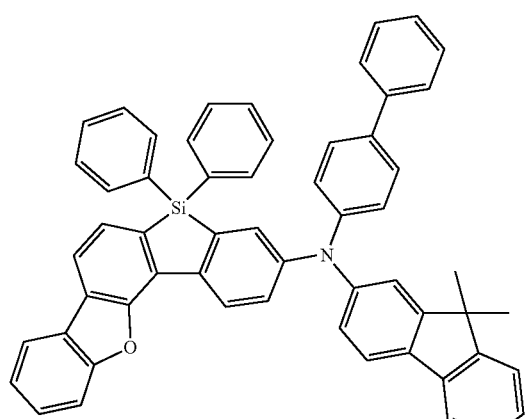
H-24
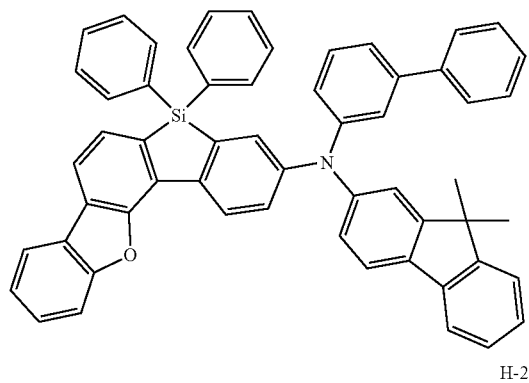
H-25
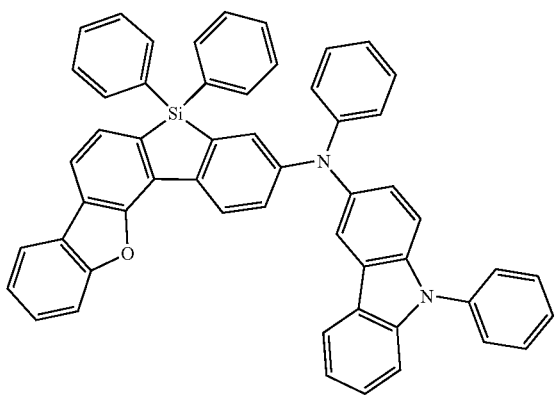
H-26
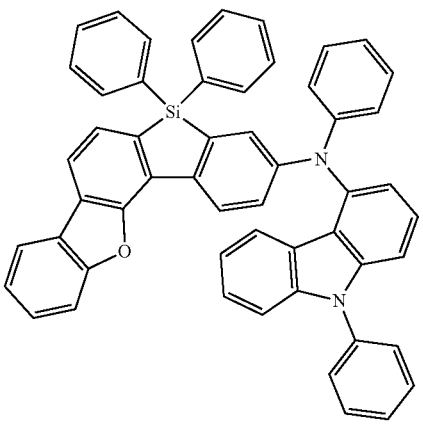
H-27
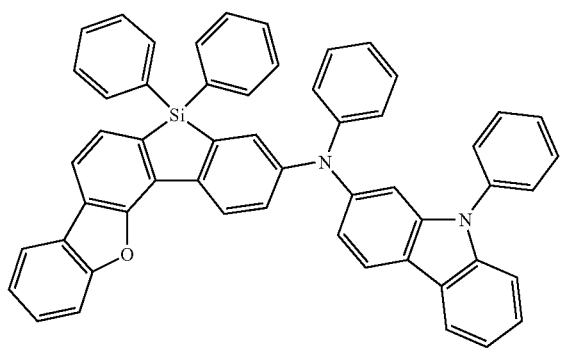
H-28
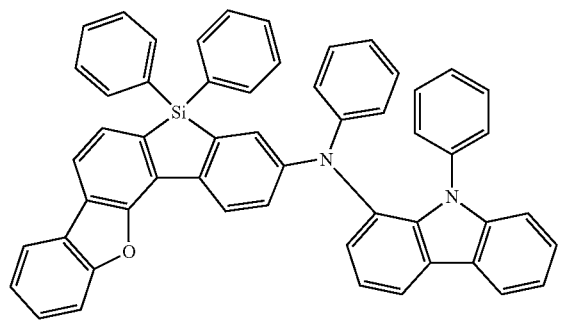
H-29
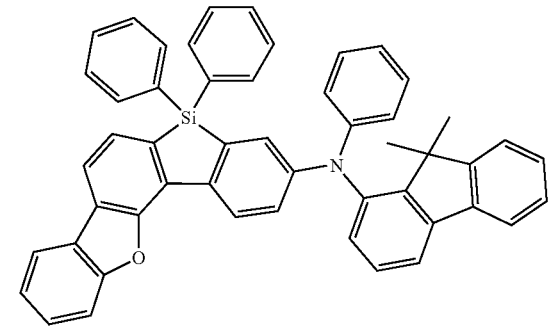

H-30
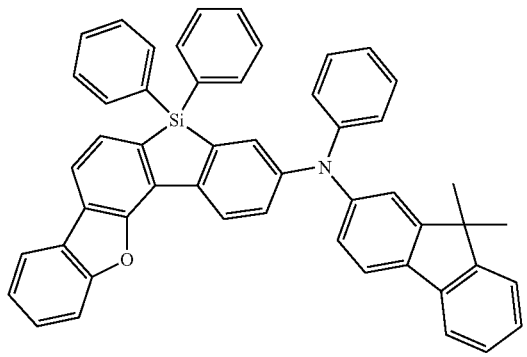
H-31
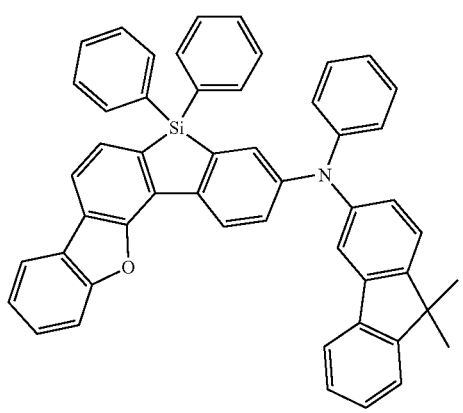
H-32
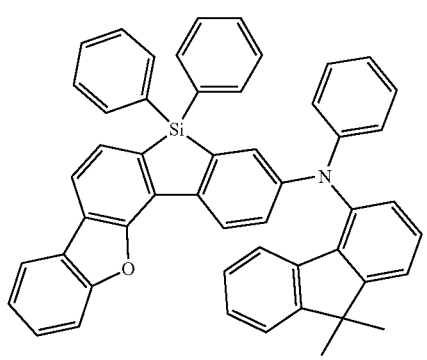
H-33
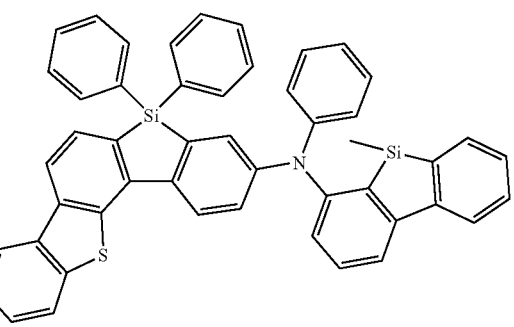
H-34
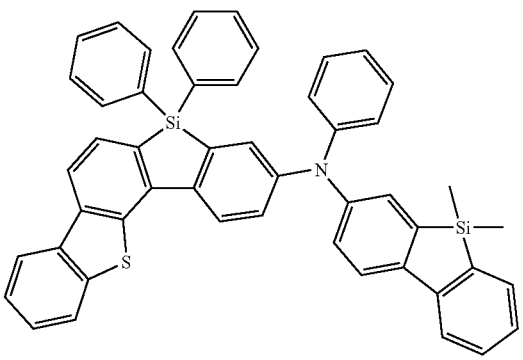
H-35
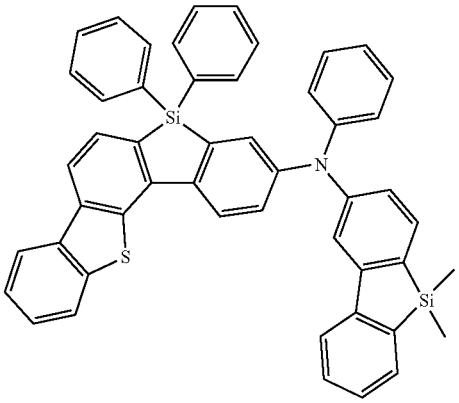
H-36
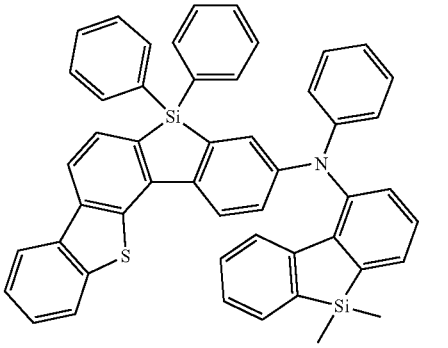
H-37
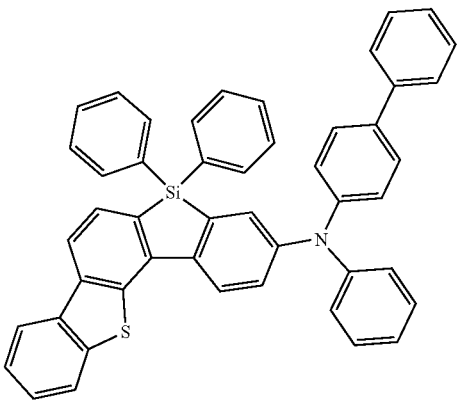

H-38
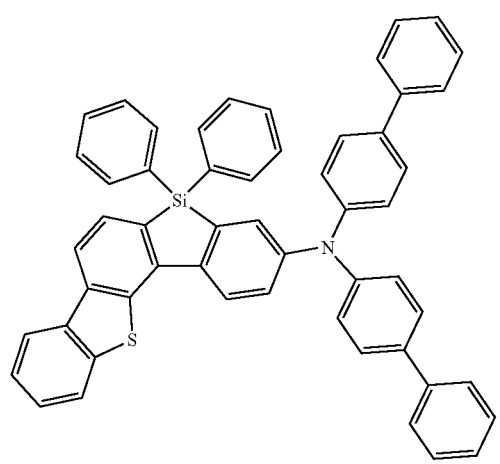
H-39
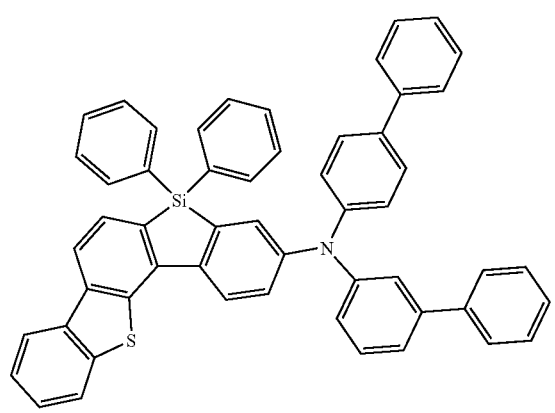
H-40
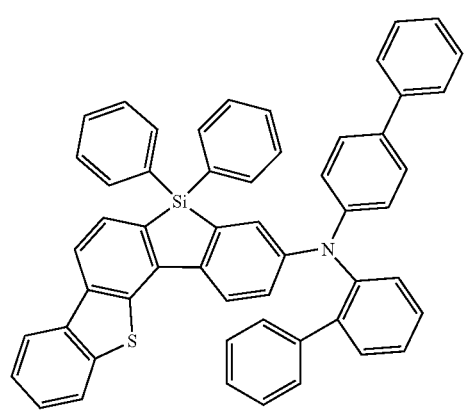
H-41
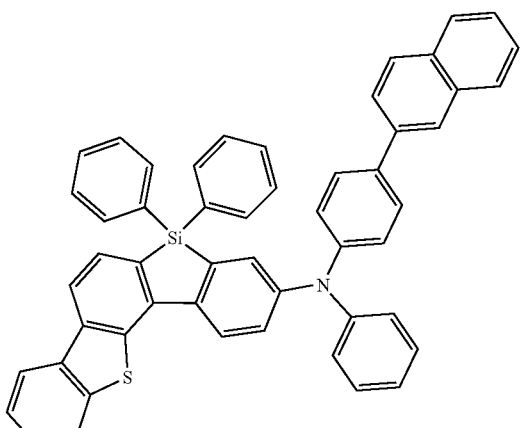
H-42
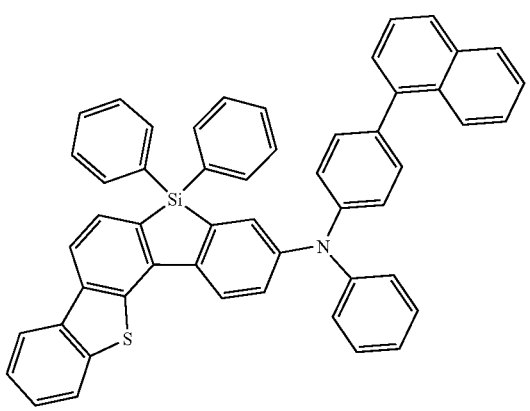
H-43
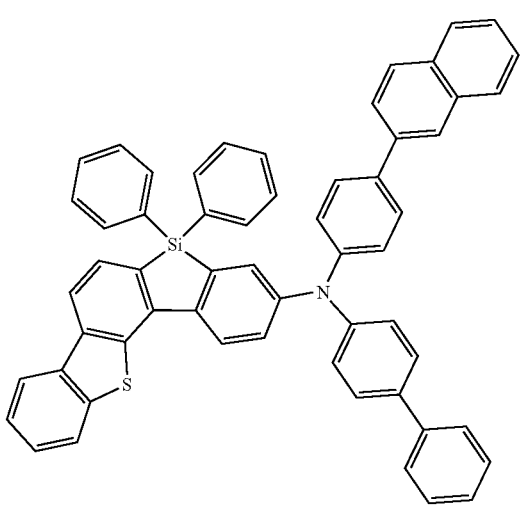

-continued
H-44
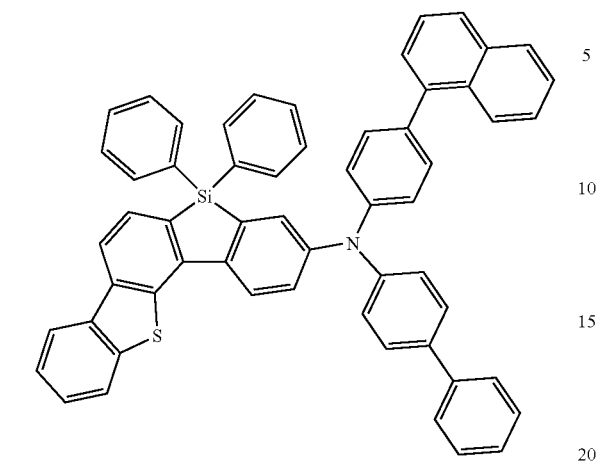
H-45
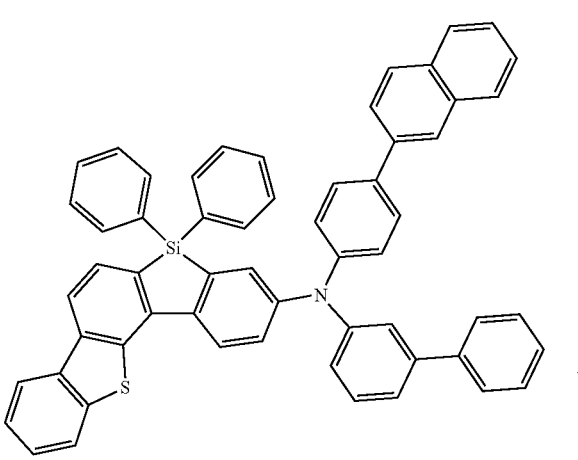
H-46
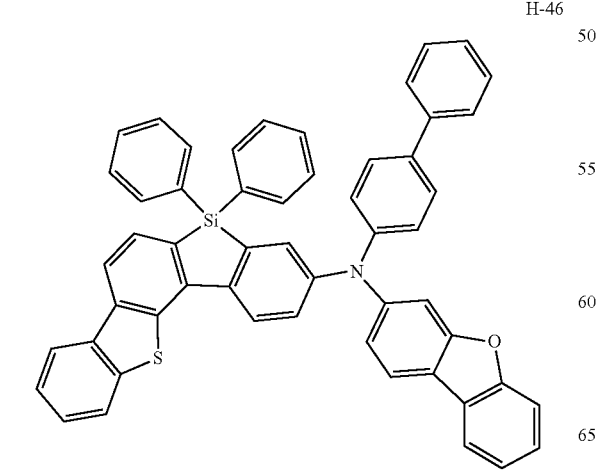
-continued
H-47
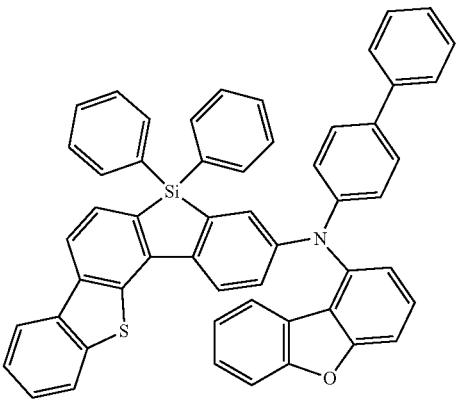
H-48
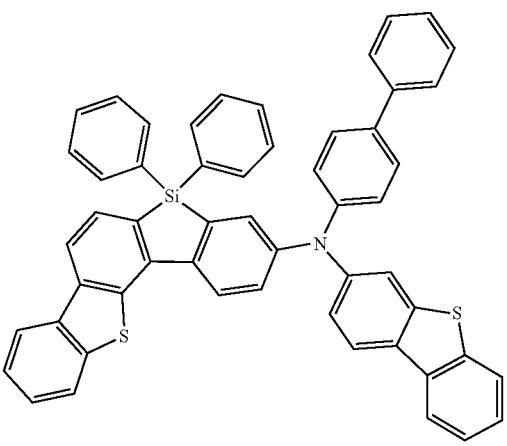
H-49
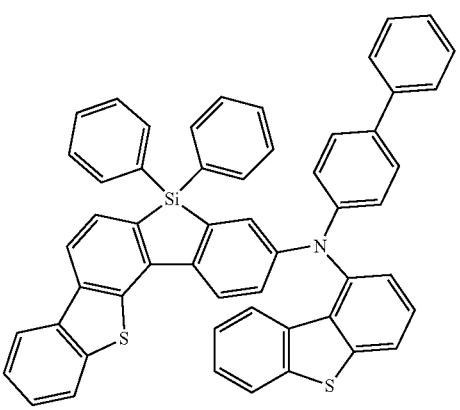
H-50
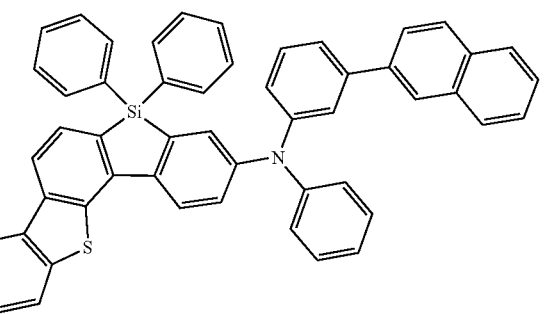

H-51
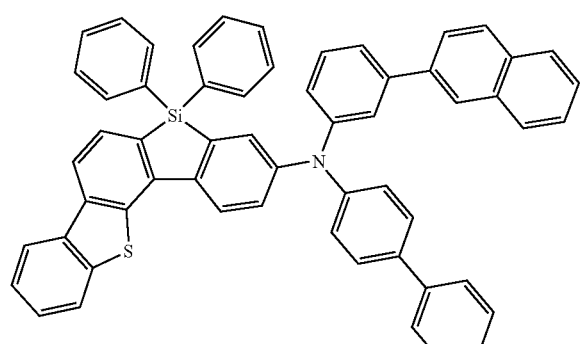
H-52
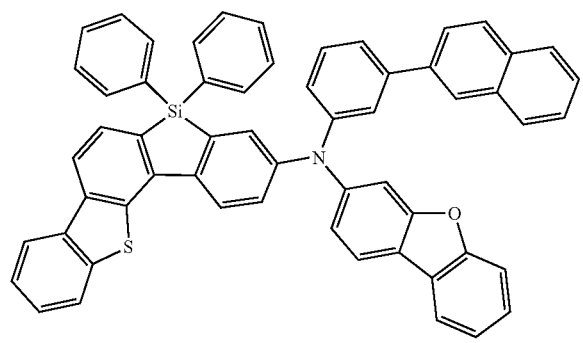
H-53
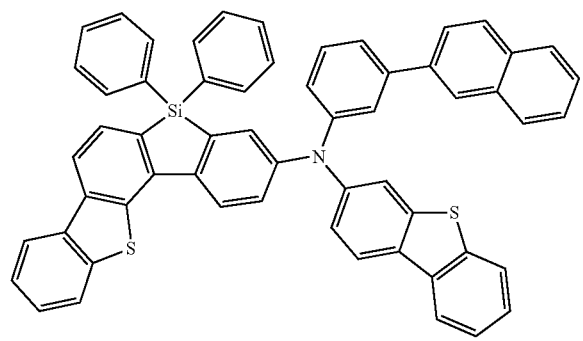
H-54
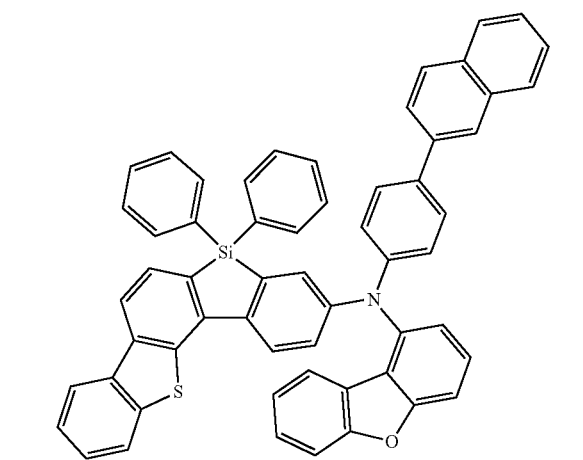
H-55
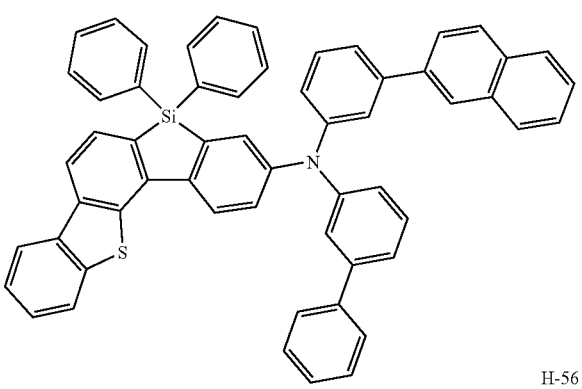
H-56
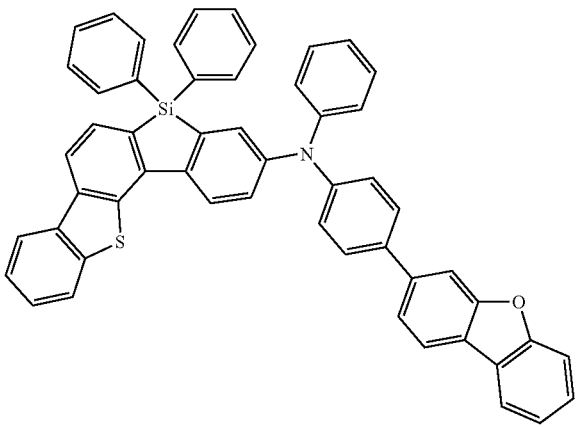
H-57
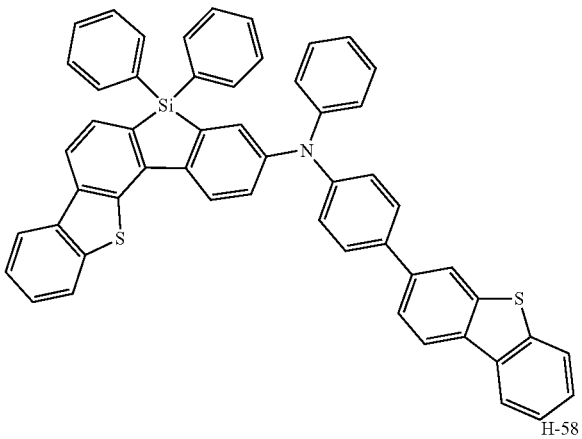
H-58
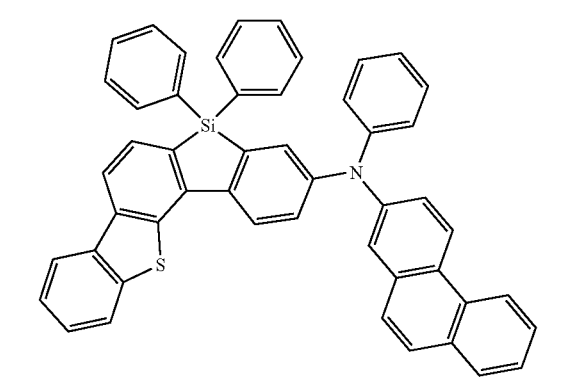

H-59
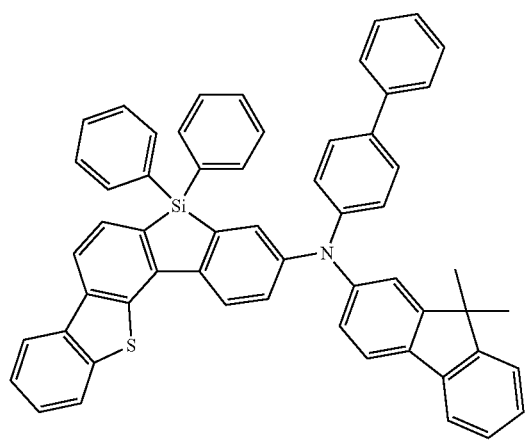
H-60
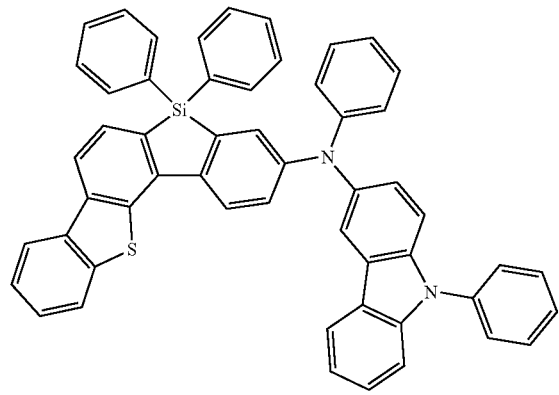
H-61
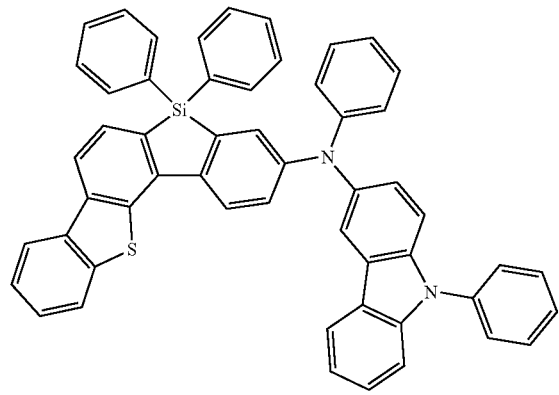
H-62
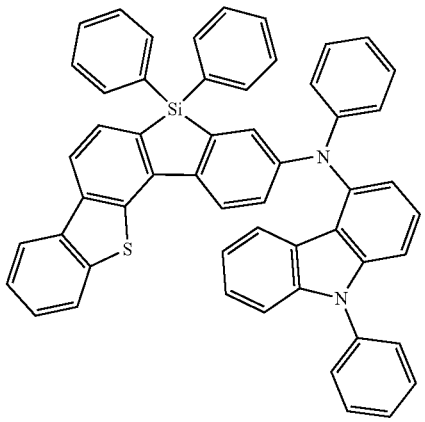
H-63
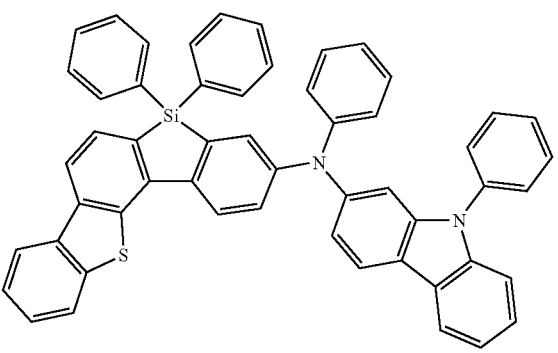
H-64
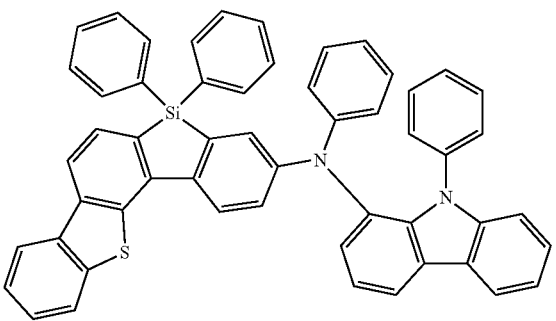
H-65
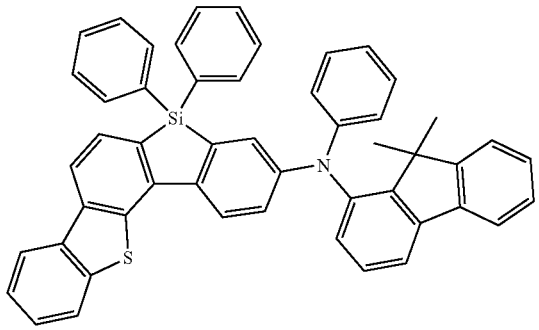

H-66

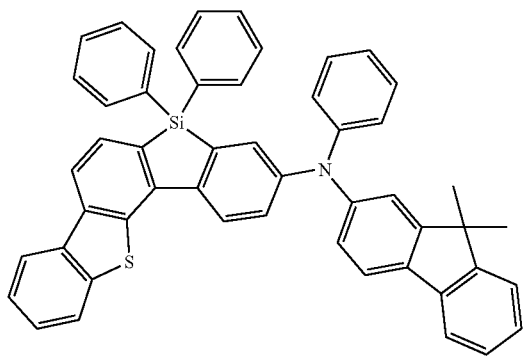

H-67

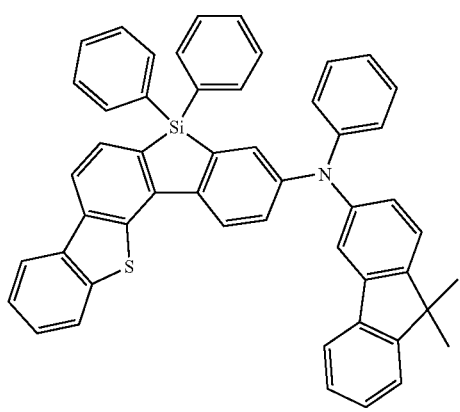

H-68

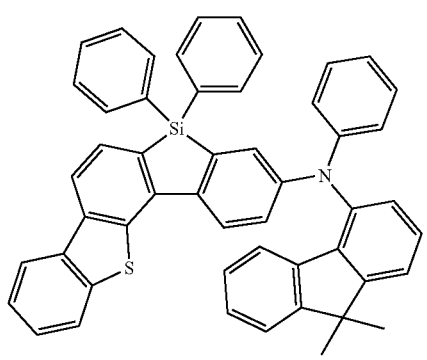

H-69

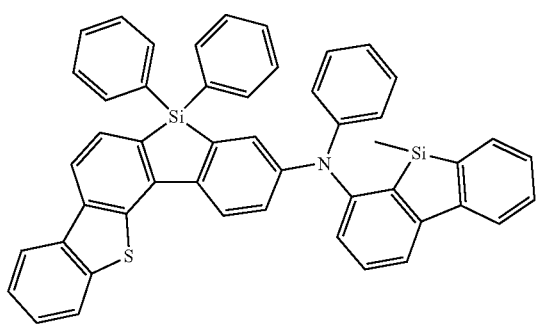

H-70

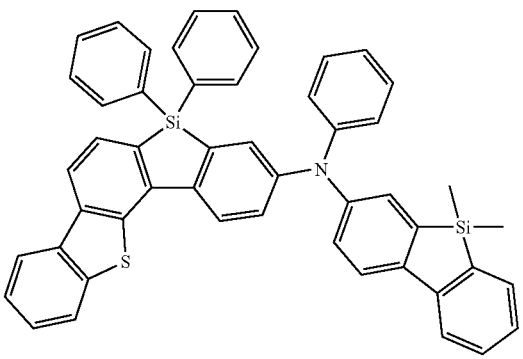

H-71

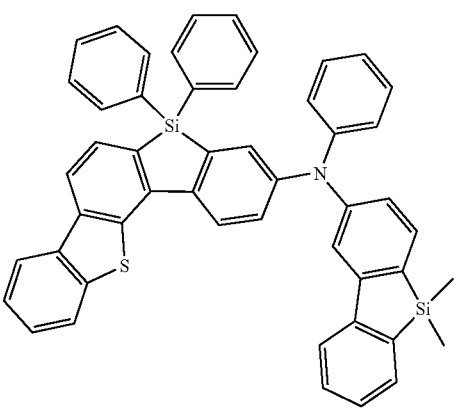

H-72

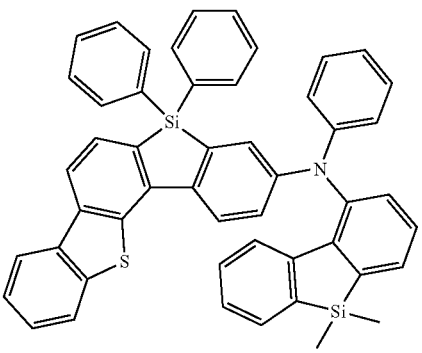

In an implementation, the composition for an organic optoelectronic device may include the first compound represented by Chemical Formula 1A-2, Chemical Formula 1A-4, Chemical Formula 1E-2, Chemical Formula 1E-4, Chemical Formula 1F-2, Chemical Formula 1F-4, Chemical Formula 1G-2, or Chemical Formula 1G-4 and the compound represented by Chemical Formula 2-2.

In an implementation, $Ar^1$ and $Ar^2$ of Chemical Formula 1A-2 and Chemical Formula 1A-4 may each independently be or include, e.g., a substituted or unsubstituted phenyl group, a substituted or unsubstituted biphenyl group, or a substituted or unsubstituted naphthyl group, $R^1$ and $R^2$ may each independently be or include, e.g., a substituted or unsubstituted C1 to C5 alkyl group or a substituted or unsubstituted phenyl group, $R^3$, $R^4$, and $R^6$ may each independently be or include, e.g., hydrogen or a substituted or unsubstituted phenyl group, and $L^1$ and $L^2$ may each independently be or include, e.g., a single bond or a substituted or unsubstituted phenylene group.

In an implementation, $Ar^1$ and $Ar^2$ of Chemical Formula 1E-2, Chemical Formula 1E-4, Chemical Formula 1F-2, Chemical Formula 1F-4, Chemical Formula 1G-2, and Chemical Formula 1G-4 may each independently be or include, e.g., a substituted or unsubstituted phenyl group, a substituted or unsubstituted biphenyl group, or a substituted or unsubstituted naphthyl group, $R^1$ and $R^2$ may each independently be or include, e.g., a substituted or unsubstituted C1 to C5 alkyl group or a substituted or unsubstituted phenyl group, $R^4$ and $R^6$ to $R^1$ may each independently be or include, e.g., hydrogen or a substituted or unsubstituted phenyl group, and $L^1$ and $L^2$ may each independently be or include, e.g., a single bond or a substituted or unsubstituted phenylene group.

The first compound and the second compound may be, e.g., included in a weight ratio of about 1:99 to about 99:1. Within the above range, an appropriate weight ratio using the electron transport capability of the first compound for an organic optoelectronic device and the hole transport capability of the second organic optoelectronic device compound may be adjusted to implement bipolar characteristics and improve efficiency and life-span. Within the above range, they may be, e.g., included in a weight ratio of about 90:10 to about 10:90, about 90:10 to about 20:80, about 90:10 to about 30:70, about 90:10 to about 40:60, or about 80:20 to about 40:60. In an implementation, they may be included in a weight ratio of about 70:30 to about 40:60, e.g., about 50:50.

In an implementation, the first compound and the second compound may be included as a host of a light emitting layer, e.g., a phosphorescent host.

The aforementioned composition for an organic optoelectronic device may be formed by a dry film forming method such as chemical vapor deposition.

Hereinafter, an organic optoelectronic device including the aforementioned composition for an organic optoelectronic device is described.

The organic optoelectronic device may be a suitable device to convert electrical energy into photoenergy and vice versa, and may be, e.g., an organic photoelectric device, an organic light emitting diode, an organic solar cell, or an organic photo-conductor drum.

Herein, an organic light emitting diode as one example of an organic optoelectronic device is described referring to drawings.

Figure 2:
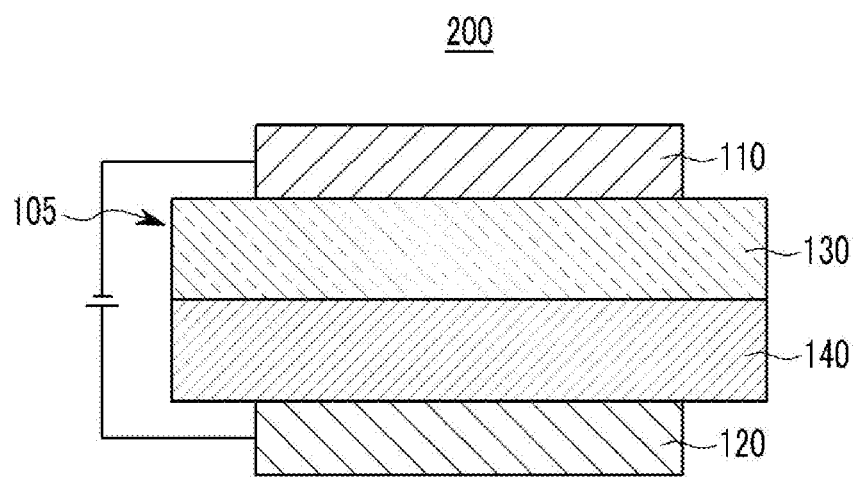

FIGS. 1 and 2 are cross-sectional views of organic light emitting diodes according to embodiments.

Referring to FIG. 1, an organic light emitting diode 100 according to an embodiment includes an anode 120 and a cathode 110 facing each other and an organic layer 105 between the anode 120 and cathode 110.

The anode 120 may be made of a conductor having a large work function to help hole injection, and may be, e.g., a metal, a metal oxide, or a conductive polymer. The anode 120 may be, e.g., a metal such as nickel, platinum, vanadium, chromium, copper, zinc, gold, or the like or an alloy thereof; a metal oxide such as zinc oxide, indium oxide, indium tin oxide (ITO), indium zinc oxide (IZO), or the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, or polyaniline.

The cathode 110 may be made of a conductor having a small work function to help electron injection, and may be, e.g., a metal, a metal oxide, or a conductive polymer. The cathode 110 may be for example a metal such as magnesium, calcium, sodium, potassium, titanium, indium, yttrium, lithium, gadolinium, aluminum silver, tin, lead, cesium, barium, or the like, or an alloy thereof, a multi-layer structure material such as LiF/Al, $LiO_2$/Al, LiF/Ca, LiF/Al, or $BaF_2$/Ca.

The organic layer 105 may include the aforementioned composition for an organic photoelectronic device.

The organic layer 105 may include the light emitting layer 130, and the light emitting layer 130 may include the aforementioned composition for an organic optoelectronic device.

The light emitting layer 130 may include, e.g., the aforementioned composition for an organic photoelectronic device as a phosphorescent host.

In addition to the aforementioned host, the light emitting layer may further include one or more compounds.

The light emitting layer may further include a dopant. The dopant may be, e.g., a phosphorescent dopant, for example a red, green. or blue phosphorescent dopant, and may be, e.g., a red phosphorescent dopant.

The composition for an organic optoelectronic device further including a dopant may be, e.g., a red light emitting composition.

The dopant may be mixed with the compound for an organic photoelectronic device or composition for an organic photoelectronic device in a small amount to cause light emission, and may be generally a material such as a metal complex that emits light by multiple excitation into a triplet or more. The dopant may be, e.g., an inorganic, organic, or organic/inorganic compound, and one or more types thereof may be used.

Examples of the dopant may include a phosphorescent dopant and examples of the phosphorescent dopant may include an organometal compound including Ir, Pt, Os, Ti, Zr, Hf, Eu, Tb, Tm, Fe, Co, Ni, Ru, Rh, Pd, or a combination thereof. The phosphorescent dopant may be, e.g., a compound represented by Chemical Formula Z.

$$L^5MX^2 \qquad \text{[Chemical Formula Z]}$$

In Chemical Formula Z, M may be a metal, and $L^5$ and $X^2$ may each independently be a ligand to form a complex compound with M.

The M may be, e.g., Ir, Pt, Os, Ti, Zr, Hf, Eu, Tb, Tm, Fe, Co, Ni, Ru, Rh, Pd, or a combination thereof, and $L^5$ and $X^2$ may be, e.g., a bidendate ligand.

The organic layer may further include an auxiliary layer in addition to the light emitting layer.

The auxiliary layer may be, e.g., a hole auxiliary layer 140.

Referring to FIG. 2, the organic light emitting diode 200 may further include a hole auxiliary layer 140 in addition to the light emitting layer 130. The hole auxiliary layer 140 may help further increase hole injection and/or hole mobility and may help block electrons between the anode 120 and the light emitting layer 130.

The hole auxiliary layer 140 may include, e.g., a compound of the following Group C.

In an implementation, the hole auxiliary layer 140 may include a hole transport layer between the anode 120 and the light emitting layer 130 and a hole transport auxiliary layer between the light emitting layer 130 and the hole transport layer and at least one of the compounds of Group C may be included in the hole transport auxiliary layer.

[Group C]
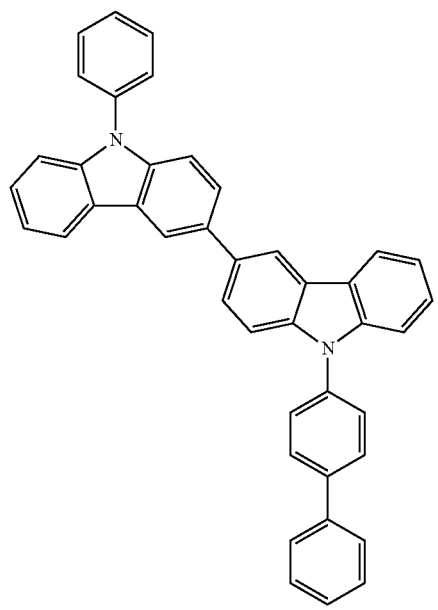
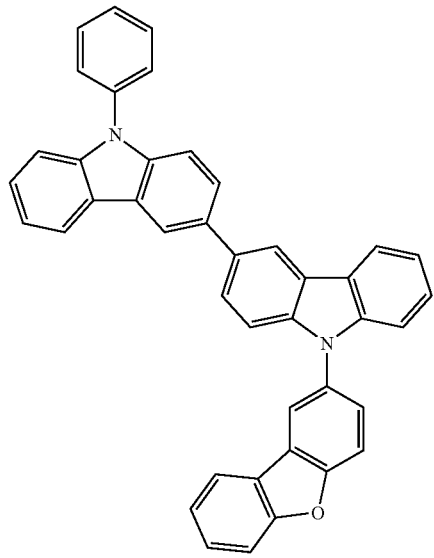
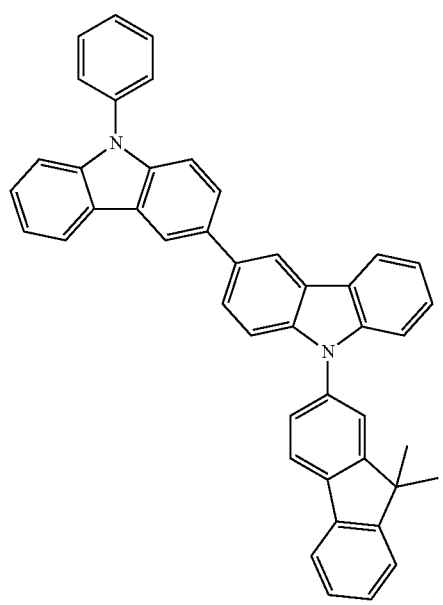
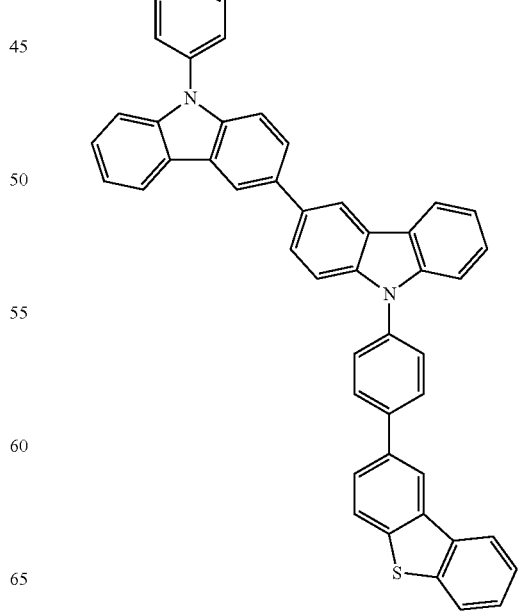

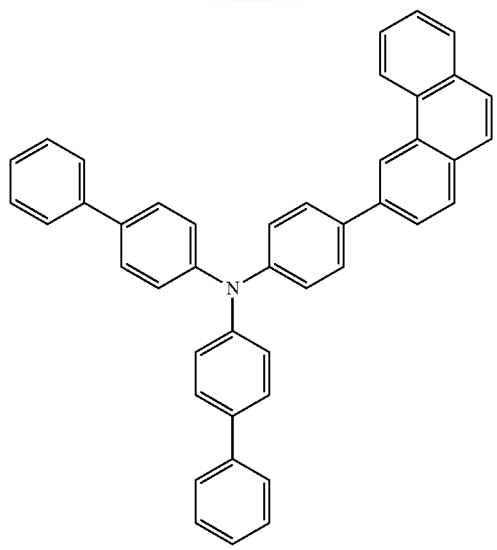
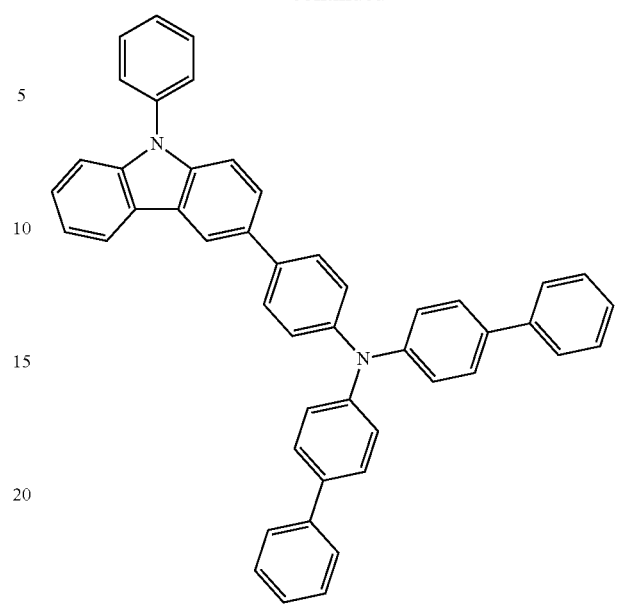
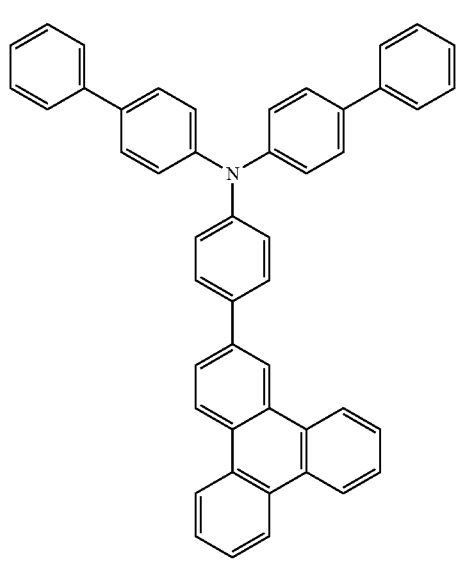
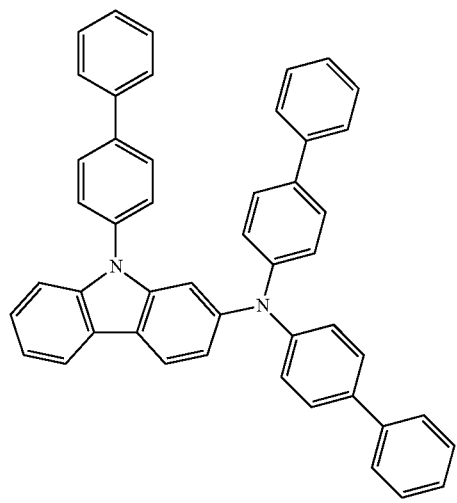
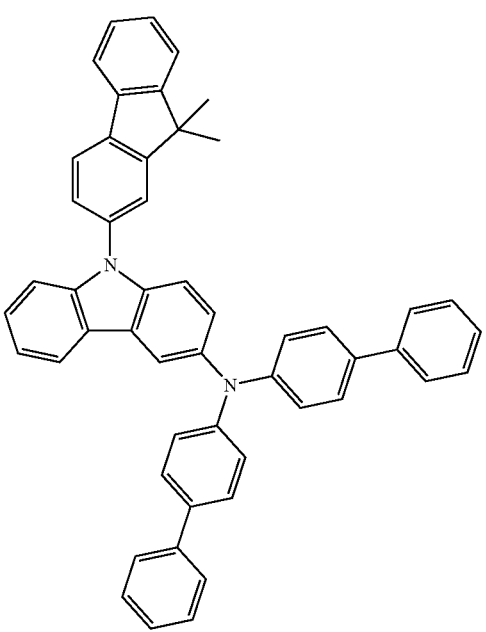

193
-continued
194
-continued
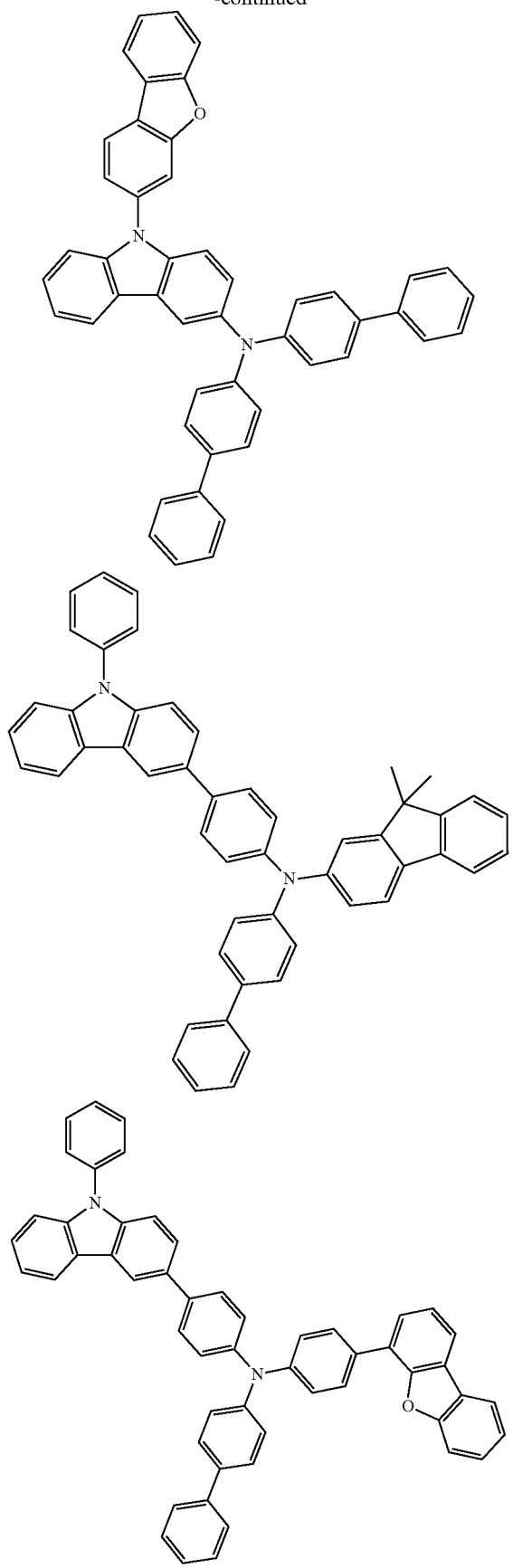
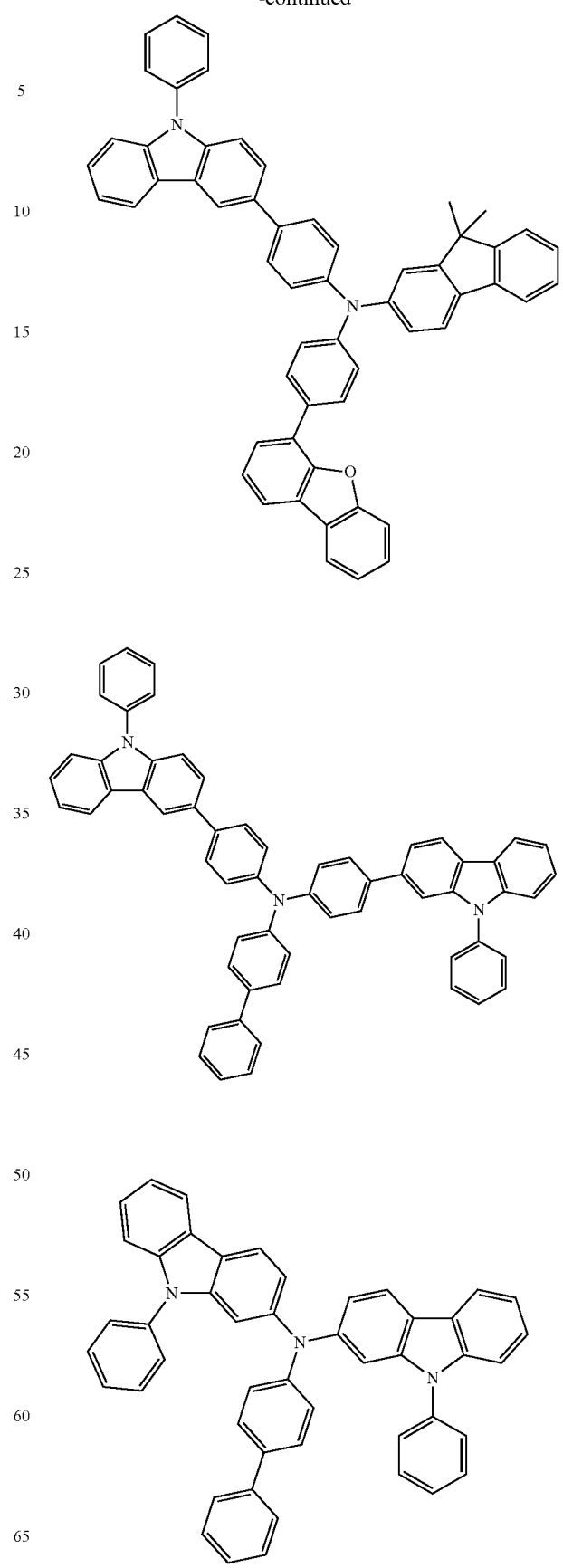

195
-continued
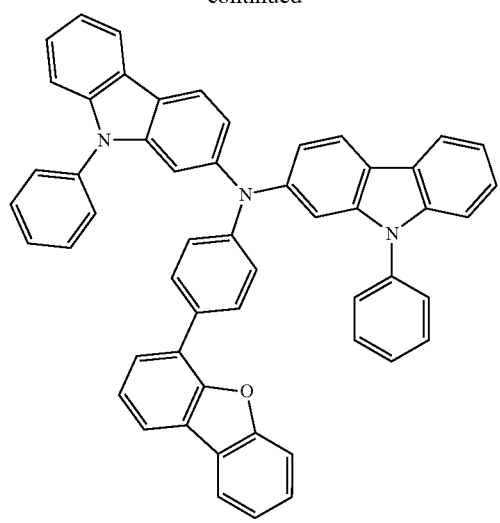
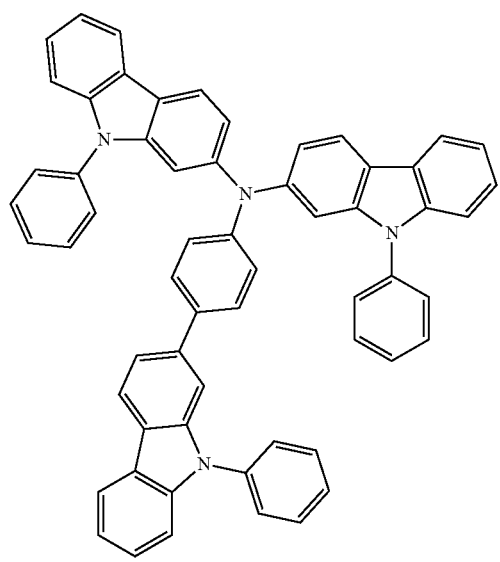
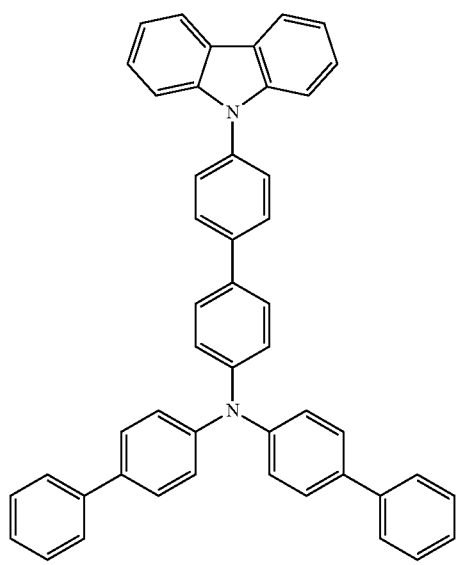
196
-continued
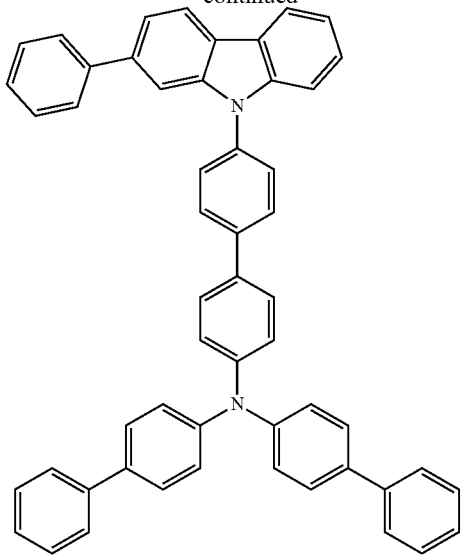
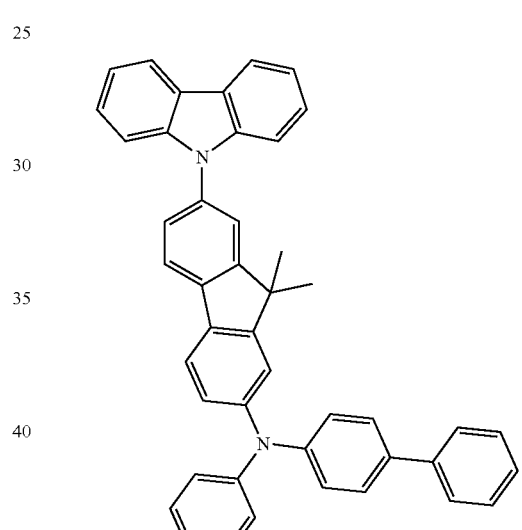
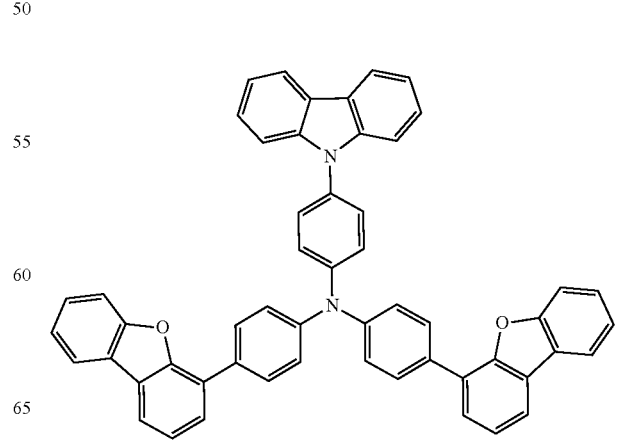

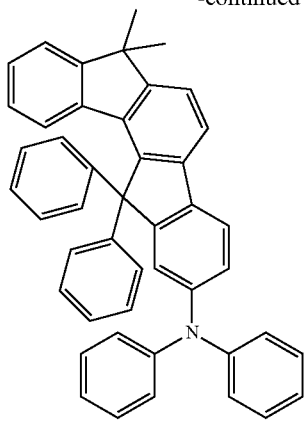
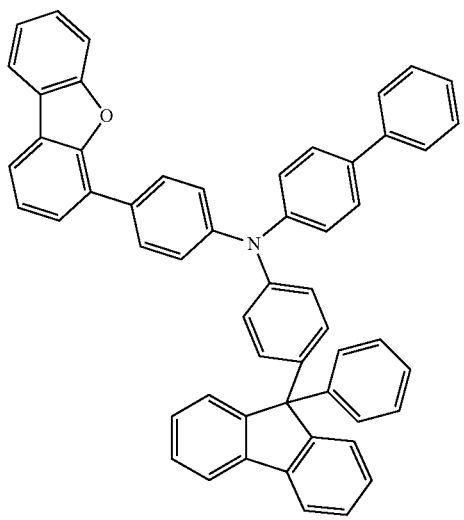
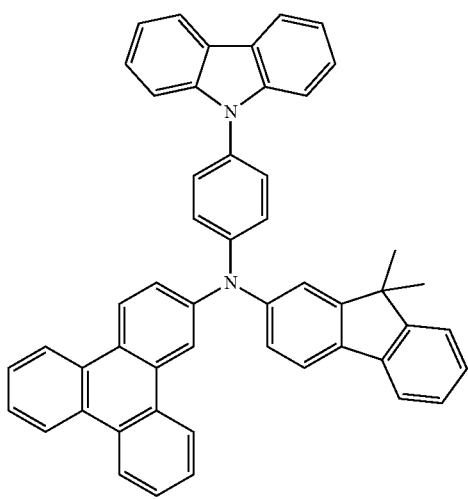
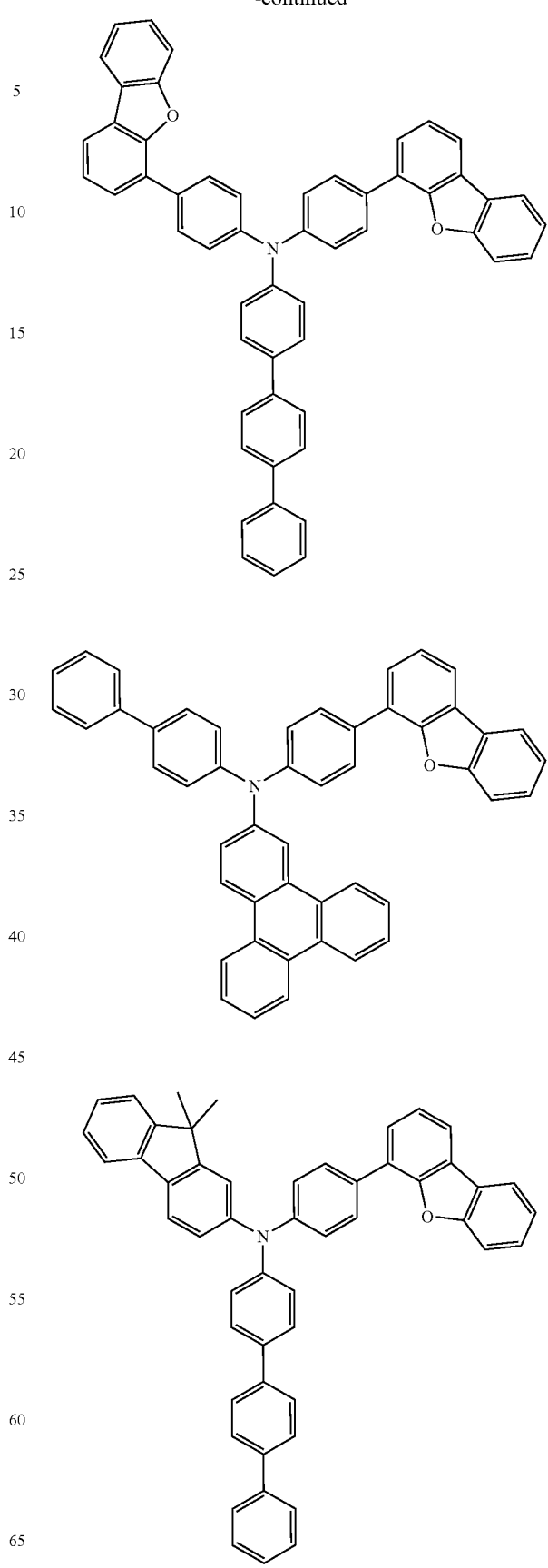

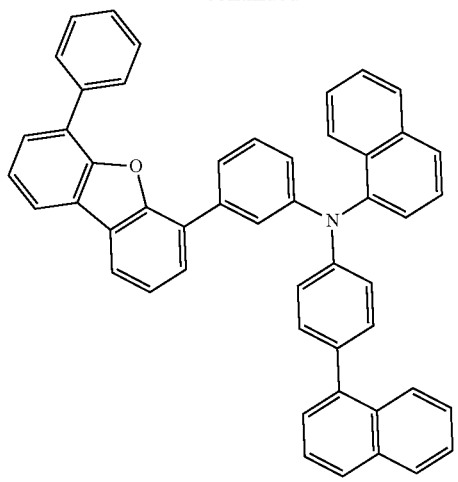
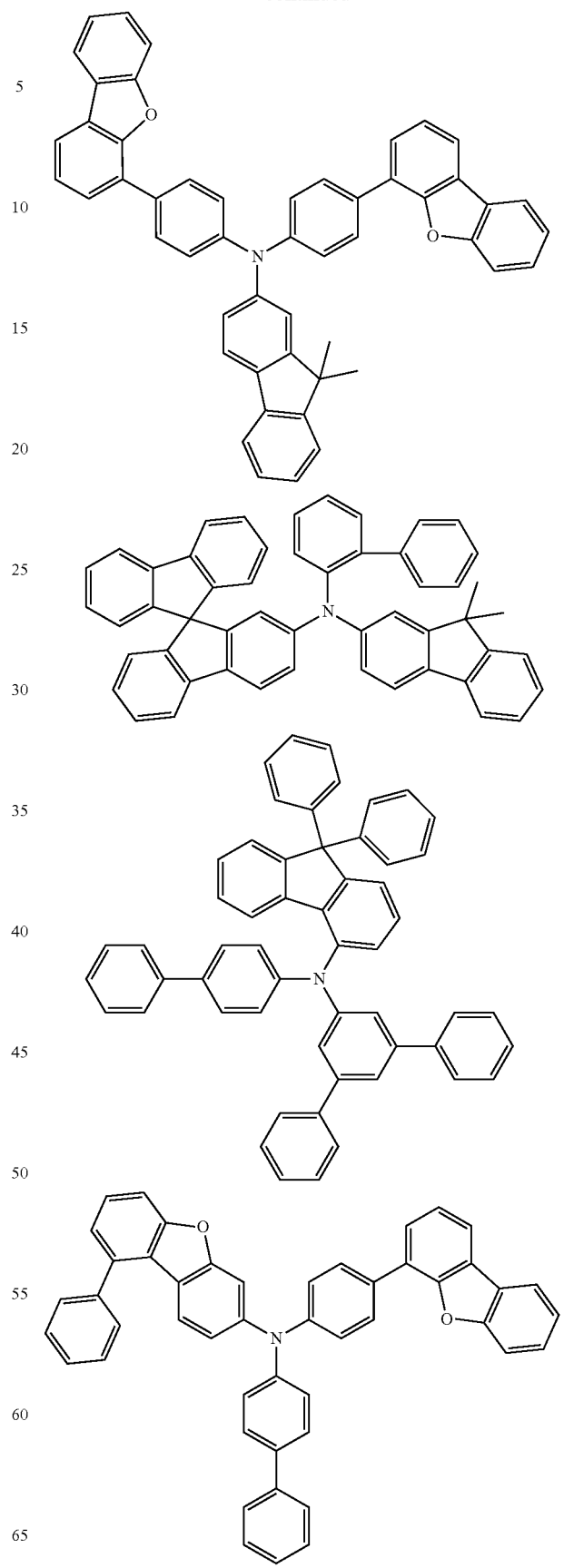

201
-continued
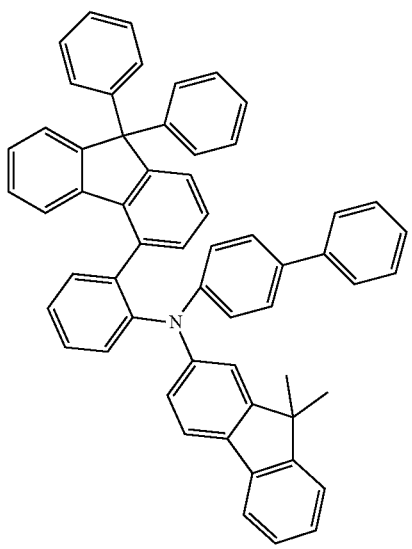
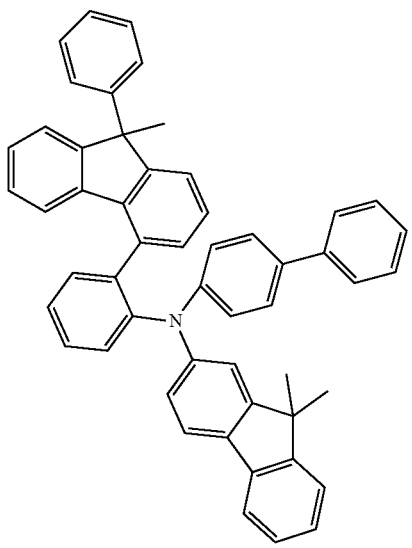
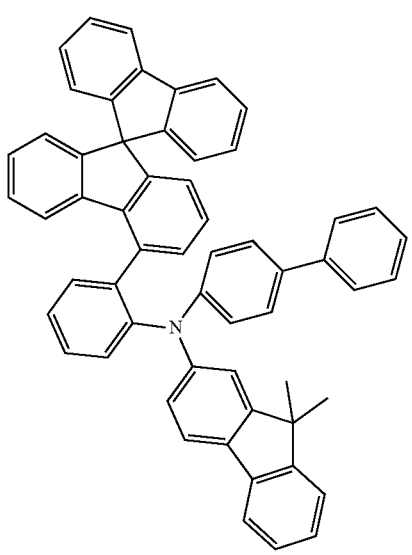
202
-continued
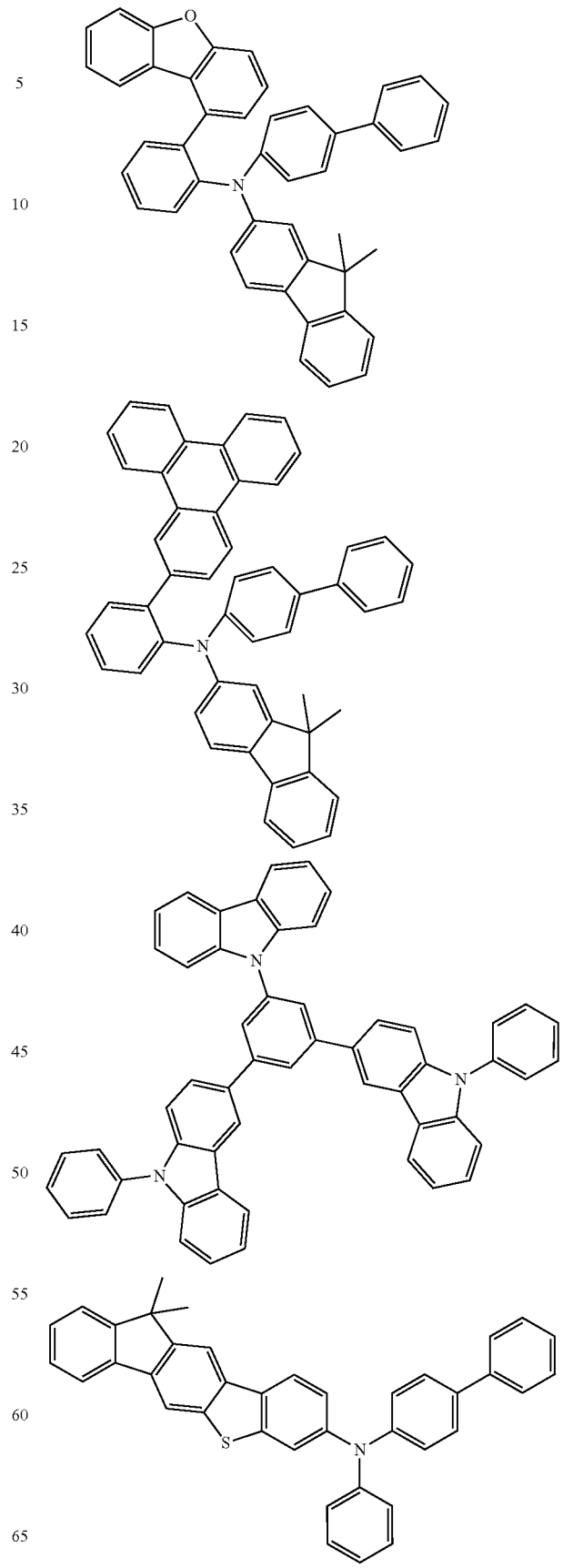

203
-continued
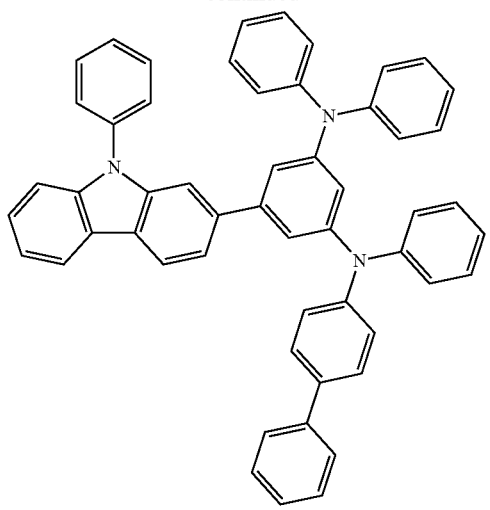
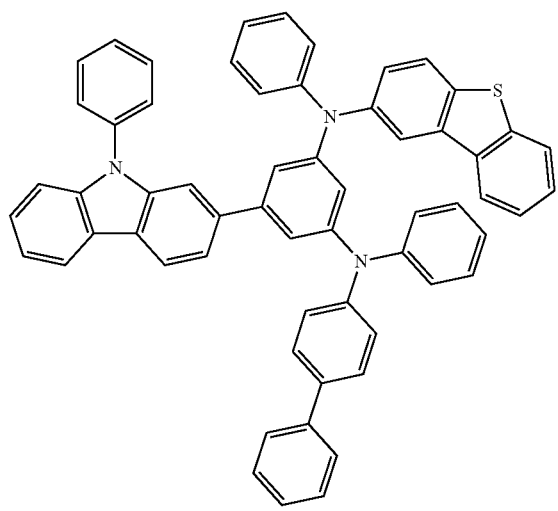
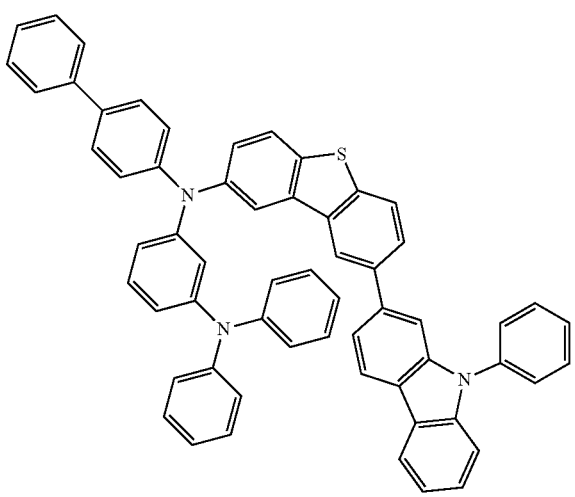
204
-continued
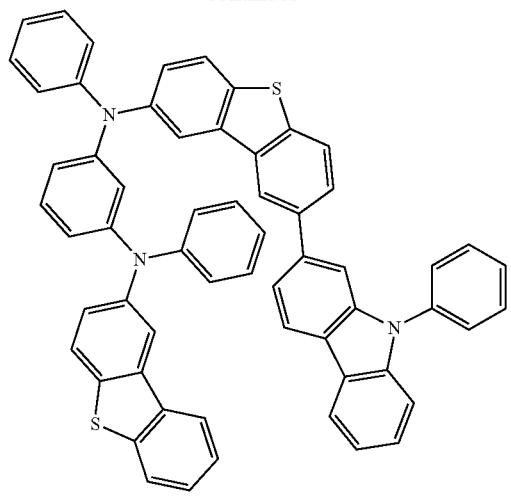
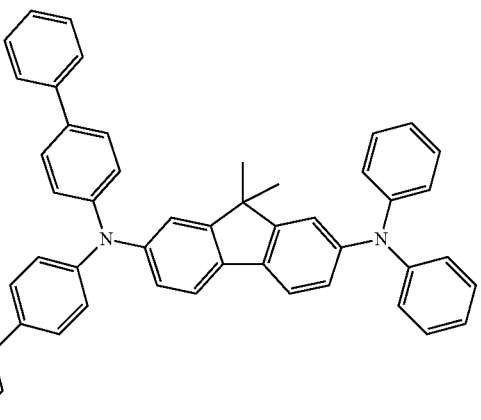

205
-continued
206
-continued
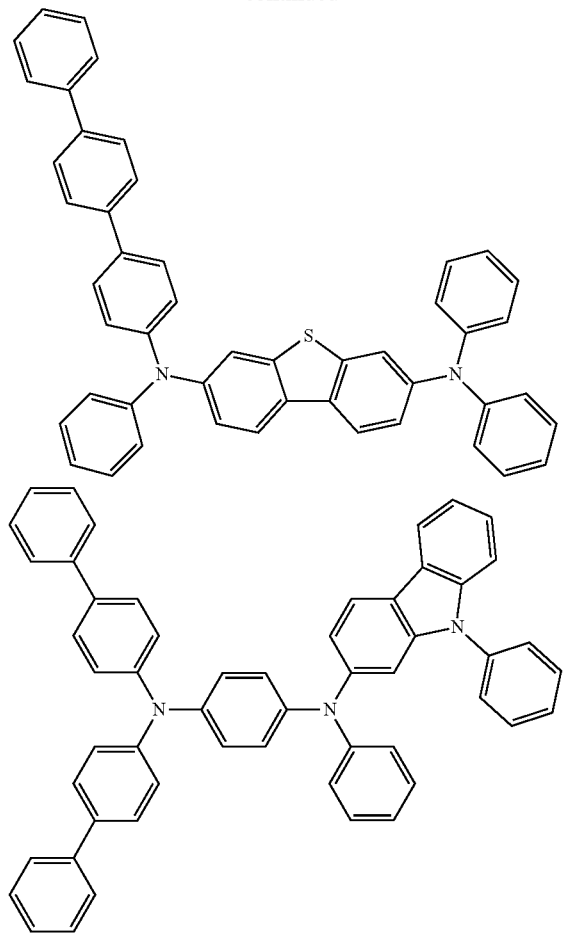
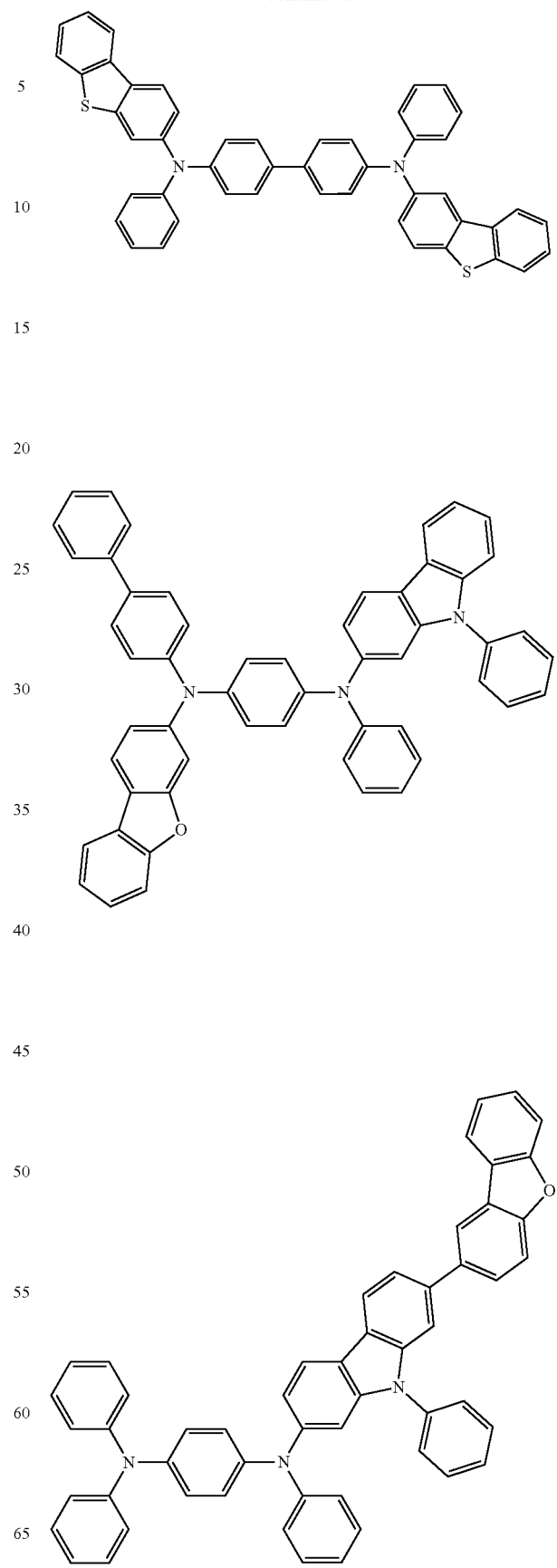

207
-continued
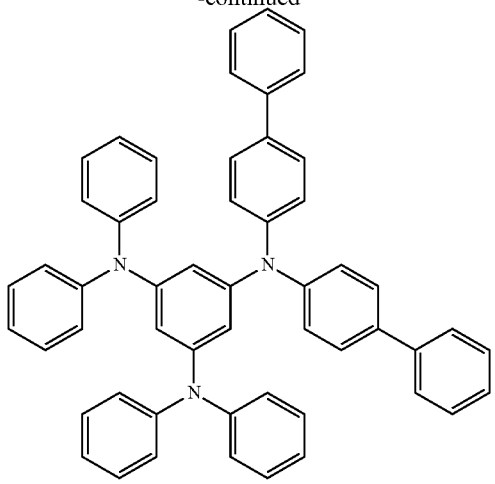
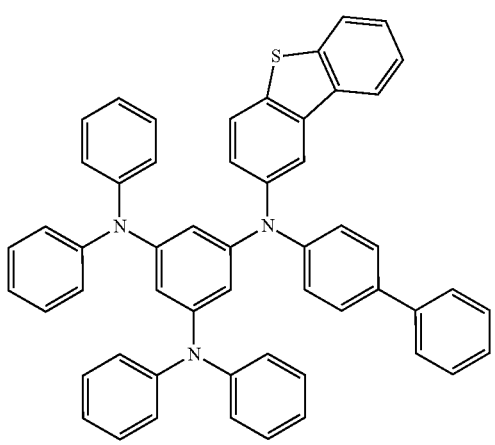
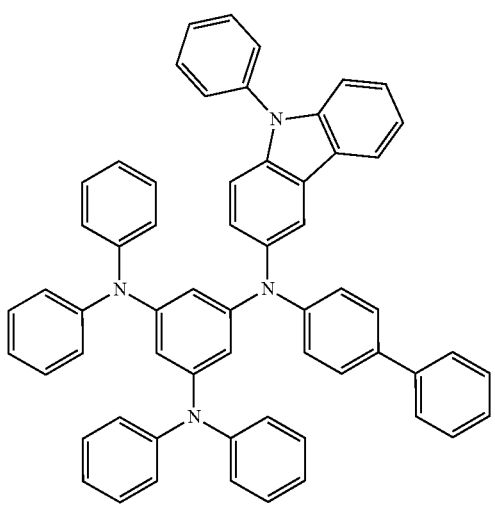
208
-continued
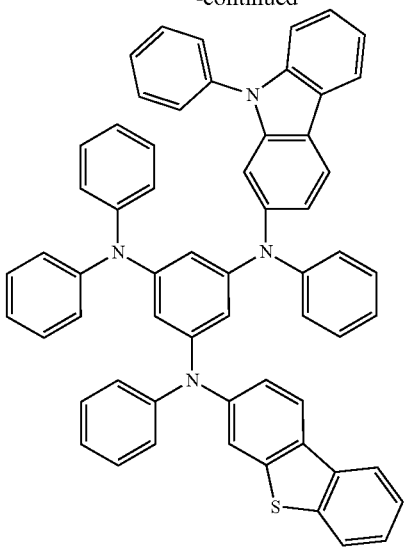
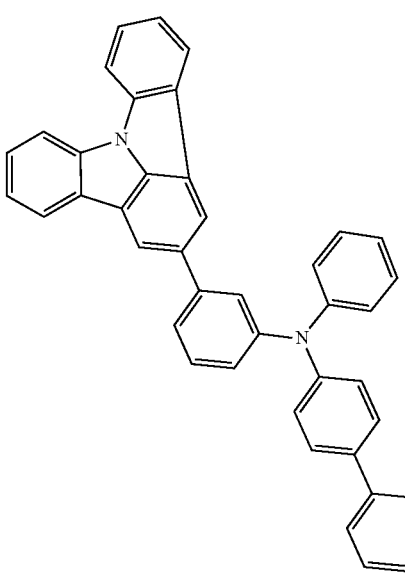
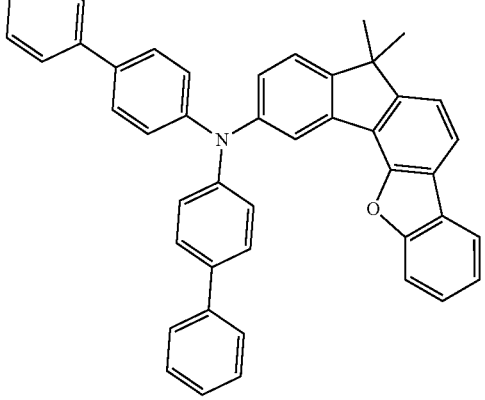

209
-continued
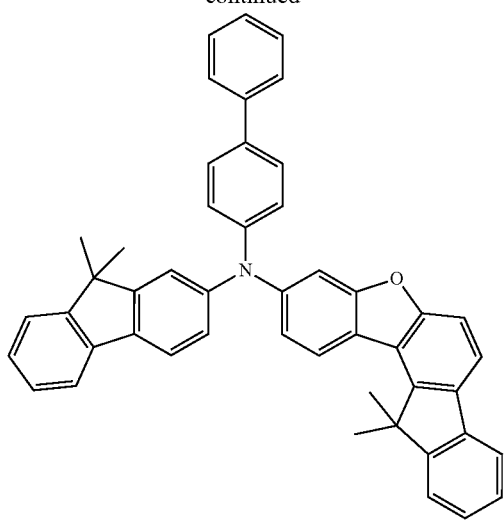
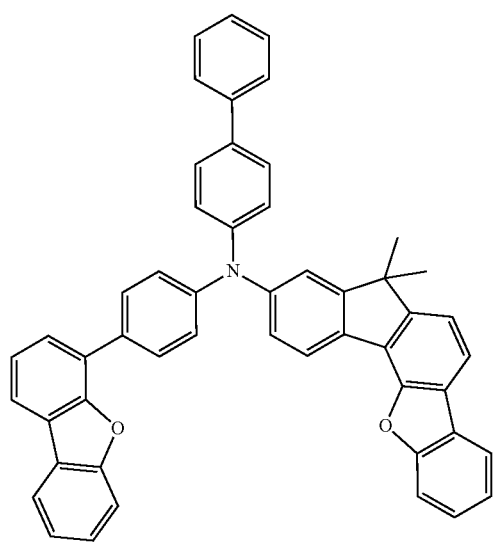
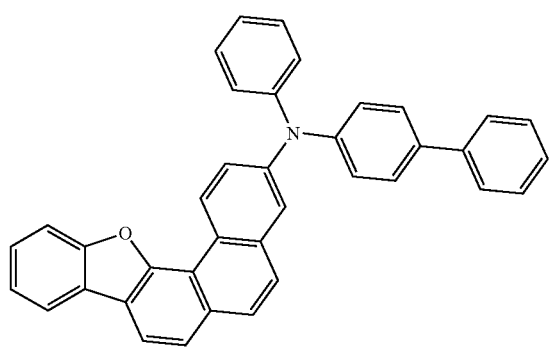
210
-continued
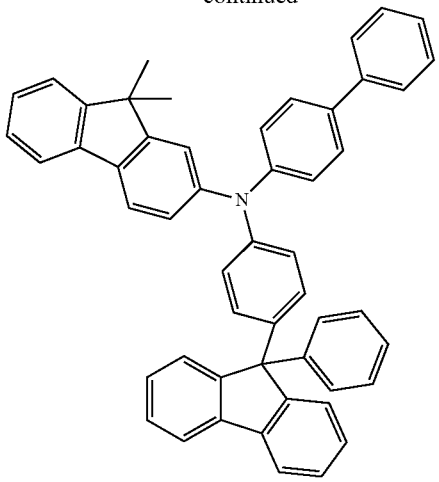
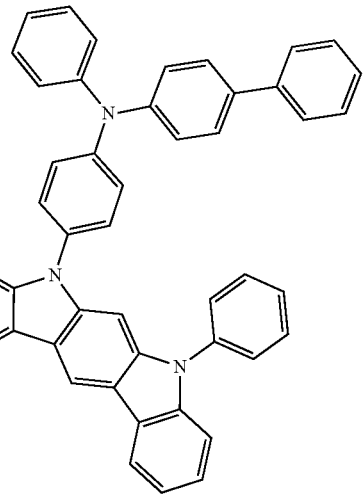
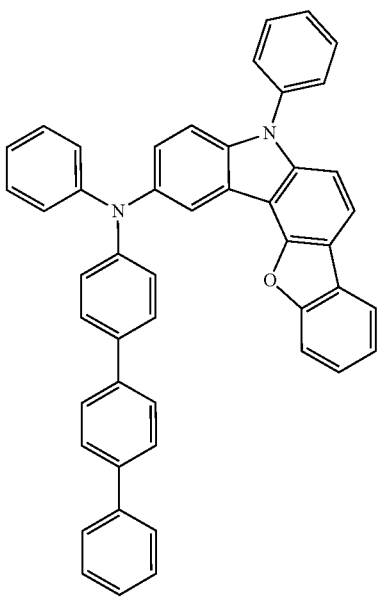

211
-continued

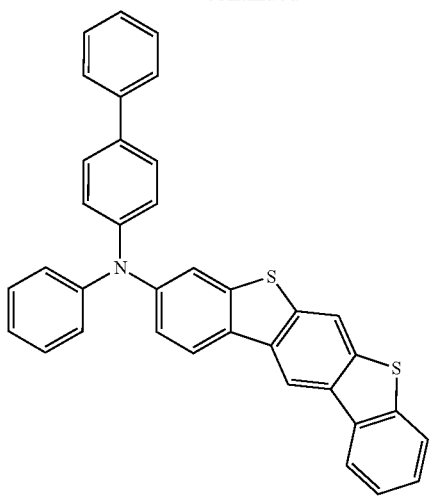

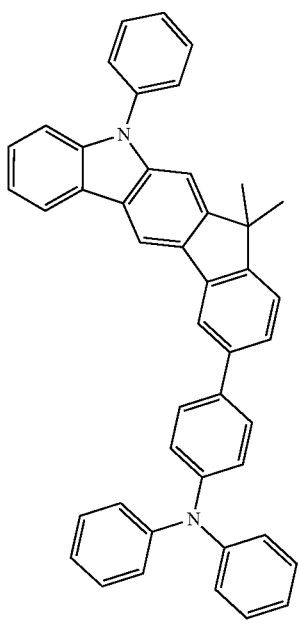

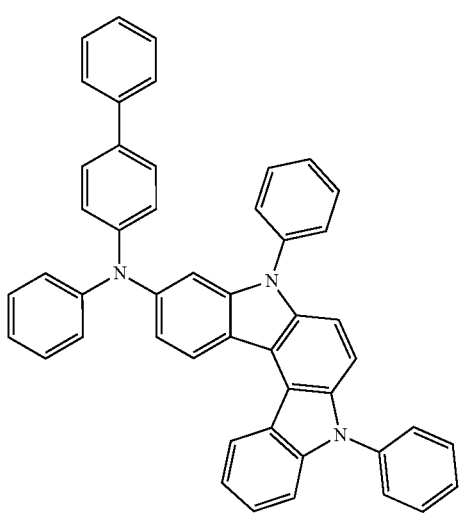

212
-continued

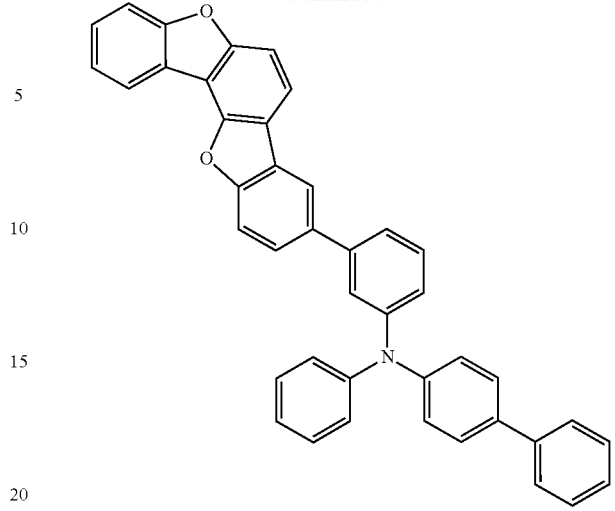

In addition to the aforementioned compounds, other suitable compounds may also be used for the hole transport auxiliary layer.

In an implementation, the organic layer 105 in FIG. 1 or 2 may be an organic light emitting diode further including an electron transport layer, an electron injection layer, or a hole injection layer.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

Hereinafter, the embodiments are illustrated in more detail with reference to examples. However, these examples are exemplary.

Hereinafter, starting materials and reactants used in Examples and Synthesis Examples were purchased from Sigma-Aldrich Co. Ltd., TCI Inc., Tokyo chemical industry or P&H tech as far as there in no particular comment or were synthesized by known methods.

(Preparation of Compound for Organic Photoelectronic Device)

A compound was synthesized through the following steps.

Synthesis of First Compound for Organic Optoelectronic Device

Synthesis Example 1: Synthesis of Compound A-2

[Reaction Scheme 1]

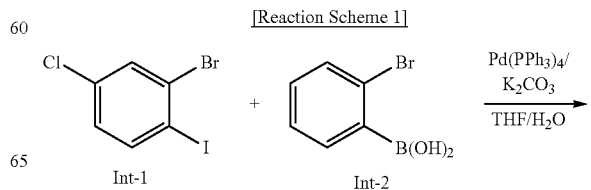

Int-1        Int-2

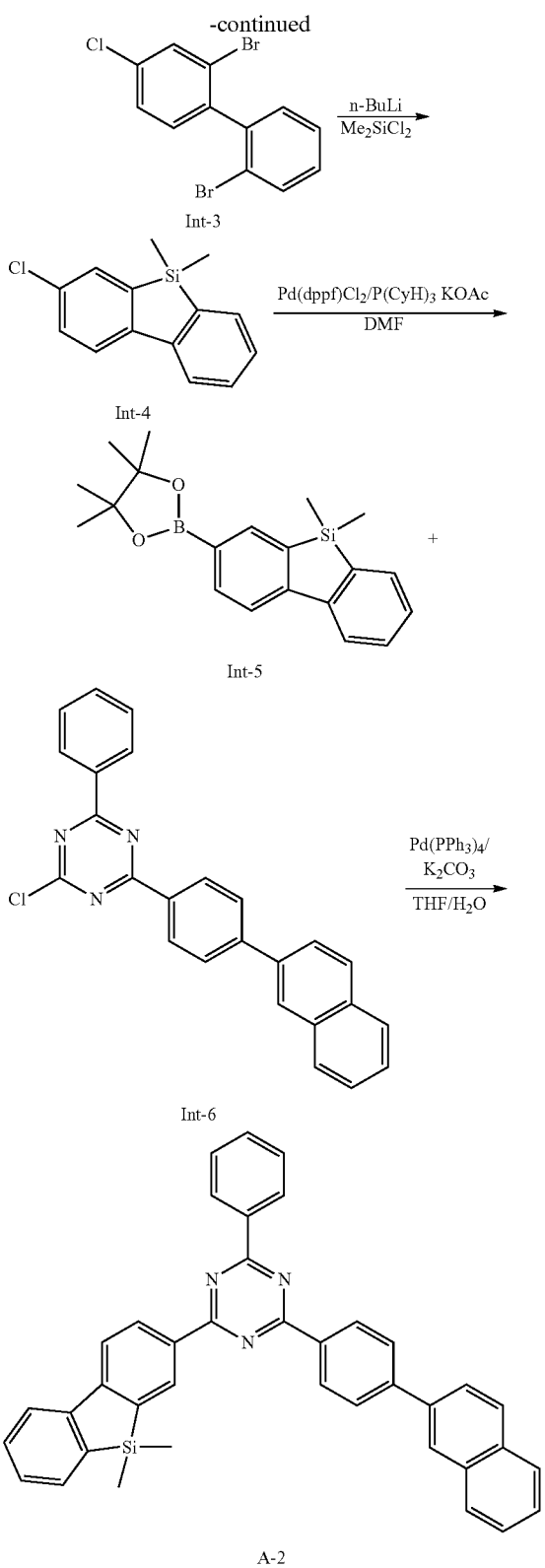

1st step: Synthesis of Intermediate Int-3

Intermediate Int-1 (100 g, 315.11 mmol) was dissolved in 1.0 L of tetrahydrofuran (THF), and Intermediate Int-2 (63.28 g, 315.11 mmol) and tetrakis(triphenylphosphine) palladium (10.92 g, 9.45 mmol) were added thereto and then, stirred. Subsequently, potassium carbonate (108.88 g, 787.77 mmol) saturated in 500 ml of water was added thereto and then, heated and refluxed at 80° C. for 12 hours. When a reaction was complete, water was added to the reaction solution and then, extracted with ethyl acetate (EA), treated with magnesium sulfate anhydrous to remove moisture, filtered, and concentrated under a reduced pressure. The obtained residue was separated and purified through flash column chromatography to obtain 86.24 g (79%) of Intermediate Int-3.

2nd Step: Synthesis of Intermediate Int-4

Intermediate Int-3 (86.24 g 248.92 mmol) was dissolved in 600 mL of tetrahydrofuran (THF), and an internal temperature thereof was decreased down to −78° C. n-BuLi (288.75 ml, 721.88 mmol) was added thereto in a dropwise fashion, while the internal temperature was maintained at −78° C., and then, stirred at the same temperature for 1 hour.

Dichlorodimethylsilane (104.31 ml, 871.24 mmol) was slowly added thereto in a dropwise fashion at −78° C. and then, stirred at ambient temperature for 12 hours. When a reaction was complete, water was added to the reaction solution and then, extracted with ethyl acetate (EA), treated with magnesium sulfate anhydrous to remove moisture, filtered, and concentrated under a reduced pressure. The obtained residue was separated and purified through flash column chromatography to obtain 43.12 g (71%) of Int-4.

3rd Step: Synthesis of Intermediate Int-5

The intermediate, Int-4 (42.0 g, 171.58 mmol) was dissolved in 500 ml of dimethyl formamide (DMF) under a nitrogen environment, and bis(pinacolato)diboron (65.35 g, 257.36 mmol), (1,1'-bis(diphenylphosphine)ferrocene)dichloropalladium (II) (7.01 g, 8.58 mmol), tricyclohexylphosphine (14.43 g, 25.74 mmol) and potassium acetate (33.68 g, 343.15 mmol) were added thereto and then, heated and refluxed at 150° C. for 24 hours. When a reaction was complete, water was added to the reaction solution, and the mixture was filtered and then, dried in a vacuum oven. The obtained residue was separated and purified through column chromatography to obtain 45 g (78%) of Intermediate Int-5.

4th Step: Synthesis of Compound A-2

Intermediate Int-5 (4.18 g 12.44 mmol) was dissolved in 40 mL of tetrahydrofuran (THF), and the intermediate, Int-6 (5.00 g, 12.20 mmol) and tetrakis(triphenylphosphine) palladium (0.42 g, 0.37 mmol) were added thereto and then, stirred. Subsequently, potassium carbonate (4.21 g, 30.49 mmol) saturated in 20 ml of water was added thereto and then, heated and refluxed at 80° C. for 12 hours. When a reaction was complete, an organic layer was separated therefrom and concentrated. The obtained mixture was added to 150 mL of methanol, and a solid crystallized therein was filtered, dissolved in monochlorobenzene, filtered through silica gel/Celite, and then, after removing an appropriate amount of an organic solvent, recrystallized with methanol to obtain 4.85 g (70%) of Compound A-2.

calcd. C39H29N3Si:C, 82.50; H, 5.15; N, 7.40; Si, 4.95; found: C, 82.50; H, 5.14; N, 7.41; Si, 4.95.

Synthesis Examples 2 to 21

Final products described in Table 3 were synthesized as an example according to Chemical Formula 1 according to a similar method to that of the 4th step of Synthesis Example 1 except that at least one of the intermediates of Int-5 and Int-6 was changed into Intermediate A shown in Table 1 and Intermediate B shown in Table 2.

TABLE 1
<Intermediate A>
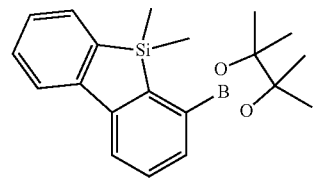
Int-7
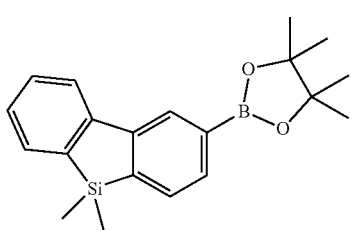 [SMILES: CC1(C)OB(c2ccc3c(c2)-c2ccccc2[Si]3(C)C)OC1(C)C]
Int-8
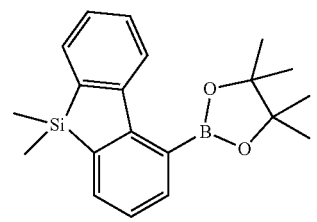
Int-9
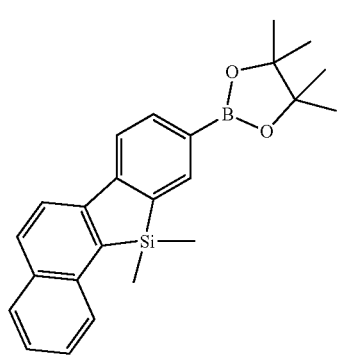 [SMILES: CC1(C)OB(c2ccc3c(c2)[Si](C)(C)c2c-3ccc3ccccc23)OC1(C)C]
Int-10
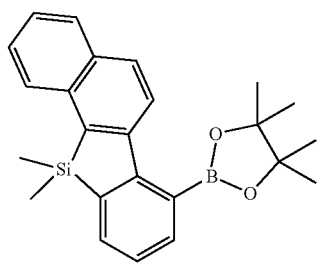 [SMILES: CC1(C)OB(c2cccc3c2-c2ccc4ccccc4c2[Si]3(C)C)OC1(C)C]
Int-11
TABLE 1-continued
<Intermediate A>
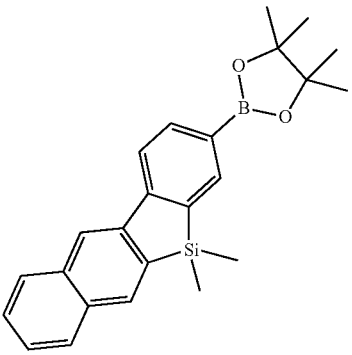 [SMILES: CC1(C)OB(c2ccc3c(c2)[Si](C)(C)c2cc4ccccc4cc2-3)OC1(C)C]
Int-12
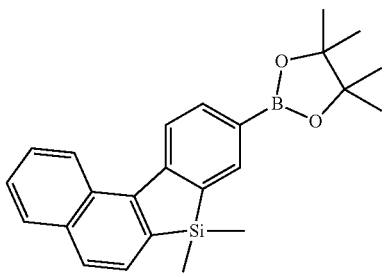 [SMILES: CC1(C)OB(c2ccc3c(c2)[Si](C)(C)c2ccc4ccccc4c2-3)OC1(C)C]
Int-13
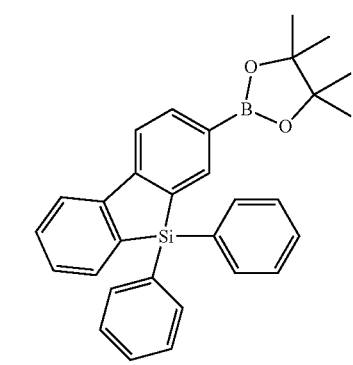 [SMILES: CC1(C)OB(c2ccc3c(c2)[Si](c2ccccc2)(c2ccccc2)c2ccccc2-3)OC1(C)C]
Int-14
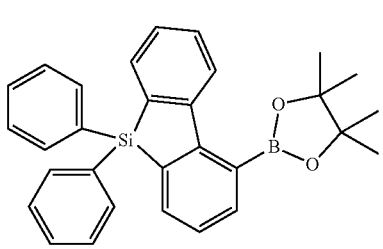 [SMILES: CC1(C)OB(c2cccc3c2-c2ccccc2[Si]3(c2ccccc2)c2ccccc2)OC1(C)C]
Int-15

TABLE 2

<Intermediate B>

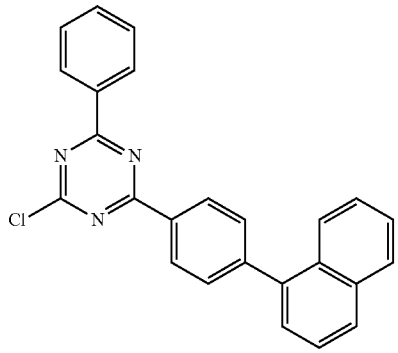 [SMILES: Clc1nc(-c2ccccc2)nc(-c2ccc(-c3cccc4ccccc34)cc2)n1]

Int-16

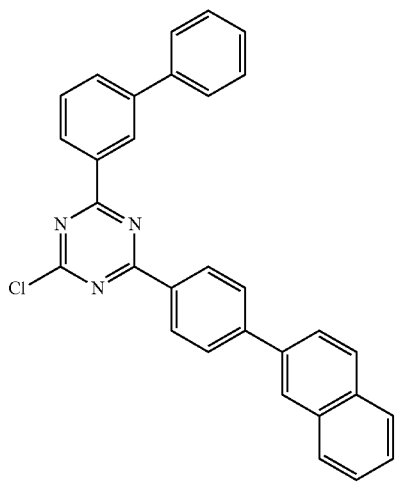 [SMILES: Clc1nc(-c2ccc(-c3ccc4ccccc4c3)cc2)nc(-c2cccc(-c3ccccc3)c2)n1]

Int-17

TABLE 2-continued

<Intermediate B>

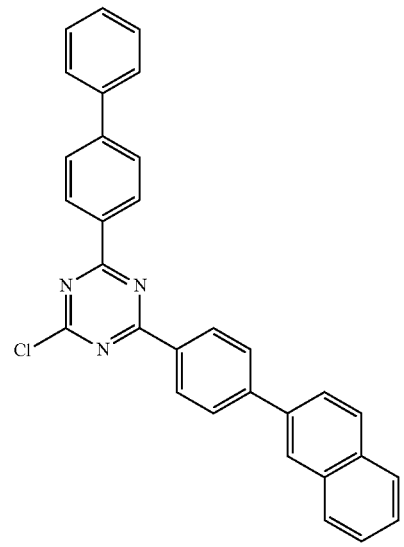 [SMILES: Clc1nc(-c2ccc(-c3ccccc3)cc2)nc(-c2ccc(-c3ccc4ccccc4c3)cc2)n1]

Int-18

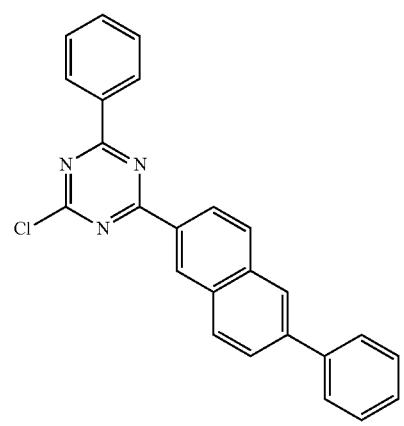 [SMILES: Clc1nc(-c2ccccc2)nc(-c2ccc3cc(-c4ccccc4)ccc3c2)n1]

Int-19

TABLE 3

<Final Products>

| Synthesis Examples | Int. A | Int. B | Final products | Yield amount (Yield) | Property data of final products |
|---|---|---|---|---|---|
| Synthesis Example 2 | Int-7 | Int-6 | Compound A-1 | 4.54 g (73%) | calcd. C39H29N3Si: C, 82.50; H, 5.15; N, 7.40; Si, 4.95 found: C, 82.50; H, 5.15; N, 7.40; Si, 4.95 |
| Synthesis Example 3 | Int-8 | Int-6 | Compound A-3 | 5.08 g (69%) | calcd. C39H29N3Si: C, 82.50; H, 5.15; N, 7.40; Si, 4.95 found: C, 82.50; H, 5.14; N, 7.41; Si, 4.95 |
| Synthesis Example 4 | Int-9 | Int-6 | Compound A-4 | 4.54 g (73%) | calcd. C39H29N3Si: C, 82.50; H, 5.15; N, 7.40; Si, 4.95 found: C, 82.51; H, 5.14; N, 7.40; Si, 4.95 |
| Synthesis Example 5 | Int-5 | Int-16 | Compound A-6 | 4.96 g (76%) | calcd. C39H29N3Si: C, 82.50; H, 5.15; N, 7.40; Si, 4.95; found: C, 82.51; H, 5.14; N, 7.41; Si, 4.94 |
| Synthesis Example 6 | Int-9 | Int-16 | Compound A-8 | 5.44 g (74%) | calcd. C39H29N3Si: C, 82.50; H, 5.15; N, 7.40; Si, 4.95 found: C, 82.50; H, 5.15; N, 7.40; Si, 4.95 |
| Synthesis Example 7 | Int-5 | Int-17 | Compound A-10 | 4.12 g (72%) | calcd. C45H33N3Si C, 83.95; H, 5.17; N, 6.53; Si, 4.36 found: C, 83.94; H, 5.16; N, 6.53; Si, 4.36 |
| Synthesis Example 8 | Int-9 | Int-17 | Compound A-12 | 5.73 g (70%) | calcd. C45H33N3Si C, 83.95; H, 5.17; N, 6.53; Si, 4.36 found: C, 83.95; H, 5.16; N, 6.53; Si, 4.37 |
| Synthesis Example 9 | Int-5 | Int-18 | Compound A-18 | 4.84 g (75%) | calcd. C45H33N3Si C, 83.95; H, 5.17; N, 6.53; Si, 4.36 found: C, 83.95; H, 5.17; N, 6.53; Si, 4.36 |
| Synthesis Example 10 | Int-5 | Int-19 | Compound A-34 | 5.04 g (68%) | calcd. C39H29N3Si: C, 82.50; H, 5.15; N, 7.40; Si, 4.95; found: C, 82.50; H, 5.14; N, 7.41; Si, 4.95 |
| Synthesis Example 11 | Int-10 | Int-6 | Compound B-2 | 5.27 g (80%) | calcd. C43H31N3Si: C, 83.60; H, 5.06; N, 6.80; Si, 4.55; found: C, 83.61; H, 5.05; N, 6.80; Si, 4.55 |

TABLE 3-continued

<Final Products>

| Synthesis Examples | Int. A | Int. B | Final products | Yield amount (Yield) | Property data of final products |
|---|---|---|---|---|---|
| Synthesis Example 12 | Int-11 | Int-6 | Compound B-4 | 4.80 g (76%) | calcd. C43H31N3Si: C, 83.60; H, 5.06; N, 6.80; Si, 4.55; found: C, 83.60; H, 5.05; N, 6.80; Si, 4.55 |
| Synthesis Example 13 | Int-10 | Int-17 | Compound B-10 | 4.00 g (72%) | calcd. C49H35N3Si: C, 84.81; H, 5.08; N, 6.06; Si, 4.05; found: C, 84.82; H, 5.08; N, 6.06; Si, 4.03 |
| Synthesis Example 14 | Int-11 | Int-17 | Compound B-12 | 6.74 g (69%) | calcd. C49H35N3Si: C, 84.81; H, 5.08; N, 6.06; Si, 4.05; found: C, 84.82; H, 5.08; N, 6.05; Si, 4.04 |
| Synthesis Example 15 | Int-12 | Int-6 | Compound C-2 | 4.81 g (72%) | calcd. C43H31N3Si: C, 83.60; H, 5.06; N, 6.80; Si, 4.55; found: C, 83.60; H, 5.06; N, 6.80; Si, 4.55 |
| Synthesis Example 16 | Int-12 | Int-17 | Compound C-10 | 5.36 g (76%) | calcd. C49H35N3Si: C, 84.81; H, 5.08; N, 6.06; Si, 4.05; found: C, 84.82; H, 5.07; N, 6.05; Si, 4.06 |
| Synthesis Example 17 | Int-13 | Int-6 | Compound D-2 | 4.39 g (72%) | calcd. C43H31N3Si: C, 83.60; H, 5.06; N, 6.80; Si, 4.55; found: C, 83.61; H, 5.05; N, 6.80; Si, 4.55 |
| Synthesis Example 18 | Int-13 | Int-17 | Compound D-10 | 8.30 g (78%) | calcd. C49H35N3Si: C, 84.81; H, 5.08; N, 6.06; Si, 4.05; found: C, 84.81; H, 5.06; N, 6.06; Si, 4.05 |
| Synthesis Example 19 | Int-14 | Int-6 | Compound E-2 | 5.15 g (75%) | calcd. C49H33N3Si: C, 85.06; H, 4.81; N, 6.07; Si, 4.06; found: C, 85.07; H, 4.81; N, 6.07; Si, 4.05 |
| Synthesis Example 20 | Int-15 | Int-6 | Compound E-4 | 4.62 g (77%) | calcd. C49H33N3Si: C, 85.06; H, 4.81; N, 6.07; Si, 4.06; found: C, 85.06; H, 4.81; N, 6.07; Si, 4.06 |
| Synthesis Example 21 | Int-14 | Int-17 | Compound E-10 | 4.85 g (72%) | calcd. C55H37N3Si: C, 86.02; H, 4.86; N, 5.47; Si, 3.66; found: C, 86.03; H, 4.86; N, 5.47; Si, 3.65 |

Synthesis of Second Compound for Organic Optoelectronic Device

Synthesis Example 22: Synthesis of Compound F-5

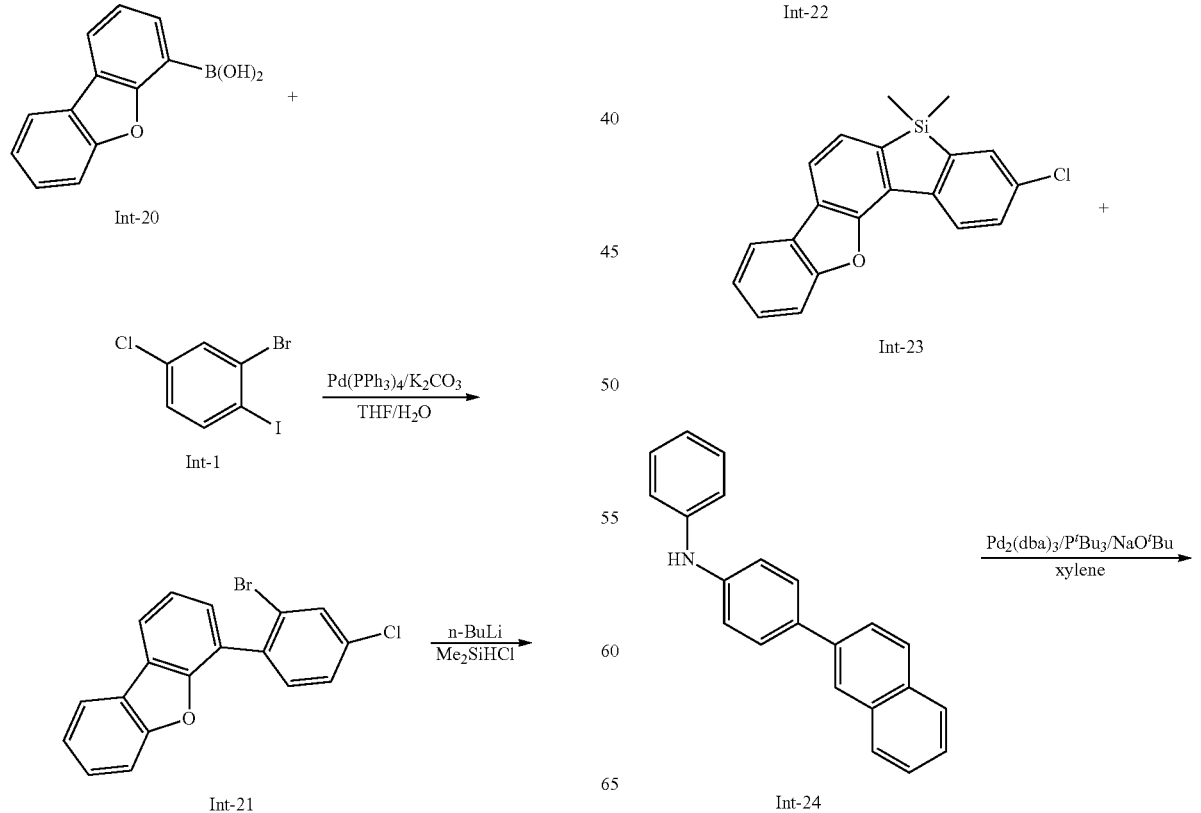

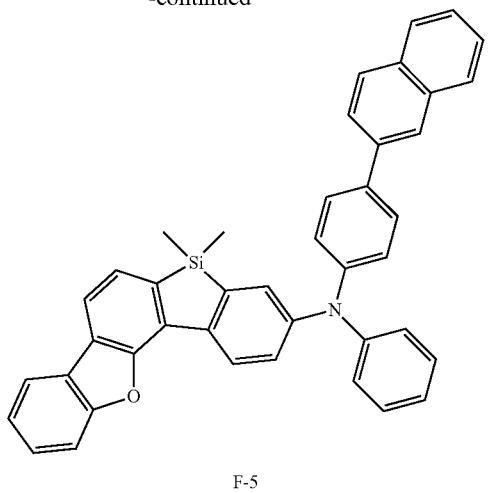

F-5

1st Step: Synthesis of Int-21

Int-1 (100 g, 275.33 mmol) was dissolved in 1.0 L of tetrahydrofuran (THF), and Int-20 (62.79 g, 275.33 mmol) and tetrakis(triphenylphosphine) palladium (9.54 g, 8.26 mmol) were added thereto and then, stirred. Subsequently, potassium carbonate (95.13 g, 688.34 mmol) saturated in 500 ml of water was added thereto and then, heated and refluxed at 80° C. for 12 hours. When a reaction was complete, water was added to the reaction solution and then, extracted with ethyl acetate (EA), treated with magnesium sulfate anhydrous to remove moisture, filtered, and concentrated under a reduced pressure. The obtained residue was separated and purified through flash column chromatography to obtain 71.88 g (73%) of Int-21.

2nd Step: Synthesis of Int-22

Int-21 (71.88 g 192.35 mmol) was dissolved in 670 mL of tetrahydrofuran (THF), and an internal temperature thereof was decreased down to −78° C. n-BuLi (104.5 ml, 261.24 mmol) was slowly added thereto in a dropwise fashion, while the internal temperature of −78° C. was maintained, and then, stirred for one hour at the same temperature.

Subsequently, chlorodimethylsilane (30.64 ml, 281.39 mmol) was slowly added thereto in a dropwise fashion at −78° C. and then, stirred at ambient temperature for 12 hours. When a reaction was complete, water was added to the reaction solution and then, extracted with ethyl acetate (EA), treated with magnesium sulfate anhydrous to remove moisture, filtered, and concentrated under a reduced pressure. The obtained residue was separated and purified through flash column chromatography to obtain 33.86 g (50%) of Int-22.

3rd Step: Synthesis of Int-23

Int-22 (33.80 g, 100.33 mmol) was dissolved in 300 mL of trifluoromethylbenzene, and di-tert-butyl peroxide (56.42 ml, 300.99 mmol) was slowly added thereto in a dropwise fashion. The obtained mixture was heated and refluxed at an internal temperature of 120° C. for 48 hours. When a reaction was complete, the reaction solution was cooled down to ambient temperature, and 200 ml of water was added thereto and then, stirred for 1 hour. The resultant was extracted with ethyl acetate (EA), treated with magnesium sulfate anhydrous to remove moisture, filtered, and concentrated under a reduced pressure. The obtained residue was separated and purified through flash column chromatography to obtain 20.16 g (60%) of Int-23.

4th Step: Synthesis of Compound F-5

2.82 g (8.42 mmol) of Int-23, 2.62 g (8.42 mmol) of Int-24, 2.42 g (25.26 mmol) of sodium t-butoxide, and 0.34 g (0.84 mmol) of tri-tert-butylphosphine were dissolved in 50 ml of xylene, and 0.38 g (0.42 mmol) of Pd$_2$(dba)$_3$ was added thereto and then, refluxed and stirred under a nitrogen atmosphere for 12 hours. When a reaction was complete, an organic layer extracted with xylene and distilled water was dried with anhydrous magnesium sulfate and filtered, and a filtrate therefrom was concentrated under a reduced pressure. A product therefrom was purified through silica gel column chromatography with normal hexane/dichloromethane (in a volume ratio of 2:1) to obtain 3.7 g (Yield: 74%) of Compound F-5.

Synthesis Examples 23 to 45

Final products described in Table 6 were synthesized as an example according to Chemical Formula 2 according to a similar method to that of the 4th step of Synthesis Example 22 except that at least one of the intermediates of Int-23 and Int-24 was changed into Intermediate C shown in Table 4 and Intermediate D shown in Table 5.

TABLE 4

<Intermediate C>

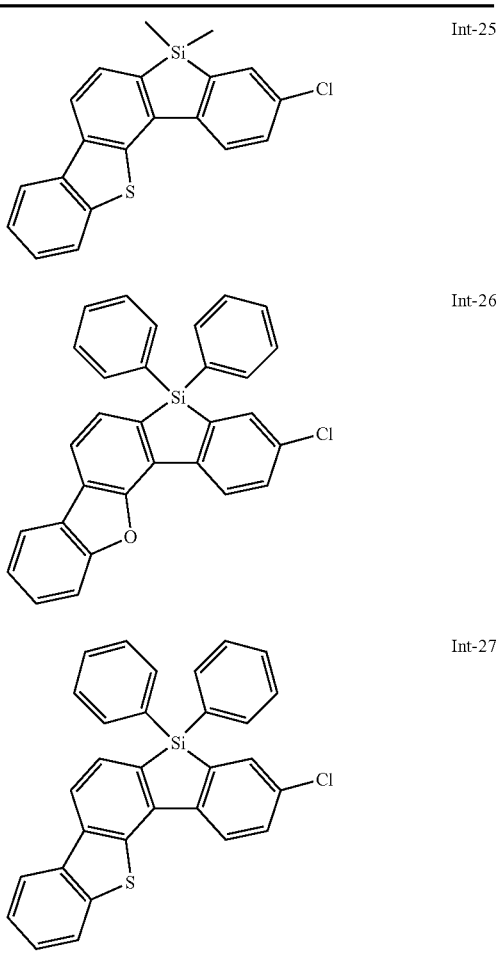

TABLE 5
<Intermediate D>
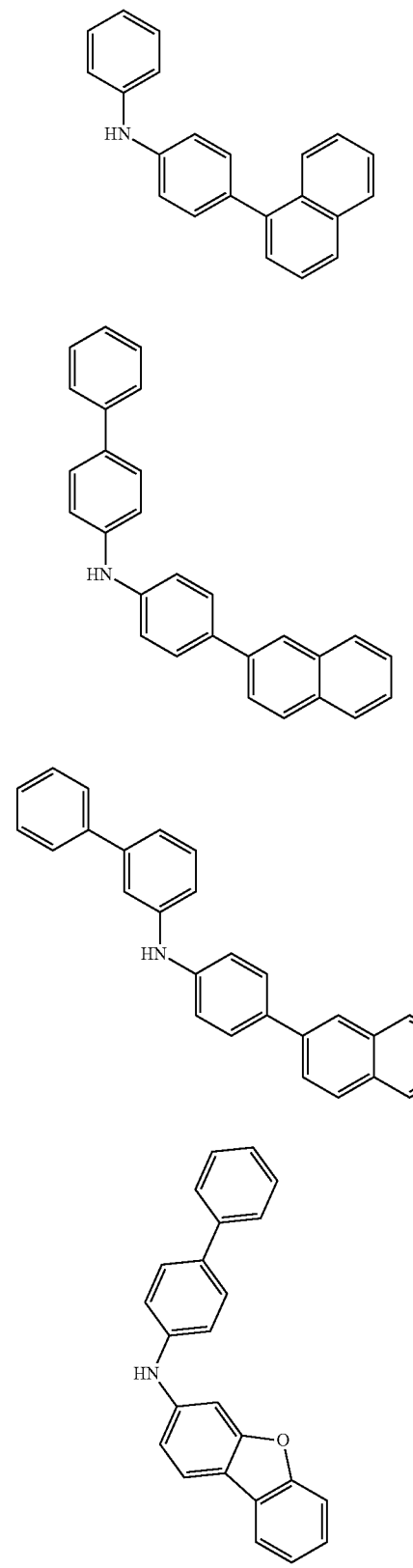
Int-28
Int-29
Int-30
Int-31
TABLE 5-continued
<Intermediate D>
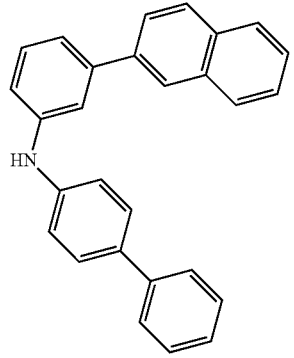 [SMILES: c1ccc(-c2ccc(Nc3cccc(-c4ccc5ccccc5c4)c3)cc2)cc1]
Int-32
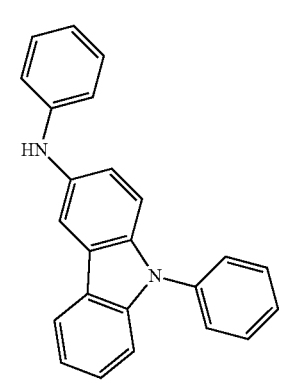 [SMILES: c1ccc(Nc2ccc3c(c2)c2ccccc2n3-c2ccccc2)cc1]
Int-33
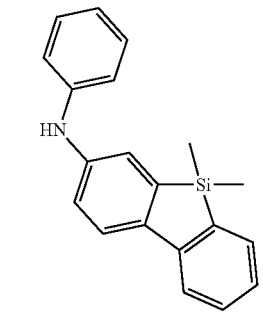 [SMILES: C[Si]1(C)c2ccccc2-c2ccc(Nc3ccccc3)cc21]
Int-34
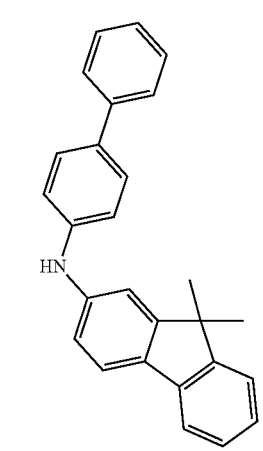 [SMILES: CC1(C)c2ccccc2-c2ccc(Nc3ccc(-c4ccccc4)cc3)cc21]
Int-35

TABLE 5-continued

<Intermediate D>

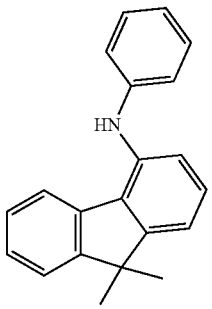 [SMILES: CC1(C)c2ccccc2-c2c(Nc3ccccc3)cccc21]

Int-36

<Intermediate D>

Int-37

TABLE 6

<Final Products>

| Synthesis Examples | Int. C | Int. D | Final products | Yield amount (Yield) | Property data of final products |
|---|---|---|---|---|---|
| Synthesis Example 23 | Int-23 | Int-28 | Compound F-6 | 3.18 g (74%) | calcd. C42H31NOSi: C, 84.95; H, 5.26; N, 2.36; 0, 2.69; Si, 4.73 found C, 84.96; H, 5.26; N, 2.36; 0, 2.69; Si, 4.72 |
| Synthesis Example 24 | Int-23 | Int-29 | Compound F-9 | 4.48 g (67%) | calcd. C48H35NOSi: C, 86.06; H, 5.27; N, 2.09; 0, 2.39; Si, 4.19 found: C, 86.06; H, 5.27; N, 2.09; 0, 2.39; Si, 4.19 |
| Synthesis Example 25 | Int-23 | Int-30 | Compound F-13 | 5.84 g (71%) | calcd. C48H35NOSi: C, 86.06; H, 5.27; N, 2.09; 0, 2.39; Si, 4.19 found: C, 86.06; H, 5.26; N, 2.10; 0, 2.39; Si, 4.19 |
| Synthesis Example 26 | Int-23 | Int-31 | Compound F-26 | 4.33 g (68%) | calcd. C44H31NO2Si: C, 83.38; H, 4.93; N, 2.21; 0, 5.05; Si, 4.43; found: C, 83.37; H, 4.92; N, 2.21; 0, 5.05; Si, 4.43 |
| Synthesis Example 27 | Int-23 | Int-32 | Compound F-35 | 4.28 g (69%) | calcd. C48H35NOSi: C, 86.06; H, 5.27; N, 2.09; 0, 2.39; Si, 4.19 found: C, 86.06; H, 5.27; N, 2.11; 0, 2.38; Si, 4.19 |
| Synthesis Example 28 | Int-23 | Int-33 | Compound F-57 | 4.47 g (71%) | calcd. C44H32N2OSi: C, 83.51; H, 5.10; N, 4.43; 0, 2.53; Si, 4.44 found: C, 83.52; H, 5.10; N, 4.43; 0, 2.53; Si, 4.43 |
| Synthesis Example 29 | Int-23 | Int-34 | Compound F-66 | 6.63 g (69%) | calcd. C40H33NOSi2 C, 80.09; H, 5.55; N, 2.33; 0, 2.67; Si, 9.36 found: C, 80.09; H, 5.55; N, 2.33; 0, 2.67; Si, 9.36 |
| Synthesis Example 30 | Int-23 | Int-35 | Compound F-71 | 6.21 g (74%) | calcd. C47H37NOSi C, 85.55; H, 5.65; N, 2.12; 0, 2.42; Si, 4.26 found: C, 85.55; H, 5.64; N, 2.13; 0, 2.42; Si, 4.26 |
| Synthesis Example 31 | Int-25 | Int-24 | Compound G-5 | 4.56 g (70%) | calcd. C42H31NSSi: C, 82.72; H, 5.12; N, 2.30; S, 5.26; Si, 4.61; found: C, 82.71; H, 5.12; N, 2.30; S, 5.26; Si, 4.61 |
| Synthesis Example 32 | Int-25 | Int-29 | Compound G-9 | 3.64 g (75%) | calcd. C48H35NSSi: C, 84.05; H, 5.14; N, 2.04; S, 4.67; Si, 4.09; found: C, 84.05; H, 5.13; N, 2.05; S, 4.67; Si, 4.09 |
| Synthesis Example 33 | Int-25 | Int-30 | Compound G-13 | 7.33 g (64%) | calcd. C48H35NSSi: C, 84.05; H, 5.14; N, 2.04; S, 4.67; Si, 4.09; found: C, 84.05; H, 5.14; N, 2.05; S, 4.67; Si, 4.08 |
| Synthesis Example 34 | Int-25 | Int-31 | Compound G-26 | 5.86 g (69%) | calcd. C44H31NOSSi: C, 81.32; H, 4.81; N, 2.16; 0, 2.46; S, 4.93; Si, 4.32; found: C, 81.32; H, 4.81; N, 2.16; 0, 2.46; S, 4.93; Si, 4.32 |
| Synthesis Example 35 | Int-25 | Int-32 | Compound G-35 | 4.11 g (67%) | calcd. C48H35NSSi: C, 84.05; H, 5.14; N, 2.04; S, 4.67; Si, 4.09; found: C, 84.05; H, 5.14; N, 2.04; S, 4.67; Si, 4.09 |
| Synthesis Example 36 | Int-25 | Int-33 | Compound G-57 | 5.92 g (69%) | calcd. C44H32N2SSi: C, 81.44; H, 4.97; N, 4.32; S, 4.94; Si, 4.33; found: C, 81.45; H, 4.96; N, 4.32; S, 4.94; Si, 4.33 |
| Synthesis Example 37 | Int-25 | Int-36 | Compound G-64 | 5.89 g (74%) | calcd. C41H33NSSi: C, 82.09; H, 5.55; N, 2.34; S, 5.34; Si, 4.68; found: C, 82.09; H, 5.55; N, 2.35; S, 5.33; Si, 4.68 |
| Synthesis Example 38 | Int-25 | Int-34 | Compound G-66 | 5.95 g (65%) | calcd. C40H33NSSi2: C, 78.00; H, 5.40; N, 2.27; S, 5.21; Si, 9.12; found: C, 78.01; H, 5.40; N, 2.27; S, 5.20; Si, 9.12 |
| Synthesis Example 39 | Int-25 | Int-35 | Compound G-71 | 5.54 g (74%) | calcd. C47H37NSSi: C, 83.51; H, 5.52; N, 2.07; S, 4.74; Si, 4.15; found: C, 83.51; H, 5.52; N, 2.07; S, 4.74; Si, 4.15 |
| Synthesis Example 40 | Int-26 | Int-24 | Compound H-5 | 7.83 g (70%) | calcd. C52H35NOSi: C, 86.99; H, 4.91; N, 1.95; 0, 2.23; Si, 3.91; found: C, 86.99; H, 4.91; N, 1.95; 0, 2.23; Si, 3.91 |
| Synthesis Example 41 | Int-26 | Int-37 | Compound H-14 | 3.44 g (74%) | calcd. C52H35NOSi: C, 86.99; H, 4.91; N, 1.95; 0, 2.23; Si, 3.91; found: C, 86.99; H, 4.91; N, 1.96; 0, 2.23; Si, 3.90 |
| Synthesis Example 42 | Int-26 | Int-33 | Compound H-25 | 6.98 g (69%) | calcd. C54H36N2OSi: C, 85.68; H, 4.79; N, 3.70; 0, 2.11; Si, 3.71; found: C, 85.68; H, 4.79; N, 3.70; 0, 2.11; Si, 3.71 |
| Synthesis Example 43 | Int-27 | Int-24 | Compound H-41 | 3.66 g (64%) | calcd. C52H35NSSi: C, 85.09; H, 4.81; N, 1.91; S, 4.37; Si, 3.83; found: C, 85.09; H, 4.81; N, 1.92; S, 4.36; Si, 3.83 |
| Synthesis Example 44 | Int-27 | Int-37 | Compound H-50 | 3.80 g (69%) | calcd. C52H35NSSi: C, 85.09; H, 4.81; N, 1.91; S, 4.37; Si, 3.83; found: C, 85.10; H, 4.81; N, 1.91; S, 4.36; Si, 3.83 |
| Synthesis Example 45 | Int-27 | Int-33 | Compound H-61 | 4.58 g (70%) | calcd. C54H36N2SSi: C, 83.90; H, 4.69; N, 3.62; S, 4.15; Si, 3.63; found: C, 83.90; H, 4.69; N, 3.62; S, 4.15; Si, 3.63 |

Synthesis of Comparative Synthesis Examples 1 to 3

Comparative Compound 1 was synthesized as a comparative example (for comparison with the compound represented by Chemical Formula 1) according to a similar method to that of the 4$^{th}$ step of Synthesis Example 1, except that the intermediate of Int-38 shown in Table 7 was used instead of the Intermediate Int-5 of Synthesis Example 1.

In addition, Comparative Compounds 2 and 3 were synthesized as comparative examples (for comparison with the compound represented by Chemical Formula 2) according to a similar method to that of the 4$^{th}$ step of Synthesis Example 22, except that the intermediate of Int-39 or Int-40 shown in Table 7 was used instead of the Intermediate of Int-23 according to Synthesis Example 22.

TABLE 7
| Comparative Synthesis Example | Intermediate of Synthesis Example 1 | Intermediate of Synthesis Example 22 | Final products | Yield amount (Yield) | Property data of final products |
|---|---|---|---|---|---|
| Comparative Synthesis Example 1 | 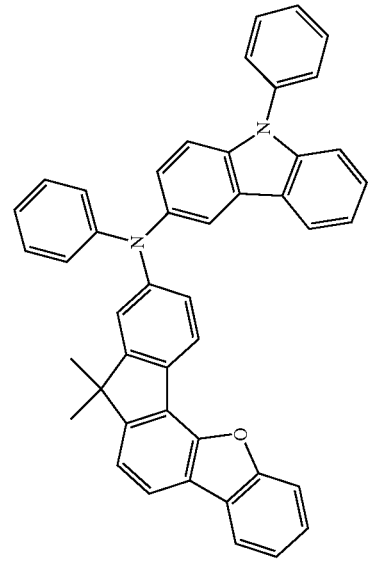<br>Int-38 | — | Comparative compound 1 | 8.38 g (76%) | calcd. C40H29N3: C, 87.08; H, 5.30; N, 7.62 found C, 87.08; H, 5.29; N, 7.63 |
| Comparative Synthesis Example 2 | — | 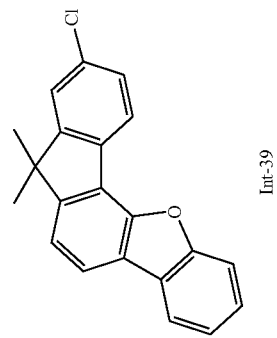<br>Int-39 | Comparative compound 2 | 5.62 g (72%) | calcd. C45H32N2O: C, 87.63; H, 5.23; N, 4.54; O, 2.59 found C, 87.64; H, 5.27; N, 4.54; O, 2.59 |

TABLE 7-continued
| Comparative Synthesis Example | Intermediate of Synthesis Example 1 | Intermediate of Synthesis Example 22 | Final products | Yield amount (Yield) | Property data of final products |
|---|---|---|---|---|---|
| Comparative Synthesis Example 3 | — | 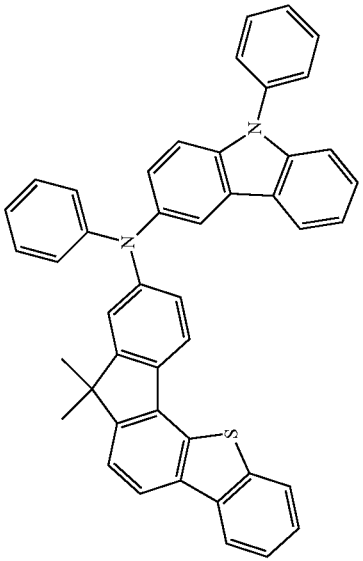<br>Int-40 | 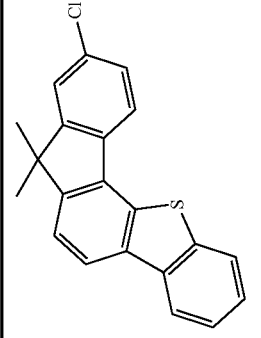<br>Comparative compound 3 | 6.90 g (71%) | calcd. C45H32N2S: C, 85.41; H, 5.10; N, 4.43; S, 5.07; found : C, 85.43; H, 5.10; N, 4.43; S, 5.05 |

(Manufacture of Organic Light Emitting Diode)

Example 1

A glass substrate coated with ITO (Indium tin oxide) at a thickness of 1,500 Å was washed with distilled water. After washing with the distilled water, the glass substrate was washed with isopropyl alcohol, acetone, or methanol, ultrasonicated and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to be 50 Å-thick on the injection layer, and then Compound C was deposited to be 700 Å-thick to form a hole transport layer. On the hole transport layer, 400 Å-thick light emitting layer was formed by using Compound A-2 obtained in Synthesis Example 1 and Compound F-57 obtained in Synthesis Example 22 simultaneously as a host and doping 2 wt % of [Ir(piq)$_2$acac] as a dopant by a vacuum-deposition. Herein, Compound A-2 and Compound F-57 were used in a weight ratio of 5:5. Subsequently, on the light emitting layer, a 300 Å-thick electron transport layer was formed by simultaneously vacuum-depositing Compound D and Liq in a weight ratio of 1:1, and on the electron transport layer, Liq and Al were sequentially vacuum-deposited to be 15 Å-thick and 1,200 Å-thick, manufacturing an organic light emitting diode.

The organic light emitting diode had a five-layered organic thin layer, and specifically the following structure.

ITO/Compound A (700 Å)/Compound B (50 Å)/Compound C (700 Å)/EML[98 wt % of Host (Compound A-2: Compound F-57=5:5 and 2 wt % of Dopant: [Ir(piq)$_2$acac]] (400 Å)/Compound D: Liq (300 Å)/Liq (15 Å)/Al (1,200 Å).

Compound A: N4,N4'-diphenyl-N4,N4'-bis(9-phenyl-9H-carbazol-3-yl) biphenyl-4,4'-diamine Compound B: 1,4,5,8,9,11-hexaazatriphenylene-hexacarbonitrile (HAT-CN)

Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl) quinoline

Examples 2 to 16, and Comparative Examples 1 to 3

Diodes of Examples 2 to 16 and Comparative Examples 1 to 3 were manufactured in the same manner as in Example 1, except that the host was changed as described in Table 8.

Evaluation

The driving voltage, efficiency, and life-span characteristics of the organic light emitting diodes according to Examples 1 and 16 and Comparative Examples 1 to 3 were evaluated. Specific measurement methods are as follows, and the results are shown in Table 8.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) was calculated by using the luminance and current density from the items (1) and (2).

(4) Measurement of Life-Span

While maintaining luminance (cd/m$^2$) at 5,000 cd/m$^2$, a time for the current efficiency (cd/A) to decrease to 90% was measured to obtain results.

(5) Measurement of Driving Voltage

Driving voltages of the organic light emitting diodes at 15 mA/cm$^2$ were measured by using a current-voltage meter (Keithley 2400).

Based on the results of Example 9, relative values of driving voltages, luminous efficiency, and life-spans were compared and evaluated, respectively.

TABLE 8

| | First host | Second host | Driving voltage (V) | Luminous efficiency (cd/A) | Luminance (cd/m$^2$) | Life-span T90 (h) |
|---|---|---|---|---|---|---|
| Example 1 | Compound A-2 | F-57 | 96% | 108% | 5000 | 120% |
| Example 2 | Compound A-4 | | 95% | 108% | 5000 | 123% |
| Example 3 | Compound A-10 | | 94% | 109% | 5000 | 124% |
| Example 4 | Compound A-12 | | 95% | 110% | 5000 | 124% |
| Example 5 | Compound B-2 | | 97% | 106% | 5000 | 121% |
| Example 6 | Compound B-4 | | 96% | 107% | 5000 | 124% |
| Example 7 | Compound C-2 | | 98% | 104% | 5000 | 110% |
| Example 8 | Compound D-2 | | 99% | 103% | 5000 | 108% |
| Example 9 | Compound E-2 | | 100% | 100% | 5000 | 100% |
| Example 10 | Compound E-4 | | 99% | 102% | 5000 | 105% |
| Example 11 | A-12 | F-5 | 94% | 107% | 5000 | 124% |
| Example 12 | | F-6 | 95% | 106% | 5000 | 129% |
| Example 13 | | F-26 | 95% | 106% | 5000 | 120% |
| Example 14 | | G-5 | 94% | 108% | 5000 | 126% |
| Example 15 | | G-64 | 93% | 109% | 5000 | 115% |
| Example 16 | | H-5 | 99% | 103% | 5000 | 105% |
| Comparative Example 1 | Comparative compound 1 | F-57 | 107% | 95% | 5000 | 94% |
| Comparative Example 2 | A-12 | Comparative Compound 2 | 106% | 95% | 5000 | 93% |
| Comparative Example 3 | A-12 | Comparative Compound 3 | 107% | 96% | 5000 | 91% |

Referring to Table 8, the compounds according to the Examples exhibited significantly improved driving, efficiency, and life-span characteristics compared with the Comparative Examples.

One or more embodiments may provide a composition for an organic optoelectronic device capable of implementing a high efficiency and long life-span organic optoelectronic device.

High efficiency and long life-span organic optoelectronic devices may be implemented.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A composition for an organic photoelectronic device, the composition comprising:
a first compound represented by Chemical Formula 1, and
a second compound represented by Chemical Formula 2:

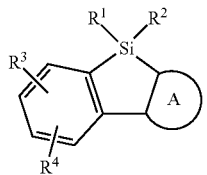

[Chemical Formula 1]

wherein:
$R^1$ and $R^2$ are each independently a substituted or unsubstituted C1 to C10 alkyl group, a substituted or unsubstituted C3 to C10 cycloalkyl group, a substituted or unsubstituted C6 to C20 aryl group, or a combination thereof, $R^3$ and $R^4$ are each independently hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof, and ring A is a moiety of the following Group A, Group A

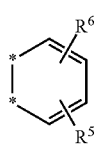

[A-1]

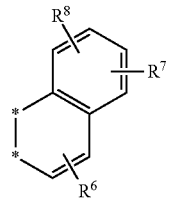

[A-2]

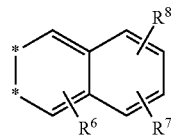

[A-3]

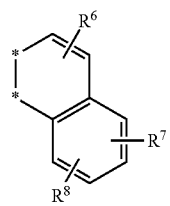

[A-4]

wherein:
$R^5$ to $R^8$ are each independently hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof,

* is a linking point, and at least one of $R^3$ to $R^8$ is a substituent represented by Chemical Formula B,

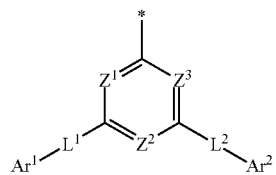

[Chemical Formula B]

wherein:
$Z^1$ to $Z^3$ are each independently N or $CR^a$, at least two of $Z^1$ to $Z^3$ being N, each $R^a$ is independently hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof, $L^1$ and $L^2$ are each independently a single bond or a substituted or unsubstituted C6 to C30 arylene group, $Ar^1$ and $Ar^2$ are each independently a substituted or unsubstituted C6 to C30 aryl group, a substituted or unsubstituted C2 to C30 heterocyclic group, or a combination thereof;

[Chemical Formula 2]

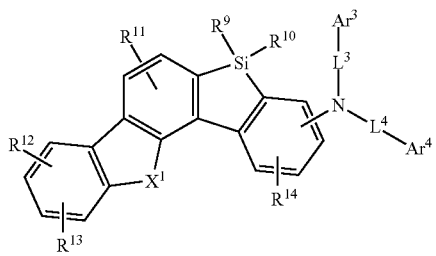

$X^1$ is O or S, $R^9$ and $R^{10}$ are each independently a substituted or unsubstituted C1 to C10 alkyl group, a substituted or unsubstituted C3 to C10 cycloalkyl group, a substituted or unsubstituted C6 to C20 aryl group, or a combination thereof, $R^{11}$ to $R^{14}$ are each independently hydrogen, deuterium, a cyano group, a halogen, a substituted or unsubstituted C1 to C30 alkyl group, a substituted or unsubstituted C6 to C30 aryl group, a substituted or unsubstituted C2 to C30 heterocyclic group, or a combination thereof, $L^3$ and $L^4$ are each independently a single bond or a substituted or unsubstituted C6 to C30 arylene group, and $Ar^3$ and $Ar^4$ are each independently a substituted or unsubstituted C6 to C30 aryl group, a substituted or unsubstituted C2 to C30 heterocyclic group, or a combination thereof.

2. The composition as claimed in claim 1, wherein:

the first compound is represented by Chemical Formula 1A, Chemical Formula 1E, Chemical Formula 1F, or Chemical Formula 1G,

[Chemical Formula 1A]

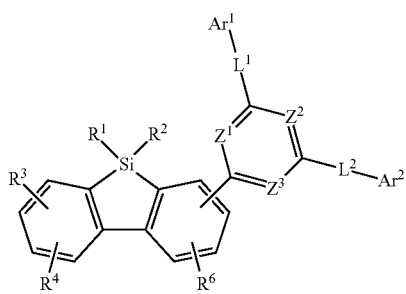

[Chemical Formula 1E]

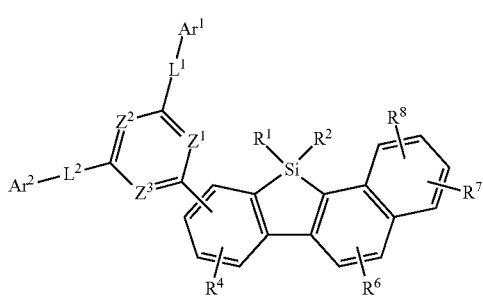

[Chemical Formula 1F]

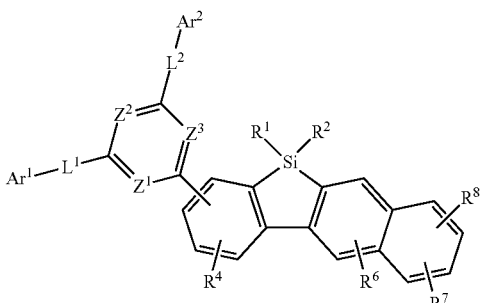

[Chemical Formula 1G]

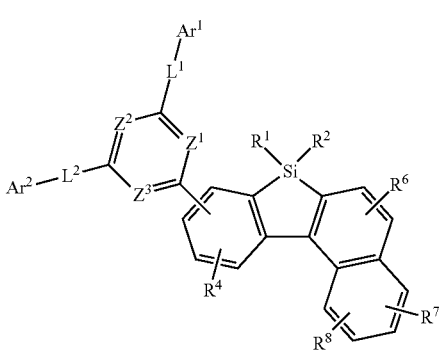

in Chemical Formula 1A and Chemical Formula 1E to Chemical Formula 1G, $R^1$ to $R^4$, $R^6$ to $R^8$, $Z^1$ to $Z^3$, $L^1$, $L^2$, $Ar^1$, and $Ar^2$ are defined the same as those of Chemical Formula 1.

3. The composition as claimed in claim 1, wherein:

the first compound is represented by Chemical Formula 1A-2, Chemical Formula 1A-4, Chemical Formula 1E-2, Chemical Formula 1E-4, Chemical Formula 1F-2, Chemical Formula 1F-4, Chemical Formula 1G-2, or Chemical Formula 1G-4:

[Chemical Formula 1A-2]

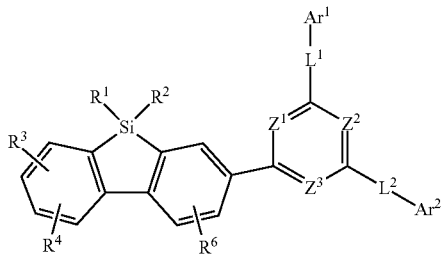

[Chemical Formula 1A-4]

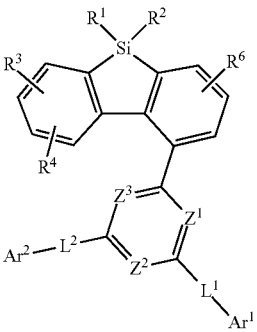

-continued

[Chemical Formula 1E-2]

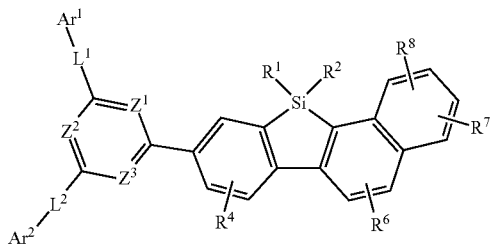

[Chemical Formula 1E-4]

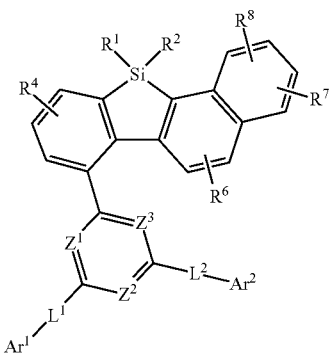

[Chemical Formula 1F-2]

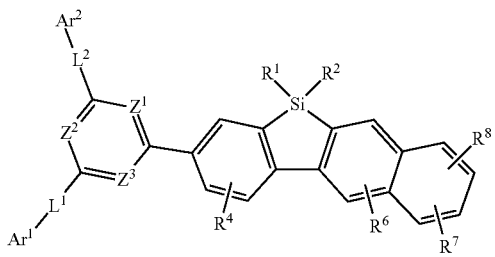

[Chemical Formula 1F-4]

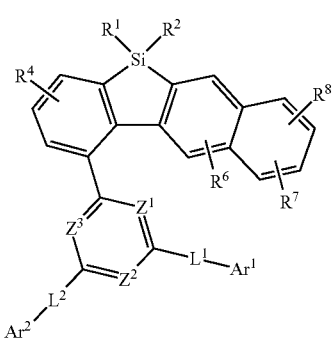

[Chemical Formula 1G-2]

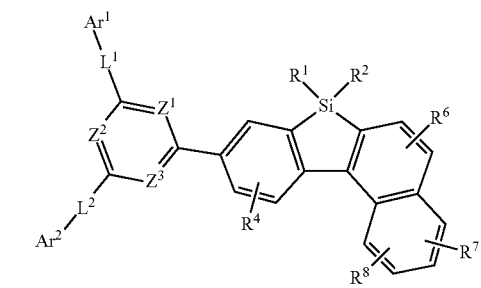

-continued

[Chemical Formula 1G-4]

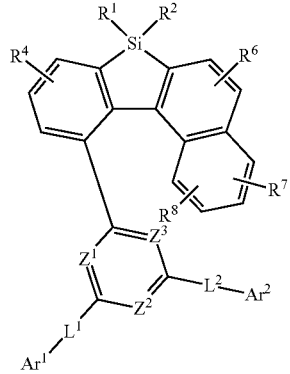

in Chemical Formula 1A-2, Chemical Formula 1A-4, Chemical Formula 1E-2, Chemical Formula 1E-4, Chemical Formula 1F-2, Chemical Formula 1F-4, Chemical Formula 1G-2, and Chemical Formula 1G-4, $R^1$ to $R^4$, $R^6$ to $R^8$, $Z^1$ to $z^3$, $L^1$, $L^2$, $Ar^1$, and $Ar^2$ are defined the same as those of Chemical Formula 1.

4. The composition as claimed in claim 3, wherein:

the first compound is represented by Chemical Formula 1A-2 or Chemical Formula 1A-4, $Ar^1$ and $Ar^2$ are each independently a substituted or unsubstituted phenyl group, a substituted or unsubstituted biphenyl group, or a substituted or unsubstituted naphthyl group, $R^1$ and $R^2$ are each independently a substituted or unsubstituted C1 to C5 alkyl group or a substituted or unsubstituted phenyl group, $R^3$, $R^4$, and $R^6$ are each independently hydrogen or a substituted or unsubstituted phenyl group, and $L^1$ and $L^2$ are each independently a single bond or a substituted or unsubstituted phenylene group.

5. The composition as claimed in claim 3, wherein:

the first compound is represented by Chemical Formula 1E-2, Chemical Formula 1E-4, Chemical Formula 1F-2, Chemical Formula 1F-4, Chemical Formula 1G-2, or Chemical Formula 1G-4, $Ar^1$ and $Ar^2$ are each independently a substituted or unsubstituted phenyl group, a substituted or unsubstituted biphenyl group, or a substituted or unsubstituted naphthyl group, $R^1$ and $R^2$ are each independently a substituted or unsubstituted C1 to C5 alkyl group or a substituted or unsubstituted phenyl group, $R^4$ and $R^6$ to $R^8$ are each independently hydrogen or a substituted or unsubstituted phenyl group, and $L^1$ and $L^2$ are each independently a single bond or a substituted or unsubstituted phenylene group.

6. The composition as claimed in claim 1, wherein:

the second compound is represented by Chemical Formula 2-2:

[Chemical Formula 2-2]

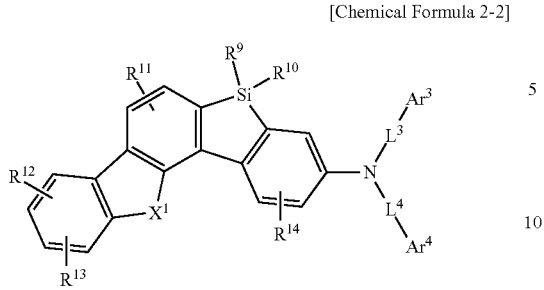

in Chemical Formula 2-2, $X^1$, $R^9$ to $R^{14}$, $L^3$, $L^4$, $Ar^3$, and $Ar^4$ are defined the same as those of Chemical Formula 2.

7. The composition as claimed in claim 6, wherein:

$Ar^3$ and $Ar^4$ are each independently a substituted or unsubstituted phenyl group, a substituted or unsubstituted biphenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted dibenzofuranyl group, a substituted or unsubstituted dibenzothiophenyl group, a substituted or unsubstituted carbazolyl group, or a substituted or unsubstituted dibenzosilole group, $L^3$ and $L^4$ are each independently a single bond, a substituted or unsubstituted phenylene group, or a substituted or unsubstituted naphthylene group, $R^9$ and $R^{10}$ are each independently a substituted or unsubstituted C1 to C5 alkyl group or a substituted or unsubstituted phenyl group, and $R^{11}$ to $R^{14}$ are each independently hydrogen or a substituted or unsubstituted phenyl group.

8. The composition as claimed in claim 6, wherein:

$Ar^3$ and $Ar^4$ are each independently a substituted or unsubstituted phenyl group, a substituted or unsubstituted biphenyl group, a substituted or unsubstituted naphthyl group, a substituted or unsubstituted fluorenyl group, a substituted or unsubstituted dibenzofuranyl group, a substituted or unsubstituted dibenzothiophenyl group, a substituted or unsubstituted carbazolyl group, or a substituted or unsubstituted dibenzosilole group, $L^3$ and $L^4$ are each independently a single bond or a substituted or unsubstituted phenylene group, $R^9$ and $R^{14}$ are each independently a substituted or unsubstituted methyl group or a substituted or unsubstituted phenyl group, and $R^{11}$ to $R^{14}$ are each hydrogen.

9. The composition as claimed in claim 1, wherein:

the first compound is represented by Chemical Formula 1A-2, Chemical Formula 1A-4, Chemical Formula 1E-2, Chemical Formula 1E-4, Chemical Formula 1F-2, Chemical Formula 1F-4, Chemical Formula 1G-2, or Chemical Formula 1G-4, the second compound is represented by Chemical Formula 2-2:

[Chemical Formula 1A-2]

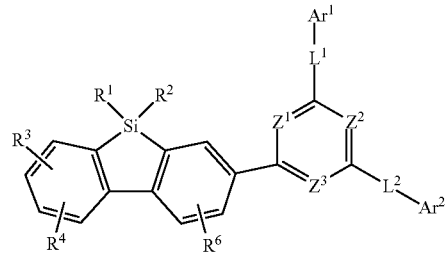

[Chemical Formula 1A-4]

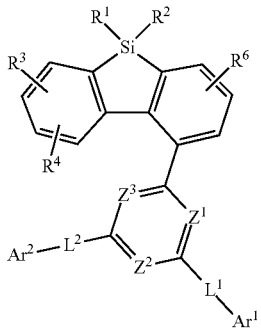

[Chemical Formula 1E-2]

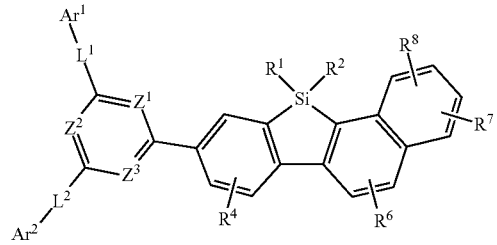

[Chemical Formula 1E-4]

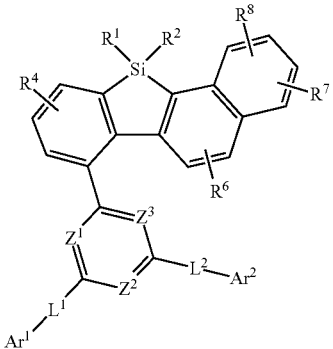

[Chemical Formula 1F-2]

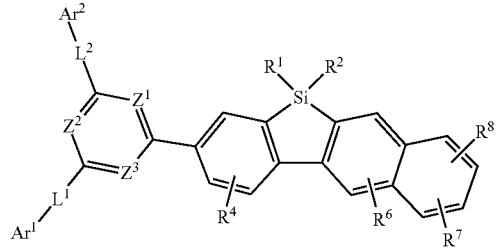

-continued

[Chemical Formula 1F-4]

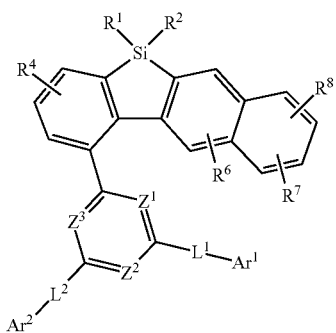

[Chemical Formula 1G-2]

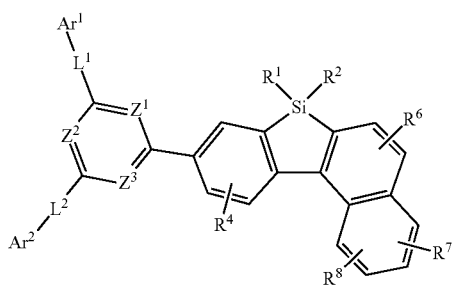

[Chemical Formula 1G-4]

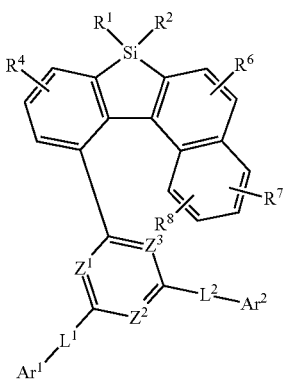

[Chemical Formula 2-2]

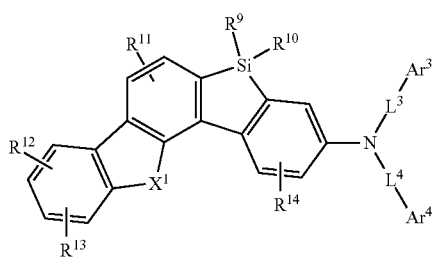

in Chemical Formula 1A-2, Chemical Formula 1A-4, Chemical Formula 1E-2, Chemical Formula 1E-4, Chemical Formula 1F-2, Chemical Formula 1F-4, Chemical Formula 1G-2, and Chemical Formula 1G-4, $R^1$ to $R^4$, $R^6$ to $R^8$, $Z^1$ to $Z^3$, $L^1$, $L^2$, $Ar^1$, and $Ar^2$ are defined the same as those of Chemical Formula 1, and in Chemical Formula 2-2, $X^1$, $R^9$ to $R^{14}$, $L^3$, $L^4$, $Ar^3$, and $Ar^4$ are defined the same as those of Chemical Formula 2.

10. The composition as claimed in claim 9, wherein:
in Chemical Formula 1A-2 and Chemical Formula 1A-4, $Ar^1$ and $Ar^2$ are each independently a substituted or unsubstituted phenyl group, a substituted or unsubstituted biphenyl group, or a substituted or unsubstituted naphthyl group, $R^1$ and $R^2$ are each independently a substituted or unsubstituted C1 to C5 alkyl group or a substituted or unsubstituted phenyl group, $R^3$, $R^4$, and $R^6$ are each independently hydrogen or a substituted or unsubstituted phenyl group, and $L^1$ and $L^2$ are each independently a single bond or a substituted or unsubstituted phenylene group,
in Chemical Formula 1E-2, Chemical Formula 1E-4, Chemical Formula 1F-2, Chemical Formula 1F-4, Chemical Formula 1G-2, and Chemical Formula 1G-4, $Ar^1$ and $Ar^2$ are each independently a substituted or unsubstituted phenyl group, a substituted or unsubstituted biphenyl group, or a substituted or unsubstituted naphthyl group, $R^1$ and $R^2$ are each independently a substituted or unsubstituted C1 to C5 alkyl group or a substituted or unsubstituted phenyl group, $R^4$ and $R^6$ to $R^8$ are each independently hydrogen or a substituted or unsubstituted phenyl group, and $L^1$ and $L^2$ are each independently a single bond or a substituted or unsubstituted phenylene group, and
in Chemical Formula 2-2, $Ar^3$ and $Ar^4$ are each independently a substituted or unsubstituted phenyl group, a substituted or unsubstituted biphenyl group, a substituted or unsubstituted naphthyl group, a substituted or unsubstituted fluorenyl group, a substituted or unsubstituted dibenzofuranyl group, a substituted or unsubstituted dibenzothiophenyl group, a substituted or unsubstituted carbazolyl group, or a substituted or unsubstituted dibenzosilole group, $L^3$ and $L^4$ are each independently a single bond or a substituted or unsubstituted phenylene group, and $R^9$ and $R^{10}$ are each independently a substituted or unsubstituted methyl group or a substituted or unsubstituted phenyl group, and $R^{11}$ to $R^{14}$ are each hydrogen.

11. An organic photoelectronic device, comprising:
an anode and a cathode facing each other; and
at least one organic layer between the anode and the cathode,
wherein:
the at least one organic layer includes a light emitting layer, and
the light emitting layer includes the composition for an organic photoelectronic device as claimed in claim 1.

12. The organic photoelectronic device as claimed in claim 11, wherein the composition for an organic photoelectronic device is a host of the light emitting layer.

13. The organic photoelectronic device as claimed in claim 11, wherein the composition includes the first compound and the second compound in a weight ratio of about 70:30 to about 40:60.

14. A display device comprising the organic photoelectronic device as claimed in claim 11.

* * * * *